United States Patent
Terasawa et al.

(10) Patent No.: US 6,646,123 B2
(45) Date of Patent: *Nov. 11, 2003

(54) PENTACYCLIC COMPOUND

(75) Inventors: Hirofumi Terasawa, Tokyo (JP); Tsunehiko Soga, Tokyo (JP); Takashi Ishiyama, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/126,653

(22) Filed: Apr. 22, 2002

(65) Prior Publication Data

US 2003/0162971 A1 Aug. 28, 2003

Related U.S. Application Data

(62) Division of application No. 09/759,378, filed on Jan. 16, 2001, which is a continuation of application No. 09/513,852, filed on Feb. 25, 2000, now Pat. No. 6,211,363, which is a continuation of application No. 08/945,276, filed as application No. PCT/JP96/01145 on Apr. 25, 1996, now Pat. No. 6,075,140.

(30) Foreign Application Priority Data

Apr. 28, 1995 (JP) .............................................. 7-106295

(51) Int. Cl.$^7$ ...................... C07D 493/08; C07D 305/14
(52) U.S. Cl. .................... 544/60; 544/148; 544/368; 546/283.7; 548/526; 549/482; 549/510
(58) Field of Search ............... 544/60, 148, 368; 546/283.7; 548/526; 549/482, 510

(56) References Cited

U.S. PATENT DOCUMENTS

| | | |
|---|---|---|
| 5,254,580 A | 10/1993 | Chen et al. |
| 5,284,864 A | 2/1994 | Holton et al. |
| 5,284,865 A | 2/1994 | Holton et al. |
| 5,475,011 A | 12/1995 | Ojima et al. |
| 5,481,010 A | 1/1996 | Ahond et al. |
| 5,599,820 A | 2/1997 | Ojima et al. |
| 5,780,653 A | 7/1998 | Tao et al. |
| 6,075,140 A | 6/2000 | Terasawa et al. |
| 6,211,363 B1 | 4/2001 | Terasawa et al. |

FOREIGN PATENT DOCUMENTS

| | | |
|---|---|---|
| JP | 6-179665 | 6/1994 |
| WO | WO 93/21173 | 10/1993 |
| WO | WO 94/21250 | 9/1994 |
| WO | WO 95/11247 | 4/1995 |
| WO | WO 95/13270 | 5/1995 |
| WO | WO 96/03395 | 2/1996 |

OTHER PUBLICATIONS

Journal of Organic Chemistry, vol. 59, No. 21, (1994) C. Shu–hui et al., p. 6156–6158.

*Primary Examiner*—Deepak Rao
(74) *Attorney, Agent, or Firm*—Sughrue Mion, PLLC

(57) ABSTRACT

The present invention relates to a novel taxol derivative having an antitumor activity which is represented by formula (1).

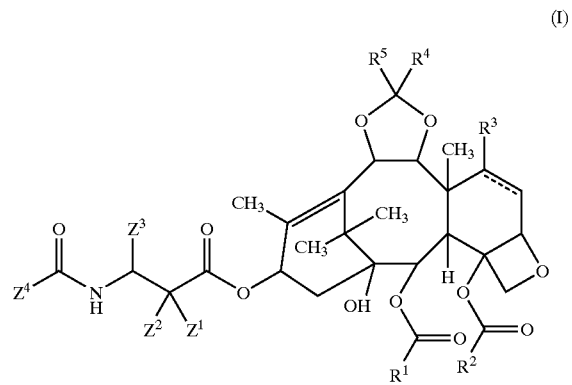

[In the formula (I), $R^1$: a phenyl group, $R^2$: an alkyl group, an alkenyl group, an alkynyl group, a cycloalkyl group or an alkoxyl group, $R^3$: a hydrogen atom, a hydroxyl group, a halogen atom, an alkoxyl group, a group —O—$R^{31}$, an acyloxy group or a group —O—CO—$R^{31}$, (in which $R^{31}$: an alkylamino group, an alkenyl group, an alkynyl group, a cycloalkyl group, an aryl group or a heterocyclic group), $R^4$ and $R^5$: a hydrogen atom, an alkyl group, an alkenyl group, an alkynyl group, an aryl group or a heterocyclic group, $Z^1$: a hydrogen atom, a hydroxyl group, a halogen atom or an alkyl group, $Z^2$: a hydrogen atom, a hydroxyl group, a halogen atom or an alkyl group, $Z^3$: an alkyl group, an alkenyl group, an alkynyl group, a cycloalkyl group, an aryl group or a heterocyclic group].

2 Claims, No Drawings

PENTACYCLIC COMPOUND

This is a divisional of application Ser. No. 09/759,378 filed Jan. 16, 2001; which is a continuation of application Ser. No. 09/513,852 now U.S. Pat. No. 6,211,363; in turn a continuation application of application Ser. No. 08/945,276, filed Oct. 22, 1997 now U.S. Pat. No. 6,075,140 which is a 371 of PCP/JP96/01145 filed Apr. 25, 1996, the disclosure of which is incorporated herein by reference.

TECHNICAL FIELD

This invention relates to a novel taxol derivative having an antitumor activity.

BACKGROUND ART

Taxol is a natural compound having the following chemical structure, which can be obtained in a small amount from a trunk or the like of *Taxus brevifolia*.

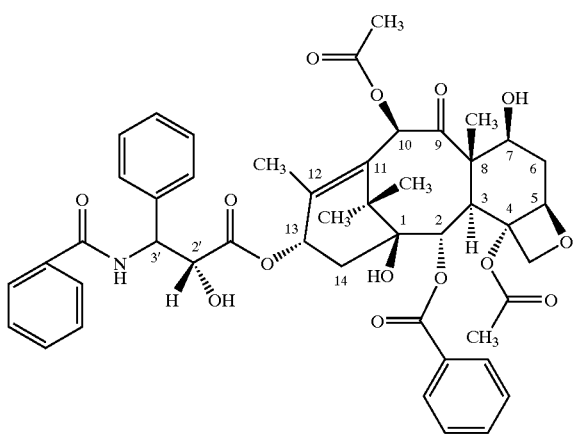

It is known that taxol has an antitumor activity and its action mechanism is based on the depolymerization inhibition action of microtubule during cell division, so that its clinical application is expected as an antitumor agent which is different from the general antitumor agents.

Though taxol can be obtained only in an extremely small amount from a natural source, reports have been published recently on the synthesis of taxol derivatives using a starting material 10-O-deacethylbaccatin III represented by the following structural formula:

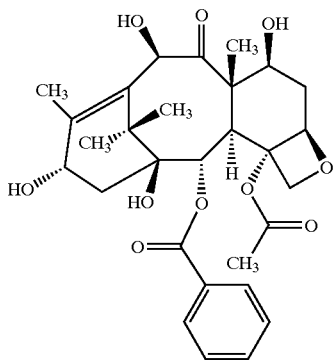

which is a taxol precursor that can be obtained in a relatively large amount from leaves and the like of taxaceous trees (cf. JP-A-3-505725; the term "JP-A" as used herein means an "unexamined published Japanese patent application"). Of such derivatives, a compound (Taxotere™) represented by the following structural formula:

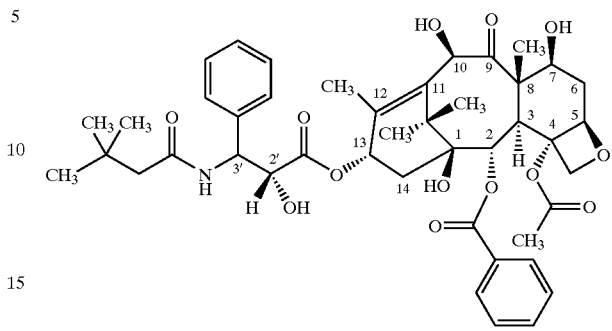

has been drawing attention as a compound which has an antitumor activity similar to or higher than that of taxol and is now under development as an antitumor agent.

Though taxol and Taxotere™ are promising compounds as antitumor agents, their clinical tests have revealed that they have low efficacy-on digestive organ cancers, especially large bowel cancers, so that great concern has been directed toward the development of a derivative having more strong antitumor effects.

DISCLOSURE OF THE INVENTION

The 9-position of taxol derivatives is generally a keto group, but some derivatives in which this position is reduced are also known. A compound having an α-configuration hydroxyl group at the 9-position has been obtained from a natural source, and various 9-position α-hydroxyl group type derivatives obtained by chemical modification of the compound have been reported (for example, see *J. Med. Chem.*, 37, 2655 (1994)). Also, it is known that a compound having a β-configuration hydroxyl group at the 9-position can be synthesized chemically by reducing 10-O-deacethylbaccatin III using a reducing agent, and various 9-position β-hydroxyl group type derivatives obtained by chemical modification of the compound have been reported (for example, see WO 94/20088).

As a result of extensive investigation, the inventors of the present invention have found that the antitumor activity of the aforementioned 9-position β-hydroxyl group type taxol derivative sharply increases when its 9-position hydroxyl group and 10-position hydroxyl group are converted into cyclic acetal type. The present invention has been accomplished on the basis of this finding.

Accordingly, present invention relates to a compound represented by the following general formula (I) or a salt thereof:

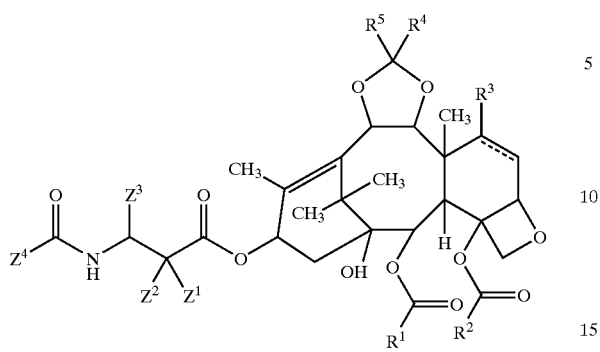

(I)

wherein

R¹ represents a phenyl group, which may have one or more substituent(s) selected from the group consisting of a halogen atom, an alkyl group and an alkoxyl group;

R² represents an alkyl group, an alkenyl group, an alkynyl group, a cycloalkyl group or an alkoxyl group, in which these alkyl, alkenyl, alkynyl, cycloalkyl and alkoxyl groups may have one or more substituent(s) selected from the group consisting of a halogen atom, a hydroxyl group, a carboxyl group, an alkoxyl group, an aryloxy group, a phenyl group, an amino group, an alkylamino group, an alkoxycarbonyl group, an an aryloxycarbonyl group, an acyl group, an acylamino group and an acyloxy group;

R³ represents a hydrogen atom, a hydroxyl group, a halogen atom, an alkoxyl group, a group —O—R³, an acyloxy group or a group —O—CO—R³¹, in which the alkoxyl and acyloxy groups may have one or more substituent(s) selected from the group consisting of a halogen atom, a hydroxyl group, a carboxyl group, a cycloalkyl group, an alkoxyl group, an aryl group, an aryloxy group, an amino group, an alkylamino group, an alkoxycarbonyl group, an aryloxycarbonyl group, an acyl group, an acylamino group, an acyloxy group and a heterocyclic group (the heterocyclic group may have one or more alkyl group(s) on the constituent atoms of its ring), wherein R³¹ represents an alkylamino group, an alkenyl group, an alkynyl group, a cycloalkyl group, an aryl group or a heterocyclic group, in which these alkylamino, alkenyl, alkynyl, cycloalkyl, aryl and heterocyclic groups may have one or more substituent(s) selected from the group consisting of a halogen atom, a hydroxyl group, a carboxyl group, an alkyl group, an alkoxyl group, an aryloxy group, a phenyl group, an amino group, an alkylamino group, an aminoalkyl group, an alkylaminoalkyl group, an alkoxycarbonyl group, an aryloxycarbonyl group, an acyl group, an acylamino group, an acyloxy group and a nitrogen-containing heterocyclic group having a size of three- to eight-membered ring (the nitrogen-containing heterocyclic group may have one or more alkyl group(s) on the constituent atoms of its ring), or R³ may form a three-membered ring together with the methyl group linked to a carbon atom adjacent to the carbon atom to which R³ is linked;

R⁴ and R⁵ each represents a hydrogen atom, an alkyl group, an alkenyl group, an alkynyl group, an aryl group or a heterocyclic group, in which these alkyl, alkenyl, alkynyl, aryl and heterocyclic groups may have one or more substituent(s) selected from the group consisting of an alkoxyl group, an amino group, an alkylamino group, an aminoalkyl group, an alkylaminoalkyl group and a nitrogen-containing saturated heterocyclic group having a size of five- or six-membered ring represented by the following formula:

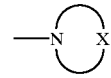

wherein X represents an oxygen atom, a sulfur atom, CH₂, CH—Y, NH or N—Y; in which Y is an alkyl group, (the heterocyclic group may have one or more alkyl group(s) on a carbon atom as a constituent atom of its ring), or R⁴ and R⁵ may form a thiocarbonyl group or a carbonyl group together with the carbon atom linked thereto;

Z¹ represents a hydrogen atom, a hydroxyl group, a halogen atom or an alkyl group;

Z² represents a hydrogen atom, a hydroxyl group, a halogen atom or an alkyl group;

Z³ represents an alkyl group, an alkenyl group, an alkynyl group, a cycloalkyl group, an aryl group or a heterocyclic group, in which these alkyl, alkenyl, alkynyl, cycloalkyl, aryl and heterocyclic groups may have one or more substituent(s) selected from the group consisting of a halogen atom, a hydroxyl group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group; and Z⁴ represents an alkyl group, an aryl group or an alkoxyl group, in which these alkyl, aryl and alkoxyl groups may have one or more substituent(s) selected from the group consisting of a halogen atom, a hydroxyl group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group;

with the proviso that the dotted line of the following moiety:

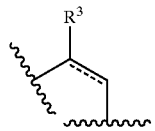

means that the corresponding bonding of the moiety may be a double bond, but R³ is not a hydroxyl group in that case.

Further, the present. invention relates to a compound having a configuration represented by the following general formula (Ia) or a salt thereof:

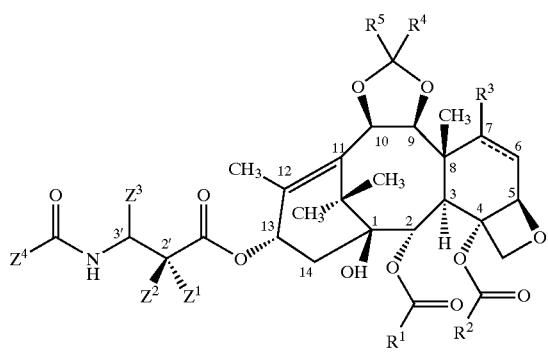

(Ia)

wherein $R^1$, $R^2$, $R^3$, $R_4$, $R^5$, $Z^1$, $Z^2$, $Z^3$ and $Z^4$ are as defined above.

Firstly, the terms used herein are described.

The term "$C_1$–$C_6$" as used herein means 1 to 6 carbon atoms, for example, "$C_2$–$C_6$ alkenyl group" means an alkenyl group having 2 to 6 carbon atoms.

Each of "alkyl group", "alkenyl group" and "alkynyl group" may be either straight chain or branched chain, preferably having 1 carbon atom (2 carbon atoms in the case of alkenyl and alkynyl groups) to 6 carbon atoms.

The term "alkoxyl group" means a group in which an alkyl group is linked to —O—, and the alkyl group may be substituted by. a phenyl group (which may have a substituent group), such as benzyloxy, phenetyloxy, p-methoxybenzyloxy and the like groups. The alkyl moiety having 1 to 6 carbon atoms is preferred.

The term "alkoxycarbonyl group" means a group in which an alkyl group is linked to the oxygen atom of —COO—, and the alkyl group may substituted by a phenyl group (which may have a substituent group), such as benzyloxycarbonyl, phenetyloxycarbonyl, p-methoxybenzyloxycarbonyl and the like groups. The alkyl moiety having 1 to 6 carbon atoms is preferred.

The term "aryl group" means a monovalent group in which one hydrogen atom is removed from the nucleus of an aromatic hydrocarbon, such as phenyl, tolyl, biphenyl, naphthyl and the like groups.

In the "aminoalkyl group", an amino group may be bonded at any position of an alkyl group, and the alkyl group preferably have 1 to 6 carbon atoms.

The term "alkylamino group" means a group in which an amino group is substituted by one alkyl group or a group in which amino group is substituted by two alkyl groups (the two alkyl groups may be the same or different from each other). The alkyl group moiety preferably have 1 to 6 carbon atoms.

The term "acyl group" means a group in which a hydrogen atom, an alkyl group or an aryl group is linked to a carbonyl group (—CO—), such as formyl, acetyl, propanoyl, benzoyl and the like groups. In this case, the alkyl group to be linked have preferably 1 to 6 carbon atoms, and a phenyl group is preferred as the aryl group to be linked.

The term "heterocyclic group" means a substituent group which has one or a plurality of at least one atom selected from the group consisting of an oxygen atom, a nitrogen atom and a sulfur atom and is derived from a monocyclic or bicyclic saturated or unsaturated heterocyclic compound, and these heterocyclic groups may be linked at any position. Examples of the monocyclic heterocyclic group include substituent groups derived from monocyclic heterocyclic compounds such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, piperazine, dioxane, pyran, morpholine and the like. Examples of the bicyclic.heterocyclic group include substituent groups derived from bicyclic heterocyclic compounds such as benzofuran, indolizine, benzothiophene, indole, naphthylidine, quinoxaline, quinazoline, chroman and the like.

The term "nitrogen-containing heterocyclic group" means a substituent group derived from a saturated or unsaturated heterocyclic compound which always has one nitrogen atom as a constituent atom of the heterocyclic group and may also have one or a plurality of atom selected from an oxygen atom, a nitrogen atom and a sulfur atom as other constituent atoms. Examples of such group include pyrrole, pyrrolidine, imidazole, pyrazole, imidazolidine, pyrazolidine, oxazole, thiazole, oxadiazole, thiadiazole, pyridine, dihydropyridine, piperidine, pyridazine, pyrimidine, pyrazine, piperazine, morpholine, thiomorpholine and the like.

The "nitrogen-containing saturated heterocyclic group having a size of five- or six-membered ring represented by the following formula:

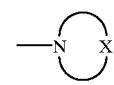

wherein X represents an oxygen atom, a sulfur atom, $CH_2$, CH—Y, NH or N—Y, in which Y is an alkyl group, (the heterocyclic group may have one or more alkyl group(s) on carbon atoms as constituent atoms of its ring)" means a substituent group derived from a saturated heterocyclic compound which always has one nitrogen atom as a constituent atom of the heterocyclic group and has a size of five- or six-membered ring, and its examples include pyrrolidine, imidazolidine, pyrazolidine, oxazolidine, thiazolidine, isooxazolidine, isothiazolidine, piperidine, piperazine, morpholine, thiomorpholine and the like.

The term "$R^3$ may form a three-membered ring together with the methyl group linked to a carbon atom adjacent to the carbon atom to which $R^3$ is linked" means that the 7- and 8-position moieties form the following structure.

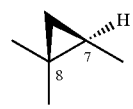

Next, each substituent group in the general formula (I) is described.

Preferred examples of the "alkyl group" and "alkoxyl group" as substituent groups of the phenyl group of $R^1$ are those which have 1 to 3 carbon atoms.

The number of substituent groups of the phenyl group of $R^1$ is preferably 1 or 2, and the substituent group is substituted preferably at the meta position.

Unsubstituted phenyl group is preferred as $R^1$. Also preferred is a phenyl group having 1 or 2 fluorine atoms, chlorine atoms, methyl groups or methoxy groups substituted at the meta position.

As $R^2$, an alkyl group, an alkoxyl group and a cycloalkyl group are preferred.

As the "alkyl group" of $R^2$, a $C_1$–$C_6$ alkyl group is preferred, and a methyl group, an ethyl group and a propyl group are particularly preferred.

As the "alkoxyl group" of $R^2_1$, a $C_1$–$C_6$ alkoxyl group is preferred, and a methoxy group and an ethoxy group are particularly preferred.

As the "cycloalkyl group" of $R^2$, a $C_3$–$C_6$ cycloalkyl group is preferred, and a cyclopropyl group is particularly preferred.

As $R^2$, a methyl group, an ethyl group, a propyl group, a methoxy group, an ethoxy group or a cyclopropyl group is particularly preferred.

As the "halogen atom" of $R^3_1$, a fluorine atom is preferred.

As $R^3$, a hydrogen atom, a fluorine atom or a hydroxyl group is particularly preferred. Also preferred as $R^3$ is a group in which a three-membered ring is formed together with the methyl group linked to a carbon atom (8-position) adjacent to the carbon atom (7-position) to which $R^3$ is linked, namely a group in which the 7- and 8-position moieties have the following structure.

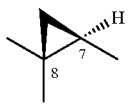

As the alkyl groups of $R^4$ and $R^5$, those having 1 to 6 carbon atoms are preferred, and a methyl group, an ethyl group and a propyl group are particularly preferred.

As the alkenyl group of $R^4$ and $R^5$, those having 2 to 6 carbon atoms are preferred, and allyl group is particularly preferred.

As the substituent group of the alkyl, alkenyl or phenyl group of $R^4$ and $R^5$, an amino group, an alkylamino group or a nitrogen-containing saturated heterocyclic group having a size of five- or six-membered ring represented by the following formula:

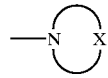

wherein X represents an oxygen atom, a sulfur atom, $CH_2$, CH—Y, NH or N—Y, in which Y is an alkyl group, (the heterocyclic group may have one or more alkyl group(s) on a carbon atom as a constituent atom of its ring) is preferred.

The alkyl moiety of the alkylamino group is preferably a $C_1$–$C_3$ alkyl group, and it may be a dialkyl substitution (in the case of dialkyl substitution, the two alkyl groups may be the same or different from each other).

As the nitrogen-containing saturated heterocyclic group having a size of five- or six-membered ring represented by the following formula:

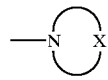

(the heterocyclic group may have one or more alkyl group(s) on a carbon atom as a constituent atom of its ring), groups derived from piperazine, morpholine, thiomorpholine, 4-$C_1$–$C_3$ alkylpiperazine are particularly preferred.

Also, methyl group is preferred as the alkyl group to be substituted on the carbon atom as a constituent atom of the ring of heterocyclic group.

A preferred example as $R^4$ and $R^5$ is a combination in which one is a hydrogen atom or an alkyl group and the other is an alkyl group, an alkenyl group or a phenyl group.

As the "halogen atom" of $Z^1$ and $Z^2_1$ a fluorine atom, a chlorine atom and a bromine atom are preferred.

As the "alkyl group" of $Z^1$ and $Z^2$, a methyl group, an ethyl group and a propyl group are preferred.

As $Z^1$, a halogen atom and a hydroxyl group are preferred, and a fluorine atom is particularly preferred as the halogen atom.

As $Z^2$, a halogen atom, a hydrogen atom or an alkyl group is preferred, in which a fluorine atom is particularly preferred as the halogen atom, and a methyl group is particularly preferred as the alkyl group.

Most preferred examples as $Z^1$ and $Z^2$ include a combination in which $Z^1$ is a fluorine atom and $Z^2$ is a fluorine atom, a combination in which $Z^1$ is a hydroxyl group and $Z^2$ is a hydrogen atom and a combination in which $Z^1$ is a hydroxyl group and $Z^2$ is a methyl group.

As $Z^3$, an aryl group, a heterocyclic group and an alkenyl group are preferred.

As the "aryl group" of $Z^3$, a phenyl group is preferred.

As the "alkenyl group" of $Z^3$, 2-methyl-1-propenyl is preferred.

As the heterocyclic group of $Z^3_1$, a monocyclic heterocyclic group is preferred, more preferably a monocyclic five- or six-membered ring heterocyclic group, such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, piperazine, dioxane, pyran, morpholine and the like.

Among the heterocyclic group of $Z^3$, a monocyclic five- or six-membered ring heterocyclic group having one oxygen atom, nitrogen atom or sulfur atom as a constituent atom of the ring structure is more preferred, and examples of such group include those which are derived from pyrrole, furan, thiophene, pyrrolidine, tetrahydrofuran, tetrahydrothiophene, pyridine, dihydropyridine, tetrahydropyran, piperidine, pyran and the like.

Among the heterocyclic group of $Z^3$, a monocyclic five- or six-membered ring unsaturated heterocyclic group having one oxygen atom, nitrogen atom or sulfur atom as a constituent atom of the ring structure is most preferred, and examples of such group include those which are derived from furan, pyridine and pyrrole.

As $Z^3$, a 2-methyl-1-propenyl group, a phenyl group, a furyl group, a pyridyl group and a pyrrolyl group are particularly preferred.

As $Z^4$, an aryl group or an alkoxyl group is preferred.

As the "aryl group" of $Z^4$, a phenyl group is preferred.

As the "alkoxyl group" of $Z^4$, a tert-butoxy group is preferred.

As $Z^4$, a phenyl group and a tert-butoxy group are particularly preferred.

Preferably, the compound of the present invention may have the following configuration.

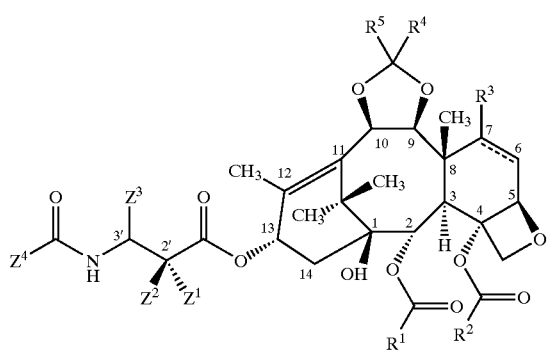

(Ia)

Configuration of the 3'-position, to which the substituent group $Z^3$ is linked, may be either of the two configurations, but preferably the same configuration of natural taxol. Also, configuration of the 7-position is either α- or β-configuration.

The taxol derivative of the present invention may be in the free form as such and in the form of an acid addition salt or a salt of carboxylic acid. Examples of the acid addition salt include inorganic acid salts such as hydrochloride, sulfate, nitrate, hydrobromate, hydroiodate, phosphate and the like and organic acid salts such as acetate, methanesulfonate, benzenesulfonate, toluenesulfonate, citrate, maleate, fumarate, lactate and the like.

Examples of the salt of carboxyl group may be either inorganic salts or organic salts, which include alkali metal salts such as lithium salt, sodium salt, potassium salt and the like, alkaline earth metal salts such as magnesium salt, calcium salt and the like, as well as ammonium salt, triethylamine salt, N-methylglucamine salt, tris-(hydroxymethyl) aminomethane salt and the like.

The following describes production process of the compound of the present invention. In the practice of the reaction, the substituent groups may be protected with protecting groups if desired, and conversion sequence of each substituent group is not particularly limited.

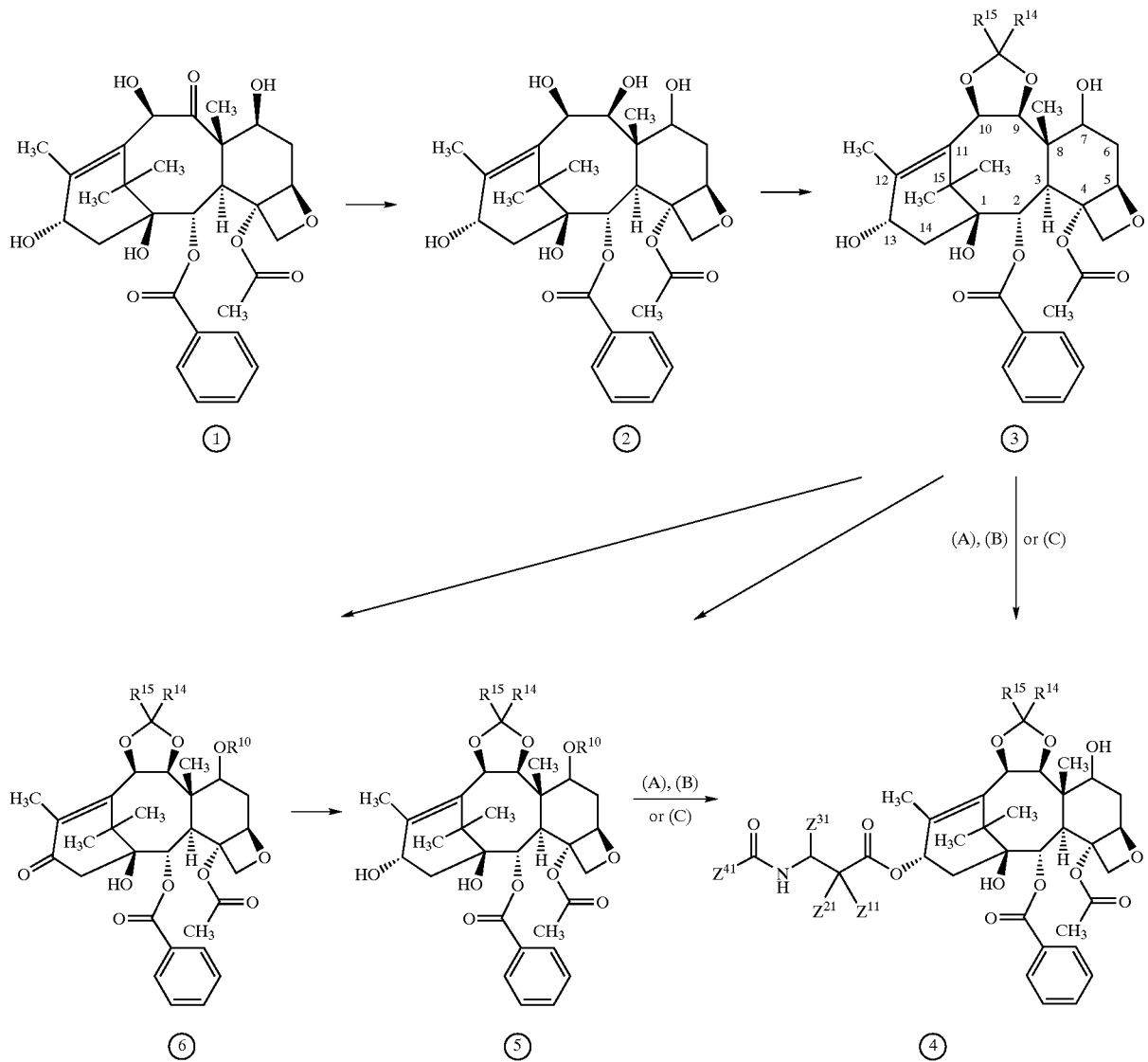

-continued

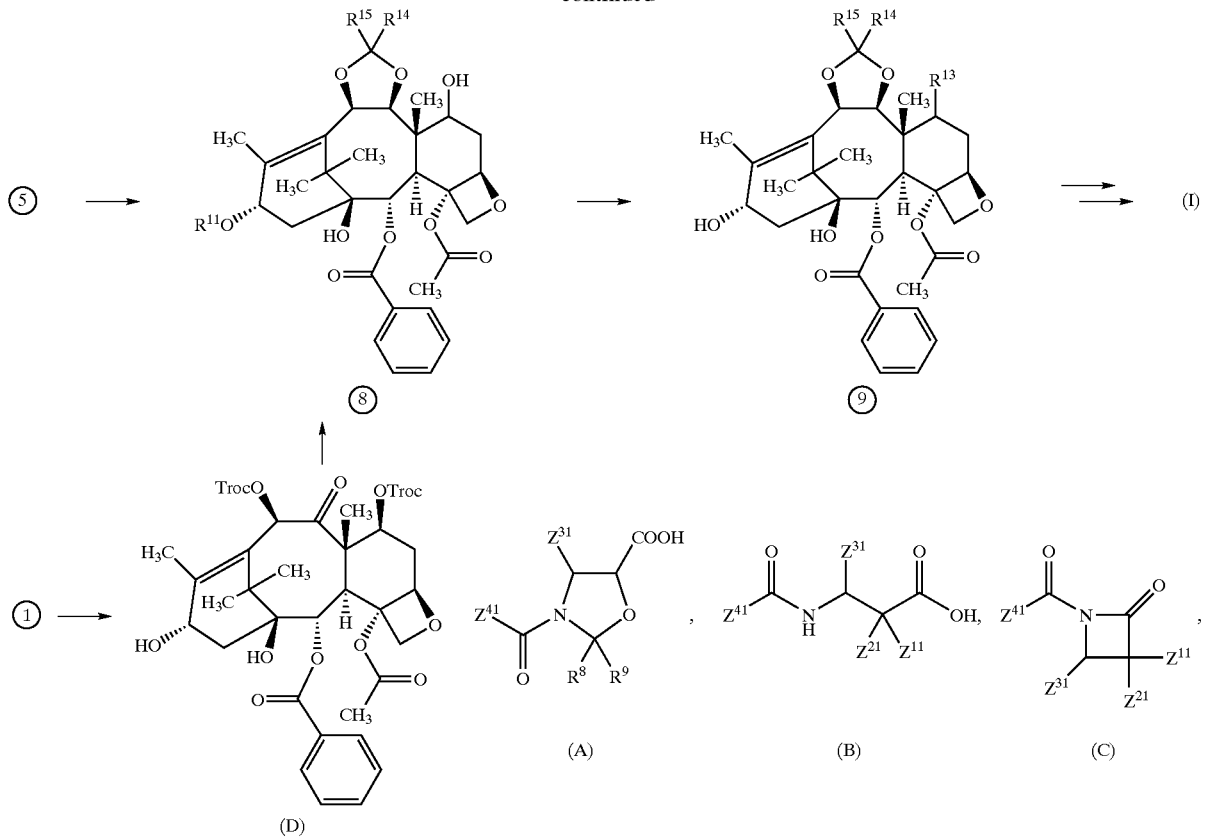

In the above reaction scheme, $R^{13}$ means $R^3$ itself or $R^3$ protected by a protecting group (when $R^3$ is substituted by a hydroxyl group, an amino group or the like or when $R^3$ is a hydroxyl group);

$R^{24}$ means $R^4$ itself or $R^4$ protected by a protecting group (when $R^4$ is substituted by an amino group or the like);

$R^{15}$ means $R^5$ itself or $R^5$ protected by a protecting group (when $R^5$ is substituted by an amino group or the like);

$Z^{11}$ means $Z^1$ itself or $Z^1$ protected by a protecting group (when $Z^1$ is a hydroxyl group);

$Z^{21}$ means $Z^2$ itself or $Z^2$ protected by a protecting group (when $Z^2$ is a hydroxyl group);

$Z^{31}$ means $Z^3$ itself or $Z^3$ protected by a protecting group (when $Z^3$ is substituted by a hydroxyl group, an amino group or the like); and $Z^{41}$ means $Z^4$ itself or $Z^4$ protected by a protecting group (when $Z^4$ is substituted by a hydroxyl group, amino group or the like).

$R^8$ and $R^9$ are independently a hydrogen atom, an alkyl group, an aryl group and the like and, in a preferred combination, both are methyl groups or one is a p-methoxyphenyl group and the other is a hydrogen atom.

$R^{10}$ and $R^{11}$ are protecting groups of the hydroxyl group.

A compound (3) is obtained by allowing a compound (2) derived from 10-O-deacetylbaccatin III (a compound (1)) to react with an aldehyde or ketone represented by $R^{14}C(=O)R^{15}$ or an acetal represented by $R^{14}R^{15}C(OR^{45})_2$ ($R^{45}$ is methyl or the like alkyl group) in the presence of an acid catalyst such as 10-camphorsulfonic acid, p-toluenesulfonic acid or the like. Next, a compound (4) is obtained by condensing the 13-position hydroxyl group of the compound (3) with a compound (A), (B) or (C) in accordance with respective ordinary method already reported.

As the condensation reaction with the compound (A) or (B), a method is known in which a carboxylic acid activating agent such as di(2-pyridyl) carbonate or dicyclohexylcarbodiimide is used in the presence of 4-dimethylaminopyridine or the like base catalyst. In this connection, when the compound (A) is used, $Z^{11}$ and $Z^{21}$ become a combination of hydrogen atom and hydroxyl group.

As the condensation reaction with the compound (C), a method is known in which sodium hexamethyldisilazide or the like base is used.

At this stage of reaction, the compound (A), (B) or (C) will react with the 7-position hydroxyl group of compound (3) in some cases. In that case, the product of interest can be separated and purified by a silica gel column chromatography or the like means. Alternatively, since a compound (5) in which a protecting group is introduced selectively into the 7-position of compound (3) can be obtained by selecting proper protecting group and reaction conditions (a high selectivity is obtained especially in the case of a carbamate type protecting group, for example, the 7-position can be selectively protected with 2,2,2-trichloroethoxycarbonyl group by carrying out the reaction with 2,2,2-trichloroethoxycarbonyl chloride in pyridine at 0° C.), the compound (4) may be synthesized by condensing the 13-position hydroxyl group of this compound (5) with the compound (A), (B) or (C) in the same manner as described above. The compound (5) can also be obtained by another method in which the 13-position hydroxyl group of compound (3) is converted into ketone using manganese dioxide or the like oxidizing agent, a protecting group is introduced into the 7-position hydroxyl group of the resulting compound to obtain a compound (6), followed by reducing the 13-position ketone again into hydroxyl group using a sodium borohydride or the like reducing agent.

After conversion or deprotection of each substituent group of the thus obtained compound (4) as occasion demands, the compound. (I) of interest can be obtained by converting the 2-position benzoyl group into $COR^1$, the 4-position acetyl group into $COR^2$ the 7-position hydroxyl group into $R^3$, and the $R^{14}$, $R^{15}$, $Z^{11}$, $Z^{21}$, $Z^{31}$ and $Z^{41}$ into $R^4$, $R^5$, $Z^1$, $Z^2$, $Z^3$ and $Z^4$, respectively. Such conversion and deprotection can be carried out by using general techniques of organic chemistry, such as the following examples.

Conversion of the 2-position benzoyl group into $COR^1$ can be effected, for example, in accordance with a method described in a literature (*Tetrahedron Letter*, 35, 8931 (1994)) in which the 2-position ester bond is selectively hydrolyzed and then acylated, by which a compound whose $R^1$ is other than a phenyl group is obtained.

Conversion of the 4-position acetyl group into $COR^2$ can be effected, for example, in accordance with a method in which a reaction with a compound represented by $R^{21}$—X ($R^{21}$ represents an alkyl group, an alkenyl group or an aryl group and X represents a halogen atom such as iodine atom, bromine atom or the like or a leaving group such as methanesulfonyl group, p-toluenesulfonyl group or the like) is carried out in the presence of sodium hexamethyldisilazide or the like base at a temperature of from −100° C. to room temperature, thereby obtaining a compound whose $R^2$ is other than a methyl group.

The compound whose $R^2$ is other than a methyl group can also be obtained by allowing the compound (6) to react with the compound represented by $R^{21}$—X in the presence of sodium hexamethyldisilazide or the like base to obtain a compound in which the 4-position acetyl group is converted into $COR^2$, subsequently reducing the 13-position hydroxyl group and finally carrying out condensation reaction with the compound (A), (B) or (C).

Conversion of the 7-position hydroxyl group into $R^3$ can be effected by various methods depending on the type of $R^3$. A compound in which $R^3$ is hydrogen can be obtained by removing the 7-position hydroxyl group by a known method (for example, see *J. Org. Chem.*, 58, 5028 (1993)). A compound in which $R^3$ is —OC(=O)$R^{31}$ can be obtained by acylating the 7-position hydroxyl group using a carboxylic acid or an acid chloride based on general techniques of organic chemistry. A compound in which $R^3$ is —OC(=O)NQ$^1$Q$^2$ ($Q^1$ and $Q^2$ are independently a hydrogen atom or an alkyl group) can be obtained by a method in which the 7-position hydroxyl group is allowed to react with a compound represented by ClC(=O)OR$^{32}$ ($R^{32}$ is p-nitropheyl or the like aryl group) and then with an amine, to react with phosgene in the presence of an amine, to react with a compound represented by ClC(=O)NQ$^1$Q$^2$ ($Q^1$ and $Q^2$ are independently a hydrogen atom or an alkyl group) or to react with an isocyanate represented by $R^{31}$N=C=O. Conversion into $R^3$ of interest can also be made by converting the 7-position hydroxyl group and then carrying out several steps of organochemical conversion.

In another process, a compound (9) is obtained by protecting the 13-position hydroxyl group of compound (5) with a protecting group $R^{11}$ which can be distinguished from the protecting group $R^{10}$, removing $R^{10}$ to obtain a compound (8), converting-the 7-position hydroxyl group of compound (8) into $R^{13}$ in the same manner as described in the foregoing and then removing the protecting group $R^{11}$. Thereafter, the 13-position hydroxyl group of compound (9) is condensed with the compound (A), (B) or (C), and then conversion and deprotection of various substituent groups are carried out to obtain the compound (I) of interest. In this connection, the compound (8) can be synthesized directly from the compound (3) by selecting proper protecting group $R^{11}$ and reaction conditions, and the compound (9) can also be synthesized directly from the compound (3) by conversion of the 7-position hydroxyl group.

A compound of interest whose $R^3$ is a halogen atom, for example, a compound whose $R^3$ is fluorine atom, can be obtained by treating a compound having a hydroxyl group at the 7-position with diethylaminosulfur trifluoride in tetrahydrofuran, methylene chloride, ethyl ether, toluene, 1,1-dimethoxyethane or a mixture solvent thereof.

The compound (8) can also be synthesized from a compound (D) which is obtained-from the compound (1). That is, the 13-position hydroxyl group of compound (D) is protected with the protecting group $R^{11}$ which can be distinguished from 2,2,2-trichloroethoxycarbonyl group, 2,2,2-trichloroethoxycarbonyl groups at the 7- and 10-positions are removed, and then the thus obtained compound is treated with a reducing agent such as tetrabutylammonium borohydride or the like to convert the 9-position ketone into hydroxyl group and allowed to react with an aldehyde, a ketone or an acetal in the same manner as described in the foregoing, thereby obtaining the compound (8).

The following compounds as the production materials can be synthesized by reported methods.

Compound (2): WO 94/20088 and others.

Compound (D): *Tetrahedron*, 422, 4451 (1986) and others.

Compound (A): *Tetrahedron Letter*, 33, 5185 (1992) and others.

Compound (B): *J. Am. Chem. Soc.*, 110, 5917 (1988) and others.

Compound (C): *Tetrahedron Letter*, 34, 4149 (1993) and others.

In the above synthesis methods, compounds in which the 7-position has β-configuration are obtained in general. Since it is known that configuration of the 7-position hydroxyl group is isomerized from to a when a taxol derivative in which the 9-position is keto group and the 7-position is not protected is treated with a base, a compound having a-configuration at the 7-position can be synthesized by reducing the 9-position keto group into a hydroxyl group after isomerization.

The compound of the present invention can be used for the treatment of various cancers such as lung cancers, digestive organ cancers, ovarial cancers, uterine cancers, breast cancers, cancers of liver, head and neck cancers, blood cancers, renal cancers, testicular tumors and the like.

The compound of the present invention can be administered as intravenous, intramuscular, subcutaneous and the like various injections or through other various routes of administration such as oral administration, percutaneous absorption and the like. Of these methods, intravenous injection by a solutions and oral administration are desirable. The solutions can be prepared by forming an acid addition with a pharmacologically acceptable acid or an alkali metal salt with sodium or the like. In the case of oral administration, the compound may be in its free form or a salt form.

Appropriate pharmaceutical preparation is selected corresponding to each administration method and prepared by usually used preparation method. Of the dosage forms of the antitumor agent of the present invention, examples of oral preparations include tablets, powders, granules, capsules, solutions, syrups, elixirs, oil or aqueous suspensions and the like. In the case of injections, stabilizing agents, antiseptics, solubilizing agents and the like may be used in the preparation. The injections which may contain these auxiliary agents may be dispensed into containers and made into solid preparations by freeze-drying or the like means to be dissolved again before using.

Liquid preparations include solutions, suspensions, emulsions and the like, and suspending agents, emulsifying agents and the like may be used as additives when these preparations are prepared.

The compound of the present invention can be used for the treatment of cancers in mammals, particularly in human. In the case of human, it may preferably be administered once a day repeatedly at appropriate intervals.

It may be administered in a dose of from about 0.5 to 50 mg, preferably from about 1 to 20 mg, per 1 m² of the body surface area.

BEST MODE FOR CARRYING OUT THE INVENTION

The present invention is now illustrated in greater detail by way of Reference Examples and Examples, but it should be understood that the present invention is not deemed to be limited thereto.

Inventive Example 1

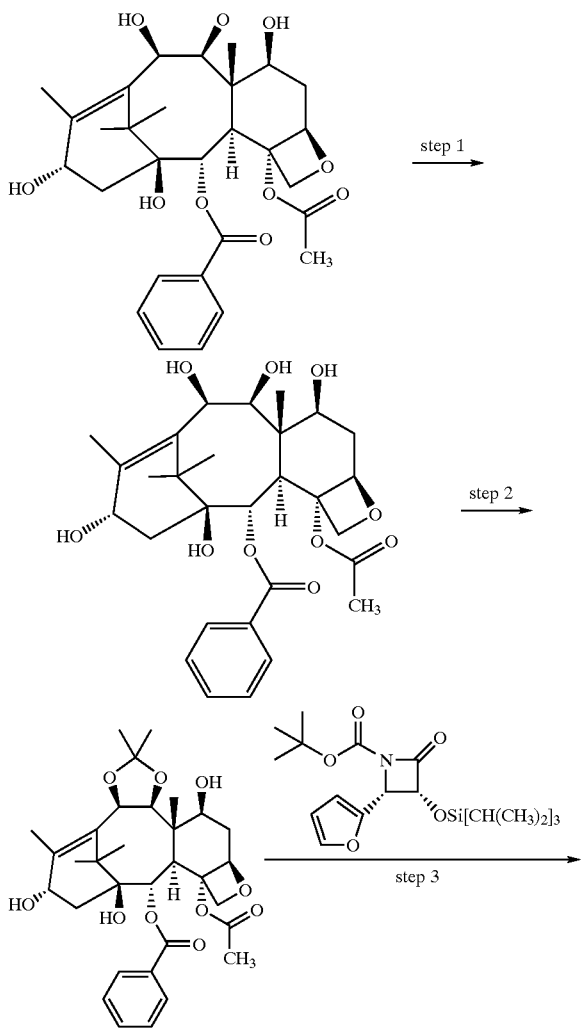

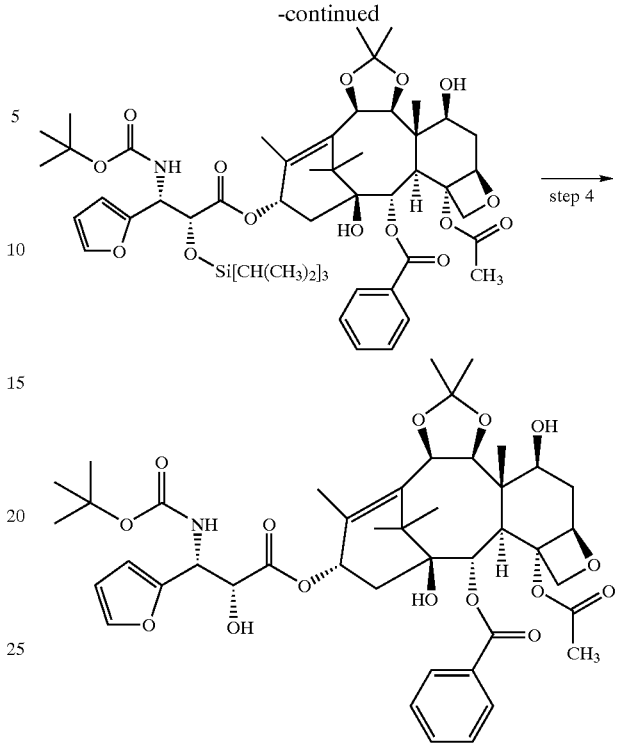

Step 1: 9β-10-Deacetyl-9-dihydrobaccatin III

A 6.98 g portion of 10-deacetylbaccatin III was dissolved in a mixture solution consisting of 200 ml of a dry methylene chloride and 200 ml of a dry 1,4-dioxane, and 12.89 of tetrabutylammonium borohydride was added to the resulting solution at room temperature and stirred for 19 hours at the same temperature. The reaction solution was cooled to 0° C. and neutralized by gradually adding dropwise 1 N hydrochloric acid. This solution was concentrated under a reduced pressure to evaporate the greater part of the organic solvents. The resulting residue was mixed with ethyl acetate and water and shaken to separate the organic layer, and the water layer was extracted with ethyl acetate. The whole organic layers were washed with a saturated brine and dried over anhydrous sodium sulfate. Thereafter, the solvent was evaporated under a reduced pressure and the resulting residue was purified by a silica gel column chromatography (developing solvent; chloroform:acetone=5:1 (v/v)) to obtain 4.794 g of the title compound as a white solid.

Rf=0.65 (chloroform:methanol=7:1 (v/v)); FAB Mass: 546 (M⁺).

Step 2: 9β-10-Deacetyl-9-dihydro-9,10-O-isopropylidenebaccatin III

A 0.4825 g portion of the compound obtained in the above step 1 was dissolved in 4.8 ml of a dry methylene chloride and 4.8 ml of a dry 1,4-dioxane, and 0.54 ml of 2,2-dimethoxypropane and 19.9 mg of camphorsulfonic acid were added to the resulting solution at room temperature and allowed to stand for 1 hour. This solution was cooled to 0° C. and adjusted to pH 7 by adding triethylamine, and then the solvent was evaporated under a reduced pressure. Thereafter, the resulting residue was purified by a silica gel column chromatography (developing solvent; chloroform:acetone=5:1 (v/v)) to obtain 0.2949 g of the title compound as a white solid.

Rf=0.36 (chloroform:acetone=6:1 (v/v)); ¹H-NMR (400 MHz, CDCl₃/TMS) δ (ppm); 1.16 (3H, s), 1.41 (3H, s), 1.57 (3H, s), 1.63 (3H, s), 1.64 (3H, s), 1.70–2.20 (4H, m), 3.04 (1H, d, J=4.9 Hz), 3.85 (1H, d, J=7.3 Hz), 4.04 (1H, br-d), 4.33 (1H, d, J=8.3 Hz), 4.39 (1H, d, J=8.3 Hz), 4.67 (1H, d, J=7.8 Hz), 4.80 (1H, br), 5.06 (1H, s), 5.58 (1H, d, J=7.3 Hz), 6.02 (1H, d, J=4.9 Hz), 7.49 (2H, t, J=7.3 Hz), 7.59 (1H, t, J=7.3 Hz), 8.13 (2H, d, J=7.3 Hz).

Step 3: 9β-13-O-[(2R,3R)-3-(tert-Butoxycarbonylamino)-3-(2-furyl)-2-(triisopropylsilyloxy)propionyl]-10-deacetyl-9-dihydro-9,10-O-isopropylidenebaccatin III A 49.8 mg portion of the compound obtained in the above step 2 and 49.0 mg of (3R,4R)-1-(tert-butoxycarbonyl)-4-(2-furyl)-3-(triisopropylsilyloxy)azetidin-2-one were dissolved in 3.4 ml of a dry tetrahydrofuran to which was subsequently added dropwise 1 N sodium hexamethyldisilazide (tetrahydrofuran solution) at −58°C. After 30 minutes, the resulting solution was mixed with saturated ammonium chloride aqueous solution at −50° C. and extracted with ethyl acetate. The extract was washed with saturated brine and dried over anhydrous sodium sulfate. Thereafter, the solvent was evaporated under a reduced pressure and the resulting residue was purified by a silica gel thin layer chromatography (developing solvent; hexane:ethyl acetate=4:1 (v/v)) to obtain 15.6 mg of the title compound as a colorless transparent syrup.

Rf=0.09 (hexane:ethyl acetate=4:1 (v/v)); $^1$H-NMR (400 MHz, CDCl$_3$/TMS) δ (ppm); 0.91–1.02 (22H, m), 1.06 (3H, s), 1.30 (3H, s), 1.39 (9H, s), 1.58 (3H, s), 1.67 (3H, s), 1.68 (3H, s), 1.76 (3H, s), 1.87 (1H, br-s), 2.15–2.23 (2H, m), 2.26–2.39 (2H, m), 2.45 (3H, s), 2.97 (1H, d, J=4.9 Hz), 3.89 (1H, d, J=7.3 Hz), 4.01–4.09 (1H, m), 4.31 (1H, d, J=8.3 Hz), 4.39 (1H, d, J=8.3 Hz), 4.68 (1H, br-d, J=6.8 Hz), 4.99 (1H, s), 5.12 (1H, s), 5.23–5.34 (2H, m), 5.53 (1H, d, J=7.3 Hz), 6.02 (1H, d, J=4.9 Hz), 6.10 (1H, br-t, J=8.0 Hz), 6.25 (1H, J=3.4 Hz), 6.34 (1H, dd, J=3.4 Hz, 1.9 Hz), 7.37 (1H, d, J=1.9 Hz), 7.48 (2H, t, J=7.3 Hz), 7.59 (1H, t, J=7.3 Hz), 8.12 (2H, d, J=7.3 Hz).

Step 4: 9β-13-O-[(2R,3R)-3-(tert-Butoxycarbonylamino)-3-(2-furyl)-2-hydroxypropionyl]-10-deacetyl-9-dihydro-9,10-O-isopropylidenebaccatin III A 44.3 mg portion of the compound obtained in the above step 3 was dissolved in 2.21 ml of a dry pyridine, and the solution was mixed with 0.44 ml of hydrogen fluoride-pyridine at 0° C., returned to room temperature and then stirred for 14 hours. The resulting solution was mixed with water cooled at 0° C., followed by extraction with ethyl acetate. The organic layer was washed with 1 N hydrochloric acid, saturated sodium bicarbonate aqueous solution and saturated brine in that order and dried over anhydrous sodium sulfate. Thereafter, the solvent was evaporated under a reduced pressure and the resulting residue was purified by a silica gel thin layer chromatography (developing solvent; chloroform:acetone=6:1 (v/v)) to obtain 33.9 mg of the title compound as a colorless transparent syrup.

Rf=0.32 (chloroform:acetone=6:1 (v/v)); Melting point: 133–135° C. (lyophilization from dioxane); $^1$H-NMR (400 MHz, CDCl$_3$/TMS) δ (ppm); 1.08 (3H, s), 1.28 (3H, s), 1.41 (9H, s), 1.58 (3H, s), 1.65 (3H, s), 1.67 (3H, s), 1.70 (3H, s), 1.83–1.94 (1H, m), 2.07–2.27 (2H, m), 2.36 (3H, s), 2.29–2.47 (1H, m), 2.94 (1H, d, J=4.9 Hz), 3.83 (1H, d, J=7.3 Hz), 4.32 (1H, d, J=8.7 Hz), 4.39 (1H, d, J=8.7 Hz), 4.65–4.76 (2H, m), 5.10 (1H, s), 5.30–5.42 (2H, m), 5.54 (1H, d, J=7.3 Hz), 6.05 (1H, d, J=4.9 Hz), 6.11 (1H, d, J=3.5 Hz), 6.36 (1H, dd, J=3.5 Hz, 1.4 Hz), 7.39 (1H, d, J=1.4 Hz), 7.48 (2H, t, J=7.3 Hz), 7.60 (1H, t, J=7.3 Hz), 8.11 (2H, d, J=7.3 Hz). FAB Mass: 840 (MH$^+$).

Inventive Example 2

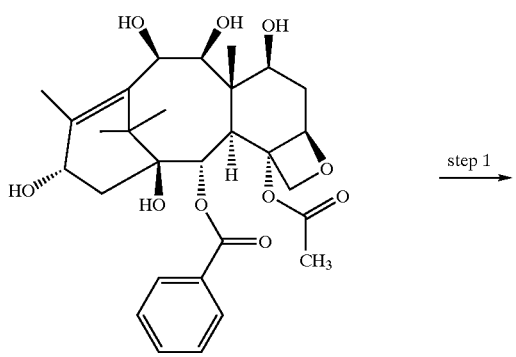

step 1

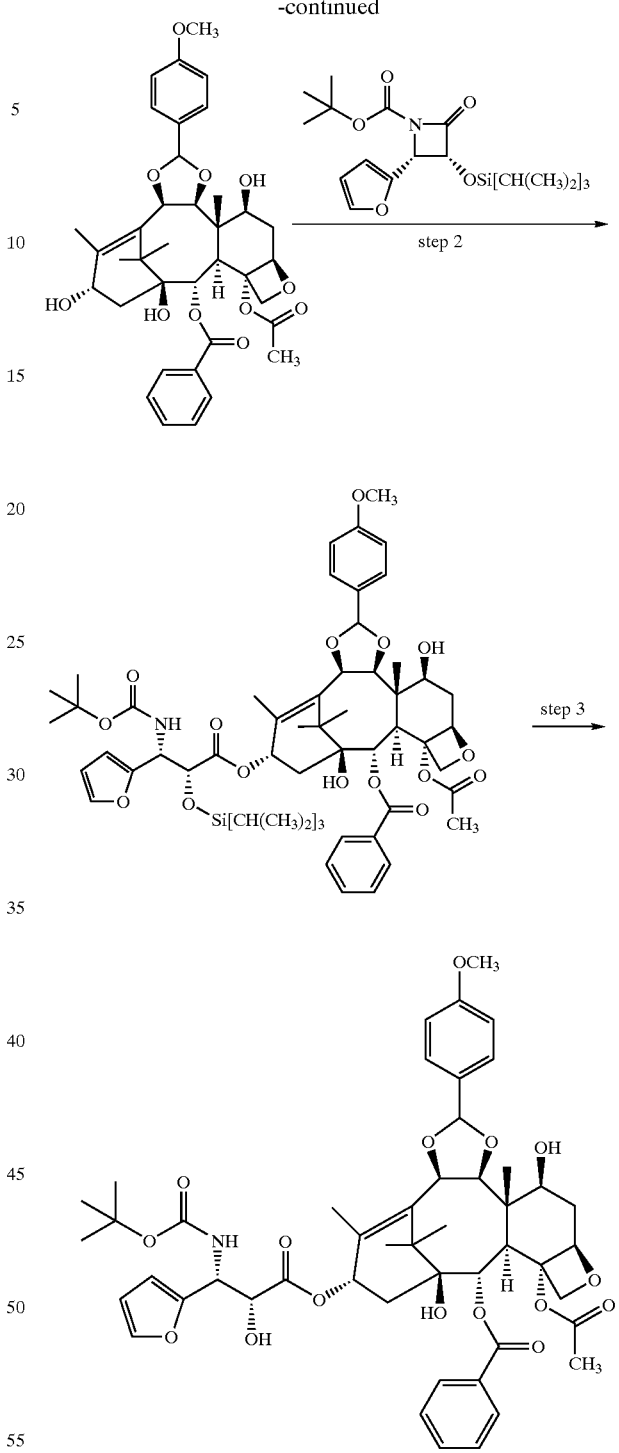

Step 1: 9β-10-Deacetyl-9-dihydro-9,10-O-(4-methoxybenzylidene)baccatin III

The compound obtained in the step 1 of Inventive Example 1 was subjected to the same reaction of the step 2 of Inventive Example 1 except that 4-methoxybenzaldehyde dimethylacetal was used in stead of 2,2-dimethoxypropane, thereby obtaining the title compound as a colorless transparent syrup.

Rf=0.24 (chloroform:acetone=10:1 (v/v)); $^1$H-NMR (400 MHz, CDCl$_3$/TMS) δ (ppm); 1.19 (3H, s), 1.50 (3H, s), 1.61 (3H, s), 1.98 (3H, s), 1.96–2.43 (m), 2.34 (3H, s), 3.10 (1H, d, J=4.9 Hz), 3.84 (3H, s), 3.98 (1H, d, J=7.3 Hz), 4.09–4.19 (1H, m), 4.31 (1H, d, J=8.3 Hz), 4.39 (1H, d, J=8.3 Hz), 4.57 (1H, d, J=7.8 Hz), 4.84 (1H, q, J=7.2 Hz), 5.07 (1H, s), 5.47 (1H, d, J=7.3 Hz), 5.80 (1H, s), 6.04 (1H, d, J=4.9 Hz), 6.93 (2H, d, J=8.8 Hz), 7.42–7.55 (4H, m), 7.60 (1H, t, J=7.4 Hz), 8.12 (2H, d, J=7.4 Hz). Step 2: 9β-13-O-[(2R,3R)-3-(tert-Butoxycarbonylamino)-3-(2-furyl)-2-(triisopropylsilyloxy) propionyl]-10-deacetyl-9-dihydro-9,10-O-(4-methoxybenzylidene)baccatin III Using the compound obtained in the above step 1 as the starting material, its reaction with (3R,4R)-1-(tert-butoxycarbonyl)-4-(2-furyl)-3-(triisopropylsilyloxy) azetidin-2-one was carried out in the same manner as described in the step 3 of Inventive Example 1, thereby obtaining the title compound as a colorless transparent syrup.

Rf=0.28 (hexane:ethyl acetate=5:2 (v/v)): $^1$H-NMR (400 MHz, CDCl$_3$/TMS) δ (ppm); 0.91–1.08 (21H, m), 1.32 (3H, s), 1.54 (3H, s), 1.72 (3H, s), 1.80 (3H, s), 1.40 (9H, s), 2.17–2.28 (2H, m), 2.36 (2H, d, J=8.2 Hz), 2.47 (3H, s), 3.02 (1H, d, J=5.0 Hz), 3.84 (3H, s), 4.00 (1H, d, J=7.8 Hz), 4.07–4.16 (1H, m), 4.29 (1H, AB type d, J=8.2 Hz), 4.39 (1H, AB type d, J=8.2 Hz), 4.61 (1H, d, J=7.8 Hz), 5.00 (1H, s), 5.12 (1H, s), 5.22–5.36 (2H, m), 5.41 (1H, d, J=7.8 Hz), 5.76 (1H, s), 6.05 (1H, d, J=5.0 Hz), 6.11 (1H, br-t, J=8.2 Hz), 6.26 (1H, d, J=3.6 Hz), 6.34 (1H, dd, J=3.6 Hz, 2.0 Hz), 6.93 (2H, d, J=8.8 Hz), 7.38 (1H, d, J=2.0 Hz), 7.43–7.53 (4H, m), 7.59 (1H, t, J=7.9 Hz), 8.02 (2H, d, J=7.9 Hz).

Step 3: 9β-13-O-[(2R,3R)-3-(tert-Butoxycarbonylamino)-3-(2-furyl)-2-hydroxypropionyl]-10-deacetyl-9-dihydro-9,10-O-(4-methoxybenzylidene)baccatin III Using the compound obtained in the above step 2 as the starting material, the reaction procedure of the step 4 of Inventive Example 1 was repeated to obtain the title compound as a colorless transparent syrup.

Rf=0.15 (chloroform:acetone=7:1 (v/v)); Melting point: 148–151° C. (lyophilization from dioxane); $^1$H-NMR (400 MHz, CDCl$_3$/TMS) δ (ppm); 1.30 (3H, s), 1.42 (9 Hz, s), 1.56 (3H, s), 1.76 (6H, s), 2.10–2.26 (3H, m), 2.36 (3H, s), 2.31–2.48 (1H, m), 2.99 (1H, d, J=4.9 Hz), 3.84 (3H, s), 3.98 (1H, d, J=7.4 Hz), 4.06–4.17 (1H, m), 4.30 (1H, AB type d, J=8.3 Hz), 4.38 (1H, AB type d, J=8.3 Hz), 4.57 (1H, d, J=8.3 Hz), 4.72 (1H, d, J=3.9 Hz), 5.11 (1H, s), 5.38 (2H, br-s), 5.43 (1H, d, J=7.4 Hz), 5.80 (1H, s), 6.07 (1H, d, J=4.9 Hz), 6.15 (1H, br-t, J=8.0 Hz), 6.32 (1H, d, J=3.8 Hz), 6.36 (1H, dd, J=3.8 Hz, 2.0 Hz), 6.93 (2H, d, J=8.8 Hz), 7.40 (1H, d, J=2.0 Hz), 7.43–7.53 (4H, m), 7.60 (1H, t, J=7.3 Hz), 8.11 (2H, d, J=7.3 Hz). FAB mass: 918 (M$^+$).

Inventive Example 3

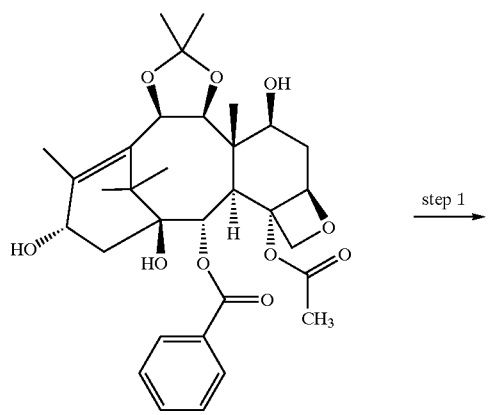

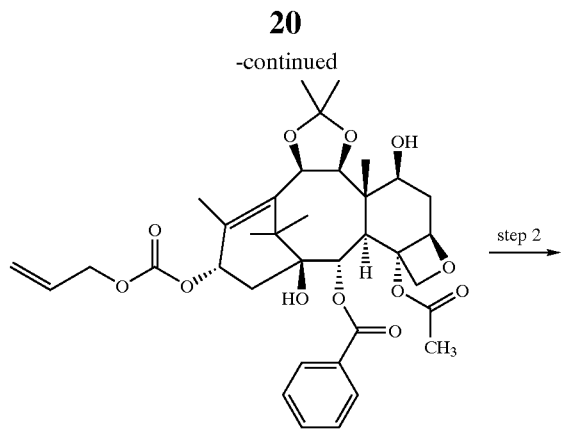

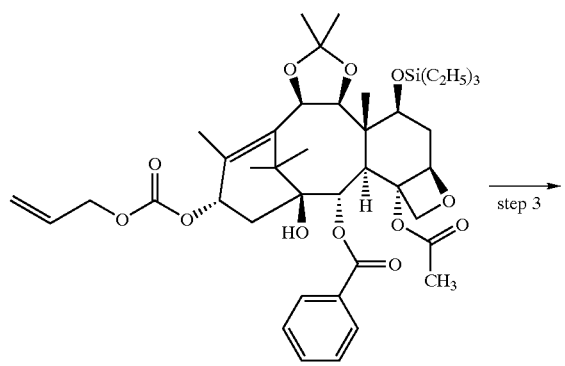

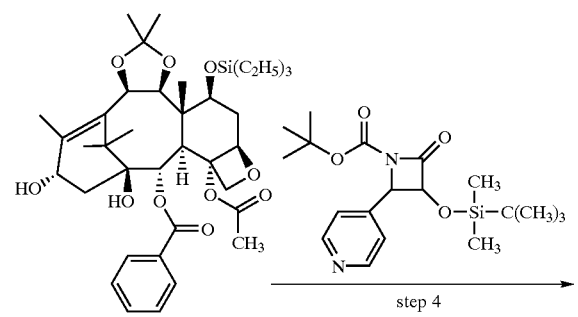

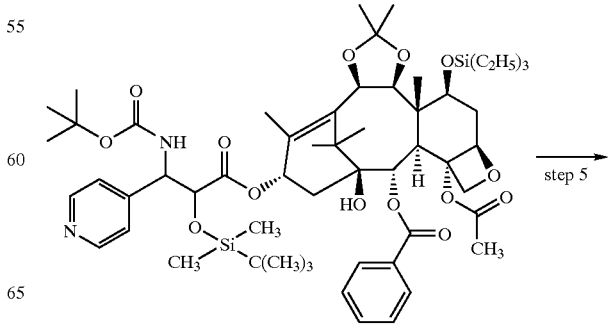

-continued

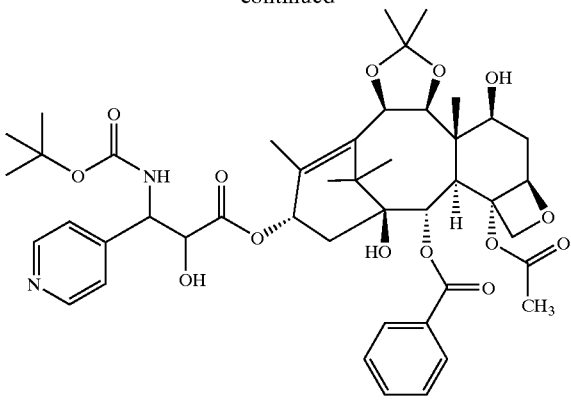

Step 1: 9β-13-O-Allyloxycarbonyl-10-deacetyl-9-dihydro-9,10-O-isopropylidenebaccatin III A 98.6 mg portion of the compound obtained in the step 2 of Inventive Example 1 was dissolved in 4.0 ml of tetrahydrofuran, 1.64 N n-butyl lithium (hexane solution, 0.31 ml) was added dropwise to the resulting solution at −78° C., and 0.025 ml of allyloxycarbonyl chloride was added thereto 5 minutes thereafter. After 30 minutes, the resulting solution was mixed with saturated ammonium chloride aqueous solution and extracted with ethyl acetate. The organic layers were washed with saturated brine and dried over anhydrous sodium sulfate. Thereafter, the solvent was evaporated under a reduced pressure and the resulting residue was purified by a silica gel column chromatography (developing solvent; hexane:ethyl acetate=5:4 (v/v)); to obtain 52.8 mg of the title compound as a colorless transparent syrup.

Rf=0.39 (hexane:ethyl acetate 5:4 (v/v)); $^1$H-NMR (400 MHz, CDCl$_3$/TMS) δ (ppm); 1.23 (3H, s), 1.40 (3H, s), 1.58 (3H, s), 1.64 (3H, s), 1.65 (3H, s), 1.80 (3H, s), 2.11–2.27 (2H, m), 2.26–2.38 (2H, m), 2.31 (3H, s); 2.98 (1H, d, J=4.8 Hz), 3.90 (1H, d, J=7.8 Hz), 4.01–4.09 (1H, m), 4.26 (1H, AB type d, J=8.3 Hz), 4.39 (1H, AB type d, J=8.3 Hz), 4.56 (1H, d, J=6:8 Hz), 4.63–4.76 (2H, m), 5.11 (1H, m), 5.28–5.44 (2H, m), 5.56 (1H, d, J=7.8 Hz), 5.85–6.05 (1H, m), 6.00 (1H, d, J=4.8 Hz), 7.47 (2H, t, J=7.8 Hz), 7.59 (1H, t, J=7.8 Hz), 8.11 (2H, d, J=7.8 Hz).

Step 2: 9β-13-O-Allyloxycarbonyl-O-deacetyl-9-dihydro-9,10-O-isopropylidene-7-O-triethylsilylbaccatin III A 52.8 mg portion of the compound obtained in the above step 1 was dissolved in 2.2 ml of a dry methylene chloride to which was subsequently added 0.036 ml of 2,6-lutidine at room temperature. After cooling to −40° C., thereto was added dropwise 0.062 ml of triethylsilyl trifluoromethanesulfonate, followed by 25 minutes of stirring. The resulting solution was mixed with saturated sodium bicarbonate aqueous solution at −40° C. and extracted with chloroform. The organic layers were washed with saturated brine and dried over anhydrous sodium sulfate. Thereafter, the solvent was evaporated under a reduced pressure and the resulting residue was purified by a silica gel column chromatography (developing solvent; hexane:ethyl acetate 4:1 (v/v)); to obtain 34.1 mg of the title compound as a colorless transparent syrup.

Rf=0.32 (hexane:ethyl acetate=3:1 (v/v)); $^1$H-NMR (400 MHz, CDCl$_3$/TMS) δ (ppm); 0.56–0.71 (6H, m), 1.15 (3H, s), 1.39 (3H, s), 1.47 (3H, s), 1.51 (3H, s), 1.58 (3H, s), 1.81 (3H, s), 2.05–2.15 (1H, m), 2.20–2.34 (2H, m), 2.30 (3H, s), 2.39 (1H, dd, J=7.6 Hz, 14.0 Hz), 3.22 (1H, d, J=5.8 Hz), 3.95 (1H, dd, J=3.4 Hz, 9.8 Hz), 4.28 (1H, AB type d, J=7.8 Hz), 4.47 (1H, AB type d, J=7.8 Hz), 4.56 (1H, br-d, J=9.3 Hz), 4.68 (2H, d, J=5.9 Hz), 4.82 (1H, t, J=7.2 Hz), 5.27–5.33 (1H, m), 5.34–5.41 (1H, m), 5.43 (1H, d, J=9.3 Hz), 5.82–6.01 (1H, m), 5.86 (1H, d, J=7.8 Hz), 5.88 (1H, t, J=7.6 Hz), 7.47 (2H, t, J=7.8 Hz), 7.58 (1H, t, J=7.8 Hz), 8.09 (2H, d, J=7.8 Hz).

Step 3: 9β-10-Deacetyl-9-dihydro-9,10-O-isopropylidene-7-O-triethyisilylbaccatin III A 32.1 mg portion of the compound obtained in the above step 2 was dissolved in 1.0 ml of tetrahydrofuran, and the solution was mixed with 0.005 ml of methanol and 4.3 mg of tetrakistriphenylphosphine palladium and stirred for 1 hour in an atmosphere of nitrogen. Thereafter, the solvent was evaporated under a reduced pressure and the resulting residue was purified by a silica gel thin layer chromatography (developing solvent; hexane:ethyl acetate 5:3 (v/v)); to obtain 17.1 mg of the title compound as a colorless transparent syrup.

Rf=0.29 (hexane:ethyl acetate=5:3 (v/v)); $^1$H-NMR (400 MHz, CDCl$_3$/TMS) δ (ppm); 0.61 (6H, q, J=7.8 Hz), 0.96 (9H, t, J=7.8 Hz), 1.11 (3H, s), 1.40 (3H, s), 1.50 (3H, s), 1.57 (3H, s), 1.59 (3H, s), 1.93 (3H, s), 1.88–2.15 (2H, m), 2.23–2.47 (2H, m), 2.32 (3H, s), 3.16 (1H, d, J=5.3 Hz), 4.17 (1H, t, J=4.8 Hz), 4.17–4.29 (1H, m), 4.20 (1H, AB type d, J=7.8 Hz), 4.29 (1H, AB type d, J=7.8 Hz), 4.73 4.88 (2H, m), 5.51 (1H, d, J=7.8 Hz), 5.91 (1H, d, J=5.3 Hz), 7.48 (2H, t, J=7.3 Hz), 7.59 (1H, t, J=7.3 Hz), 8.14 (2H, d, J=7.3 Hz).

Step 4: 9β-13-O-[3-(tert-Butoxycarbonylamino)-2-(tert-butyldimethylsilyloxy)-3-(4-pyridyl)propionyl]-10-deacetyl-9-dihydro-9,10-O-isopropylidene-7-O-triethylsilylbaccatin III Using the compound obtained in the above step 3 as the starting material, its reaction with cis-1-(tert-butoxycarbonyl)-3-(tert-butyldimethylsilyloxy)-4-(4-pyridyl)azetidin-2-one was carried out in the same manner as described in the step 3 of Inventive Example 1 to obtain the title compound in the form of a colorless transparent syrup as a mixture of two diastereoisomers in which relative configuration of the 2'- and 3'-positions was threo (syn) form.

Rf=0.32 (hexane:ethyl acetate=5:4 (v/v)); $^1$H-NMR (400 MHz, CDCl$_3$/TMS) δ (ppm); −0.30–0.37 (m), 0.60–1.02 (m), 1.25–1.88 (m), 2.10–2.58 (m), 2.24 and 2.54 (total 3H, each s), 3.10 and 3.15 (total 1H, each d, J=5.4 Hz, J=5.9 Hz), 3.92–4.18 (m), 4.21–4.60 (m), 4.84 and 4.94 (total 1H, each t, J=6.3 Hz, J=4.8 Hz), 5.21–5.68 (m), 5.88 and 5.94 (total 1H, each d, J=5.9 Hz, J=5.4 Hz), 6.18–6.30 (m), 7.18–7.64 (m), 8.11 (2H, d, J=7.3 Hz), 8.52–8.70 (m).

Step 5: 9β-13-O-[3-(tert-Butoxycarbonylamino)-2-hydroxy-3-(4-pyridyl)propionyl]-10-deacetyl-9-dihydro-9,10-O-isopropylidenebaccatin III A 27.1 mg portion of the compound obtained in the above step 4 was dissolved in 1.35 ml of pyridine to which was subsequently added dropwise 0.27 ml of hydrogen fluoride-pyridine at 0° C., followed by 6 hours of stirring at room temperature. After adding water cooled to 0° C., the resulting solution was extracted with ethyl acetate. The organic layer was washed with saturated brine and dried over anhydrous sodium sulfate. Thereafter, the solvent was evaporated under a reduced pressure and the resulting residue was purified by a silica gel thin layer chromatography (chloroform:methanol=12:1 (v/v)); to obtain a low polarity isomer A and a high polarity isomer B of the two diastereoisomers of the title compound in which relative configuration of the 2'- and 3'-positions was threo (syn) form, each as a colorless transparent syrup.

Isomer A

Rf=0.27 (chloroform:methanol 12:1 (v/v)); Melting point: 157–159° C. (lyophilization from dioxane); $^{1}$H-NMR (400 MHz, CDCl$_3$/TMS) δ (ppm); 1.24 (3H, s), 1.40 (3H, s), 1.51 (3H, s), 1.58 (3H, s), 1.63 (3H, s), 1.66 (3H, s), 1.42 (9H, s), 1.92 (1H, br-s), 1.96–2.02 (2H, m), 2.16–2.41 (2H, m), 2.30 (3H, s), 2.89 (1H, d, J=4.4 Hz), 3.77 (1H, d, J=7.4 Hz), 4.03–4.12 (1H, m), 4.35 (1H, AB type d, J=8.8 Hz), 4.38 (1H, AB type d, J=8.8 Hz), 4.63 (1H, s), 4.68 (1H, d, J=8.3 Hz), 5.11 (1H, s), 5.30 (1H, br-d, J=9.8 Hz), 5.52 (1H, br-d, J=7.4 Hz), 5.74 (1H, br-d, J=9.8 Hz), 6.06 (1H, d, J=4.4 Hz), 6.10 (1H, t, J=7.8 Hz), 7.35 (2H, d, J=5.9 Hz), 7.47 (2H, t, J=7.8 Hz), 7.60 (1H, t, J=7.8 Hz), 8.10 (2H, d, J=7.8 Hz), 8.59 (2H, d, J=5.9 Hz). FAB mass: 851 (MH$^+$).

Isomer B

Rf=0.25 (chloroform:methanol 12:1 (v/v)); Melting point: 160–163° C. (.lyophilization from dioxane); $^{1}$H-NMR (400 MHz, CDCl$_3$/TMS) δ (ppm); 1.29 (3H, s), 1.40 (3H, s), 1.59 (3H, s), 1.63 (3H, s), 1.68 (3H, s), 1.81 (3H, s), 1.40 (9H, s), 1.92 (1H, br-s), 2.05–2.42 (4H, m), 2.19 (3H, s), 2.93 (1H, d, J=4.9 Hz), 3.83 (1H, d, J=7.3 Hz), 4.03–4.13 (1H, m), 4.32 (1H, AB type d, J=8.3 Hz), 4.39 (1H, AB type d, J=8.3 Hz), 4.51 (1H, br-s), 4.73 (1H, d, J=7.3 Hz), 5.18 (1H, s like), 5.30 (1H, br-d, J=8.4 Hz), 5.46–5.61 (2H, m), 6.06 (1H, d, J=4.9 Hz), 6.23 (1H, m), 7.42 (2H, d, J=6.8 Hz), 7.46 (2H, t, J=7.6 Hz), 7.60 (1H, t, J=7.6 Hz), 8.10 (2H, d, J=7.6 Hz), 8.62 (2H, d, J=6.8 Hz). FAB mass: 851 (MH$^+$).

Inventive Example 4

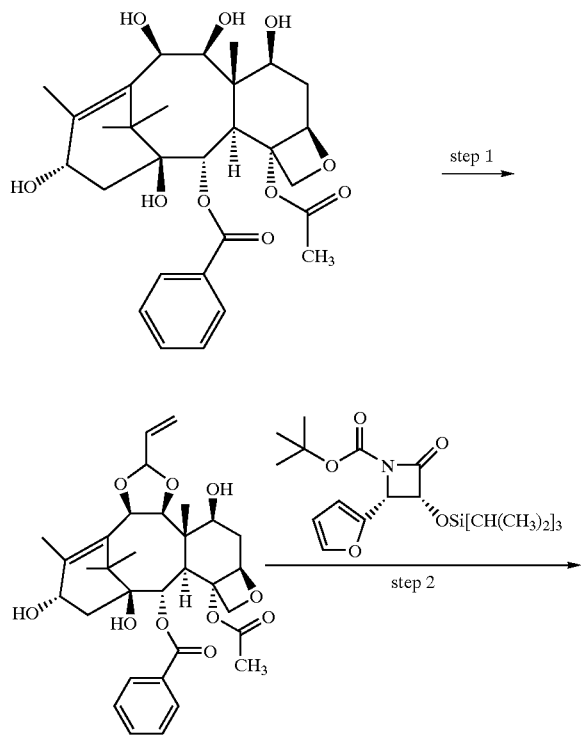

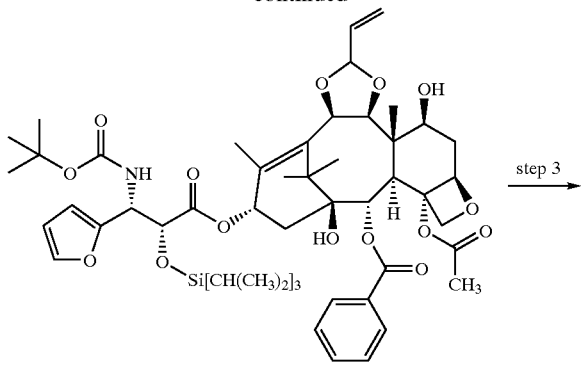

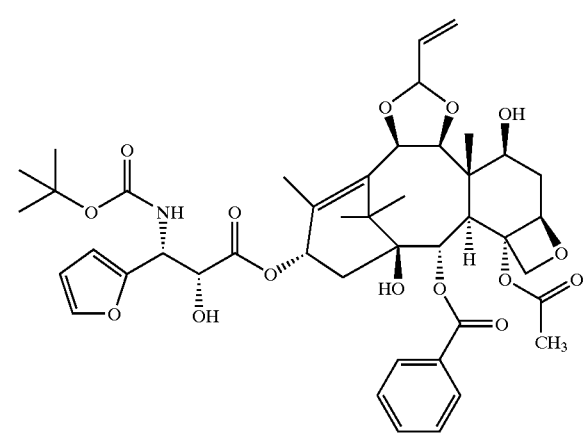

Step 1: 9β-10-Deacetyl-9-dihydro-9,10-O-(2-propenylidene)baccatin III

Using the compound obtained in the step 1 of Inventive Example 1 as the starting material, the reaction procedure of the step 2 of Inventive Example 1 was repeated, except that acrolein diethylacetal was used in stead of 2,2-dimethoxypropane, to obtain the title compound.

Rf=0.30 (chloroform:acetone=5:1 (v/v)); $^{1}$H-NMR (400 MHz, CDCl$_3$/TMS) δ (ppm); 1.17 (3H, s), 1.62 (3H, s), 1.65 (3H, s), 1.92 (3H, s), 1.82 (1H, s), 1.98 (1H, dd, J=16.0 Hz, 6.8 Hz), 2.09–2.42 (3H, m), 2.34 (3H, s), 3.05 (1H, d, J=4.4 Hz), 3.89 (1H, d, J=6.8 Hz), 4.06–4.16 (1H, m), 4.32 (1H, AB type d, J=8.3 Hz), 4.40 (1H, AB type d, J=8.3 Hz), 4.59 (1H, d, J=7.8 Hz), 4.82 (1H, br-q, J=6.8 Hz), 5.07 (1H, s), 5.22 (1H, d, J=6.3 Hz), 5.30 (1H, d, J=6.8 Hz), 5.45 (1H, d, J=10.3 Hz), 5.56 (1H, d, J=17.6 Hz), 6.04 (1H, d, J=4.4 Hz), 5.96–6.11 (1H, m), 7.48 (2H, t, J=7.3 Hz), 7.60 (1H, t, J=7.3 Hz), 8.13 (2H, d, J=7.3 Hz).

Step 2: 9β-13-O-[(2R,3R)-3-(tert-Butoxycarbonylamino)-3-(2-furyl)-2-(triisopropylsilyloxy)propionyl]-10-deacetyl-9-dihydro-9,10-O-(2-propenylidene)baccatin III Using the compound obtained in the above step 1 as the starting material, the reaction procedure of the step 3 of Inventive Example 1 was repeated to obtain the title compound.

Rf=0.16 (chloroform:acetone=12:1 (v/v)); $^1$H-NMR (400 MHz, CDCl$_3$/TMS) δ (ppm); 0.91–1.03 (21H, m), 1.30 (3H, s), 1.64 (3H, s), 1.68 (3H, s), 1.75 (3H, s), 1.40 (9H, s), 1.89 (1H, s), 2.21 (2H, m), 2.33 (2H, d, J=8.8 Hz), 2.46 (3H, s), 2.96 (1H, d, J=4.9 Hz), 3.91 (1H, d, J=6.9 Hz), 4.05–4.14 (1H, m), 4.30 (1H, AB type d, J=8.3 Hz), 4.40 (1H, AB type d, J=8.3 Hz), 4.63 (1H, d, J=8.3 Hz), 5.00 (1H, s), 5.12 (1H, s), 5.19 (1H, d, J=6.4 Hz), 5.24 (1H, d, J=6.9 Hz), 5.22–5.34 (2H, m), 5.45 (1H, d, J=10.3 Hz), 5.57 (1H, d, J=17.5 Hz), 5.94–6.15 (2H, m), 6.05 (1H, d, J=4.9 Hz), 6.25 (1H, d, J=2.9 Hz), 6.34 (1H, dd, J=2.9 Hz, 1.9 Hz), 7.37 (1H, d, J=1.9 Hz), 7.47 (2H, t, J=7.8 Hz), 7.59 (1H, t, J=7.8 Hz), 8.12 (2H, d, J=7.8 Hz).

Step 3: 9β-13-O-[(2R,3R)-3-(tert-Butoxycarbonylamino)-3-(2-furyl)-2-hydroxypropionyl]-10-deacetyl-9-dihydro-9,10-O-(2-propenylidene)baccatin III Using the compound obtained in the above step 2 as the starting material, the reaction procedure of the step 4 of Inventive Example 1 was repeated to obtain the title compound as a colorless transparent syrup.

Rf=0.05 (chloroform:acetone=12:1 (v/v)); Melting point: 147–150° C. (lyophilization from dioxane); $^1$H-NMR (400 MHz, CDCl$_3$/TMS) δ (ppm); 1.28 (3H, s), 1.62 (3H, s), 1.69 (3H, s), 1.71 (3H, s), 1.41 (9H, s), 2.05–2.26 (3H, m), 2.29–2.44 (1H, m), 2.35 (3H, s), 2.93 (1H, d, J=4.9 Hz), 3.89 (1H, d, J=6.8 Hz), 4.04–4.16 (1H, m), 4.32 (1H, AB type d, J=8.3 Hz), 4.39 (1H, AB type d, J=8.3 Hz), 4.71 (1H, s), 5.10 (1H, s), 5.22 (1H, d, J=5.9 Hz), 5.27 (1H, d, J=6.8 Hz), 5.32–5.46 (2H, m), 5.46 (1H, d, J=10.8 Hz), 5.57 (1H, d, J=17.6 Hz), 5.97–6.19 (2H, m), 6.08 (1H, d, J=4.9 Hz), 6.32 (1H, d, J=1.9 Hz), 6.36 (1H, dd, J=3.0 Hz, 1.9 Hz), 7.39 (1H, d, J=3.0 Hz), 7.48 (2H, t, J=7.8 Hz), 7.60 (1H, t, J=7.8 Hz), 8.10 (2H, d, J=7.8 Hz). FAB mass: 838 (MH$^+$).

Inventive Example 5

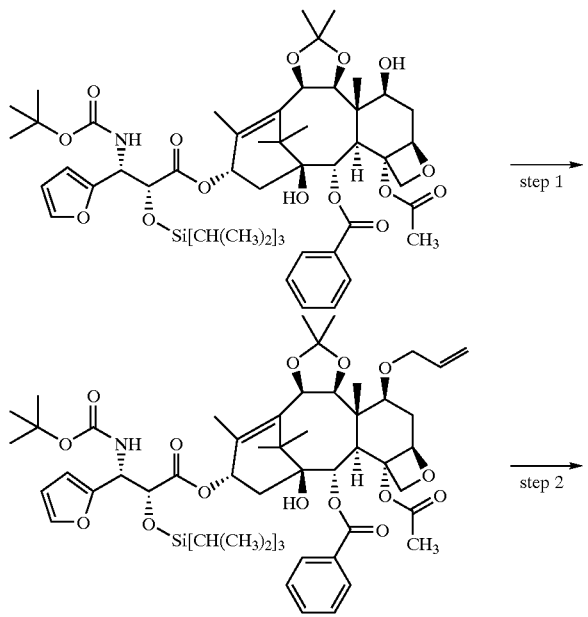

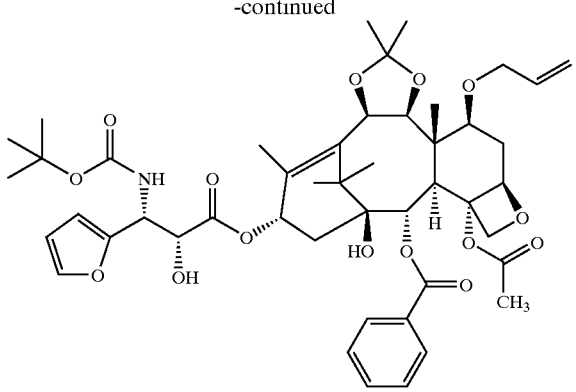

Step 1: 9β-7-O-Allyl-13-O-[(2R,3R)-3-(tert-butoxycarbonylamino)-3-(2-furyl)-2-(triisopropylsilyloxy)propionyl]-10-deacetyl-9-dihydro-9,10-O-isopropylidenebaccatin III A 34.4 mg portion of the compound obtained in the step 3 of Inventive Example 1 was dissolved in 1.4 ml of tetrahydrofuran to which was subsequently added dropwise 1 N sodium hexamethyldisilazide (tetrahydrofuran solution, 0.14 ml) at −50° C. Five minutes thereafter, the resulting solution was mixed with 0.020 ml of allyl iodide at the same temperature and stirred for 1.5 hours and then mixed again with 0.020 ml of allyl iodide at −42° C. and stirred for 1.5 hours. This mixture solution was mixed with saturated ammonium chloride aqueous solution at −40° C. and extracted with ethyl acetate. The organic layer was washed with saturated brine and dried over anhydrous sodium sulfate. Thereafter, the solvent was evaporated under a reduced pressure and the resulting residue was purified by a silica gel thin layer chromatography (developing solvent; hexane:ethyl acetate 5:1 (v/v)); to obtain, from an area of Rf=0.12 on the gel, 2.6 mg of a colorless transparent syrup of the title compound in which the 7-position hydroxyl group was etherificated.

Also, an area of Rf=0.27 on the gel gave 4.2 mg of a compound in which the 4-position acetyl group was converted into allyl group.

Rf=0.12 (hexane:ethyl acetate=6:1 (v/v)); $^1$H-NMR (400 MHz, CDCl$_3$/TMS) δ (ppm); 0.90–1.02 (m), 1.22 (3H, s), 1.36 (3H, s), 1.38 (9H, s), 1.51 (3H, s), 1.53 (3H, s), 1.57 (3H, s), 1.77 (3H, s), 2.02–2.48 (4H, m), 2.44 (3H, s), 3.23 (1H, d, J=5.8 Hz), 3.45 (1H, dd, J=2.9 Hz, 9.8 Hz), 3.84 (1H, dd, J=12.7 Hz, 5.4 Hz), 4.17 (1H, dd, J=12.7 Hz, 5.4 Hz), 4.26 (1H, AB type d, J=7.8 Hz), 4.56 (1H, AB type d, J=7.8 Hz), 4.32 (1H, d, J=8.8 Hz), 4.82 (1H, t, J=6.4 Hz), 4.96 (1H, s), 5.14 (1H, dd, J=10.3 Hz, 1.0 Hz), 5.21–5.36 (2H, m), 5.42 (1H, d, J=8.8 Hz), 5.87 (1H, d, J=5.8 Hz), 5.82–5.98 (1H, m), 6.14 (1H, br-t, J=8.4 Hz), 6.24 (1H, d, J=2.9 Hz), 6.34 (1H, dd, J=2.9 Hz, 1.0 Hz), 7.37 (1H, d, J=1.0 Hz), 7.47 (2H, t, J=7.8 Hz), 7.56 (1H, t, J=7.8 Hz), 8.10 (2H, d, J=7.8 Hz).

Step 2: 9β-7-O-Allyl-13-O-[(2R,3R)-3-(tert-butoxycarbonylamino)-3-(2-furyl)-2-hydroxypropionyl]-10-deacetyl-9-dihydro-9,10-O-isopropylidenebaccatin III Using the compound obtained in the above step 1 as the starting material, the reaction procedure of the step 4 of Inventive Example 1 was repeated to obtain the title compound as a colorless transparent syrup.

Rf=0.68 (chloroform:acetone=12:1 (v/v)); Melting point: 112–115° C. (lyophilization from dioxane); $^1$H-NMR (400 MHz, CDCl$_3$/TMS) δ (ppm); 1.23 (3H, s), 1.25 (3H, s), 1.39 (3H, s), 1.40 (9H, s), 1.46–1.61 (6H, m), 1.73 (3H, s), 1.68–1.82 (1H, m), 2.08–2.40 (3H, m), 2.35 (3H, s), 3.12

(1H, d, J=3.9 Hz), 3.44–3.56 (1H, m), 3.83 (1H, dd, J=13.0 Hz, 6.0 Hz), 4.17 (1H, dd, J=13.0 Hz, 4.8 Hz), 4.23 (1H, d, J=7.8 Hz), 4.56 (1H, d, J=8.3 Hz), 4.70 (1H, d, J=3.5 Hz), 4.83 (1H, t, J=4.9 Hz), 5.12 (1H, d, J=8.8 Hz), 5.27 (1H, d, J=16.1 Hz), 5.35 (1H, br-s), 5.46 (1H, d, J=8.3 Hz), 5.82–5.98 (1H, m), 5.92 (1H, d, J=3.9 Hz), 6.14 (1H, br-t, J=8.4 Hz), 6.31 (1H, d, J=2.9 Hz), 6.37 (1H, dd, J=2.9 Hz, 1.5 Hz), 7.40 (1H, d, J=1.5 Hz), 7.47 (2H, t, J=7.8 Hz), 7.58 (1H, t, J=7.8 Hz), 8.11 (2H, d, J=7.8 Hz). FAB Mass: 880 (M+).

Inventive Example 6

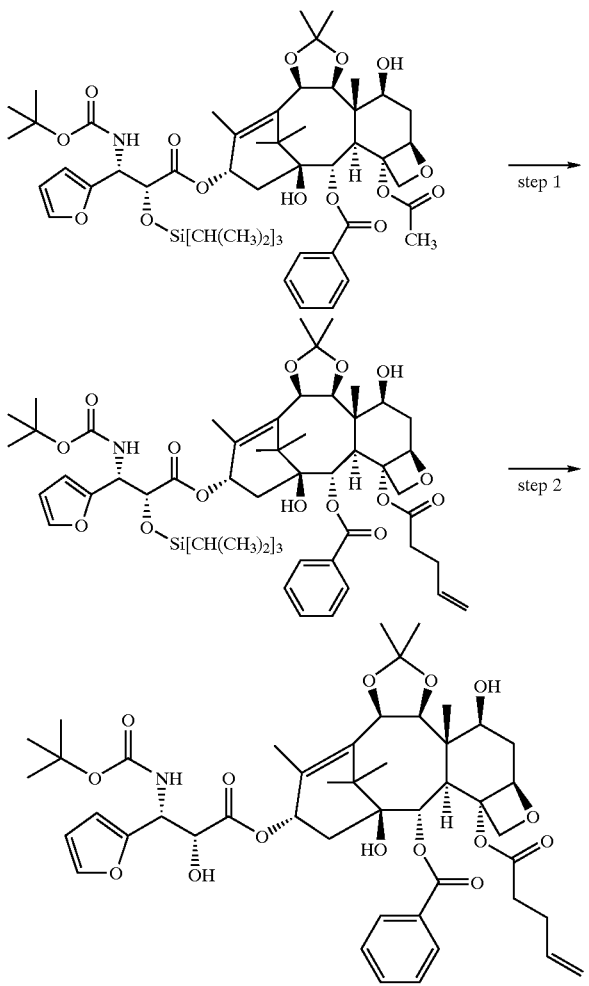

Step 1: 9β-13-O-[(2R,3R)-3-(tert-Butoxycarbonylamino)-3-(2-furyl)-2-(triisopropylsilyloxy)propionyl]-4,10-dideacetyl-9-dihydro-9,10-O-7isopropylidene-4-O-(4-pentenoyl)baccatin III By the reaction procedure of the step 1 of Inventive Example 5, 4.2 mg of the title compound in which the 4-position acetyl group was converted into allyl group was obtained from an area of Rf=0.27 on the gel.

Rf=0.27 (hexane:ethyl acetate=6:1 (v/v)); $^1$H-NMR (400 MHz, CDCl$_3$/TMS) δ (ppm); 0.91–1.04 (m), 1.23 (3H, s), 1.36 (3H, s), 1.37 (9H, s), 1.47 (3H, s), 1.50–1.60 (6H, m), 1.76 (3H, s), 2.09 (1H, ddd, J=5.2 Hz, 8.8 Hz, 14.4 Hz), 2.15–2.31 (2H, m), 2.40 (1H, dd, J=8.8 Hz, 15.2 Hz), 2.53–2.64 (2H, m), 2.71 (1H, q, J=7.6 Hz), 2.87 (1H, q, J=7.6 Hz), 3.18 (1H, d, J=5.4 Hz), 3.92 (1H, dd, J=8.8 Hz, 3.4 Hz), 4.26 (1H, AB type d, J=8.3 Hz), 4.51 (1H, AB type d, J=8.3 Hz), 4.41 (1H, br-d, J=8.3 Hz), 4.76 (1H, t, J=6.4 Hz), 4.96 (1H, s), 5.03 (1H, q, J=10.8 Hz), 5.14 (1H, dd, J=17.1 Hz, 1.0 Hz), 5.21–5.33 (2H, m), 5.40 (1H, d, J=8.3 Hz), 5.81–5.97 (1H, m), 5.89 (1H, d, J=5.4 Hz), 6.10 (1H, t, J=8.8 Hz), 6.25 (1H, d, J=3.4 Hz), 6.35 (1H, dd, J=3.4 Hz, 2.8 Hz), 7.36 (1H, d, J=2.8 Hz), 7.48 (2H, t, J=7.3 Hz), 7.57 (1H, t, J=7.3 Hz), 8.12 (2H, d, J=7.3 Hz).

Step 2: 9β-13-O-[(2R,3R)-3-(tert-Butoxycarbonylamino)-3-(2-furyl)-2-hydroxypropionyl]-4,10-dideacetyl-9-dihydro-9,10-O-isopropylidene-4-O-(4-pentenoyl)baccatin III Using the compound obtained in the above step 1 as the starting material, the reaction procedure of the step 4 of Inventive Example 1 was repeated to obtain the title compound.

Rf=0.20 (chloroform:acetone=10:1 (v/v)); Melting point: 105–110° C. (lyophilization from dioxane); $^1$H-NMR (400 MHz, CDCl$_3$/TMS) δ (ppm); 1.25 (3H, s), 1.28 (3H, s), 1.40 (9H, s), 1.58 (3H, s), 1.64 (3H, s), 1.67 (3H, s), 1.70 (3H, s), 2.07–2.28 (3H, m), 2.30–2.41 (1H, m), 2.49–2.66 (3H, m), 2.69–2.80 (1H, m), 2.94 (1H, d, J=4.4 Hz), 3.66 (1H, br-s), 3.84 (1H, d, J=5.4 Hz), 4.06 (1H, m), 4.33 (1H, AB type d, J=8.3 Hz), 4.38 (1H, AB type d, J=8.3 Hz), 4.64–4.73 (2H, m), 4.99–5.10 (2H, m), 5.13 (1H, dd, J=1.0 Hz, 17.0 Hz), 5.31 (1H, s), 5.54 (1H, d, J=8.3 Hz), 5.75–5.89 (1H, m), 6.05 (1H, d, J=4.4 Hz), 6.10 (1H, br-t, J=7.2 Hz), 6.32 (1H, d, J=3.4 Hz), 6.36 (1H, dd, J=3.4 Hz, 1.5 Hz), 7.39 (1H, d, J=1.5 Hz), 7.48 (2H, t, J=7.4 Hz), 7.61 (1H, t, J=7.4 Hz), 8.13 (2H, d, J=7.4 Hz). FAB Mass: 880 (M$^+$).

Inventive Example 7

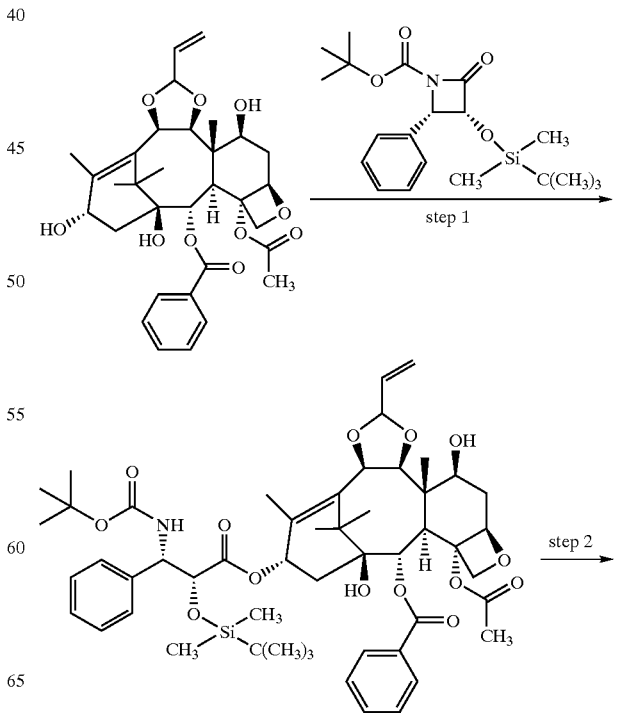

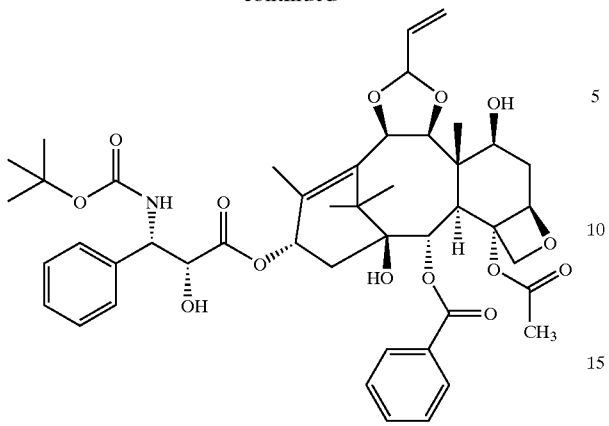

Step 1: 9β-13-O-[(2R,3S)-3-(tert-Butoxycarbonylamino)-2-(tert-butyldimethylsilyloxy)-3-phenylpropionyl]-10-deacetyl-9-dihydro-9,10-O-(2-propenylidene)baccatin III Using the compound obtained in the step 1 of Inventive Example 4 as the starting material, its reaction with (3R, 4S)-1-(tert-butoxycarbonyl)-3-(tert-butyldimethylsilyloxy)-4-phenylazetidin-2-one was carried out in the same manner as described in the step 3 of Inventive Example 1 to obtain the title compound as a colorless transparent syrup.

Rf=0.35 (chloroform:acetone=7:1 (v/v)); $^1$H-NMR (400 MHz, CDCl$_3$/TMS) δ (ppm); −0.33 (3H, s), −0.11 (3H, s), 0.74 (9H, s), 1.33 (3H, s), 1.38 (9H, s), 1.64 (3H, s), 1.69 (3H, s), 1.73 (3H, s), 1.85 (1H, s), 2.13–2.28 (3H, m), 2.33 (1H, dd, J=9.3 Hz, 14.6 Hz), 2.53 (3H, s), 2.96 (1H, d, J=4.9 Hz), 3.91 (1H, d, J=7.3 Hz), 4.04–4.14 (1H, m), 4.33 (1H, AB type d, J=8.3 Hz), 4.40 (1H, AB type d, J=8.3 Hz), 4.53 (1H, s), 4.59 (1H, d, J=7.8 Hz), 5.13 (1H, s), 5.19 (1H, d, J=5.9 Hz), 5.23 (1H, d, J=7.3 Hz), 5.30 (1H, br-d, J=8.8 Hz), 5.45 (1H, d, J=10.3 Hz), 5.57 (1H, d, J=17.6 Hz), 5.96–6.10 (1H, m), 6.04 (1H, d, J=4.9 Hz), 6.20 (1H, t, J=8.8 Hz), 7.18–7.41 (5H, m), 7.48 (2H, t, J=7.8 Hz), 7.60 (1H, t, J=7.8 Hz), 8.13 (2H, d, J=7.8 Hz).

Step 2: 9β-13-O-[ (2R,3S)-3-(tert-Butoxycarbonylamino)-2-hydroxy-3-phenylpropionyl]-10-deacetyl-9-dihydro-9,10-O-(2-propenylidene)baccatin III Using the compound obtained in the above step 1 as the starting material, the reaction procedure of the step 4 of Inventive Example 1 was repeated to obtain the title compound.

Rf=0.30 (chloroform:acetone=5:1 (v/v)); Melting point: 145–150° C. (lyophilization from dioxane); $^1$H-NMR (400 MHz, CDCl$_3$/TMS) δ (ppm); 1.26 (3H, s), 1.40 (9H, s), 1.61 (6H, s), 1.68 (3H, s), 1.91 (1H, s), 2.00–2.36 (3H, m), 2.30 (3H, s), 2.39 (1H, dd, J=9.8 Hz, 15.2 Hz), 2.90 (1H, d, J=4.9 Hz), 3.85 (1H, d, J=6.8 Hz), 4.06–4.15 (1H, m), 4.16 (1H, br-s), 4.32 (1H, AB type d, J=8.8 Hz), 4.38 (1H, AB type d, J=8.8 Hz), 4.57 (1H, d, J=8.3 Hz), 4.62 (1H, br-s), 5.10 (1H, s), 5.22 (1H, d, J=6.3 Hz), 5.26 (1H, d, J=6.8 Hz), 5.30 (1H, br-d, J=9.7 Hz), 5.97–6.13 (2H, m), 6.07 (1H, d, J=4.3 Hz), 7.20–7.45 (5H, m), 7.47 (2H, t, J=7.4 Hz), 7.60 (1H, t, J=7.4 Hz), 8.10 (2H, d, J=7.4 Hz). FAB Mass: 848 (MH$^+$).

Inventive Example 8

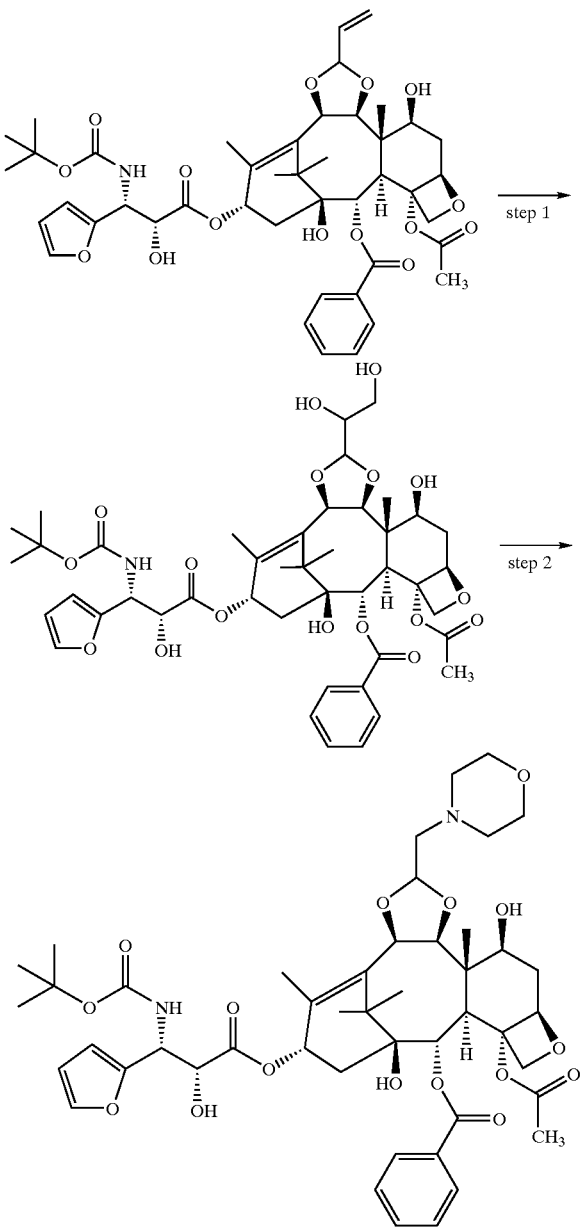

Step 1: 9β-13-O-[(2R,3R)-3-(tert-Butoxycarbonylamino)-3-(2-furyl)-2-hydroxypropionyl]-10-deacetyl-9-dihydro-9,10-O-(2,3-dihydroxypropylidene)baccatin III A 35.1 mg portion of the compound obtained in the step 3 of Inventive Example 4 was dissolved in 1.1 ml of tetrahydrofuran and 0.35 ml of a distilled water, and the solution was mixed with 26.8 mg of N-morpholine-N-oxide and 4.8 mg of osmium tetraoxide at room temperature. This, 21 hours thereafter, was mixed with sodium sulfite aqueous solution and extracted with ethyl acetate. The organic layer was washed with saturated brine and dried over anhydrous sodium sulfate. Thereafter, the solvent was evaporated under a reduced pressure and the resulting residue was purified by a silica gel thin layer chromatography (developing solvent; chloroform:methanol=10:1 (v/v)) to obtain 14.1 mg of the title compound as a colorless transparent syrup.

Rf=0.25 (chloroform:methanol=8:1 (v/v)); $^1$H-NMR (400 MHz, CDCl$_3$/TMS) δ (ppm); 1.27 (3H, s), 1.29 (3H, s), 1.41

(9H, s), 1.63 (3H, s), 1.69 (3H, s), 1.70 (3H, s), 2.00–2.55 (m), 2.36 (3H, s), 2.93 (1H, d, J=4.9 Hz), 3.70–4.00 (m), 4.05–4.18 (1H, m), 4.30 (1H, AB type d, J=8.8 Hz), 4.38 (1H, AB type d, J=8.8 Hz), 4.71 (1H, s), 4.75–4.92 (2H, m), 5.10 (1H, s), 5.26 (1H, d, J=4.9 Hz), 5.35 (1H, br-d, J=9.7 Hz), 6.03 (1H, d, J=7.3 Hz), 6.08–6.16 (1H, m), 6.31 (1H, d, J=3.4 Hz), 6.36 (1H, dd, J=3.4 Hz, 1.5 Hz), 7.39 (1H, d, J=1.5 Hz), 7.42–7.67 (3H, m), 8.02–8.17 (2H, m).

Step 2: 9β-13-O-[(2R,3R)-3-(tert-Butoxycarbonylamino)-3-(2-furyl)-2-hydroxypropionyl]-10-deacetyl-9-dihydro-9,10-O-(2-morpholinoethylidene)baccatin III A 14.1 mg portion of the compound obtained in the above step 1 was dissolved in a tetrahydrofuran-water-methanol (1:1:1 (v/v)) mixture solvent, and the solution was mixed with 19.7 mg of sodium metaperiodate at room temperature and stirred for 30 minutes. This solution was cooled to 0° C., mixed with brine and extracted with ethyl acetate. After washing the thus obtained extract with saturated brine and subsequently drying over anhydrous sodium sulfate, the solvent was evaporated under a reduced pressure. The resulting residue was dried in vacuo and dissolved in 1.3 ml of ethanol, and the resulting solution was mixed with 0.10 ml of acetic acid, 0.14 ml of morpholine and 13.9 mg of sodium cyanoborohydride at room temperature and stirred for 1 hour. The reaction solution was mixed with saturated sodium bicarbonate aqueous solution and saturated brine, and extracted with ethyl acetate. The thus obtained extract was washed with saturated brine and dried over anhydrous sodium sulfate. Thereafter, the solvent was evaporated under a reduced pressure and the resulting residue was purified by a silica gel thin layer chromatography (developing solvent; chloroform:methanol=12:1 (v/v)) to obtain 10.4 mg of the title compound as a colorless transparent syrup.

Rf=0.56 (chloroform:methanol=10:1 (v/v)); Melting point: 149–152° C. (lyophilization from dioxane); $^1$H-NMR (400 MHz, CDCl$_3$/TMS) δ (ppm); 1.27 (3H, s), 1.41 (9H, s), 1.60 (3H, s), 1.65 (3H, s), 1.69 (3H, s), 1.89 (1H, s), 2.08–2.26 (3H, m), 2.35 (3H, s), 2.31–2.43 (1H, m), 2.54–2.70 (4H, m), 2.74 (1H, dd, J=5.4 Hz, 13.7 Hz), 2.82 (1H, dd, J=3.9 Hz, 13.7 Hz), 2.92 (1H, d, J=4.7 Hz), 3.69–3.79 (4H, m), 3.80 (1H, d, J=6.9 Hz), 3.87–3.94 (1H, broad), 4,04–4.11 (1H, m), 4.31 (1H, AB type d, J=8.3 Hz), 4.39 (1H, AB type d, J=8.3 Hz), 4.67 (1H, d, J=8.3 Hz), 4.71 (1H, s), 5.02 (1H, dd, J=5.4 Hz, 3.9 Hz), 5.11 (1H, s), 5.20 (1H, d, J=6.9 Hz), 5.30–5.42 (2H, m), 6.04 (1H, d, J=4.7 Hz), 6.11 (1H, br-t, J=8.0 Hz), 6.31 (1H, d, J=3.4 Hz), 6.36 (1H, dd, J=3.4 Hz, 2.0 Hz), 7.39 (1H, d, J=2.0 Hz), 7.48 (2H, t, J=7.8 Hz), 7.60 (1H, t, J=7.8 Hz), 8.11 (2H, d, J=7.8 Hz). FAB Mass: 911 (M$^+$).

Inventive Example 9

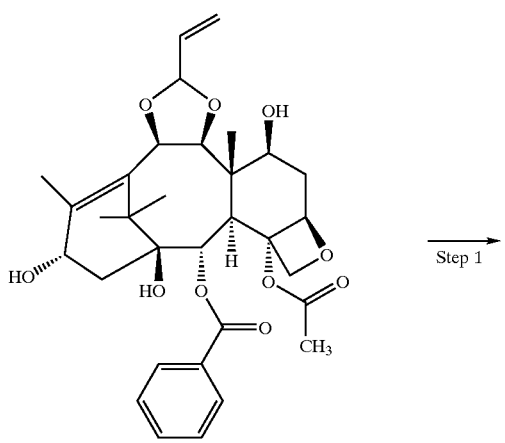

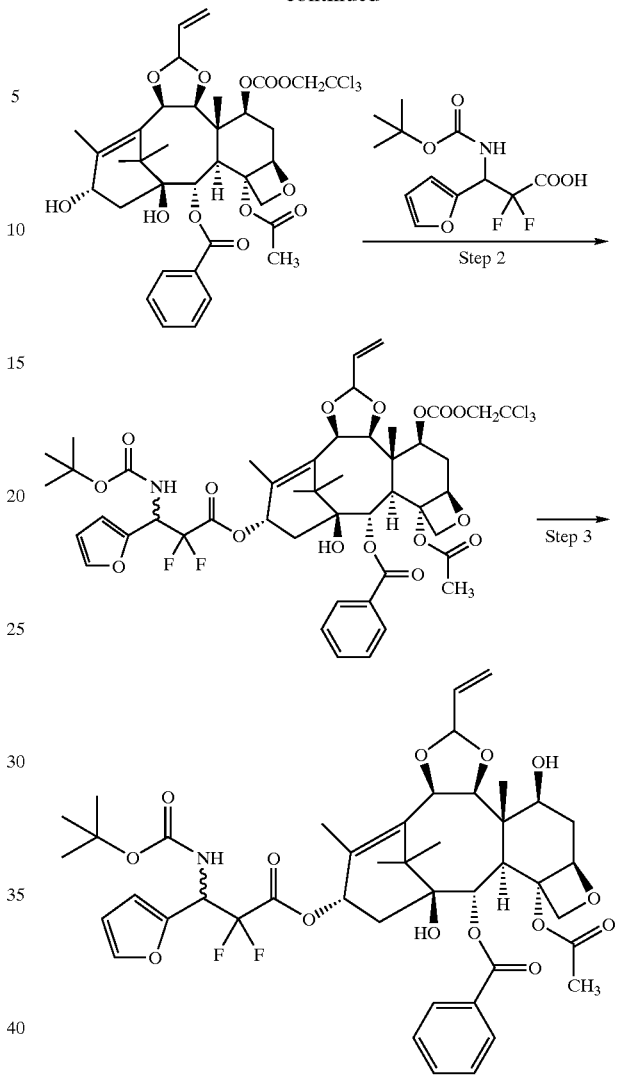

Step 1: 9β-10-Deacetyl-9-dihydro-9,10-O-(2-propenylidene)-7-O-(2,2,2-trichloroethoxycarbonyl)baccatin III A 100.4 mg portion of the compound obtained in the step 1 of Inventive Example 4 was dissolved in 3.0 ml of pyridine to which was subsequently added dropwise 0.025 ml of 2,2,2-trichloroethoxycarbonyl chloride at 0° C. After 30 minutes, 0° C.-cooled water was added thereto and the resulting solution was extracted with ethyl acetate. The thus obtained extract was washed with 1 N hydrochloric acid, saturated sodium bicarbonate aqueous solution and saturated brine in that order and dried over anhydrous sodium sulfate. Thereafter, the solvent was evaporated under a reduced pressure and the resulting residue was purified by a silica gel column chromatography (developing solvent; chloroform:acetone=6:1 (v/v)) to obtain 116.7 mg of the title compound as a colorless transparent syrup.

Rf=0.48 (chloroform:acetone=5:1 (v/v)); $^1$H-NMR (400 MHz, CDCl$_3$/TMS) δ (ppm); 1.16 (3H, s), 1.60 (3H, s), 1.62 (3H, s), 1.96 (3H, s), 1.80 (1H, s), 1.91–2.00 (1H, m), 2.20 (1H, dt, J=16.0 Hz, 4.4 Hz), 2.29–2.43 (2H, m), 2.35 (3H, s), 3.20 (1H, d, J=4.9 Hz), 3.97 (1H, d, J=7.3 Hz), 4.31 (1H, AB type d, J=8.3 Hz), 4.44 (1H, AB type d, J=8.3 Hz), 4.66 (1H, AB type d, J=11.7 Hz), 4.83 (1H, AB type d, J=11.7 Hz), 4.76–4.89 (2H, m), 5.15 (1H, dd, J=5.3 Hz, 3.4 Hz), 5.19

(1H, d, J=5.9 Hz), 5.34 (1H, d, J=7.3 Hz), 5.46 (1H, d, J=10.3 Hz), 5.57 (1H, d, J=17.5 Hz), 5.98 (1H, d, J=4.9 Hz), 6.04 (1H, ddd, J=17.5 Hz, 10.3 Hz, 5.9 Hz), 7.48 (2H, t, J=7.4 Hz), 7.59 (1H, t, J=7.4 Hz), 8.13 (2H, d, J=7.4 Hz).

Step 2: 9β-13-O-[3-(tert-Butoxycarbonylamino)-2,2-difluoro-3-(2-furyl)propionyl]-10-deacetyl-9-dihydro-9,10-O-(2-propenylidene)-7-O-(2,2,2-trichloroethoxycarbonyl) baccatin III A 0.2041 g portion of 3-(tert-butoxycarbonylamino)-2,2-difluoro-3-(2-furyl)propionic acid was dissolved in 4.0 ml of toluene, and the solution was mixed with 0.1516 g of di-2-pyridyl carbonate at room temperature. After 20 minutes, 2.0 ml toluene suspension of 0.1167 g of the compound obtained in the above step 1 was added thereto, 39.9 mg of 4-dimethylaminopyridine was further added thereto, and the mixture was stirred for 16 hours at 65° C. After cooling to room temperature, the reaction solution was mixed with water and extracted with ethyl acetate. The thus obtained extract was washed with saturated brine and dried over anhydrous sodium sulfate. Thereafter, the solvent was evaporated under a reduced pressure and the resulting residue was purified by a silica gel column chromatography (developing solvent; chloroform:acetone=20:1 (v/v)) to obtain 75.5 mg of the title compound as a colorless transparent syrup.

Rf=0.44 (chloroform:acetone=20:1 (v/v)); $^1$H-NMR (400 MHz, CDCl$_3$/TMS) δ (ppm); 1.28 (3H, s), 1.43 (9H, s), 1.47 (3H, s), 1.62 (3H, s), 1.64 (3H, s), 1.90 (1H, broad s), 2.19–2.40 (6H, m), 3.13 (1H, d, J=4.7 Hz), 3.95–4.01 (1H, m), 4.31 (1H, AB type d, J=8.3 Hz), 4.39 (1H, AB type d, J=8.3 Hz), 4.67 (1H, AB type d, J=11.7 Hz), 4.85 (1H, AB type d, J=11.7 Hz), 4.87–4.94 (1H, m), 5.08–5.17 (2H, m), 5.28 (1H, t, J=8.3 Hz), 5.38 (1H, br-d, J=8.8 Hz), 5.46 (1H, d, J=10.2 Hz), 5.56 (1H, d, J=17.5 Hz), 5.58–5.73 (1H, m), 5.96 (1H, d, J=4.7 Hz), 6.04 (1H, ddd, J=17.5 Hz, 10.2 Hz, 5.9 Hz), 6.12–6.28 (1H, m), 6.31–6.46 (2H, m), 7.38–7.51 (3H, m), 7.60 (1H, t, J=7.4 Hz), 8.06–8.14 (2H, m).

Step 3: 9β-13-O-[3-(tert-Butoxycarbonylamino)-2,2-difluoro-3-(2-furyl)propionyl]-10-deacetyl-9-dihydro-9,10-O-(2-propenylidene)baccatin III A 75.5 mg portion of the compound obtained in the above step 2 was dissolved in 6.0 ml of an acetic acid-methanol (1:1 (v/v)) mixture solvent, and the solution was mixed with 0.1728 g of zinc powder at room temperature and stirred for 30 minutes at 62° C. The solid matter was filtered off. The resulting filtrate was concentrated under a reduced pressure, diluted with ethyl acetate, washed with saturated sodium bicarbonate aqueous solution and saturated brine, and then dried over anhydrous sodium sulfate. Thereafter, the solvent was evaporated under a reduced pressure and the resulting residue was purified by a silica gel thin layer chromatography (developing solvent; chloroform:acetone=7:1 (v/v)) to obtain 14.7 mg of the title compound as a colorless transparent syrup.

Rf=0.30 (chloroform:acetone=8:1 (v/v)); Melting point; 124–127° C. (lyophilization from dioxane); $^1$H-NMR (400 MHz, CDCl$_3$/TMS) δ (ppm); 1.30 (3H, s), 1.43 (9H, s), 1.62 (6H, s), 1.89 (1H, s), 2.16–2.35 (4H, m), 2.26 (3H, s), 2.92 (1H, d, J=4.9 Hz), 3.83–3.94 (1H, m), 4.04–4.10 (1H, m), 4.28 (1H, AB type d, J=8.3 Hz), 4.40 (1H, AB type d, J=8.3 Hz), 4.60 (1H, br-d, J=8.3 Hz), 5.12 (1H, s), 5.17–5.28 (2H, m), 5.31–5.41 (1H, m), 5.45 (1H, d, J=10.7 Hz), 5.56 (1H, d, J=17.6 Hz), 5.55–5.72 (1H, m), 5.94–6.07 (1H, m), 6.03 (1H, d, J=4.9 Hz), 6.12–6.25 (1H, m), 6.35–6.46 (2H, m), 7.42 (1H, s), 7.48 (2H, t, J=7.3 Hz), 7.60 (1H, t, J=7.3 Hz), 8.06–8.14 (2 H, m). FAB Mass: 858 (M$^+$).

Inventive Example 10

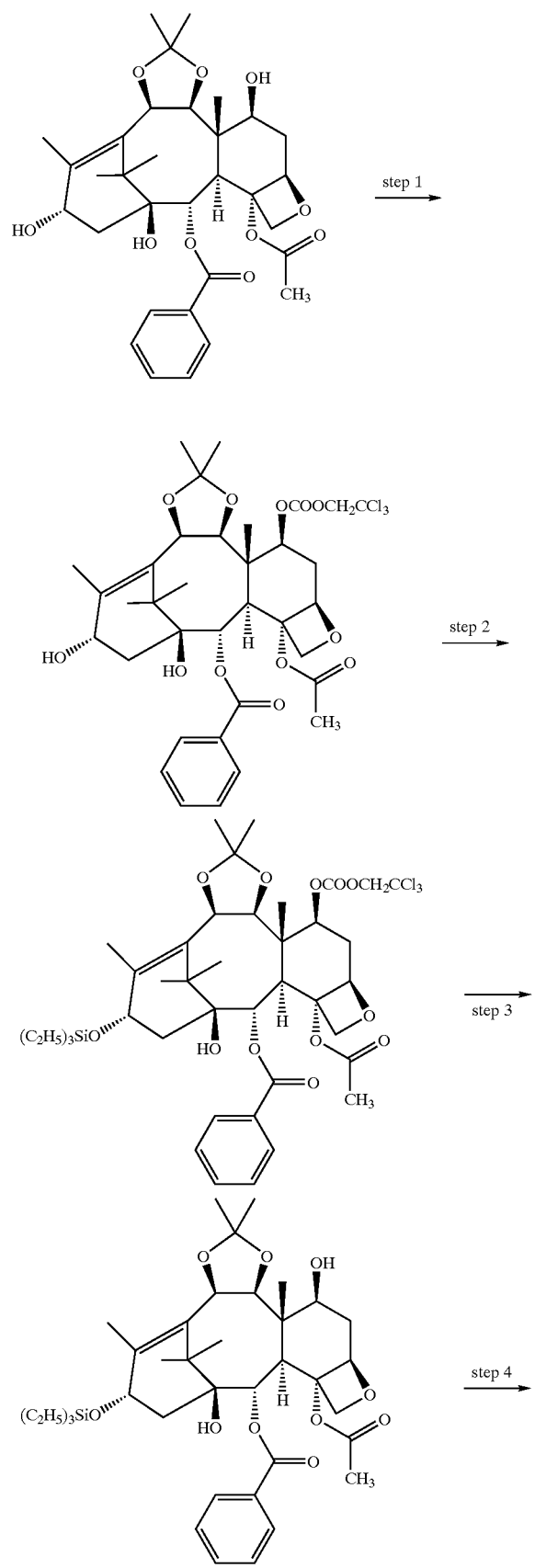

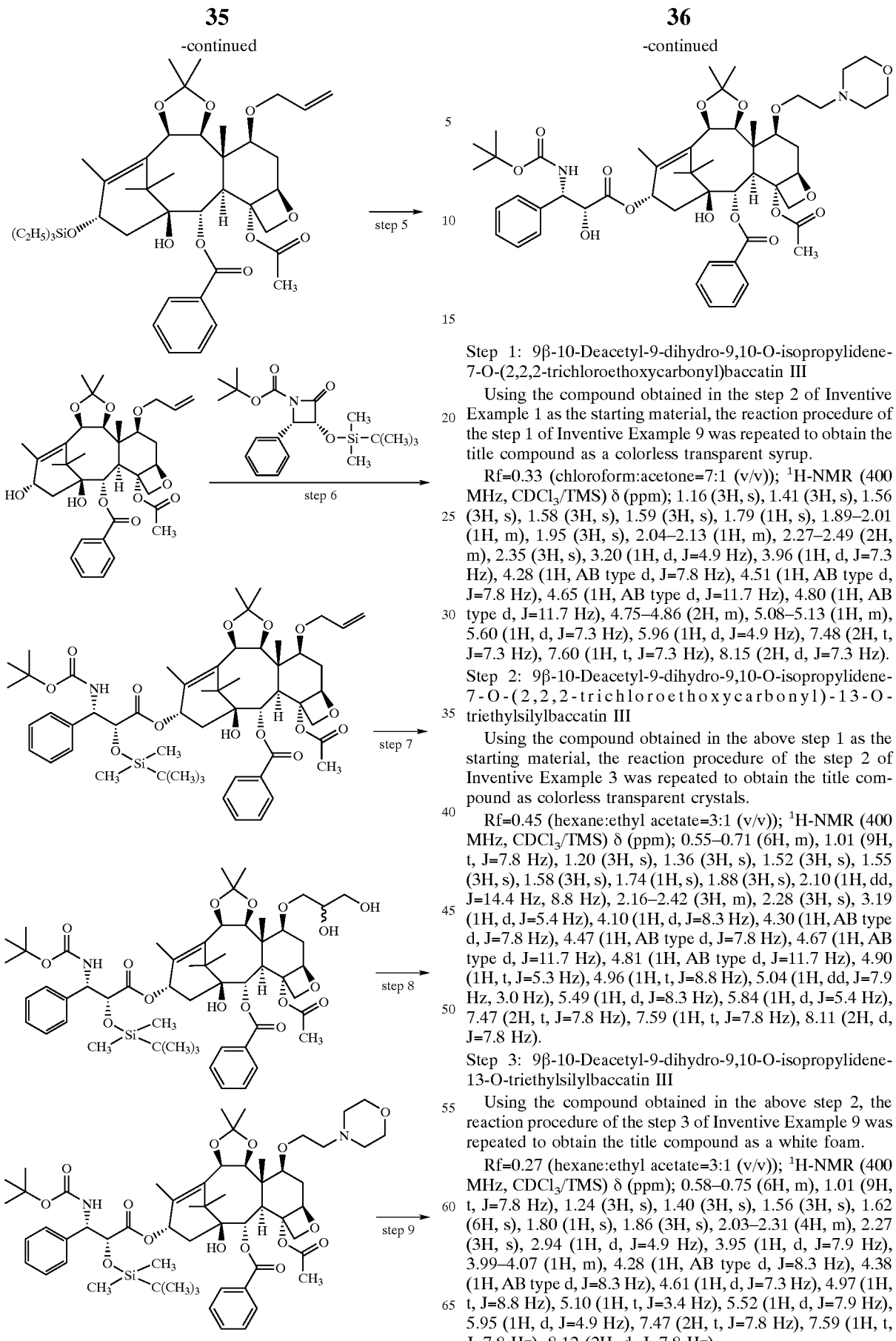

Step 1: 9β-10-Deacetyl-9-dihydro-9,10-O-isopropylidene-7-O-(2,2,2-trichloroethoxycarbonyl)baccatin III Using the compound obtained in the step 2 of Inventive Example 1 as the starting material, the reaction procedure of the step 1 of Inventive Example 9 was repeated to obtain the title compound as a colorless transparent syrup.

Rf=0.33 (chloroform:acetone=7:1 (v/v)); $^1$H-NMR (400 MHz, CDCl$_3$/TMS) δ (ppm); 1.16 (3H, s), 1.41 (3H, s), 1.56 (3H, s), 1.58 (3H, s), 1.59 (3H, s), 1.79 (1H, s), 1.89–2.01 (1H, m), 1.95 (3H, s), 2.04–2.13 (1H, m), 2.27–2.49 (2H, m), 2.35 (3H, s), 3.20 (1H, d, J=4.9 Hz), 3.96 (1H, d, J=7.3 Hz), 4.28 (1H, AB type d, J=7.8 Hz), 4.51 (1H, AB type d, J=7.8 Hz), 4.65 (1H, AB type d, J=11.7 Hz), 4.80 (1H, AB type d, J=11.7 Hz), 4.75–4.86 (2H, m), 5.08–5.13 (1H, m), 5.60 (1H, d, J=7.3 Hz), 5.96 (1H, d, J=4.9 Hz), 7.48 (2H, t, J=7.3 Hz), 7.60 (1H, t, J=7.3 Hz), 8.15 (2H, d, J=7.3 Hz).

Step 2: 9β-10-Deacetyl-9-dihydro-9,10-O-isopropylidene-7-O-(2,2,2-trichloroethoxycarbonyl)-13-O-triethylsilylbaccatin III Using the compound obtained in the above step 1 as the starting material, the reaction procedure of the step 2 of Inventive Example 3 was repeated to obtain the title compound as colorless transparent crystals.

Rf=0.45 (hexane:ethyl acetate=3:1 (v/v)); $^1$H-NMR (400 MHz, CDCl$_3$/TMS) δ (ppm); 0.55–0.71 (6H, m), 1.01 (9H, t, J=7.8 Hz), 1.20 (3H, s), 1.36 (3H, s), 1.52 (3H, s), 1.55 (3H, s), 1.58 (3H, s), 1.74 (1H, s), 1.88 (3H, s), 2.10 (1H, dd, J=14.4 Hz, 8.8 Hz), 2.16–2.42 (3H, m), 2.28 (3H, s), 3.19 (1H, d, J=5.4 Hz), 4.10 (1H, d, J=8.3 Hz), 4.30 (1H, AB type d, J=7.8 Hz), 4.47 (1H, AB type d, J=7.8 Hz), 4.67 (1H, AB type d, J=11.7 Hz), 4.81 (1H, AB type d, J=11.7 Hz), 4.90 (1H, t, J=5.3 Hz), 4.96 (1H, t, J=8.8 Hz), 5.04 (1H, dd, J=7.9 Hz, 3.0 Hz), 5.49 (1H, d, J=8.3 Hz), 5.84 (1H, d, J=5.4 Hz), 7.47 (2H, t, J=7.8 Hz), 7.59 (1H, t, J=7.8 Hz), 8.11 (2H, d, J=7.8 Hz).

Step 3: 9β-10-Deacetyl-9-dihydro-9,10-O-isopropylidene-13-O-triethylsilylbaccatin III Using the compound obtained in the above step 2, the reaction procedure of the step 3 of Inventive Example 9 was repeated to obtain the title compound as a white foam.

Rf=0.27 (hexane:ethyl acetate=3:1 (v/v)); $^1$H-NMR (400 MHz, CDCl$_3$/TMS) δ (ppm); 0.58–0.75 (6H, m), 1.01 (9H, t, J=7.8 Hz), 1.24 (3H, s), 1.40 (3H, s), 1.56 (3H, s), 1.62 (6H, s), 1.80 (1H, s), 1.86 (3H, s), 2.03–2.31 (4H, m), 2.27 (3H, s), 2.94 (1H, d, J=4.9 Hz), 3.95 (1H, d, J=7.9 Hz), 3.99–4.07 (1H, m), 4.28 (1H, AB type d, J=8.3 Hz), 4.38 (1H, AB type d, J=8.3 Hz), 4.61 (1H, d, J=7.3 Hz), 4.97 (1H, t, J=8.8 Hz), 5.10 (1H, t, J=3.4 Hz), 5.52 (1H, d, J=7.9 Hz), 5.95 (1H, d, J=4.9 Hz), 7.47 (2H, t, J=7.8 Hz), 7.59 (1H, t, J=7.8 Hz), 8.12 (2H, d, J=7.8 Hz).

Step 4: 9β-7-O-Allyl-10-deacetyl-9-dihydro-9,10-O-isopropylidene-13-O-triethylsilylbaccatin III A 0.2400 g portion of the compound obtained in the above step 3 was dissolved in 7.2 ml of a dry tetrahydrofuran to which was subsequently added dropwise 1.64 N butyl lithium (hexane solution, 0.315 ml) at −50° C. After 17 minutes of the dropwise addition, the resulting solution was mixed with allyl iodide (0.15 ml) dissolved in dimethyl sulfoxide (1.80 ml), and the mixture was stirred at 0° C. for 1.5 hours. The mixture solution was mixed with saturated ammonium chloride aqueous solution at 0° C. and extracted with ethyl acetate. The thus obtained extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=10:3 (v/v)) to obtain 0.1358 g of the title compound as a white solid.

Rf=0.41 (hexane:ethyl acetate=3:1 (v/v)); $^1$H-NMR (400 MHz, CDCl$_3$/TMS) δ (ppm); 0.59–0.74 (6H, m), 1.01 (9H, t, J=7.8 Hz), 1.37 (3H, s), 1.43 (3H, s), 1.50 (3H, s), 1.57 (3H, s), 1.65 (1H, s), 1.87 (3H, s), 2.00–2.14 (2H, m), 2.21–2.47 (2H, m), 2.28 (3H, s), 3.26 (1H, d, J=5.8 Hz), 3.42 (1H, dd, J=11.7 Hz, 3.4 Hz), 3.85 (1H, dd, J=12.7 Hz, 5.4 Hz), 4.18 (1H, dd, J=12.7 Hz, 5.4 Hz), 4.29 (1H, AB type d, J=7.8 Hz), 4.54 (1H, AB type d, J=7.8 Hz), 4.40 (1H, d, J=9.8 Hz), 4.82 (1H, t, J=8.3 Hz), 4.93 (1H, t, J=8.3 Hz), 5.16 (1H, dd, J=10.3 Hz, 1.5 Hz), 5.32 (1H, dd, J=17.1 Hz, 1.5 Hz), 5.41 (1H, d, J=9.8 Hz), 5.77 (1H, d, J=5.8 Hz), 5.85–6.00 (1H, m), 7.46 (2H, t, J=7.3 Hz), 7.58 (1H, t, J=7.3 Hz), 8.07 (2H, d, J=7.3 Hz).

Step 5: 9β-7-O-Allyl-10-deacetyl-9-dihydro-9,10-O-isopropylidenebaccatin III

Using the compound obtained in the above step 4, the reaction procedure of the step 4 of Inventive Example 1 was repeated to obtain the title compound as a colorless transparent syrup.

Rf=0.05 (hexane:ethyl acetate=2:1 (v/v)); $^1$H-NMR (400 MHz, CDCl$_3$/TMS) δ (ppm); 1.12 (3H, s), 1.40 (3H, s), 1.54 (3H, s), 1.55 (3H, s), 1.58 (3H, s), 1.74 (1H, s), 1.94 (3H, s), 1.99–2.38 (4H, m), 2.3 (3H, s), 3.22 (1H, d, J=5.4 Hz), 3.57 (1H, dd, J=6.9 Hz, 2.5 Hz), 3.83 (1H, dd, J=12.4 Hz, 5.6 Hz), 4.09–4.27 (2H, m), 4.23 (1H, d, J=7.7 Hz), 4.60 (1H, d, J=7.7 Hz), 4.72–4.88 (2H, m), 5.11 (1H, dd, J=10.3 Hz, 1.4 Hz), 5.26 (1H, dd, J=17.0 Hz, 1.4 Hz), 5.52 (1H, d, J=7.3 Hz), 5.81–5.96 (2H, m), 7.46 (2H, t, J=7.8 Hz), 7.58 (1H, t, J=7.8 Hz), 8.12 (2H, d, J=7.8 Hz).

Step 6: 9β-7-O-Allyl-13-O-[(2R,3S)-3-(tert-butoxycarbonylamino)-2-(tert-butyldimethylsilyloxy)-3-phenylpropionyl]-10-deacetyl-9-dihydro-9,10-O-isopropylidenebaccatin III Using the compound obtained in the above step 5, its reaction with 1-(tert-butoxycarbonyl)-3-(tert-butyidimethylsilyloxy)-4-phenylazetidin-2-one was carried out in accordance with the reaction procedure of the step 3 of Inventive Example 1 to obtain the title compound as a colorless transparent syrup.

Rf=0.17 (hexane:ethyl acetate=2:1 (v/v)); $^1$H-NMR (400 MHz, CDCl$_3$/TMS) δ (ppm); −0.32 (3H, s), −0.12 (3H, s), 0.74 (9H, s), 1.25 (3H, s), 1.36 (3H, s), 1.36 (9H, s), 1.51 (3H, s), 1.53 (3H, s), 1.57 (3H, s), 1.75 (3H, s), 2.06–2.12 (2H, m), 2.15–2.35 (1H, m), 2.42 (1H, dd, J=14.7 Hz, 9.8 Hz), 2.53 (3H, s), 3.22 (1H, d, J=5.9 Hz), 3.46 (1H, dd, J=9.8 Hz, 2.0 Hz), 3.85 (1H, dd, J=12.2 Hz, 5.4 Hz), 4.18 (1H, dd, J=12.2 Hz, 5.8 Hz), 4.28 (1H, AB type d, J=8.3 Hz), 4.58 (1H, AB type d, J=8.3 Hz), 4.33 (1H, d, J=8.8 Hz), 4.50 (1H, s), 4.83 (1H, t, J=6.8 Hz), 5.15 (1H, dd, J=10.7 Hz, 1.4 Hz), 5.22–5.36 (1H, m), 5.31 (1H, dd, J=17.2 Hz, 1.4 Hz), 5.40 (1H, d, J=8.8 Hz), 5.41–5.54 (1H, m), 5.87 (1H, d, J=5.9 Hz), 5.81–5.98 (1H, m), 6.22 (1H, t, J=8.8 Hz), 7.19–7.42 (5H, m), 7.47 (2H, t, J=7.3 Hz), 7.57 (1H, t, J=7.3 Hz), 8.11 (2H, d, J=7.3 Hz).

Step 7: 9β-13-O-[(2R,3S)-3-(tert-Butoxycarbonylamino)-2-(tert-butyldimethylsilyloxy)-3-phenylpropionyl]-10-deacetyl-9-dihydro-7-O-(2,3-dihydroxypropyl)-9,10-O-isopropylidenebaccatin III Using the compound obtained in the above step 6, the reaction procedure of the step 1 of Inventive Example 8 was repeated to obtain the title compound as a colorless transparent syrup.

Rf=0.29 (chloroform:acetone=4:1 (v/v)); $^1$H-NMR (400 MHz, CDCl$_3$/TMS) δ (ppm); −0.32 (3H, s), −0.11 (3H, s), 0.74 (9H, s), 1.31 (3H, s), 1.37 (9H, s), 1.39 (3H, s), 1.52 (3H, s), 1.57 (3H, s), 1.60 (3H, s), 1.74 (3H, s), 1.94–2.42 (m), 2.53 (3H, s), 3.03 and 3.06 (total 1H, each d, J=4.9 Hz), 3.45–3.81 (m), 3.88–4.02 (m), 4.21–4.38 (m), 4.47 (d, J=7.7 Hz), 4.50–4.58 (m), 4.90–5.01 (m), 5.23–5.36 (m), 5.40–5.54 (m), 5.92 and 5.94 (total 1H, each d, J=4.9 Hz), 5.94 (d, J=4.9 Hz), 7.21–7.40 (5H, m), 7.48 (2H, t, J=7.8 Hz), 7.59 (1H, t, J=7.8 Hz), 8.13 (2H, d, J=7.8 Hz).

Step 8: 9β-13-O-[(2R,3S)-3-(tert-Butoxycarbonylamino)-2-(tert-butyldimethylsilyloxy)-3-phenylpropionyl]-10-deacetyl-9-dihydro-7-O-(2-morpholinoethyl)-9,10-O-isopropylidenebaccatin III Using the compound obtained in the above step 7, the reaction procedure of the step 2 of Inventive Example 8 was repeated to obtain the title compound as a colorless transparent syrup.

Rf=0.74 (chloroform:methanol=12:1 (v/v)); $^1$H-NMR (400 MHz, CDCl$_3$/TMS) δ (ppm); −0.33 (3H, s), −0.12 (3H, s), 0.74 (9H, s), 1.26 (3H, s), 1.35 (9H, s), 1.39 (3H, s), 1.50 (3H, s), 1.52 (3H, s), 1.57 (3H, s), 1.74 (3H, s), 1.59–1.80 (4H, m), 2.05–2.33 (3H, m), 2.36–2.52 (3H, m), 2.52 (3H, s), 3.18 (1H, d, J=5.4 Hz), 3.35–3.49 (2H, m), 3.60–3.84 (5H, m), 4.19–4.33 (1H, m), 4.26 (1H, AB type d, J=8.3 Hz), 4.55 (1H, AB type d, J=8.3 Hz), 4.50 (1H, s), 4.83 (1H, t, J=6.4 Hz), 5.30 (1H, br-d, J=8.0 Hz), 5.86 (1H, d, J=5.4 Hz), 6.22 (1H, t, J=8.8 Hz), 7.28–7.41 (5H, m), 7.48 (2H, t, J=7.8 Hz), 7.58 (1H, t, J=7.8 Hz), 8.11 (2H, d, J=7.8 Hz).

Step 9: 9β-13-O-[(2R,3S)-3-(tert-Butoxycarbonylamino)-2-hydroxy-3-phenylpropionyl]-10-deacetyl-9-dihydro-7-O-(2-morpholinoethyl)-9,10-O-isopropylidenebaccatin III Using the compound obtained in the above step 8, the reaction procedure of the step 4 of Inventive Example 1 was repeated to obtain the title compound as a colorless transparent syrup.

Rf=0.23 (chloroform:methanol=15:1 (v/v)); Melting point: 128–133° C. (lyophilization from dioxane); $^1$H-NMR (400 MHz, CDCl$_3$/TMS) δ (ppm); 1.23 (3H, s), 1.39 (9H, s), 1.41 (3H, s), 1.51 (3H, s), 1.58 (6H, s), 1.59 (3H, s), 1.50–1.86 (2H, m), 1.81 (1H, br-s), 1.96–2.47 (4H, m), 2.30 (3H, s), 2.48–2.62 (4H, m), 3.03 (1H, d, J=4.0 Hz), 3.32–3.43 (1H, m), 3.46–3.57 (1H, m), 3.59–3.84 (4H, m), 4.07–4.23 (2H, m), 4.52 (1H, d, J=7.8 Hz), 4.60 (1H, s), 4.83 (1H, s), 5.22–5.33 (1H, br-d, J=8.4 Hz), 5.46 (1H, d, J=7.8 Hz), 5.59 (1H, br-d, J=8.4 Hz), 5.93 (1H, d, J=4.0 Hz), 6.10 (1H, t, J=8.3 Hz), 7.21–7.43 (5H, m), 7.47 (2H, t, J=7.8 Hz), 7.59 (1H, t, J=7.8 Hz), 8.11 (2H, d, J=7.8 Hz).

Inventive Example 11

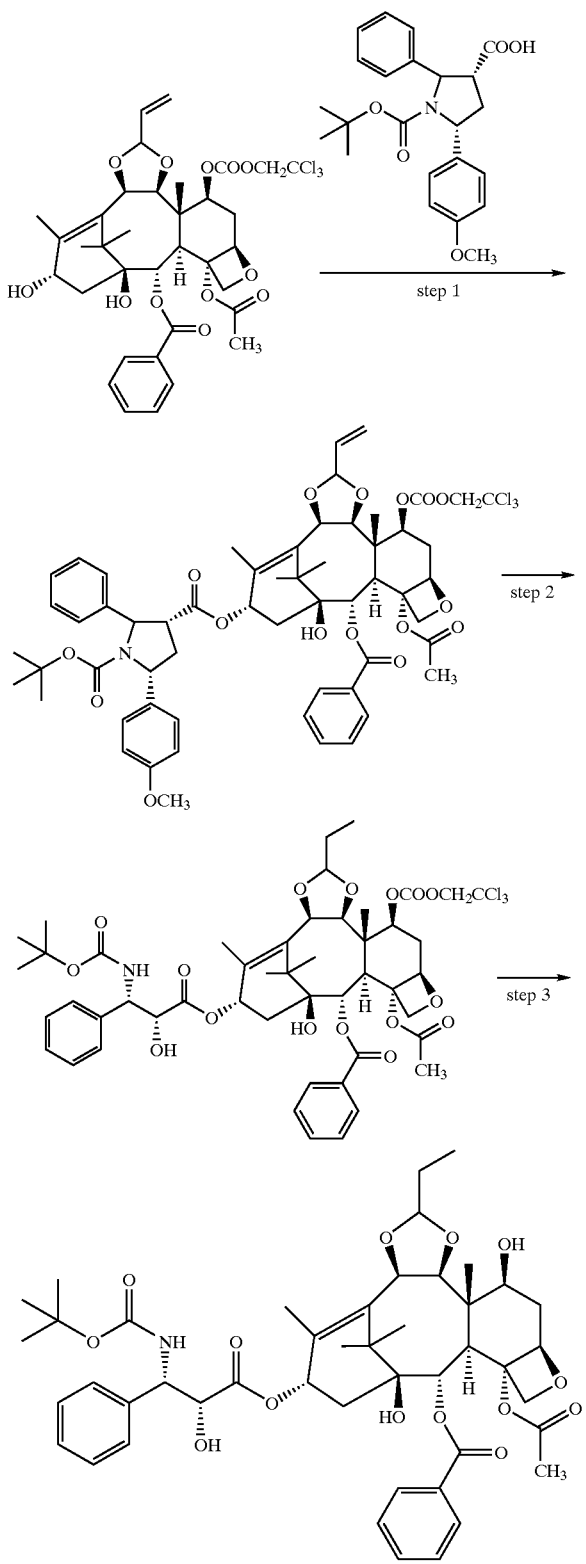

Step 1: 9β-13-O-[(2R,3S)-N-(tert-Butoxycarbonyl)-N,O-(4-methoxybenzylidene)-3-phenylisoserinyl]-10-deacetyl-9-dihydro-9,10-O-(2-propenylidene)-7-O-(2,2,2-trichloroethoxycarbonyl)baccatin III A 70.1 mg portion of (2R,3S)-N-(tert-Butoxycarbonyl)-N,O-(4-methoxybenzylidene)-3-phenylisoserine was dissolved in a mixture solvent consisting of 2.1 ml of a dry methylene chloride and 2.1 ml of a dry toluene, and the solution was mixed with 34.0 mg of dicyclohexylcarbodiimide at 0° C. After 12 minutes of the mixing, thereto was added dropwise 2.5 ml of a dry methylene chloride solution containing 78.1 mg of the compound obtained in the step 1 of Inventive Example 9, followed by the addition of 4.2 mg of 4-dimethylaminopyridine and subsequent 2 hours of stirring at room temperature. After cooling to 0° C., the reaction mixture was filtered and the filtered material was washed with toluene. The resulting filtrate was diluted with chloroform, washed with water and saturated brine and then dried over anhydrous sodium sulfate. Thereafter, the solvent was evaporated under a reduced pressure and the resulting residue was purified by a silica gel thin layer chromatography (developing solvent; chloroform:acetone=20:1 (v/v)) to obtain 68.9 mg of the title compound as a white glassy substance.

Rf=0.18 (chloroform:acetone=20:1 (v/v)); $^1$H-NMR (400 MHz, CDCl$_3$/TMS) δ (ppm); 1.05 (12H, s), 1.24 (3H, s), 1.45 (3H, br-s), 1.58 (3H, s), 1.74 (3H, br-s), 1.77 (1H, s), 2.07 (1H, d, J=14.7 Hz, J=8.3 Hz), 2.13–2.35 (3H, m), 3.04 (1H, d, J=4.9 Hz), 3.81 (3H, s), 3.93 (1H, d, J=7.8 Hz), 4.24 (1H, d, J=8.3 Hz), 4.35 (1H, d, J=8.3 Hz), 4.58 (1H, d, J=4.9 Hz), 4.65 (1H, d, J=11.7 Hz), 4.79 (1H, t, J=4.9 Hz), 4.83 (1H, d, J=11.7 Hz), 5.03 (1H, dd, J=6.9 Hz, J=4.0 Hz), 5.10 (1H, d, J=5.9 Hz), 5.20 (1H, d, J=7.8 Hz), 5.34–5.48 (1H, br), 5.45 (1H, d, J=10.2 Hz), 5.55 (1H, d, J=17.1 Hz), 5.87 (1H, d, J=4.9 Hz), 5.93–6.1 (2H, m), 6.25–6.46 (1H, br), 6.90 (2H, d, J=8.8 Hz), 7.32–7.52 (7H, m), 7.47 (2H, t, J=7.3 Hz), 7.60 (1H, t, J=7.3 Hz), 8.05 (2H, d, J=7.3 Hz).

Step 2: 9β-13-O-[(2R,3S)-3-(tert-Butoxycarbonylamino)-2-hydroxy-3-phenylpropionyl]-10-deacetyl-9-dihydro-9,10-O-propylidene)-7-O-(2,2,2-trichloroethoxycarbonyl)baccatin III A 68.9 mg portion of the compound obtained in the above step 1 was dissolved in 3.4 ml of ethanol, and the solution was mixed with 8.6 mg of 10% palladium hydroxide at room temperature and stirred for 5 hours in an atmosphere of hydrogen. Then, the resulting solution was again mixed with 8.6 mg of 10% palladium hydroxide and stirred for 2 hours. The atmosphere of the reaction system was replaced by nitrogen, and the reaction solution was filtered. After washing the filtered material with ethyl acetate, the solvent in the filtrate was evaporated under a reduced pressure and the resulting residue was purified by a silica gel thin layer chromatography (developing solvent; chloroform:acetone=20:1 (v/v)) to obtain 28.4 mg of the title compound in a white glassy form.

Rf=0.40 (chloroform:acetone=20:1 (v/v)); $^1$H-NMR (400 MHz, CDCl$_3$/TMS) δ (ppm); 1.03 (3H, t, J=7.8 Hz), 1.25 (3H, s), 1.40 (9H, s), 1.59 (3H, s), 1.61 (3H, s), 1.64 (3H, s), 1.74–1.93 (3H, m), 2.01–2.23 (2H, m), 2.30 (3H, s), 2.30–2.45 (2H, m), 3.04 (1H, d, J=4.9 Hz), 3.88 (1H, d, J=7.3 Hz), 4.21–4.34 (2H, m), 4.43 (1H, d, J=8.3 Hz), 4.62 (1H, br-s), 4.65 (1H, d, J=12.2 Hz), 4.76 (1H, t, J=5.4 Hz), 4.85 (1H, d, J=12.2 Hz), 4.90 (1H, br-s), 5.14 (1H, br-t, J=4.4 Hz), 5.24 (1H, d, J=7.3 Hz), 5.31 (1H, d, J=9.2 Hz), 5.66 (1H, d, J=9.2 Hz), 6.00 (1H, d, J=4.9 Hz), 6.09 (1H, t, J=7.8 Hz), 7.20–7.46 (5H, m), 7.47 (2H, t, J=7.3 Hz), 7.60 (1H, t, J=7.3 Hz), 8.12 (2H, d, J=7.3 Hz).

Step 3: 9β-13-O-[(2R,3S)-3-(tert-Butoxycarbonylamino)-2-hydroxy-3-phenylpropionyl]-10-deacetyl-9-dihydro-9,10-O-propylidenebaccatin III A 28.4 mg portion of the compound obtained in the above step 2 was dissolved in 2.8 ml of a dioxane-methanol-acetic acid (1:1:1 (v/v)) mixture solvent, and the solution was mixed with 66.2 mg of zinc powder and stirred at room temperature for 5 hours and then at 55° C. for 16 hours. The reaction mixture was filtered as such, the filtered material was washed with chloroform and then the solvent in the filtrate was evaporated under a reduced pressure. The thus obtained residue was diluted with ethyl acetate, washed with saturated sodium bicarbonate aqueous solution and saturated brine and then dried over anhydrous sodium sulfate. Thereafter, the solvent was evaporated under a reduced pressure and the resulting residue was purified by a silica gel thin layer chromatography (developing solvent; chloroform:acetone=10:1 (v/v)) to obtain 10.8 mg of the title compound in a white glassy form.

Rf=0.18 (chloroform: acetone=20:1 (v/v)); Melting point 132–139° C. (lyophilization from dioxane); $^1$H-NMR (400 MHz, CDCl$_3$/TMS) δ (ppm); 1.04 (3H, t, J=7.9 Hz), 1.26 (6H, s), 1.40 (9H, s), 1.60 (3H, s), 1.66 (3H, s), 1.73–1.91 (2H, m), 1.88 (1H, s), 1.98–2.14 (2H, m), 2.17–2.33 (1H, m), 2.30 (3H, s), 2.37 (1H, dd, J=15.1 Hz, J=9.7 Hz), 2.91 (1H, d, J=4.8 Hz), 3.78 (1H, d, J=7.3 Hz), 4.02–4.19 (2H, m), 4.33 (1H, d, J=8.3 Hz), 4.37 (1H, d, J=8.3 Hz), 4.55–4.68 (2H, m), 4.80 (1H, t, J=5.4 Hz), 5.10 (1H, s like), 5.19 (1H, d, J=7.3 Hz), 5.29 (1H, br-d, J=8.3 Hz), 5.63 (1H, br-d, J=8.3 Hz), 6.05 (1H, d, J=4.8 Hz), 6.08 (1H, t, J=8.8 Hz), 7.20–7.45 (5H, m), 7.47 (2H, t, J=7.8 Hz), 7.60 (1H, t, J=7.8 Hz), 8.10 (2H, d, J=7.8 Hz). FAB Mass: 850 (M$^+$+1).

Inventive Example 12

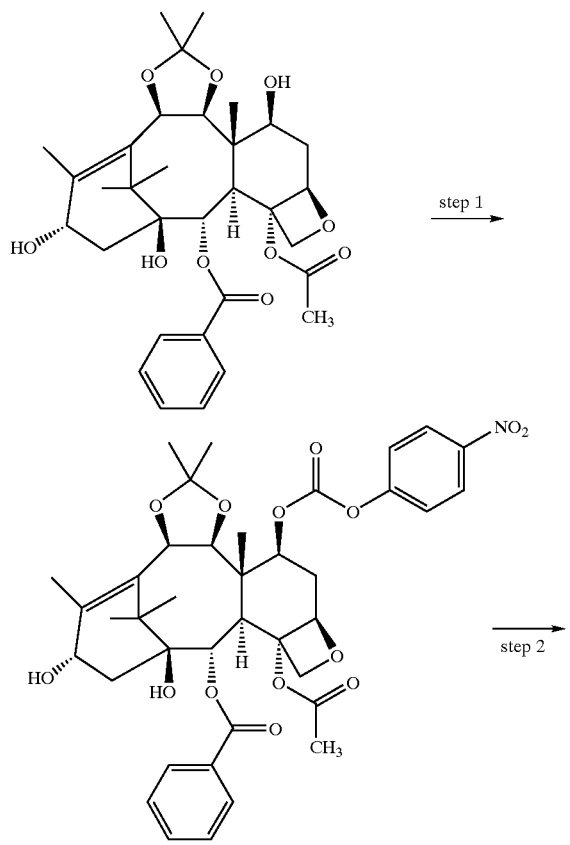

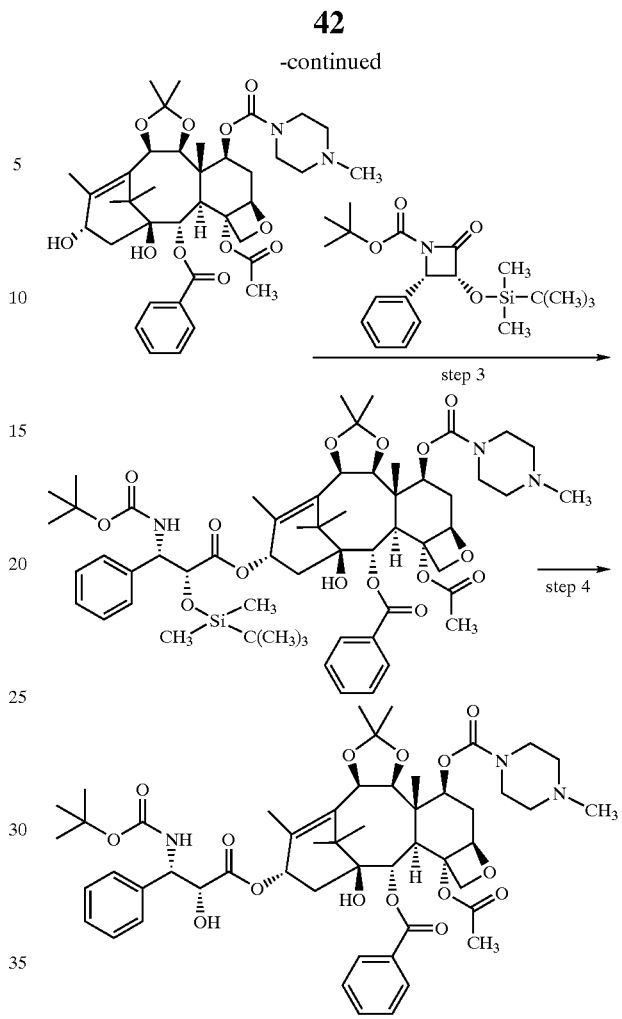

Step 1: 9β-10-Deacetyl-9-dihydro-9,10-O-isopropylidene-7-O-(4-nitrophenoxycarbonyl)baccatin III A 70 mg portion of the compound obtained in the step 2 of Inventive Example 1 was dissolved in 2 ml of a dry tetrahydrofuran and cooled to −78° C. Thereto was then added dropwise 0.16 ml of n-butyl lithium (1.64 mol/ml solution in hexane) at the same temperature. After completion of the dropwise addition, the mixture was stirred for 10 minutes at the same temperature. Next, thereto was added dropwise 1 ml of tetrahydrofuran solution containing 29 mg of 4-nitrophenyl chloroformate at the same temperature. After 1 hour of stirring, the reaction solution was gradually warmed up to 0° C. and stirred for 2 hours. The reaction solution was mixed with saturated ammonium chloride aqueous solution, and diluted and extracted with ethyl acetate. The thus obtained extract was washed with saturated brine and dried over anhydrous magnesium sulfate. Thereafter, the solvent was evaporated under a reduced pressure and the resulting residue was purified by a silica gel thin layer chromatography (developing solvent; chloroform:acetone=97:3 (v/v)) to obtain 23 mg of the title compound.

$^1$H-NMR (CDCl$_3$/TMS) δ (ppm); 1.18 (3H, s), 1.43 (3H, s), 1.57 (3H, s), 1.59 (3H, s), 1.62 (3H, s), 1.63–1.80 (1H, m), 1.90–2.09 (2H, m), 1.96 (3H, s), 2.25–2.41 (1H, m), 2.36 (3H, s), 3.18 (1H, d, J=5 Hz), 3.94 (1H, d, J=7 Hz), 4.18 (1H, J=8 Hz), 4.25 (1H, 8 Hz), 4.78–4.89 (1H, m), 4.83–4.88 (1H, m), 5.13–5.17 (1H, m), 5.63 (1H, d, J=7 Hz), 5.94 (1H, d, J=5 Hz), 7.31 (2H, d, J=9 Hz), 7.49 (2H, t, J=8 Hz), 7.55–7.60 (1H, m), 8.12 (2H, d, J=7 Hz), 8.21 (2H, d, J=9 Hz).

Step 2: 9β-10-Deacetyl-9-dihydro-9,10-O-isopropylidene-7-O-[(4-methylpiperazin-1-yl)carbonyl]baccatin III A 37 mg portion of the compound obtained in the above step 1 was dissolved in 2 ml of acetonitrile to which was subsequently added dropwise 50 mg of N-methylpiperazine at room temperature. After 5 hours of stirring at the same temperature, the solvent was evaporated under a reduced pressure and the resulting residue was purified by a silica gel thin layer chromatography (developing solvent; chloroform:methanol=95:5 (v/v)) to obtain 9 mg of the title compound.

$^1$H-NMR (CDCl$_3$/TMS) δ (ppm); 1.14 (3H, s), 1.38 (3H, s), 1.52 (3H, s), 1.55 (3H, s), 1.56 (3H, s), 1.68–1.80 (1H, m), 1.95 (3H, s), 2.01 2.16 (2H, m), 2.27 (3H, s), 2.24 2.38 (5H, m), 2.34 (3H, s), 3.24 (1H, d, J=5 Hz), 3.30–3.57 (4H, m), 4.04 (1H, d, J=8 Hz), 4.29 (1H, J=8 Hz), 4.43 (1H, 8 Hz), 4.79–4.87 (1H, m), 4.84 (1H, d, J=4 Hz), 5.16–5.19 (1H, m), 5.56 (1H, d, J=8 Hz), 5.92 (1H, d, J=5 Hz), 7.49 (2H, t, J=8 Hz), 7.61 (1H, t, J=8 Hz), 8.15 (2H, d, J=7 Hz).

Step 3: 9β-13-O-[(2R,3S)-3-(tert-Butoxycarbonylamino)-2-(tert-butyldimethylsilyloxy)-3-phenylpropionyl]-10-deacetyl-9-dihydro-9,10-O-isopropylidene-7-O-[(4-methylpiperazin-1-yl)carbonyl]baccatin III Using the compound obtained in the above step 2 as the starting material, its reaction with 1-(tert-butoxycarbonyl)-3-(tert-butyldimethylsilyloxy)-4-phenylazetidin-2-one was carried out in accordance with the reaction procedure of the step 3 of Inventive Example 1 to obtain the title compound as a white amorphous solid.

$^1$H-NMR (CDCl$_3$/TMS) δ (ppm); −0.33 (3H, s), −0.12 (3H, s), 0.74 (9H, s), 1.25 (3H, s), 1.28 (3H, s), 1.33 (6H, s), 1.36 (3H, s), 1.53 (3H, s), 1.55 (9H, s), 1.63–1.80 (1H, m), 1.75 (3H, s), 2.00–2.20 (2H, m), 2.31 (3H, s), 2.20–2.45 (5H, m), 2.54 (3H, s), 3.21 (1H, d, J=5 Hz), 3.39 3.64 (4H, m), 4.12 (1H, d, J=9 Hz), 4.32 (1H, d, J=8 Hz), 4.47 (1H, d, J=8 Hz), 4.52 (1H, brs), 4.91 (1H, m), 5.10 (1H, m), 5.28–5.33 (1H, m), 5.44 (1H, d, J=9 Hz), 5.42–5.49 (1H, m), 5.89 (1H, d, J=5 Hz), 6.20–6.23 (1H, m), 7.23–7.40 (5H, m), 7.50 (2H, t, J=8 Hz), 7.60 (1H, t, J=8 Hz), 8.14 (2H, d, J=8 Hz).

Step 4: 9β-13-O-[(2R,3S)-3-(tert-Butoxycarbonylamino)-2-hydroxy-3-phenylpropionyl]-10-deacetyl-9-dihydro-9,10-O-isopropylidene-7-O-[(4-methylpiperazin-1-yl)carbonyl]baccatin III A 13 mg portion of the compound obtained in the above step 3 was dissolved in 1 ml of distilled pyridine to which was subsequently added dropwise 0.2 ml of hydrogen fluoride-pyridine at 0° C. After completion of the dropwise addition, this solution was warmed up to room temperature and stirred overnight. The reaction solution was diluted with water and then extracted with ethyl acetate. The thus obtained extract was washed with saturated brine and dried over anhydrous magnesium sulfate. Thereafter, the solvent was evaporated under a reduced pressure and the resulting residue was purified by a silica gel thin layer chromatography (developing solvent; chloroform:methanol=95:5 (v/v)) to obtain 5 mg of the title compound.

$^1$H-NMR (CDCl$_3$/TMS) δ (ppm); 1.24 (3H, s), 1.37 (3H, s), 1.39 (3H, s), 1.53 (3H, s), 1.56 (9H, s), 1.60–1.80 (1H, m), 1.62 (3H, s), 2.00–2.20 (2H, m), 2.20–2.42 (5H, m), 2.26 (3H, s), 2.32 (3H, s), 3.09 (1H, d, J=5 Hz), 3.31–3.58 (4H, m), 4.03 (1H, d, J=9 Hz), 4.27 (1H, d, J=8 Hz), 4.41 (1H, d, J=8 Hz), 4.62 (1H, br-s), 4.88 (1H, m), 5.16 (1H, m), 5.30 (1H, m), 5.49 (1H, d, J=7 Hz), 5.59 (1H, m), 5.95 (1H, m), 6.10 (1H, br-t, J=8 Hz), 7.23–7.40 (5H, m), 7.49 (2H, t, J=8 Hz), 7.61 (1H, t, J=7 Hz), 8.13 (2H, d, J=7 Hz).

Inventive Example 13

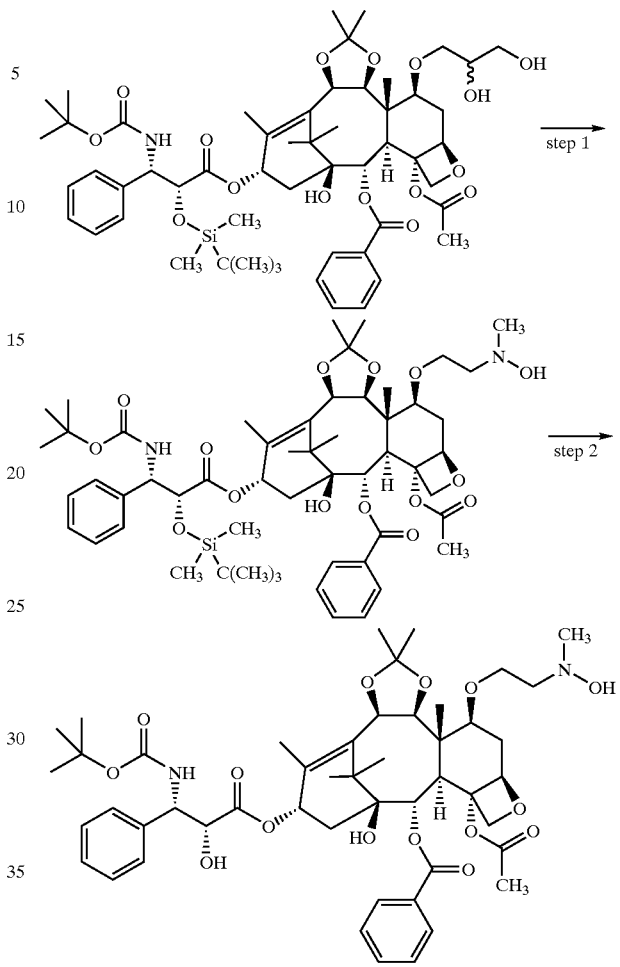

Step 1: 9β-13-O-[(2R,3S)-3-(tert-Butoxycarbonylamino)-2-(tert-butyldimethylsilyloxy)-3-phenylpropionyl]-10-deacetyl-9-dihydro-9,10-O-isopropylidene-7-O-(2-dimethylaminoethyl)baccatin III Using the compound obtained in the step 7 of Inventive Example 10 as the starting material, the reaction procedure of the step 2 of Inventive Example 8 was repeated except that dimethylamine was used in stead of morpholine, thereby obtaining the title compound as a white glassy solid.

Rf=0.53 (chloroform:methanol=5:1 (v/v)); $^1$H-NMR (400 MHz, CDCl$_3$/TMS) δ (ppm); −0.32 (3H, s), −0.11 (3H, s), 0.75 (9H, s), 1.27 (3H, s), 1.36 (9H, s), 1.40 (3H, s), 1.52 (3H, s), 1.55 (3H, s), 1.57 (3H, s), 1.74 (3H, s), 2.09–2.26 (2H, m), 2.31–2.51 (8H, m), 2.53 (3H, s), 2.63–2.86 (2H, m), 3.13 (1H, d, J=5.3 Hz), 3.46–3.63 (2H, m), 3.76–3.89 (1H, br), 4.12–4.25 (1H, br), 4.28 (1H, d, J=7.8 Hz), 4.49 (1H, d, J=7.8 Hz), 4.52 (1H, br), 4.90 (1H, t, J=4.4 Hz), 5.22–5.36 (1H, m), 5.38–5.52 (2H, m), 5.88 (1H, d, J=5.3 Hz), 6.21 (1H, t, J=8.5 Hz), 7.19–7.41 (5H, m), 7.50 (2H, t, J=7.4 Hz), 7.59 (1H, t, J=7.4 Hz), 8.11 (2H, d, J=7.4 Hz).

Step 2: 9β-13-O-[(2R,3S)-3-(tert-Butoxycarbonylamino)-2-hydroxy-3-phenylpropionyl]-10-deacetyl-9-dihydro-9,10-O-isopropylidene-7-O-(2-dimethylaminoethyl)baccatin III Using the compound obtained in the above step 1, the reaction procedure of the step 5 of Inventive Example 3 was repeated to obtain the title compound as a white glassy solid.

Rf=0.32 (chloroform:acetone=20:1 (v/v)); Melting point 119–1210C (lyophilization from dioxane); $^1$H-NMR (400

MHz, CDCl₃/TMS) δ (ppm); 1.22 (3H, s), −1.38. (9H, s), 1.41 (3H, s), 1.51 (3H, s), 1.58 (9H, s), 1.80 (1H, s), 2.04–2.37 (10H, m), 2.26 (3H, s), 2.52 (2H, t like, J=5.9 Hz), 3.04 (1H, d, J=4.4 Hz), 3.31–3.43 (1H, m), 3.46–3.57 (1H, m), 3.70–3.81 (1H, m), 4.14–4.28 (1H, br), 4.20 (1H, d, J=7.8 Hz), 4.51 (1H, d, J=7.8 Hz), 4.60 (1H, s like), 4.84 (1H, t like, J=5.0 Hz), 5.27 (1H, br-d, J=8.0 Hz), 5.46 (1H, d, J=7.6 Hz), 5.59 (1H, br-d, J=8.0 Hz), 5.92 (1H, d, J=4.4 Hz), 6.10 (1H, t, J=7.8 Hz), 7.21–7.43 (5H, m), 7.47 (2H, t, J=7.8 Hz), 7.59 (1H, t, J=7.8 Hz), 8.11 (2H, d, J=7.8 Hz). FAB Mass: 921 (M⁺).

Inventive Example 14

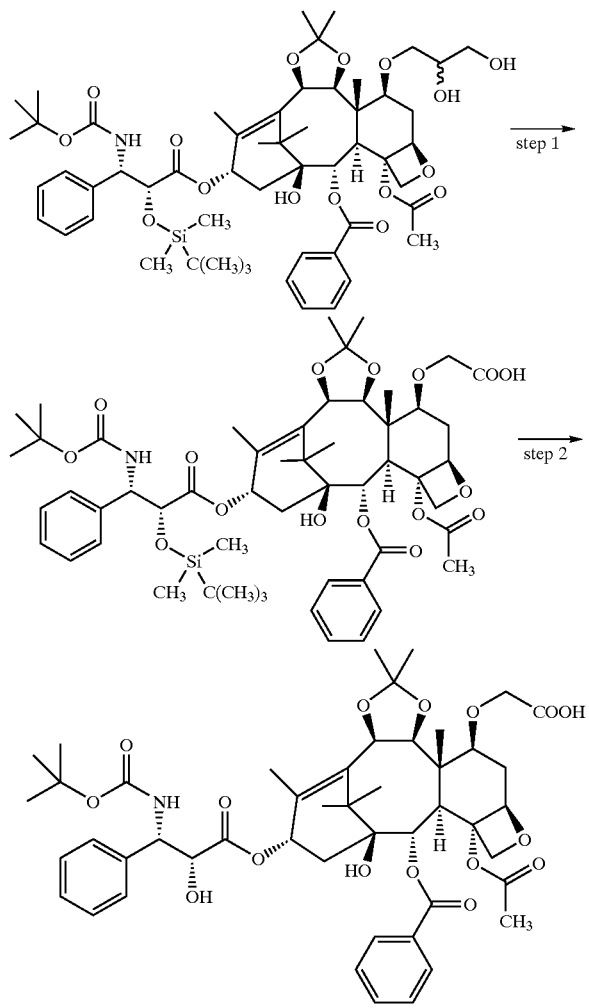

Step 1: 9β-13-O-[(2R,3S)-3-(tert-Butoxycarbonylamino)-2-(tert-butyldimethylsilyloxy)-3-phenylpropionyl]-10-deacetyl-9-dihydro-7-O-carboxymethyl-9,10-O-isopropylidenebaccatin III A 67.2 mg portion of the compound obtained in the step 7 of Inventive Example 10 was dissolved in 3 ml of a tetrahydrofuran-methanol-water (1:1:1 (v/v)) mixture solvent, and the solution was mixed with 55.3 mg of sodium metaperiodate at room temperature and stirred for 1 hour. This solution was mixed with 0° C.-cooled water and extracted with ethyl acetate. The thus obtained extract was washed with saturated brine and dried over anhydrous sodium sulfate. The solvent was evaporated under a reduced pressure, and a 22.0 mg portion of 48.0 mg of the thus obtained residue was dissolved in 1.65 ml of dioxane and 0.55 ml of water, mixed with 5.6 mg of sulfamic acid and 5.3 mg of sodium chlorite at room temperature and then stirred for 30 minutes. The reaction solution was mixed with water and extracted with ethyl acetate. The thus obtained extract was washed with saturated brine and dried over anhydrous sodium sulfate. Thereafter, the solvent was evaporated under a reduced pressure and the resulting residue was purified by a silica gel thin layer chromatography. (developing solvent; chloroform:methanol=15:1 (v/v)) to obtain 21.3 mg of the title compound as a white solid.

Rf=0.39 (chloroform:methanol=10:1 (v/v)); ¹H-NMR (400 MHz, CDCl₃/TMS) δ (ppm); −0.32 (3H, s), −0.11 (3H, s), 0.74 (9H, s), 1.33 (3H, s), 1.37 (9H, s), 1.39 (3H, s), 1.58 (6H, s), 1.63 (3H, s), 1.74 (3H, s), 1.81 (1H, s), 2.02–2.40 (4H, m), 2.54 (3H, s), 3.04 (1H, d, J=4.9 Hz), 3.68 (1H, br), 3.80–4.03 (2H, m), 4.33 (1H, d, J=7.8 Hz), 4.54 (1H, d, J=7.8 Hz), 4.44–4.62 (1H, m), 5.05 (1H, br), 5.30 (1H, d, J=8.3 Hz), 5.45 (1H, d, J=8.3 Hz), 5.52 (1H, d, J=7.3 Hz), 5.94 (1H, d, J=4.9 Hz), 6.20 (1H, t, J=8.8 Hz), 7.18–7.42 (5H, m), 7.49 (2H, t, J=7.9 Hz), 7.60 (1H, t, J=7.9 Hz), 8.12 (2H, d, J=7.9 Hz).

Step 2: 9β-13-O-[(2R,3S)-3-(tert-Butoxycarbonylamino)-2-hydroxy-3-phenylpropionyl]-10-deacetyl-9-dihydro-7-O-carboxymethyl-9,10-O-isopropylidenebaccatin III Using the compound obtained in the above step 1 as the starting material, the reaction procedure of the step 5 of Inventive Example 3 was repeated to obtain the title compound as a white glassy solid.

Rf=0.40 (chloroform:methanol=10:1 (v/v)); Melting point 157–160° C. (lyophilization from dioxane); ¹H-NMR (400 MHz, CDCl₃/TMS) δ (ppm); 1.27 (3H, s), 1.40 (3H, s), 1.41 (9H, s), 1.53 (3H, s), 1.56 (3H, s), 1.58 (3H, s), 1.63 (3H, s), 1.86 (1H, s), 1.92–2.13 (2H, m), 2.26–2.44 (2H, m), 2.32 (3H, s), 2.95 (1H, d, J=4.4 Hz), 3.71 (1H, br-s), 3.78 (1H, br-d, J=6.0 Hz), 3.90 (1H, d, J=6.6 Hz), 3.97–4.11 (1H, br), 4.29 (1H, d, J=8.3 Hz), 4.30–4.44 (1H, m), 4.54 (1H, d, J=8.3 Hz), 4.62 (1H, br-s), 5.04 (1H, br-s), 5.27 (1H, d, J=8.3 Hz), 5.53 (1H, d, J=6.8 Hz), 5.60 (1H, d, J=8.3 Hz), 5.97 (1H, d, J=4.4 Hz), 6.10 (1H, t, J=7.8 Hz), 7.22–7.43 (5H, m), 7.47 (2H, t, J=7.8 Hz), 7.60 (1H, t, J=7.8 Hz), 8.10 (2H, d, J=7.8 Hz). FAB Mass: 908 (M⁺+1).

Inventive Example 15

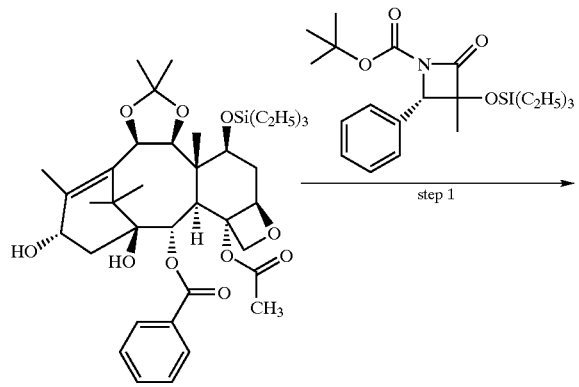

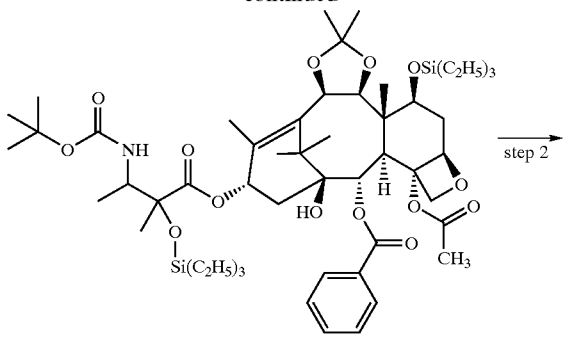

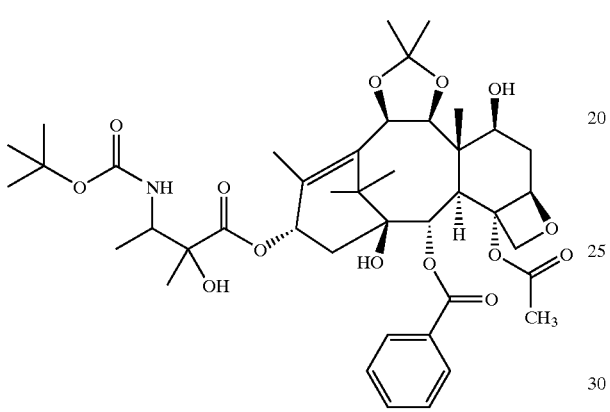

Step 1: 9β-13-O-[ 3-(tert-Butoxycarbonylamino)-2-methyl-2-triethylsilyloxy-3-phenylpropionyl]-10-deacetyl-9-dihydro-9,10-isopropylidene-7-O-triethylsilylbaccatin III Using the compound obtained in the step 3 of Inventive Example 3 as the starting material, its reaction with cis-1-(tert-butoxycarbonyl)-3-methyl-4-phenyl-3-(triethylsilyloxy)azetidin-2-one was carried out in accordance with the reaction procedure of the step 3 of Inventive Example 1 to obtain the title compound as a colorless glassy solid.

$^1$H-NMR (400 MHz, CDCl$_3$/TMS) δ (ppm); 0.50–0.72 (12H, m), 0.87 (9H, t, J=8 Hz), 0.97 (9H, t, J=8 Hz), 1.29 (9H, s), 1.34 (3H, s), 1.38 (3H, s), 1.41 (3H, s), 1.51 (3H, s), 1.57 (3H, s), 1.59 (3H, s), 1.73 (3H, s), 2.00–2.18 (3H, m), 2.34 (1H, dd, J=15 Hz, 10 Hz), 2.64 (3H, s), 3.07 (1H, d, J=5.5 Hz), 4.00 (1H, dd, J=8 Hz, 3.5 Hz), 4.24 (1H, d, J=8 Hz), 4.34 (1H, br-d, J=8 Hz), 4.56 (1H, d, J=8 Hz), 4.86 (1H, t, J=5.5 Hz), 4.98 (1H, d, J=10 Hz), 5.42 (1H, d, J=9 Hz), 5.52 (1H, d, J=10 Hz), 5.91 (1H, d, J=5.5 Hz), 6.28 (1H, t, J=9 Hz), 7.27–7.36 (10H, m), 7.48 (2H, t, J=7.5 Hz), 7.58 (1H, t, J=7.5 Hz), 8.15 (2H, d, J=7.5 Hz).

Step 2: 9β-13-O-[3-(tert-Butoxycarbonylamino)-2-hydroxy-2-methyl-3-phenylpropionyl]-10-deacetyl-9-dihydro-9,10-O-isopropylidenebaccatin III Reaction of the compound obtained in the above step 1 was carried out in the same manner as described in the step 4 of Inventive Example 1 to obtain the title compound as a colorless glassy solid.

Melting point 180–182° C. (lyophilization from dioxane); $^1$H-NMR (400 MHz, CDCl$_3$/TMS) δ (ppm); 1.32 (3H, s), 1.35 (9H, s), 1.40 (6H, s), 1.58 (3H, s), 1.60 (3H, s), 1.64 (3H, s), 1.68 (3H, s), 2.08–2.31 (4H, m), 2.51 (3H, s), 2.91 (1H, d, J=4.5 Hz), 3.80 (1H, d, J=7 Hz), 3.99 (1H, s), 4.08 (1H, m), 4.36 (1H, AB type d, J=9 Hz), 4.39 (1H, AB type, J=9 Hz), 4.70 (1H, d, J=8 Hz), 5.01 (1H, d, J=10 Hz), 5.11 (1H, br-s), 5.50 (1H, d, J=7 Hz), 5.67 (1H, d, J=10 Hz), 6.05 (1H, d, J=4.5 Hz), 6.22 (1H, t, J=8 Hz), 7.28–7.41 (10H, m), 7.48 (2H, t, J=7.5 Hz), 7.60 (1H, t, J=7.5 Hz), 8.13 (1H, d, J=7.5 Hz). FAB Mess: 865 (M$^+$+1).

Inventive Example 16

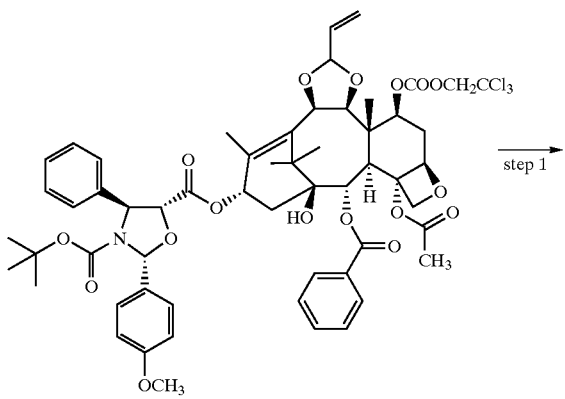

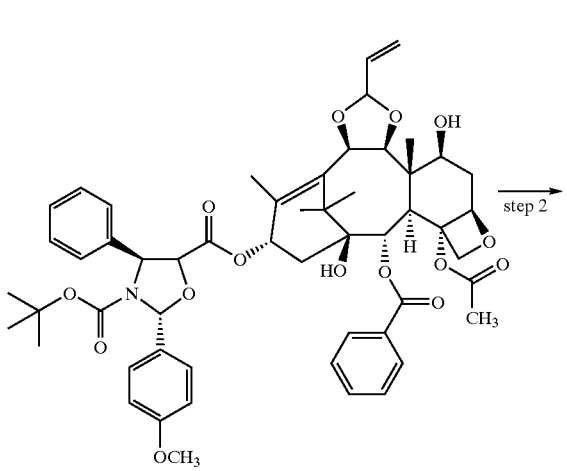

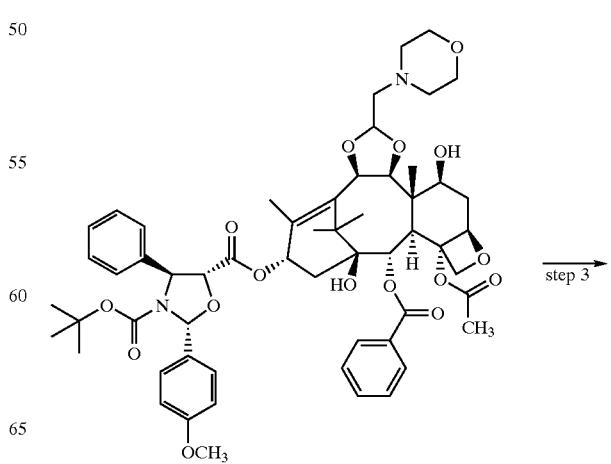

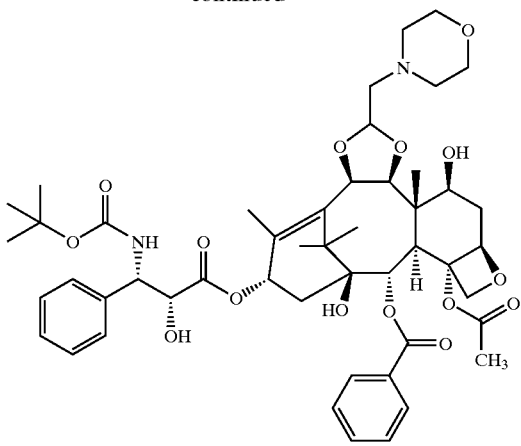

Step 1: 9β-13-O-[ (2R,3S)-N-(tert-Butoxycarbonyl)-N,O-(4-methoxybenzylidene)-3-phenylisoserinyl]-10-deacetyl-9-dihydro-9,10-O-(propenylidene)baccatin III Using the compound obtained in the step 1 of Inventive Example 11 as the starting material, the reaction procedure of the step 3 of Inventive Example 11 was repeated to obtain the title compound as a glassy solid.

Rf=0.35 (chloroform:acetone=15:1 (v/v)); $^1$H-NMR (400 MHz, CDCl$_3$/TMS) δ (ppm); 1.04 (12H, s), 1.27 (3H, s), 1.43 (3H, br s), 1.64 (3H, s), 1.72 (3H, br s), 1.83 (1H, s), 1.97–2.27 (4H, m), 2.82 (1H, d, J=5.3 Hz), 3.81 (3H, s), 3.85 (1H, d, J=7.4 Hz), 3.96–4.07 (1H, m), 4.22 (1H, d, J=8.3 Hz), 4.32 (1H, d, J=8.3 Hz), 4.48 (1H, d, J=7.4 Hz), 4.58 (1H, d, J=5.4 Hz), 4.98 (1H, s like), 5.17 (2H, d, J=5.9 Hz), 5.32–5.49 (1H, br), 5.44 (1H, d, J=10.8 Hz), 5.55 (1H, d, J=17.8 Hz), 5.90–6.12 (3H, m), 6.22–6.47 (1H, br), 6.90 (2H, d, J=8.8 Hz), 7.31–7.50 (9H, m), 7.59 (1H, t, J=7.4 Hz), 8.03 (2H, d, J =7.4 Hz).

Step 2: 9β-13-O-[(2R,3S)-N-(tert-Butoxycarbonyl)-N,O-(4-methoxybenzylidene)-3-phenylisoserinyl]-10-deacetyl-9-dihydro-9,10-O-(2-N-morpholinoethylidene)baccatin III A 149.4 mg portion of the compound obtained in the above step 1 was dissolved in a mixture solvent consisting of 4.48 ml of tetrahydrofuran and 1.49 ml of water, and the solution was mixed with 87.2 mg of N-methylmorpholine-N-oxide and 7.8 mg of osmium tetraoxide at room temperature and stirred for 8 hours in the dark, followed by further addition of 3.6 mg of osmium tetraoxide and subsequent 16 hours of stirring. This mixture solution was mixed with sodium sulfite aqueous solution, stirred at room temperature for 10 minutes and then extracted with ethyl acetate. The thus obtained extract was washed with saturated brine and dried over anhydrous sodium sulfate, and the solvent was evaporated under a reduced pressure. The resulting residue was dissolved in 4.1 ml of a tetrahydrofuran-water-methanol (1:1:1 (v/v)) mixture solvent, and the solution was mixed with 118.6 mg of sodium metaperiodate at room temperature and stirred for 40 minutes. The resulting solution was cooled to 0° C., mixed with cold water and saturated brine, and then extracted with ethyl acetate. The thus obtained extract was washed with saturated brine and dried over anhydrous sodium sulfate. The solvent was evaporated under a reduced pressure, and a 65.2 mg portion of 126.2 mg of the thus obtained residue was dissolved in 4 ml of ethanol, mixed with 0.04 ml of acetic acid, 0.059 ml of morpholine and 14.0 mg of 10% palladium hydroxide at room temperature and then stirred for 5 hours in an atmosphere of hydrogen. Thereafter, the atmosphere in the reaction system was replaced by nitrogen, its contents were filtered, the resulting filtrate was evaporated under a reduced pressure and the thus obtained residue was purified by a silica gel thin layer chromatography (developing solvent; chloroform:acetone= 5:1 (v/v)) to obtain 18.4 mg of the title compound as a colorless transparent syrup.

Rf=0.17 (chloroform:acetone=5:1 (v/v)); $^1$H-NMR (400 MHz, CDCl$_3$/TMS) δ (ppm); 1.04 (3H, s), 1.27 (3H, s), 1.41 (3H, br s), 1.56 (3H, s), 1.61 (3H, s), 1.71 (3H, br-s), 1.99–2.25 (4H, m), 2.52–2.86 (7H, m), 3.66–3.86 (5H, m), 3.81 (3H, s), 4.00 (1H, br-s), 4.21 (1H, d, J=8.3 Hz), 4.32 (1H, d, J=8.3 Hz), 4.57 (1H, d, J=4.9 Hz), 4.92–5.03 (2H, m), 5.10 (1H, d, J=7.4 Hz), 5.40 (1H, br), 5.93 (1H, d, J=4.9 Hz), 6.05 (1H, br), 6.20–6.48 (1H, br), 6.90 (2H, d, J=8.8 Hz), 7.31–7.51 (9H, m), 7.60 (1H, t, J=7.3 Hz), 8.03 (2H, d, J=7.3 Hz).

Step 3: 9β-13-O-[(2R,3S)-3-(tert-Butoxycarbonylamino)-2-hydroxy-3-phenylpropionyl-10-deacetyl-9-dihydro-9,10-O-(2-morpholinoethylidene)baccatin III Using the compound obtained in the above step 2, the reaction procedure of the step 2 of Inventive Example 11 was repeated to obtain the title compound as a colorless transparent syrup.

Rf=0.20 (chloroform:acetone=15:1 (v/v)); Melting point: 129–132° C. (lyophilization from dioxane); $^1$H-NMR (400 MHz, CDCl$_3$/TMS) δ (ppm); 1.26 (6H, s), 1.40 (9H, s), 1.59 (3H, s), 1.65 (3H, s), 1.88 (1H, s), 1.96–2.46 (4H, m), 2.30 (3H, s), 2.50–2.70 (4H, m), 2.74 (1H, dd, J=18.4 Hz, J=4.4 Hz), 2.83 (1H, dd, J=18.4 Hz, J=4.4 Hz), 2.90 (1H, d, J=4.9 Hz), 3.63–3.86 (5H, m), 4.02–4.18 (2H, m), 4.32 (1H, d, J=8.3 Hz), 4.38 (1H, d, J=8.3 Hz), 4.63 (1H, s like), 4.66 (1H, d, J=8.3 Hz), 5.02 (1H, t, J=3.9 Hz), 5.10 (1H, s like), 5.19 (1H, d like, J=6.9 Hz), 5.29 (1H, d, J=10.0 Hz), 5.61 (1H, d, J=10.0 Hz), 6.00–6.13 (2H, m), 7.19–7.53 (7H, m), 7.59 (1H, t, J=7.3 Hz), 8.11 (2H, d, J=7.3 Hz). FAB Mass: 921 (M$^+$).

The following compounds were synthesized in the same manner.

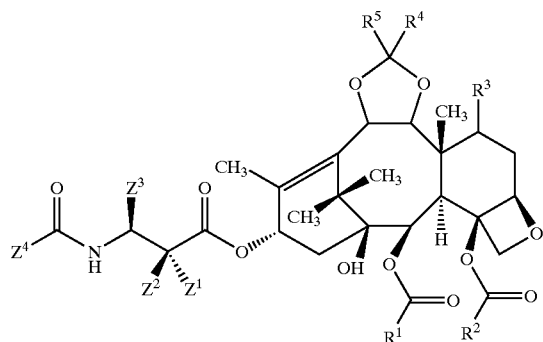

| Example No. | R¹ | R² | R³ | R⁴ | R⁵ | $Z^1$ | $Z^2$ | $Z^3$ | $Z^4$ |
|---|---|---|---|---|---|---|---|---|---|
| 17 | Ph | CH₃ | βOH | —CH₂NHCH₂Ph | H | OH | H | Ph | OC(CH₃)₃ |
| 18 | Ph | CH₃ | βOH | —CH₂—N(thiomorpholine) | H | OH | H | Ph | OC(CH₃)₃ |
| 19 | Ph | CH₃ | βOH | —CH₂N(CH₃)₂ | H | OH | H | Ph | OC(CH₃)₃ |
| 20 | Ph | (CH₂)₂CH₃ | βOH | —CH=CH₂ | H | OH | H | 2-furyl | OC(CH₃)₃ |
| 21 | Ph | (CH₂)₂CH₃ | βOH | —CH=CH₂ | H | OH | H | Ph | OC(CH₃)₃ |
| 22 | Ph | (CH₂)₂CH₃ | βOH | —CH₂—N(morpholine) | H | OH | H | 2-furyl | OC(CH₃)₃ |
| 23 | Ph | (CH₂)₂CH₃ | βOH | —CH₂—N(morpholine) | H | OH | H | Ph | OC(CH₃)₃ |
| 24 | Ph | CH₂CH₃ | βOH | —CH=CH₂ | H | OH | H | 2-furyl | OC(CH₃)₃ |
| 25 | Ph | CH₂CH₃ | βOH | —CH₂—N(morpholine) | H | OH | H | 2-furyl | OC(CH₃)₃ |
| 26 | Ph | CH₂CH₃ | βOH | —CH=CH₂ | H | OH | H | Ph | OC(CH₃)₃ |
| 27 | Ph | CH₂CH₃ | βOH | —CH₂—N(morpholine) | H | OH | H | Ph | OC(CH₃)₃ |
| 28 | Ph | CH₃ | βOH | —CH=CH₂ | H | F | F | 2-furyl | OC(CH₃)₃ |
| 29 | Ph | CH₃ | βOH | —CH₂—N(morpholine) | H | F | F | 2-furyl | OC(CH₃)₃ |
| 30 | Ph | CH₃ | βOCH₃ | —CH=CH₂ | H | OH | H | Ph | OC(CH₃)₃ |
| 31 | Ph | CH₃ | βOH | —CH=CH₂ | H | OH | H | —CH=C(CH₃)₂ | OC(CH₃)₃ |
| 32 | Ph | CH₃ | βOH | —CH=CH—CH₂—O—CH₂—Ph | H | OH | H | Ph | OC(CH₃)₃ |

-continued

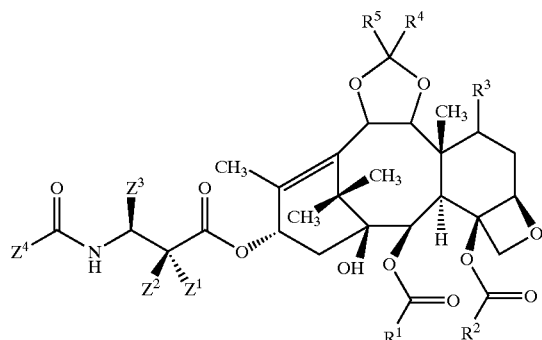

| Example No. | R¹ | R² | R³ | R⁴ | R⁵ | Z¹ | Z² | Z³ | Z⁴ |
|---|---|---|---|---|---|---|---|---|---|
| 33 | Ph | CH₃ | βOH | —(CH₂)₃—O—CH₂Ph | H | OH | H | Ph | OC(CH₃)₃ |
| 34 | Ph | CH₃ | βOH | —(CH₂)₃—N(morpholino) | H | OH | H | Ph | OC(CH₃)₃ |
| 35 | Ph | CH₃ | βOH | —(CH₂)₃—N(morpholino) | H | OH | H | 2-furyl | OC(CH₃)₃ |
| 36 | Ph | (CH₂)₂CH₃ | βOH | —CH₂NHCH₂Ph | H | OH | H | 2-furyl | OC(CH₃)₃ |
| 37 | Ph | (CH₂)₂CH₃ | βOH | —CH₂N(CH₃)₂ | H | OH | H | 2-furyl | OC(CH₃)₃ |
| 38 | Ph | CH₃ | βOH | —CH₂CH=CH₂ | H | OH | H | Ph | OC(CH₃)₃ |
| 39 | Ph | (CH₂)₂CH₃ | βOH | CH₃ | CH₃ | OH | H | 4-pyridyl | OC(CH₃)₃ |
| 40 | Ph | CH₃ | βOH | —CH₂—N(thiazolidinyl) | H | OH | H | Ph | OC(CH₃)₃ |
| 41 | Ph | CH₃ | βOH | —CH₂NHCH₂(4-pyridyl) | H | OH | H | Ph | OC(CH₃)₃ |
| 42 | Ph | CH₃ | βOH | —CH₂NH(CH₂)₂N(morpholino) | H | OH | H | Ph | OC(CH₃)₃ |
| 43 | Ph | CH₃ | βOH | —CH₂NH-cyclopropyl | H | OH | H | Ph | OC(CH₃)₃ |
| 44 | Ph | CH₃ | βOH | —CH₂N(Et)₂ | H | OH | H | Ph | OC(CH₃)₃ |
| 45 | Ph | CH₃ | βOH | —CH₂NH(CH₂)₂OH | H | OH | H | Ph | OC(CH₃)₃ |
| 46 | Ph | CH₃ | βOH | —CH₂—N(aziridinyl) | H | OH | H | Ph | OC(CH₃)₃ |

-continued

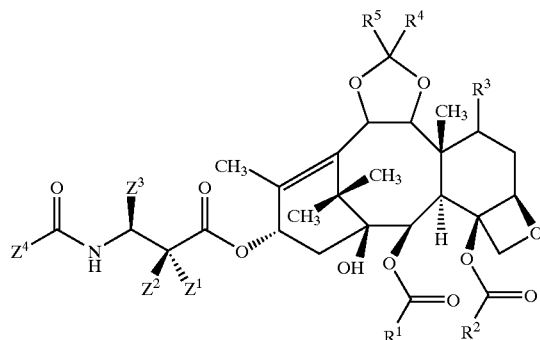

| Example No. | $R^1$ | $R^2$ | $R^3$ | $R^4$ | $R^5$ | $Z^1$ | $Z^2$ | $Z^3$ | $Z^4$ |
|---|---|---|---|---|---|---|---|---|---|
| 47 | Ph | $CH_3$ | βOH | $CH_3$ | $CH_3$ | OH | $CH_3$ | 4-pyridyl | $OC(CH_3)_3$ |
| 48 | Ph | $CH_2CH_3$ | βOH | $CH_3$ | $CH_3$ | OH | H | 4-pyridyl | $OC(CH_3)_3$ |
| 49 | Ph | cyclopropyl | βOH | —CH=$CH_2$ | H | OH | H | 2-furyl | $OC(CH_3)_3$ |
| 50 | Ph | $CH_3$ | βOH | —$CH_2NH_2$ | H | OH | H | Ph | $OC(CH_3)_3$ |
| 51 | Ph | cyclopropyl | βOH | —$CH_2$-morpholino | H | OH | H | 2-furyl | $OC(CH_3)_3$ |
| 52 | Ph | cyclopropyl | βOH | —CH=$CH_2$ | H | OH | H | Ph | $OC(CH_3)_3$ |
| 53 | Ph | cyclopropyl | βOH | —$CH_2$-morpholino | H | OH | H | Ph | $OC(CH_3)_3$ |
| 54 | Ph | $(CH_2)_2CH_3$ | βOH | $CH_3$ | $CH_3$ | OH | $CH_3$ | 4-pyridyl | $OC(CH_3)_3$ |
| 55 | Ph | cyclopropyl | βOH | $CH_3$ | $CH_3$ | OH | H | 4-pyridyl | $OC(CH_3)_3$ |
| 56 | Ph | cyclopropyl | βOH | —CH=$CH_2$ | H | OH | $CH_3$ | 2-furyl | $OC(CH_3)_3$ |
| 57 | Ph | cyclopropyl | βOH | —$CH_2$-morpholino | H | OH | $CH_3$ | 2-furyl | $OC(CH_3)_3$ |
| 58 | Ph | cyclopropyl | βOH | —CH=$CH_2$ | H | OH | H | 4-pyridyl | $OC(CH_3)_3$ |

-continued

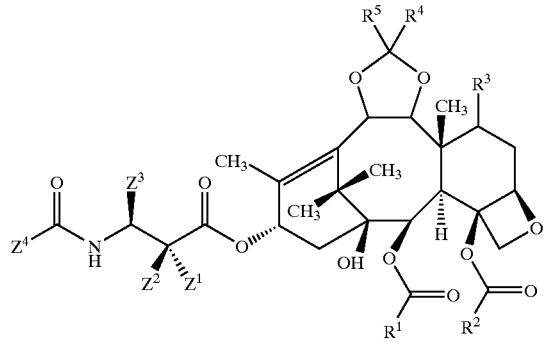

| Example No. | $R^1$ | $R^2$ | $R^3$ | $R^4$ | $R^5$ | $Z^1$ | $Z^2$ | $Z^3$ | $Z^4$ |
|---|---|---|---|---|---|---|---|---|---|
| 59 | Ph | $CH_3$ | H | $CH_3$ | $CH_3$ | OH | H | 4-pyridyl | $OC(CH_3)_3$ |
| 60 | Ph | △ | βOH | $CH_3$ | $CH_3$ | OH | $CH_3$ | 4-pyridyl | $OC(CH_3)_3$ |
| 61 | Ph | △ | H | —CH=$CH_2$ | H | OH | H | Ph | $OC(CH_3)_3$ |
| 62 | Ph | △ | H | —CH=$CH_2$ | H | OH | H | 2-furyl | $OC(CH_3)_3$ |
| 63 | Ph | △ | H | —$CH_2$—morpholino | H | OH | H | Ph | $OC(CH_3)_3$ |
| 64 | Ph | △ | H | —$CH_2$—morpholino | H | OH | H | 2-furyl | $OC(CH_3)_3$ |
| 65 | Ph | △ | H | $CH_3$ | $CH_3$ | OH | $CH_3$ | 4-pyridyl | $OC(CH_3)_3$ |
| 66 | Ph | △ | βOH | $CH_3$ | $CH_3$ | OH | $CH_3$ | 2-pyridyl | $OC(CH_3)_3$ |
| 67 | Ph | $CH_3$ | H | $CH_3$ | H | OH | H | 2-furyl | $OC(CH_3)_3$ |
| 68 | Ph | $CH_3$ | H | —CH=$CH_2$ | H | OH | H | Ph | $OC(CH_3)_3$ |
| 69 | Ph | △ | βOH | $CH_3$ | $CH_3$ | OH | H | 2-pyridyl | $OC(CH_3)_3$ |
| 70 | Ph | △ | H | $CH_3$ | $CH_3$ | OH | H | 4-pyridyl | $OC(CH_3)_3$ |

-continued

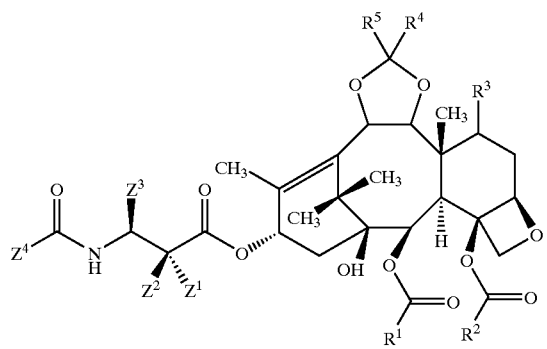

| Example No. | R¹ | R² | R³ | R⁴ | R⁵ | Z¹ | Z² | Z³ | Z⁴ |
|---|---|---|---|---|---|---|---|---|---|
| 71 | Ph | $CH_3$ | αF | —$CH_2$—N(morpholine) | H | OH | H | Ph | $OC(CH_3)_3$ |
| 72 | Ph | $CH_3$ | αF | $CH_3$ | $CH_3$ | OH | H | 4-pyridyl | $OC(CH_3)_3$ |
| 73 | Ph | $CH_3$ | αF | —$CH_2$—N(morpholine) | H | OH | H | 2-furyl | $OC(CH_3)_3$ |
| 74 | Ph | $CH_3$ | H | —$CH_2$—N(morpholine) | H | OH | H | Ph | $OC(CH_3)_3$ |
| 75 | Ph | $CH_3$ | H | $CH_3$ | H | OH | H | 4-pyridyl | $OC(CH_3)_3$ |
| 76 | Ph | cyclopropyl | βOH | $CH_3$ | $CH_3$ | OH | $CH_2CH_3$ | 4-pyridyl | $OC(CH_3)_3$ |
| 77 | Ph | $CH_3$ | H | —CH=$CH_2$ | H | OH | H | 2-furyl | $OC(CH_3)_3$ |
| 78 | Ph | $CH_3$ | βOH | $CH_3$ | $CH_3$ | OH | $CH_2CH_3$ | 4-pyridyl | $OC(CH_3)_3$ |
| 79 | Ph | $CH_3$ | H | —$CH_2$—N(morpholine) | H | OH | H | 2-furyl | $OC(CH_3)_3$ |
| 80 | Ph | $CH_3$ | H | $CH_3$ | $CH_3$ | OH | H | 2-pyridyl | $OC(CH_3)_3$ |
| 81 | Ph | $(CH_2)_2CH_3$ | αF | —$CH_2$—N(morpholine) | H | OH | H | 2-furyl | $OC(CH_3)_3$ |

-continued

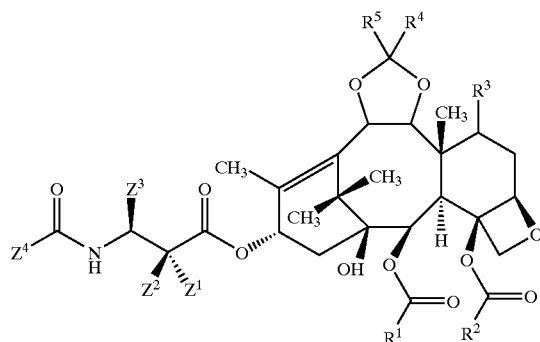

| Example No. | R¹ | R² | R³ | R⁴ | R⁵ | Z¹ | Z² | Z³ | Z⁴ |
|---|---|---|---|---|---|---|---|---|---|
| 82 | Ph | $CH_3$ | H | $CH_3$ | $CH_3$ | OH | $CH_3$ | 2-pyridyl | $OC(CH_3)_3$ |
| 83 | Ph | $CH_2CH_3$ | βOH | $CH_3$ | $CH_3$ | OH | H | 2-pyridyl | $OC(CH_3)_3$ |
| 84 | Ph | $CH_3$ | βOH | $CH_3$ | $CH_3$ | OH | $CH_3$ | 2-pyridyl | $OC(CH_3)_3$ |
| 85 | Ph | $CH_2CH_3$ | βOH | $CH_3$ | $CH_3$ | OH | $CH_3$ | 2-pyridyl | $OC(CH_3)_3$ |
| 86 | Ph | $CH_3$ | βOH | $CH_3$ | $CH_3$ | OH | H | 2-pyridyl | $OC(CH_3)_3$ |
| 87 | Ph | $CH_3$ | βOH | —CH=$CH_2$ | H | OH | $CH_3$ | 2-pyridyl | $OC(CH_3)_3$ |
| 88 | Ph | $CH_3$ | βOH | —$CH_2$—morpholinyl | H | OH | $CH_3$ | 2-pyridyl | $OC(CH_3)_3$ |
| 89 | Ph | cyclopropyl | H | —CH=$CH_2$ | H | OH | H | Ph | Ph |
| 90 | Ph | $CH_2CH_3$ | βOH | $CH_3$ | $CH_3$ | OH | $CH_3$ | 4-pyridyl | $OC(CH_3)_3$ |
| 91 | Ph | cyclopropyl | H | —$CH_2$—morpholinyl | H | OH | H | Ph | Ph |
| 92 | Ph | $OCH_2CH_3$ | βOH | —CH=$CH_2$ | H | OH | H | Ph | $OC(CH_3)_3$ |
| 93 | Ph | $OCH_2CH_3$ | βOH | —CH=$CH_2$ | H | OH | H | 2-furyl | $OC(CH_3)_3$ |

-continued

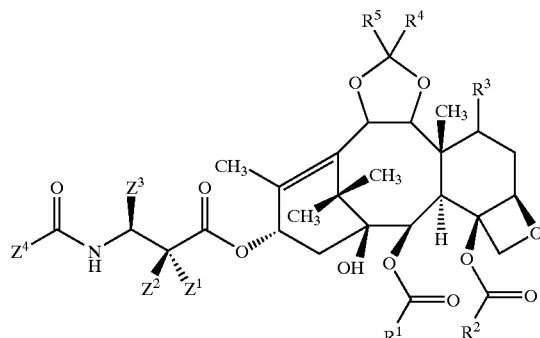

| Example No. | $R^1$ | $R^2$ | $R^3$ | $R^4$ | $R^5$ | $Z^1$ | $Z^2$ | $Z^3$ | $Z^4$ |
|---|---|---|---|---|---|---|---|---|---|
| 94 | Ph | $OCH_2CH_3$ | βOH | —$CH_2$—N(morpholino) | H | OH | H | Ph | $OC(CH_3)_3$ |
| 95 | Ph | $CH_3$ | H | $CH_3$ | $CH_3$ | OH | $CH_3$ | 4-pyridyl | $OC(CH_3)_3$ |
| 96 | Ph | $OCH_2CH_3$ | βOH | —$CH_2$—N(morpholino) | H | OH | H | 2-furyl | $OC(CH_3)_3$ |
| 97 | Ph | $CH_3$ | H | —CH=$CH_2$ | H | OH | H | 2-thienyl | $OC(CH_3)_3$ |
| 98 | Ph | $CH_3$ | H | —$CH_2$—N(morpholino) | H | OH | H | 2-thienyl | $OC(CH_3)_3$ |
| 99 | Ph | $OCH_2CH_3$ | βOH | $CH_3$ | $CH_3$ | OH | H | 2-pyridyl | $OC(CH_3)_3$ |
| 100 | Ph | $OCH_2CH_3$ | βOH | $CH_3$ | $CH_3$ | OH | H | 4-pyridyl | $OC(CH_3)_3$ |
| 101 | Ph | $OCH_2CH_3$ | βOH | $CH_3$ | $CH_3$ | OH | $CH_3$ | 4-pyridyl | $OC(CH_3)_3$ |
| 102 | Ph | $CH_3$ | H | (CH_3)_2C=S | — | OH | H | Ph | $OC(CH_3)_3$ |
| 103 | Ph | $CH_3$ | αF | $CH_3$ | $CH_3$ | OH | H | 2-pyridyl | $OC(CH_3)_3$ |
| 104 | Ph | $CH_3$ | H | —$CH_2$—N(N'-methylpiperazino) | H | OH | H | 2-furyl | $OC(CH_3)_3$ |

-continued

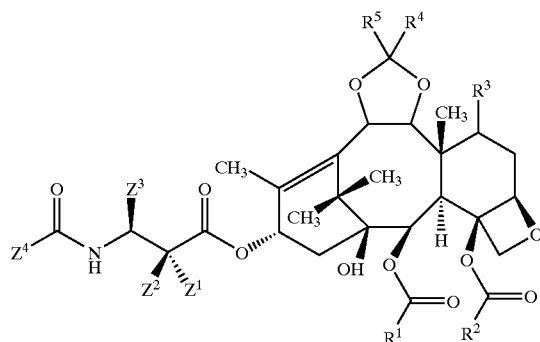

| Example No. | R¹ | R² | R³ | R⁴ | R⁵ | Z¹ | Z² | Z³ | Z⁴ |
|---|---|---|---|---|---|---|---|---|---|
| 105 | Ph | CH₃ | H | CH₂N(CH₃)₂ | H | OH | H | 2-furyl | OC(CH₃)₃ |
| 106 | Ph | OCH₂CH₃ | βOH | CH₃ | CH₃ | OH | CH₃ | 2-pyridyl | OC(CH₃)₃ |
| 107 | Ph | (CH₂)₂CH₃ | βOH | —CH₂—N(piperazinyl)NCH₃ | H | OH | H | 2-furyl | OC(CH₃)₃ |
| 108 | Ph | OCH₂CH₃ | βOH | —CH₂—N(morpholinyl) | H | OH | H | 2-thienyl | OC(CH₃)₃ |
| 109 | Ph | OCH₂CH₃ | βOH | —CH₂—N(piperazinyl)NCH₃ | H | OH | H | 2-thienyl | OC(CH₃)₃ |
| 110 | Ph | cyclopropyl | βOH | —CH=CH₂ | H | OH | H | 2-furyl | Ph |
| 111 | Ph | cyclopropyl | βOH | —CH₂—N(piperazinyl)NCH₃ | H | OH | H | 2-furyl | OC(CH₃)₃ |
| 112 | Ph | cyclopropyl | βOH | CH₂N(CH₃)₂ | H | OH | H | 2-furyl | OC(CH₃)₃ |
| 113 | Ph | cyclopropyl | βOH | —CH₂—N(morpholinyl) | H | OH | H | 2-furyl | Ph |
| 114 | Ph | OCH₂CH₃ | H | —CH₂—N(morpholinyl) | H | OH | H | 2-furyl | OC(CH₃)₃ |
| 115 | Ph | OCH₂CH₃ | H | CH₂N(CH₃)₂ | H | OH | H | 2-furyl | OC(CH₃)₃ |

Ph: Phenyl group.

Inventive Example 17

9β-9,10-O-(2-Benzylaminoethylidene)-13-O-[(2R, 3S)-3-(tert-butoxycarbonylamino)-2-hydroxy-3-phenylpropionyl]-10-deacetyl-9-dihydrobaccatin III Melting point: 125–128° C. (lyophilization from dioxane); $^1$H-NMR (400 MHz, CDCl$_3$/TMS) δ (ppm); 1.25 (3H, s), 1.40 (9H, s), 1.56 (6H, s), 1.63 (3H, s), 1.80–2.45 (5H, m), 2.30 (3H, s), 2.89 (1H, d, J=4.9 Hz), 2.99 (2H, d, J=4.9 Hz), 3.80 (1H, d, J=6.8 Hz), 3.88 (2H, s), 4.08 (1H, br s), 4.31 (1H, d, J=8.3 Hz), 4.37 (1H, d, J=8.3 Hz), 4.62 (1H, s), 5.00 (1H, t, J=4.9 Hz), 5.10 (1H, s), 5.21 (1H, d, J=6.8 Hz), 5.29 (1H, d, J=8.8 Hz), 5.64 (1H, d, J=8.8 Hz), 6.00–6.15 (2H, m), 7.22–7.56 (7H, m), 7.60 (1H, t, J=7.3 Hz), 8.10 (2H, d, J=7.3 Hz). FAB mass: 941 (MH$^+$).

Inventive Example 18

9β-13-O-[(2R,3S)-3-(tert-Butoxycarbonylamino)-2-hydroxy-3-phenylpropionyl]-10-deacetyl-9-dihydro-9,10-O-[2-(4-thiomorpholinyl)ethylidene]baccatin III Melting point: 149–152° C. (lyophilization from dioxane); $^1$H-NMR (400 MHz, CDCl$_3$/TMS) δ (ppm); 1.26 (3H, s), 1.40 (9H, s), 1.56 (3H, s), 1.58 (3H, s), 1.64 (3H, s), 1.88 (1H, s), 2.00–2.45 (3H, m), 2.30 (3H, s), 2.62–2.96 (11H, m), 3.77 (1H, d, J=7.3 Hz), 4.03–4.21 (2H, m), 4.31 (1H, d, J=8.8 Hz), 4.38 (1H, d, J=8.8 Hz), 4.57–4.70 (2H, m), 4.99 (1H, t, J=4.9 Hz), 5.10 (1H, s), 5.18 (1H, d, J=6.9 Hz), 5.29 (1H, d, J=8.3 Hz), 5.62 (1H, d, J=8.3 Hz), 6.00–6.17 (2H, m), 7.23–7.46 (7H, m), 7.60 (1H, t, J=7.4 Hz), 8.10 (2H, d, J=7.4 Hz). FAB mass: 937 (MH$^+$).

Inventive Example 19

9β-13-O-[(2R,3S)-3-(tert-Butoxycarbonylamino)-2-hydroxy-3-phenylpropionyl]-10-deacetyl-9-dihydro-9,10-O-(2-dimethylaminoethylidene)baccatin III Melting point: 148–149° C. (lyophilization from dioxane); $^1$H-NMR (400 MHz, CDCl$_3$/TMS) δ (ppm); 1.24 (3H, s), 1.38 (9H, s), 1.55 (3H, s), 1.58 (3H, s), 1.64 (3H, s), 1.87 (1H, s), 1.9–2.43 (4H, m), 2.28 (3H, s), 2.35 (6H, s), 2.67 (1H, dd, J=13.2 Hz, J=7.8 Hz), 2.75 (1H, dd, J=13.2 Hz, J=3.4 Hz), 2.88 (1H, d, J=4.9 Hz), 3.76 (1H, d, J=7.3 Hz), 4.07 (1H, br s), 4.30 (1H, d, J=8.8 Hz), 4.36 (1H, d, J=8.8 Hz), 4.60 (2H, br s), 4.98 (1H, dd, J=5.4 Hz, J=3.4 Hz), 5.08 (1H, s), 5.18 (1H, d, J=7.3 Hz), 5.27 (1H, d, J=9.3 Hz), 5.61 (1H, d, J=9.3 Hz), 6.00–6.18 (2H, m), 7.20–7.55 (7H, m), 7.60 (1H, t, J=7.8 Hz), 8.09 (2H, d, J=7.8 Hz). FAB mass: 879 (MH$^+$).

Inventive Example 20

9β-4-O-Butanoyl-13-O-[(2R,3R)-3-(tert-butoxycarbonylamino)-3-(2-furyl)-2-hydroxypropionyl]-4,10-dideacetyl-9-dihydro-9,10-O-(2-propenylidene)baccatin III Melting point: 125–128° C. (lyophilization from dioxane); $^1$H-NMR (400 MHz, CDCl$_3$/TMS) δ (ppm); 1.02 (3H, t, J=7.3 Hz), 1.28 (3H, s), 1.41 (9H, s), 1.62 (3H, s), 1.69 (3H, s), 1.71 (3H, s), 1.75–1.94 (2H, m), 1.81 (1H, s), 2.10–2.28 (3H, m), 2.29–2.52 (3H, m), 2.54–2.68 (1H, m), 2.94 (1H, d, J=4.9 Hz), 3.79–3.95 (1H, br), 3.89 (1H, d, J=6.8 Hz), 4.04–4.16 (1H, m), 4.32 (1H, d, J=8.7 Hz), 4.39 (1H, d, J=8.7 Hz), 4.59 (1H, d, J=8.3 Hz), 4.70 (1H, s), 5.05 (1H, s), 5.21 (1H, d, J=5.8 Hz), 5.27 (1H, d, J=6.8 Hz), 5.27–5.40 (2H, m), 5.46 (1H, d, J=10.2 Hz), 5.57 (1H, d, J=17.5 Hz), 6.04 (1H, ddd, J=17.5 Hz, J=10.2 Hz, J=5.8 Hz), 6.08 (1H, d, J=4.9 Hz), 6.05–6.15 (1H, m), 6.33 (1H, d, J=2.9 Hz), 6.36 (1H, dd, J=2.9 Hz, J=1.9 Hz), 7.39 (1H, d, J=1.9 Hz), 7.47 (2H, t, J=7.8 Hz), 7.61 (1H, t, J=7.8 Hz), 8.12 (2H, d, J=7.8 Hz). FAB mass: 866 (MH$^+$).

Inventive Example 21

9β-4-O-Butanoyl-13-O-[(2R,3S)-3-(tert-butoxycarbonylamino)-2-hydroxy-3-phenyl-propionyl]-4,10-dideacetyl-9-dihydro-9,10-O-(2-propenylidene)baccatin III Melting point: 127–130° C. (lyophilization from dioxane); $^1$H-NMR (400 MHz, CDCl$_3$/TMS) δ (ppm); 0.99 (3H, t, J=7.3Hz), 1.26 (3H, s), 1.29 (3H, s), 1.40 (3H, s), 1.61 (3H, s), 1.67 (3H, s), 1.73–1.88 (2H, m), 1.92 (1H, br s), 2.00–2.46 (3H, m), 2.91 (1H, d, J=4.9 Hz), 3.86 (1H, d, J=6.8 Hz), 4.09 (1H, br s), 4.32 (1H, d, J=8.8 Hz), 4.38 (1H, d, J=8.8 Hz), 4.50–4.68 (2H, m), 5.04 (1H, s like), 5.21 (1H, d, J=6.4 Hz), 5.21–5.32 (2H, m), 5.45 (1H, d, J=10.7 Hz), 5.56 (1H, d, J=17.1 Hz), 5.62 (1H, d, J=9.8 Hz), 5.97–6.12 (3H, m), 7.22–7.52 (7H, m), 7.60 (1H, t, J=7.8 Hz), 8.11 (2H, d, J=7.8 Hz). FAB mass: 876 (MH$^+$).

Inventive Example 22

9β-4-O-Butanoyl-13-O-[(2R,3R)-3-(tert-Butoxycarbonylamino)-3-(2-furyl)-2-hydroxypropionyl]-4,10-dideacetyl-9-dihydro-9,10-O-(2-morpholinoethylidene)baccatin III Melting point: 123–125° C. (lyophilization from dioxane); $^1$H-NMR (400 MHz, CDCl$_3$/TMS) δ (ppm); 1.01 (3H, t, J=7.3 Hz), 1.27 (3H, s), 1.40 (9H, s), 1.61 (3H, s), 1.65 (3H, s), 1.69 (3H, s), 1.77–1.92 (2H, m), 1.88 (1H, s), 2.08–2.26 (2H, m), 2.31–2.60 (7H, m), 2.74 (1H, dd, J=18.0 Hz, J=4.4 Hz), 2.83 (1H, dd, J=18.0 Hz, J=4.0 Hz), 2.93 (1H, d, J=4.9 Hz), 3.73 (4H, t, J=4.9 Hz), 3.82 (1H, d, J=6.9 Hz), 4.05–4.12 (1H, m), 4.31 (1H, d, J=8.3 Hz), 4.39 (1H, d, J=8.3 Hz), 4.64–4.73 (2H, m), 5.02 (1H, t, J=4.0 Hz), 5.06 (1H, s like), 5.20 (1H, d, J=6.9 Hz), 5.33 (2H, s), 6.04 (1H, d, J=4.9 Hz), 6.08 (1H, br t, J=8.0 Hz), 6.33 (1H, d, J=3.5 Hz), 6.36 (1H, dd, J=3.5 Hz, J=1.9 Hz), 7.39 (1H, d, J=1.9 Hz), 7.48 (2H, t, J=7.8 Hz), 7.61 (1H, t, J=7.8 Hz), 8.12 (2H, d, J=7.8 Hz). FAB mass: 939 (MH$^+$).

Inventive Example 23

9β-4-O-Butanoyl-13-O-[(2R,3S)-3-(tert-butoxycarbonylamino)-2-hydroxy-3-phenylpropionyl]-4,10-dideacetyl-9-dihydro-9,10-O-(2-morpholinoethylidene)baccatin III Melting point: 130–132° C. (lyophilization from dioxane); $^1$H-NMR (400 MHz, CDCl$_3$/TMS) δ (ppm); 0.99 (3H, t, J=7.3 Hz), 1.26 (3H, s), 1.40 (9H, s), 1.60 (3H, s), 1.64 (3H, s), 1.72–1.79 (2H, m), 1.80 (1H, s), 2.01–2.26 (3H, m), 2.30–2.43 (2H, m), 2.49–2.70 (5H, m), 2.75 (1H, dd, J=13.2 Hz, J=4.9 Hz), 2.83 (1H, dd, J=13.2 Hz, J=3.9 Hz), 2.89 (1H, d, J=4.4 Hz), 3.74 (4H, t, J=4.4 Hz), 3.78 (1H, d, J=7.4 Hz), 4.01–4.12 (2H, m), 4.32 (1H, d, J=8.7 Hz), 4.38 (1H, d, J=8.7 Hz), 4.62 (1H, br s), 4.66 (1H, d, J=8.3 Hz), 4.99–5.09 (2H, m), 5.19 (1H, d, J=6.8 Hz), 5.27 (1H, d, J=9.3 Hz), 5.60 (1H, d, J=9.3 Hz), 5.60 (1H, d, J=9.3 Hz), 5.98–6.10 (2H, m), 7.20–7.52 (7H, m), 7.61 (1H, t, J=7.3 Hz), 8.12 (2H, d, J=7.3 Hz). FAB mass: 949 (MH$^+$).

Inventive Example 24

9β-13-O-[(2R,3R)-3-(tert-Butoxycarbonylamino)-3-(2-furyl)-2-hydroxypropionyl]-4,10-dideacetyl-9-dihydro-4-O-propanoyl-9,10-O-(2-propenylidene)baccatin III Melting point: 135–137° C. (lyophilization from dioxane); $^1$H-NMR (400 MHz, CDCl$_3$/TMS) δ (ppm); 1.29

(3H, s), 1.34 (3H, t, J=7.8 Hz), 1.40 (9H, s), 1.63 (3H, s), 1.69 (3H, s), 1.71 (3H, s), 1.90 (1H, s), 2.10–2.26 (3H, m), 2.31–2.44 (1H, m), 2.51–2.73 (2H, m), 2.94 (1H, d, J=4.9 Hz), 3.91 (1H, d, J=7.4 Hz), 4.09 (1H, br), 4.32 (1H, d, J=8.8 Hz), 4.40 (1H, d, J=8.8 Hz), 4.55 (1H, br d, J=7.4 Hz), 4.69 (1H, s), 5.03 (1H, s like), 5.21 (1H, d, J=5.9 Hz), 5.26 (1H, d, J=7.4 Hz), 5.29–5.39 (2H, m), 5.45 (1H, d, J=10.7 Hz), 5.57 (1H, d, J=17.6 Hz), 5.97–6.06 (3H, m), 6.33 (1H, d, J=2.9 Hz), 6.36 (1H, dd, J=2.9 Hz, J=2.0 Hz), 7.39 (1H, d, J=2.0 Hz), 7.47 (2H, t, J=7.8 Hz), 7.60 (1H, t, J=7.8 Hz), 8.13 (2H, d, J=7.8 Hz). FAB mass: 852 (MH$^+$).

Inventive Example 25

9β-13-O-[(2R,3R)-3-(tert-Butoxycarbonylamino)-3-(2-furyl)-2-hydroxypropionyl]-4,10-dideacetyl-9-dihydro-9,10-O-(2-morpholinoethylidene)-4-O-propionylbaccatin III Melting point: 145–148° C. (lyophilization from dioxane); $^1$H-NMR (400 MHz, CDCl$_3$/TMS) δ (ppm); 1.28 (3H, s), 1.32 (3H, t, J=7.6 Hz), 1.40 (9H, s), 1.61 (3H, s), 1.66 (3H, s), 1.70 (3H, s), 1.89 (1H, s), 2.09–2.26 (3H, m), 2.51–2.70 (6H, m), 2.75 (1H, dd, J=12.4 Hz, J=5.6 Hz), 2.82 (1H, dd, J=12.4 Hz, J=4.0 Hz), 2.93 (1H, d, J=4.9 Hz), 3.74 (4H, t, J=4.4 Hz), 3.83 (1H, d, J=7.4 Hz), 4.04–4.12 (1H, m), 4.32 (1H, d, J=8.3 Hz), 4.41 (1H, d, J=8.3 Hz), 4.66 (1H, d, J=8.3 Hz), 4.66 (1H, s), 4.99–5.08 (2H, m), 5.20 (1H, d, J=7.4 Hz), 5.32 (2H, s like), 6.05 (1H, d, J=4.9 Hz), 6.10 (1H, br t, J=7.8 Hz), 6.33 (1H, d, J=3.4 Hz), 6.36 (1H, dd, J=3.4 Hz, J=2.0 Hz), 7.39 (1H, d, J=2.0 Hz), 7.48 (2H, t, J=7.8 Hz), 7.61 (1H, t, J=7.8 Hz), 8.13 (2H, d, J=7.8 Hz). FAB mass: 925 (MH$^+$).

Inventive Example 26

9β-13-O-[(2R,3S)-3-(tert-Butoxycarbonylamino)-2-hydroxy-3-phenylpropionyl]-4,10-dideacetyl-9-dihydro-9,10-O-(2-propenylidene)4-O-propionylbaccatin III Melting point: 190–192° C. (lyophilization from dioxane); $^1$H-NMR (400 MHz, CDCl$_3$/TMS) δ (ppm); 1.27 (3H, s), 1.30 (3H, t, J=7.8 Hz), 1.40 (9H, s), 1.59 (6H, br s), 1.61 (3H, s), 1.68 (3H, s), 1.90 (1H, s), 2.02–2.24 (3H, m), 2.29–2.70 (4H, m), 2.91 (1H, d, J=4.4 Hz), 3.87 (1H, d, J=6.9 Hz), 3.99–4.16 (2H, m), 4.32 (1H, d, J=8.3 Hz), 4.40 (1H, d, J=8.3 Hz), 4.55 (1H, d, J=8.3 Hz), 4.61 (1H, br s), 5.03 (1H, s like), 5.19–5.32 (1H, m), 5.21 (1H, d, J=6.4 Hz), 5.25 (1H, d, J=6.9 Hz), 5.45 (1H, d, J=10.7 Hz), 5.50–5.62 (1H, m), 5.56 (1H, d, J=17.1 Hz), 5.99–6.13 (3H, m), 7.12–7.50 (7H, m), 7.60 (1H, t, J=7.3 Hz), 8.12 (2H, d, J=7.3 Hz). FAB mass: 862 (MH$^+$).

Inventive Example 27

9β-13-O-[(2R,3S)-3-(tert-Butoxycarbonylamino)-2-hydroxy-3-phenylpropionyl]-4,10-dideacetyl-9-dihydro-9,10-O-(2-morpholinoethylidene)-4-O-propionylbaccatin III Melting point: 137–139° C. (lyophilization from dioxane); $^1$H-NMR(400 MHz, CDCl$_3$/TMS) δ (ppm); 1.25 (3H, s), 1.27 (3H, s), 1.29 (3H, t, J=7.3 Hz), 1.39 (9H, s), 1.58 t3H, s), 1.65 (3H, s), 1.88 (1H, s), 2.02–2.26 (3H, m), 2.36 (1H, dd, J=14.0 Hz, J=10.0 Hz), 2.42–2.71 (4H, m), 2.75 (1H, dd, J=14.0 Hz, J=4.8 Hz), 2.83 (1H, dd, J=14.0 Hz, J=3.8 Hz), 2.90 (1H, d, J=4.4 Hz), 3.74 (1H, d, J=4.4 Hz), 3.79 (1H, d, J=6.8 Hz), 3.92–4.13 (2H, br), 4.32 (1H, d, J=8.8 Hz), 4.40 (1H, d, J=8.8 Hz), 4.56–4.67 (2H, m), 5.03 (1H, s like), 5.19 (1H, d, J=6.8 Hz), 5.22 (1H, br d, J=9.2 Hz), 5.55 (1H, d, J=9.2 Hz), 5.98–6.12 (2H, m), 7.11–7.50 (7H, m), 7.61 (1H, t, J=7.3 Hz), 8.12 (2H, d, J=7.3 Hz). FAB mass: 935 (MH$^+$).

Inventive Example 28

9-13-O-[(3S)-3-(tert-Butoxycarbonylamino)-2,2-difluoro-3-(2-furyl)propionyl]-10-deacetyl-9-dihydro-9,10-O-(2-propenylidene)baccatin III Melting point: 176–178° C. (lyophilization from dioxane); $^1$H-NMR (400 MHz, CDCl$_3$/TMS) δ (ppm); 1.30 (s), 1.44 (9H, s), 1.62 (s), 1.69 (s), 2.32 (s), 2.93 (1H, d, J=5 Hz), 3.89 (1H, d, J=7 Hz), 4.08 (1H, m), 4.28 (1H, d, J=8.5 Hz), 4.40 (1H, d, J=8.5 Hz), 4.61 (1H, d, J=8.5 Hz), 5.13 (1H, br), 5.20 (1H, d, J=6 Hz), 5.23 (1H, d, J=7 Hz), 5.38 (1H, d, J=12 Hz), 5.45 (1H, d, J=l1 Hz, ), 5.56 (1H, d, J=17 Hz), 5.67 (1H, m), 6.03 (2H, m), 6.21 (1H, t, J=9 Hz), 6.39 (1H, dd, J=3 Hz, 2 Hz), 6.44 (1H, d, J=3 Hz), 7.43 (1H, d, J=2 Hz), 7.48 (2H, t, J=7.5 Hz), 7.61 (1H, t, J=7.5 Hz), 8.11 (2H, d, J=7.5 Hz). FAB mass: 858 (M+).

Inventive Example 29

9β-13-O-[(3S)-3-(tert-Butoxycarbonylamino)-2,2-difluoro-3-(2-furyl)propionyl]-10-deacetyl-9-dihydro-9,10-O-(2-morpholinoethylidene)baccatin III Melting point: 142–144° C. (lyophilization from dioxane); $^1$H-NMR (400 MHz, CDCl$_3$/TMS) δ (ppm); 1.30 (s), 1.44 (9H, s), 1.61 (s), 1.66 (s), 2.19 (2H, m), 2.28 (2H, m), 2.32 (3H, s), 2.62 (4H, m), 2.74 (1H, dd, J=13.5 Hz, 5 Hz), 2.81 (1H, dd, J=13.5 Hz, 5 Hz), 2.91 (1H, d, J=5 Hz), 3.73 (4H, t, J=4.5 Hz), 3.81 (1H, d, J=7.5 Hz), 4.07 (1H, br), 4.28 (1H, d, J=8.5 Hz), 4.41 (1H, d, J=8.5 Hz), 4.72 (1H, d, J=8.5 Hz), 5.01 (1H, t, J=4.5 Hz), 5.14 (1H, br), 5.16 (1H, d, J=7.5 Hz), 5.38 (1H, d, J=9 Hz), 5.67 (1H, m), 6.01 (1H, d, J=5 Hz), 6.20 (1H, t, J=9 Hz), 6.39 (1H, dd, J=3 Hz, 2 Hz), 6.43 (1H, d, J=3 Hz), 7.43 (1H, d, J=2 Hz), 7.49 (2H, t, J=7.5 Hz), 7.61 (1H, t, J=7.5 Hz), 8.11 (2H, d, J=7.5 Hz). FAB mass: 931 (M$^+$).

Inventive Example 30

9β-13-O-[(2R,3S)-3-(tert-Butoxycarbonylamino)-2-hydroxy-3-phenylpropionyl]-10-deacetyl-9-dihydro-7-O-methyl-9,10-O-(2-propenylidene)baccatin III Melting point: 137–140° C. (lyophilization from dioxane); $^1$H-NMR (400 MHz, CDCl$_3$/TMS) δ (ppm); 1.20 (3H, s), 1.40 (9H, br s), 1.57 (3H, s), 1.59 (3H, s), 1.65 (3H, s), 1.86 (1H, s), 1.95–2.50 (4H, m), 2.27 (3H, s), 3.07 (1H, d, J=4.9 Hz), 3.33–3.42 (1H, s), 3.38 (3H, s), 4.29 (1H, d, J=8.1 Hz), 4.32–4.40 (1H, br), 4.36 (1H, d, J=8.1 Hz), 4.46 (1H, d, J=7.8 Hz), 4.62 (1H, br s), 4.89 (1H, br d, J=5.4 Hz), 5.17 (1H, d, J=5.9 Hz), 5.25–5.38 (1H, m), 5.34 (1H, d, J=8.3 Hz), 5.48 (1H, d, J=10.3 Hz), 5.59 (1H, d, J=17.6 Hz), 5.66 (1H, br d, J=9.3 Hz), 5.96 (1H, d, J=4.9 Hz), 6.08 (1H, br t, J=7.8 Hz), 6.17 (1H, ddd, J=5.9, 10.3, 17.6 Hz), 7.26–7.44 (5H, m), 7.46 (2H, t, J=7.3 Hz), 7.59 (1H, t, J=7.3 Hz), 8.09 (2H, d, J=7.3 Hz). FAB mass: 862 (MH$^+$).

Inventive Example 31

9β-13-O-[(2R,3S)-3-(tert-Butoxycarbonylamino)-2-hydroxy-5-methyl-4-hexenoyl]-10-deacetyl-9-dihydro-9,10-O-(2-propenylidene)baccatin III Melting point: 122–127° C. (lyophilization from dioxane); $^1$H-NMR (400 MHz, CDCl$_3$/TMS) δ (ppm); 1.25

(3H, s), 1.40 (9H, s), 1.62 (3H, s), 1.69 (3H, s), 1.75 (6H, s), 1.77 (3H, s), 2.04–2.38 (4H, m), 2.11 (3H, s), 2.63 (1H, s), 2.96 (1H, d, J=7.5 Hz), 4.11 (1H, m), 4.29 (1H, br), 4.36 (2H, ABq, J=8.5 Hz), 4.58 (1H, d, J=8.2 Hz), 4.83 (1H, dt, J=9.1 Hz, 2.3 Hz), 4.96 (1H, br), 5.12 (1H, s), 5.22 (1H, d, J=6.1 Hz), 5.27 (1H, d, J=7.9 Hz), 5.28 (1H, d, J=6.1 Hz), 5.45 (1H, d, J=10.5 Hz), 5.57 (1H, d, J=17.1 Hz), 5.94–6.12 (3H, m), 7.46 (2H, t, J=7.8 Hz), 7.50 (1H, t, J=7.3 Hz), 8.04 (2H, d, J=6.8 Hz). FAB mass: 826 (MH$^+$).

Inventive Example 32

9β-9,10-O-[(2E)-4-Benzyloxy-2-butenylidene]-13-O-[(2R,3S)-3-(tert-butoxycarbonylamino)-2-hydroxy-3-phenylpropionyl]-10-deacetyl-9-dihydrobaccatin III Melting point: 112–115° C. (lyophilization from dioxane); $^1$H-NMR (400 MHz, CDCl$_3$/TMS) δ (ppm); 1.25 (3H, s), 1.40 (9H, s), 1.59 (3H, br s), 1.62 (3H, s), 1.68 (3H, s), 1.90 (1H, s), 2.00–2.35 (3H, m), 2.29 (3H, s), 2.37 (1H, dd, J=15.2 Hz, J=9.8 Hz), 2.90 (1H, d, J=4.4 Hz), 3.85 (1H, d, J=6.9 Hz), 4.10 (2H, d, J=4.4 Hz), 4.14 (1H, br), 4.32 (1H, d, J=8.3 Hz), 4.37 (1H, d, J=8.3 Hz), 4.56 (2H, s), 4.62 (1H, br), 5.09 (1H, s like), 5.21–5.36 (3H, m), 5.64 (1H, br d, J=9.8 Hz), 5.95 (1H, dd, J=15.6 Hz, J=5.8 Hz), 6.04–6.16 (3H, m), 7.25–7.45 (10H, m), 7.47 (2H, t, J=7.8 Hz), 7.60 (1H, t J=7.8 Hz), 8.10 (2H, d, J=7.8 Hz). FAB mass: 968 (MH$^+$).

Inventive Example 33

9β-9,10-O-(4-Benzyloxybutylidene)-13-O-((2R,3S)-3-(tert-butoxycarbonylamino)-2-hydroxy-3-phenylpropionyl]-10-deacetyl-9-dihydrobaccatin III Melting point: 102–105° C. (lyophilization from dioxane); $^1$H-NMR (400 MHz, CDCl$_3$/TMS) δ (ppm); 1.25 (6H, s), 1.40 (9H, s), 1.60 (3H, s), 1.64 (3H, s), 1.74–1.97 (5H, m), 2.01–2.43 (4H, m), 2.30 (3H, s), 2.90 (1H, d, J=4.4 Hz), 3.54 (2H, t, J=6.3 Hz), 3.77 (1H, d, J=6.8 Hz), 4.05–4.18 (2H, m), 4.33 (1H, d, J=8.3 Hz), 4.37 (1H, d, J=8.3 Hz), 4.53 (2H, s), 4.59–4.70 (2H, m), 4.88 (1H, t, J=5.4 Hz), 5.10 (1H, s like), 5.18 (1H, d, J=6.8 Hz), 5.30 (1H, br d, J=9.5 Hz), 5.64 (1H, br d, J=9.5 Hz), 6.02–6.14 (2H, m), 7.22–7.43 (10H, m), 7.47 (2H, t, J=7.8 Hz), 7.60 (1H, t, J=7.8 Hz), 8.10 (2H, d, J=7.8 Hz). FAB mass: 970 (MH$^+$).

Inventive Example 34

9β-13-O-[(2R,3S)-3-(tert-Butoxycarbonylamino)-2-hydroxy-3-phenylpropionyl]-10-deacetyl-9-dihydro-9,10-O-(4-morpholinobutylidene)baccatin III Melting point: 128–131° C. (lyophilization from dioxane); $^1$H-NMR (400 MHz, CDCl$_3$/TMS) δ (ppm); 1.25 (3H, s), 1.40 (9H, s), 1.53–1.74 (2H, m), 1.60 (3H, s), 1.65 (6H, s), 1.81–1.93 (3H, m), 2.03–2.56 (9H, m), 2.30 (3H, s), 2.90 (1H, d, J=4.4 Hz), 3.74 (4H, m), 3.78 (1H, d, J=6.9 Hz), 4.05–4.12 (1H, br), 4.32 (1H, d, J=8.8 Hz), 4.37 (1H, d, J=8.8 Hz), 4.59–4.68 (2H, m), 4.87 (1H, t, J=5.3 Hz), 5.10 (1H, s like), 5.18 (1H, d, J=6.9 Hz), 5.28 (1H, br d, J=9.2 Hz), 5.63 (1H, br d, J=9.2 Hz), 6.05 (1H, d, J=4.4 Hz), 6.08 (1H, t, J=8.3 Hz), 7.23–7.43 (5H, m), 7.47 (2H, t, J=7.8 Hz), 7.60 (1H, t, J=7.8 Hz), 8.10 (2H, d, J=7.8 Hz). FAB mass: 949 (MH$^+$).

Inventive Example 35

9β-13-O-[(2R,3R)-3-(tert-Butoxycarbonylamino)-3-(2-furyl)-2-hydroxypropionyl]-10-deacetyl-9-dihydro-9,10-O-(4-morpholinobutylidene)baccatin III Melting point: 127–130° C. (lyophilization from dioxane); $^1$H-NMR (400 MHz, CDCl$_3$/TMS) δ (ppm); 1.27 (3H, s), 1.41 (9H, s), 1.54–1.95 (m), 1.61 (3H, s), 1.65 (3H, s), 1.70 (3H, s), 2.05–2.26 (3H, m), 2.35 (3H, s), 2.30–2.57 (6H, m), 2.93 (1H, d, J=5.3 Hz), 3.74 (4H, t, J=4.4 Hz), 3.81 (1H, d, J=7.4 Hz), 4.07 (1H, br), 4.32 (1H, d, J=8.3 Hz), 4.39 (1H, d, J=8.3 Hz), 4.65 (1H, br), 4.71 (1H, s), 4.87 (1H, t, J=5.4 Hz), 5.10 (1H, s like), 5.20 (1H, d, J=7.4 Hz), 5.32–5.43 (2H, m), 6.05 (1H, d, J=5.3 Hz), 6.10 (1H, t, J=6.8 Hz), 6.318 (1H, d, J=2.9 Hz), 6.36 (1H, dd, J=2.9 Hz, J=1.9 Hz), 7.39 (1H, d, J=1.9 Hz), 7.47 (2H, t, J=7.8 Hz), 7.60 (1H, t, J=7.8 Hz), 8.11 (2H, d, J=7.8H). FAB mass: 939 (MH$^+$).

Inventive Example 36

9β-9,10-O-(2-Benzylaminoethylidene)-4-O-butanoyl-13-O-[(2R,3R)-3-(tert-butoxycarbonylamino)-3-(2-furyl)-2-hydroxypropionyl)-4,10-dideacetyl-9-dihydrobaccatin III Melting point: 111–115° C. (lyophilization from dioxane); $^1$H-NMR (400 MHz, CDCl$_3$/TMS) δ (ppm); 1.01 (3H, t, J=7.3 Hz), 1.27 (3H, s), 1.40 (9H, s), 1.58 (3H, s), 1.63 (3H, s), 1.70 (3H, s), 1.74–2.70 (12H, m), 2.93 (1H, d, J=4.4 Hz), 2.98 (1H, d, J=4.9 Hz), 3.85 (1H, d, J=7.8 Hz), 3.89 (2H, s), 4.07 (1H, s like), 4.31 (1H, d, J=8.3 Hz), 4.38 (1H, d, J=8.3 Hz), 4.69 (1H, d, J=1.9 Hz), 5.01 (1H, t, J=5.4 Hz), 5.05 (1H, s like), 5.22 (1H, d, J=7.8 Hz), 5.31 (1H, br d, J=9.8 Hz), 5.37 (1H, br d, J=9.8 Hz), 6.02 (1H, d, J=4.4 Hz), 6.08 (1H, br t, J=7.8 Hz), 6.32 (1H, d, J=3.4 Hz), 6.36 (1H, dd, J=3.4 Hz, J=1.9 Hz), 7.20–8.41 (6H, m), 7.47 (2H, t, J=7.3 Hz), 7.60 (1H, t, J=7.3 Hz), 8.12 (2H, d, J=7.3 Hz). FAB mass: 959 (MH$^+$).

Inventive Example 37

9β-4-O-Butanoyl-13-O-[(2R,3R)-3-(tert-butoxycarbonylamino)-3-(2-furyl)-2-hydroxypropionyl]-4,10-dideacetyl-9-dihydro-9,10-O-(2-dimethylaminoethylidene)baccatin III Melting point: 125–128° C. (lyophilization from dioxane); $^1$H-NMR (400 MHz, CDCl$_3$/TMS) δ (ppm); 1.01 (3H, t, J=6.8 Hz), 1.28 (3H, s), 1.40 (9H, s), 1.55–1.93 (4H, m), 1.61 (3H, s), 1.67 (3H, s), 1.70 (3H, s), 2.10–2.26 (3H, m), 2.38 (6H, s), 2.30–2.70 (3H, m), 2.71 (1H, dd, J=12.8 Hz, J=6.0 Hz), 2.80 (1H, dd, J=12.8 Hz, J=3.6 Hz), 2.93 (1H, d, J=4.9 Hz), 3.82 (1H, d, J=7.3 Hz), 4.08 (1H, br), 4.32 (1H, d, J=8.3 Hz), 4.39 (1H, d, J=8.3 Hz), 4.70 (1H, s), 5.01 (1H, t like, J=3.9 Hz), 5.05 (1H, s like), 5.21 (1H, d, J=7.3 Hz), 5.33 (2H, br s), 6.05 (1H, d, J=4.9 Hz), 6.08 (1H, br t, J=8.0 Hz), 6.33 (1H, d, J=3.4 Hz), 6.36 (1H, dd, J=3.4 Hz, J=1.9 Hz), 7.39 (1H, d, J=1.9 Hz), 7.47 (2H, t, J=7.3 Hz), 7.61 (1H, d, J=7.3 Hz), 8.12 (2H, d, J=7.3 Hz). FAB mass: 897 (MH$^+$).

Inventive Example 38

9β-13-O-(2R,3S)-3-(tert-Butoxycarbonylamino)-2-hydroxy-3-phenylpropionyl)-10-deacetyl-9-dihydro-9,10-O-(3-butenylidene)baccatin III $^1$H-NMR (400 MHz, CDCl$_3$/TMS) δ (ppm); 1.26 (3H, s), 1.40 (9H, br), 1.43 (3H, s), 1.62 (3H, s), 1.66 (3H, s), 1.89 (1H, s), 2.01–2.44 (4H, m), 2.30 (3H, s), 2.58 (2H, t, J=6.3 Hz), 2.91 (1H, d, J=4.4 Hz), 3.80 (1H, d, J=7.3 Hz), 4.10 (1H, br), 4.33 (1H, d, J=8.8 Hz), 4.38 (1H, d, J=8.8 Hz), 4.58–4.71 (2H, m), 4.89 (1H, t, J=5.3 Hz), 5.08–5.35 (5H, m), 5.63 (1H, br d, J=10.0 Hz), 5.81–5.93 (1H, m), 6.03–6.13 (2H, m), 7.20–7.53 (7H, m), 7.60 (1H, t, J=7.3 Hz), 8.11 (2H, d, J=7.3 Hz).

Inventive Example 39

9β-4-O-Butanoyl-13-O-[(2R,3S)-3-(tert-butoxycarbonylamino)-2-hydroxy-3-(4-pyridyl)propionyl]-4,10-dideacetyl-9-dihydro-9,10-O-isopropylidenebaccatin III Melting point: 108–109° C. (lyophilization from dioxane); $^1$H-NMR-(400 MHz, CDCl$_3$/TMS) δ (ppm); 1.03 (3H, t, J=6.8 Hz), 1.24 (3H, s), 1.40 (3H, s), 1.42 (9H, s), 1.58 (3H, s), 1.62 (3H, s), 1.63 (3H, s), 1.66 (3H, s), 1.84 (2H, q, J=6.8 Hz), 2.10–2.37 (5H, m), 2.54 (2H, m), 2.90 (1H, d, J=4.4 Hz), 3.85 (1H, d, J=6.8 Hz), 4.09 (1H, br), 4.37 (2H, s like), 4.62 (1H, s), 4.70 (1H, d, J=8.3 Hz), 5.06 (1H, s), 5.29 (1H, d, J=8.8 Hz), 5.51 (1H, d, J=6.8 Hz), 5.52 (1H, d, J=8.8 Hz), 6.07 (2H, br), 7.37 (2H, d, J=5.4 Hz), 7.47 (1H, t, J=7.8 Hz), 7.61 (1H, t, J=7.8 Hz), 8.12 (2H, d, J=7.3 Hz), 8.60 (2H, d, 5.9 Hz). FAB mass: 879 (M$^+$).

Inventive Example 40

9β-13-O-[(2R,3S)-3-(tert-Butoxycarbonylamino)-2-hydroxy-3-phenylpropionyl]-10-deacetyl-9-dihydro-9,10-O-[2-(N-thiazolidino)ethylidene]baccatin III Melting point: 114–117° C. (lyophilization from dioxane); $^1$H-NMR (400 MHz, CDCl$_3$/TMS) δ (ppm); 1.26 (3H, s), 1.40 (9H, s), 1.57 (3H, s), 1.62 (3H, br), 1.65 (3H, s), 1.90 (1H, s), 2.02–2.45 (4H, m), 2.32 (3H, s), 2.75–3.24 (7H, m), 3.80 (1H, d, J=7.3 Hz), 4.31 (1H, d, J=8.3 Hz), 4.37 (1H, d, J=8.3 Hz), 4.60–4.70 (2H, m), 5.05 (1H, t, J=4.3 Hz), 5.10 (1H, s), 5.23 (1H, d, J=6.8 Hz), 5.29 (1H, d, J=9.0 Hz), 5.62 (1H, d, J=9.0 Hz), 6.00–6.14 (2H, m), 7.24–7.46 (5H, m), 7.47 (2H, t, J=7.8 Hz), 7.60 (1H, t, J=7.8 Hz), 8.10 (2H, d, J=7.8 Hz). FAB mass: 923 (MH$^+$).

Inventive Example 41

9β-13-O-[(2R,3S)-3-(tert-Butoxycarbonylamino)-2-hydroxy-3-phenylpropionyl]-10-deacetyl-9-dihydro-9,10-O-[2-(4-pyridylmethylamino)ethylidene]baccatin III Melting point: 138–141° C. (lyophilization from dioxane); $^1$H-NMR (400 MHz, CDCl$_3$/TMS) δ (ppm); 1.26 (3H, s), 1.40 (9H, s), 1.58 (3H, s), 1.63 (6H, s), 1.90 (1H, s), 2.01–2.43 (4H, m), 2.30 (3H, s), 2.89 (1H, d, J=4.9 Hz), 2.99 (1H, d, J=4.9 Hz), 3.82 (1H, d, J=7.3 Hz), 3.91 (1H, s), 4.08 (1H, br), 4.31 (1H, d, J=8.8 Hz), 4.38 (1H, d, J=8.8 Hz), 4.58–4.74 (2H, m), 5.00 (1H, t, J=4.9 Hz), 5.10 (1H, s), 5.23 (1H, d, J=7.3 Hz), 5.28 (1H, d, J=9.7 Hz), 5.61 (1H, d, J=9.7Hz), 6.03 (1H, d, J=4.9 Hz), 6.10 (1H, t, J=7.9 Hz), 7.21–7.51 (9H, m), 7.61 (1H, t, J=7.4 Hz), 8.10 (2H, d, J=7.4 Hz), 8.56 (2H, d, J=5.9 Hz). FAB mass: 942 (MH$^+$).

Inventive Example 42

9β-13-O-[(2R,3S)-3-(tert-Butoxycarbonylamino)-2-hydroxy-3-phenylpropionyl]-10-deacetyl-9-dihydro-9,10-O-[2-(2-morpholinoethylamino)ethylidene]baccatin III Melting point: 124–127° C. (lyophilization from dioxane); $^1$H-NMR (400 MHz, CDCl$_3$/TMS) δ (ppm); 1.26 (3H, s), 1.40 (9H, s), 1.57 (3H, s), 1.60 (3H, s), 1.65 (3H, s), 2.02–2.60 (12H, m), 2.30 (3H, s), 2.75–2.87 (2H, m), 2.90 (2H, d, J=4.9 Hz), 2.99 (1H, d, J=4.9 Hz), 3.72 (4H, t, J=4.4 Hz), 3.81 (1H, d, J=7.3 Hz), 4.08 (1H, s), 4.32 (1H, d, J=8.3 Hz), 4.37 (1H, d, J=8.3 Hz), 4.62 (1H, s), 4.98 (1H, t, J=4.9 Hz), 5.10 (1H, s), 5.22 (1H, d, J=7.3 Hz), 5.29 (1H, br d, J=9.3 Hz), 5.62 (1H, br d, J=9.3 Hz), 6.04 (1H, d, J=4.9 Hz), 6.09 (1H, t, J=7.3 Hz), 7.18–7.52 (7H, m), 7.60 (1H, t, J=7.4 Hz), 8.10 (2H, d, J=7.4 Hz). FAB mass: 964 (MH$^+$).

Inventive Example 43

9β-13-O-((2R,3S)-3-(tert-Butoxycarbonylamino)-2-hydroxy-3-phenylpropionyl]-9,10-O-[2-(cyclopropylamino)ethylidene]-10-deacetyl-9-dihydrobaccatin III Melting point: 139–142° C. (lyophilization from dioxane); $^1$H-NMR (400 MHz, CDCl$_3$/TMS) δ (ppm); 0.35–0.54 (4H, m), 1.26 (3H, s), 1.40 (9H, s), 1.57 (3H, s), 1.61 (3H, s), 1.68 (3H, s), 1.89 (1H, br), 2.02–2.44 (5H, m), 2.30 (3H, s), 2.90 (1H, d, J=4.9 Hz), 3.05 (2H, d, J=5.3 Hz), 3.80 (1H, d, J=7.4 Hz), 4.10 (1H, s), 4.32 (1H, d, J=8.3 Hz), 4.38 (1H, d, J=8.3 Hz), 4.62 (1H, s), 4.96 (1H, t, J=5.3 Hz), 5.10 (1H, s), 5.21 (1H, d, J=7.4 Hz), 5.29 (1H, br d, J=8.8 Hz), 5.62 (1H, br d, J=8.8 Hz), 6.00–6.12 (2H, m), 7.19–7.52 (5H, m) 7.60 (1H, t, J=7.8 Hz), 8.10 (2H, d, J=7.8 Hz). FAB mass: 891 (MH$^+$).

Inventive Example 44

9β-13-O-[(2R,3S)-3-(tert-Butoxycarbonylamino)-2-hydroxy-3-phenylpropionyl]-10-deacetyl-9 10-O-[2-(diethylamino)ethylidene]-9-dihydrobaccatin III Melting point: 132–135° C. (lyophilization from dioxane); $^1$H-NMR (400 MHz, CDCl$_3$/TMS) δ (ppm); 1.08 (6H, t, J=7.3 Hz), 1.25 (3H, s), 1.40 (9H, s), 1.60 (3H, s), 1.62 (3H, s), 1.67 (3H, s), 1.88 (1H, s), 1.99–2.43 (4H, m), 2.29 (3H, s), 2.60–2.73 (4H, m), 2.80–2.93 (2H, m), 2.89 (1H, d, J=4.9 Hz), 3.77 (1H, d, J=6.8 Hz), 4.10 (1H, br), 4.32 (1H, d, J=8.8 Hz), 4.37 (1H, d, J=8.8 Hz), 4.58–4.69 (2H, m), 4.97 (1H, br), 5.10 (1H, s), 5.20 (1H, d, J=6.8 Hz), 5.29 (1H, d, J=8.8 Hz), 5.62 (1H, d, J=8.8 Hz), 6.01–6.12 (2H, m), 7.24–7;52 (7H, m), 7.60 (1H, t, J=7.3 Hz), 8.10 (2H, d, J=7.3 Hz). FAB mass: 907 (MH$^+$).

Inventive Example 45

9β-13-O-[(2R,3S)-3-(tert-Butoxycarbonylamino)-2-hydroxy-3-phenylpropionyl]-10-deacetyl-9-dihydro-9,10-O-[2-(2-hydroxyethylamino)ethylidene]baccatin III Melting point: 149–151° C. (lyophilization from dioxane); $^1$H-NMR (400 MHz, CDCl$_3$/TMS) δ (ppm); 1.26 (3H, s), 1.40 (9H, s), 1.57 (3H, s), 1.60 (3H, s), 1.64 (3H, s), 1.89–2.47 (m), 2.30 (3H, s), 2.83–2.96 (3H, m), 3.00 (2H, d, J=4.9 Hz), 3.67 (2H, t, J=4.9 Hz), 3.81 (1H, d, J=7.3 Hz), 4.08 (1H, s), 4.31 (1H, d, J=8.8 Hz), 4.37 (1H, d, J=88z), 4.62 (1H, s), 4.97 (1H, t, J=4.9 Hz), 5.10 (1H, s), 5.22 (1H, d, J=7.3 Hz), 5.28 (1H, d, J=9.8 Hz), 5.64 (1H, d, J=9.8 Hz), 6.04 (1H, d, J=4.9 Hz), 7.21–7.51 (7H, m), 7.60 (1H, t, J=7.3 Hz), 8.10 (2H, d, J=7.3 Hz). FAB mass: 895 (MH$^+$).

Inventive Example 46

9β-9,10-O-[2-(N-Aziridino)ethylidene]-13-O-[(2R,3S)-3-(tert-butoxycarbonylamino)-2-hydroxy-3-phenylpropionyl]-10-deacetyl-9-dihydrobaccatin III $^1$H-NMR (400 MHz, CDCl$_3$/TMS) δ (ppm); 1.35 (3H, s), 1.42 (9H, s), 1.53 (3H, s), 1.68 (3H, s), 1.78 (3H, s), 1.70–2.00 (2H, m), 2.12–2.48 (6H, m), 2.42 (3H, s), 2.48–2.58 (1H, m), 2.64–2.73 (1H, m), 2.96 (1H, d, J=4.5 Hz), 3.86 (1H, d, J=7.0 Hz), 4.03–4.11 (1H, m), 4.31 (1H, d, J=8.3 Hz), 4.41 (1H, d, J=8.3 Hz), 4.65 (1H, d, J=8.5 Hz), 5.03–5.32 (4H, m), 5.40–5.55 (2H, m), 6.01 (1H, d, J=4.5 Hz), 6.14–6.25 (2H, m), 7.20–7.45 (5H, m), 7.49 (2H, t, J=7.5 Hz), 7.60 (1H, t, J=7.5 Hz), 8.14 (2H, d, J=7.5 Hz). FAB mass: 859 (MH$^+$–H2O).

Inventive Example 47

9β-13-O-[3-(tert-Butoxycarbonylamino)-2-hydroxy-2-methyl-3-(4-pyridyl)propionyl]-10-deacetyl-9-dihydro-9,10-O-(isopropylidene)baccatin III Melting point: 170–174° C. (lyophilization from dioxane); $^1$H-NMR (400 MHz, CDCl$_3$/TMS) δ (ppm); 1.30 (s), 1.37 (9H, s), 1.40 (s), 1.43 (s), 1.58 (s), 1.63 (s), 1.68 (s), 2.05 (1H, m), 2.09 (1H, m), 2.21 (1H, m), 2.25 (1H, m), 2.47 (3H, s), 2.90 (1H, d, J=4 Hz), 3.77 (1H, d, J=7 Hz), 4.08 (1H, br), 4.32 (1H, br), 4.38 (2H, s), 4.69 (1H, d, J=8.5 Hz), 5.00 (1H, d, J=10 Hz), 5.11 (1H, br), 5.48 (1H, d, J=7 Hz), 5.78 (1H, d, J=10 Hz), 6.05 (1H, d, J=4 Hz), 6.23 (1H, t), 7.36 (2H, s-d), 7.48 (2H, t, J=7.5 Hz), 7.61 (1H, t, J=7.5 Hz), 8.12 (2H, d, J=7.5 Hz), 8.59 (2H, s-d). FAB mass: 865 (M$^+$).

Inventive Example 48

9β-13-O-[(2R,3S)-3-(tert-Butoxycarbonylamino)-2-hydroxy-3-(4-pyridyl)propionyl]-4,10-dideacetyl-9-dihydro-9,10-O-isopropylidene-4-O-propionylbaccatin III Melting point: 140–147° C. (lyophilization from dioxane); $^1$H-NMR (400 MHz, CDCl$_3$/TMS) δ (ppm); 1.25 (3H, s), 1.33 (3H, t, J=7.8 Hz), 1.41 (9H, s), 1.42 (3H, s), 1.53 (3H, s), 1.63 (3H, s), 1.66 (6H, s), 2.07–2.36 (4H, m), 2.40–2.57 (2H, m), 2.91 (1H, d, J=4.9 Hz), 3.80 (1H, d, J=7.3 Hz), 4.08 (1H, br), 4.38 (2H, ABq, J=15.6 Hz), 4.62 (1H, s), 4.72 (1H, d, J=7.9 Hz), 5.04 (1H, s), 5.28 (1H, d, J=8.5 Hz), 5.52 (1H, d, J=7.3 Hz), 5.70 (1H, d, J=8.5 Hz), 6.07 (2H, br), 7.36 (2H, s), 7.47 (2H, t, J=7.8 Hz), 7.61 (1H, t, J=7.3 Hz), 8.13 (2H, d, J=7.3 Hz), 8.60 (2H, br). FAB mass: 865 (M$^+$).

Inventive Example 49

9β-13-O-[(2R,3R)-3-(tert-Butoxycarbonylamino)-3-(2-furyl)-2-hydroxypropionyl]-4-O-cyclopropanecarbonyl-4,10-dideacetyl-9-dihydro-9,10-O-(2-propenylidene)baccatin III Melting point: 225–228° C. (lyophilization from dioxane); $^1$H-NMR (400 MHz, CDCl$_3$/TMS) δ (ppm); 1.04–1.16 (2H, m), 1.27 (3H, s), 1.41 (9H, s), 1.60 (3H, s), 1.60–1.75 (2H, m), 1.68 (3H, s), 1.74 (3H, s), 1.92 (1H, s), 2.03–2.32 (3H, m), 2.41 (1H, dd, J=14.0 Hz, J=9.6 Hz), 2.92 (1H, d J=4.4 Hz), 3.88 (1H, d, J=7.3 Hz), 3.96–4.14 (2H, m), 4.27 (1H, d, J=8.8 Hz), 4.33 (1H, d, J=8.8 Hz), 4.56 (1H, d, J=7.8 Hz), 4.71 (1H, s like), 5.05 (1H, s like), 5.22 (1H, d, J=5.8 Hz), 5.28 (1H, d, J=7.3 Hz), 5.37 (2H, s like), 5.45 (1H, d, J=10.3 Hz), 5.56 (1H, d, J=17.1 Hz), 5.97–6.15 (3H, m), 6.27–6.40 (2H, m), 7.36 (1H, s like), 7.48 (2H, t, J=7.8 Hz), 7.60 (1H, t, J=7.8 Hz), 8.05 (2H, d, J=7.8 Hz). FAB mass: 864 (MH$^+$).

Inventive Example 50

9β-9,10-O-(2-Aminoethylidene)-13-O-[(2R,3S)-3-(tert-butoxycarbonylamino)-2-hydroxy-3-phenylpropionyl]-10-deacetyl-9-dihydrobaccatin III Melting point: 155–158° C. (lyophilization from dioxane); $^1$H-NMR (400 MHz, CDCl$_3$/TMS) δ (ppm); 1.26 (3H, s), 1.40 (9H, s), 1.58 (3H, s), 1.60 (3H, s), 1.65 (3H, s), 2.00–2.44 (4H, m), 2.30 (3H, s), 2.90 (1H, d, J=4.9 Hz), 3.02 (2H, d, J=4.4 Hz), 3.82 (1H, d, J=7.4 Hz), 4.09 (1H, s like), 4.32 (1H, d, J=8.3 Hz), 4.37 (1H, d, J=8.3 Hz), 4.62 (1H, s like), 4.84 (1H, t, J=4.9 Hz), 5.10 (1H, s), 5.23 (1H, d, J=7.4 Hz), 5.28 (1H, d, J=9.2 Hz), 5.62 (1H, d, J=9.2 Hz), 6.04 (1H, d, J=4.9 Hz), 6.08 (1H, t, J=8.3 Hz), 7.20–7.56 (7H, m), 7.47 (1H, t, J=7.8 Hz), 8.10 (2H, d, J=7.8 Hz). FAB mass: 851 (MH$^+$).

Inventive Example 51

9β-13-O-[(2R,3R)-3-(tert-Butoxycarbonylamino)-3-(2-furyl)-2-hydroxypropionyl]-4-O-cyclopropanecarbonyl-4,10-dideacetyl-9-dihydro-9,10-O-(2-morpholinoethylidene)baccatin III Melting point: 147–148° C. (lyophilization from dioxane); $^1$H-NMR (400 MHz, CDCl$_3$/TMS) δ (ppm); 1.01–1.19 (2H, m), 1.27 (3H, s), 1.41 (9H, s), 1.58 (3H, s), 1.65 (3H, s), 1.72 (3H, s), 1.92 (1H, s), 2.04–2.32 (3H, m), 2.40 (1H, dd, J=15.1 Hz, J=9.2 Hz), 2.52–2.70 (4H, m), 2.74 (1H, dd, J=13.1 Hz, J=4.8 Hz), 2.90 (1H, d, J=4.9 Hz), 3.73 (4H, t like, J=4.9 Hz), 3.81 (1H, d, J=6.8 Hz), 4.06 (1H, br), 4.26 (1H, d, J=8.8 Hz), 4.33 (1H, d, J=8.8 Hz), 4.66 (1H, d, J=8.3 Hz), 4.71 (1H, s), 4.89–5.09 (2H, m), 5.21 (1H, d, J=7.4 Hz), 5.37 (2H, m), 6.01–6.10 (2H, m), 6.29–6.39 (2H, m), 7.36 (1H, s like), 7.48 (2H, t, J=7.8 Hz), 7.60 (1H, t, J=7.8 Hz), 8.05 (2H, d, J=7.8 Hz). FAB mass: 937 (MH$^+$).

Inventive Example 52

9β-13-O-[(2R,3S)-3-(tert-Butoxycarbonylamino)-2-hydroxy-3-phenylpropionyl]-4-O-cyclopropanecarbonyl-4,10-dideacetyl-9-dihydro-9,10-O-(2-propenylidene)baccatin III Melting point: 218–220° C. (lyophilization from dioxane); $^1$H-NMR (400 MHz, CDCl$_3$/TMS) δ (ppm); 1.00–1.10 (2H, m), 1.20–1.45 (2H, m), 1.25 (3H, s), 1.40 (3H, s), 1.50–1.80 (2H, m), 1.58 (3H, s), 1.95 (1H, s), 2.07–2.24 (3H, m), 2.41 (1H, dd, J=15.1 Hz, J=9.8 Hz), 2.88 (1H, d, J=3.9 Hz), 3.86 (1H, d, J=6.9 Hz), 4.08 (1H, br), 4.26 (1H, d, J=8.7 Hz), 4.31 (1H, d, J=8.7 Hz), 4.53 (1H, br d, J=7.9 Hz), 5.04 (1H, s), 5.21 (1H, d, J=6.3 Hz), 5.25–5.33 (2H, m), 5.44 (1H, d, J=10.7 Hz), 5.56 (l1H, d, J=17.0 Hz), 5.609 (1H, d, J=8.8 Hz), 5.96–6.12 (3H, m), 7.24–7.51 (7H, m), 7.60 (1H, t, J=7.3 Hz), 7.60 (1H, t, J=7.3 Hz), 8.03 (2H, d, J=7.3 Hz). FAB mass: 874 (MH$^+$).

Inventive Example 53

9β-13-O-[(2R,3S)-3-(tert-Butoxycarbonylamino)-2-hydroxy-3-phenylpropionyl]-4-O-cyclopropanecarbonyl-4,10-dideacetyl-9-dihydro-9,10-O-(2-morpholinoethylidene)baccatin III Melting point: 146–147° C. (lyophilization from dioxane); $^1$H-NMR (400 MHz, CDCl$_3$/TMS) δ (ppm); 0.96–1.02 (2H, m), 1.24 (3H, s), 1.18 1.40 (2H, m), 1.40 (9H, s), 1.57 (6H, s), 1.64 (3H, s), 1.90–2.15 (4H, m), 2.30–2.98 (8H, m), 3.61–3.83 (5H, m), 4.06 (1H, br), 4.26 (1H, d, J=8.3 Hz), 4.31 (1H, d, J=8.3 Hz), 4.50–4.74 (2H, m), 4.92–5.03 (2H, m), 5.20 (1H, d, J=6.4 Hz), 5.27 (1H, d, J=9.3 Hz), 5.68 (1H, d, J=9.3 Hz), 5.89–6.15 (2H, m), 7.17–7.52 (7H, m), 7.60 (1H, t, J=7.3 Hz), 8.03 (2H, d, J=7.3 Hz). FAB mass: 947 (MH$^+$).

Inventive Example 54

9β-13-O-[3-(tert-Butoxycarbonylamino)-2-hydroxy-2-methyl-3-(4-pyridyl)propionyl]-4-O-butanoyl-4,10-dideacetyl-9-dihydro-9,10-O-isopropylidenebaccatin III Melting point: 160–163° C. (lyophilization from dioxane); $^1$H-NMR (400 MHz, CDCl$_3$/TMS) δ (ppm); 1.11

(3H, t, J=7.5 Hz), 1.29 (s), 1.37 (9H, s), 1.40 (s), 1.42 (s), 1.58 (s), 1.64 (s), 1.67 (s), 1.92 (1H, m), 2.07 (2H, m), 2.24 (2H, m), 2.56 (1H, m), 2.71 (1H, m), 2.92 (1H, s-d), 3.77 (1H, d, J=7 Hz), 4.08 (1H, br), 4.30 (1H, br), 4.38 (2H, s), 4.71 (1H, d, J=8 Hz), 5.00 (1H, d, J=10 Hz), 5.06 (1H, br), 5.48 (1H, d, J=7 Hz), 5.80 (1H, d, J=10 Hz), 6.06 (1H, s-d), 6.20 (1H, t-br), 7.37 (2H, d, J=5 Hz), 7.48 (2H, t, J=7.5 Hz), 7.61 (1H, t, J=7.5 Hz), 8.14 (2H, d, J=7.5 Hz), 8.59 (2H, d, J=5 Hz). FAB mass: 893 ($M^+$).

Inventive Example 55

9β-13-O-[(2R,3S)-3-(tert-Butoxycarbonylamino)-2-hydroxy-3-(4-pyridyl)propionyl]-4-O-cyclopropanecarbonyl-4,10-dideacetyl-9-dihydro-9,10-O-isopropylidenebaccatin III Melting point: 128–134° C. (lyophilization from dioxane); $^1$H-NMR (400 MHz, CDCl$_3$/TMS) δ (ppm); 1.23 (3H, s), 1.26 (4H, s), 1.41 (3H, s), 1.42 (3H, s), 1.48 (9H, s), 1.53 (3H, s), 1.60 (3H, s), 1.66 (3H, s), 1.92–2.37 (5H, m), 2.88 (1H, d, J=5.3 Hz), 3.76 (1H, d, J=7.3 Hz), 4.06 (1H, m), 4.30 (2H, s), 4.60 (1H, br), 4.68 (1H, d, J=8.3 Hz), 5.06 (1H, s), 5.27 (1H, d, J=8.0 Hz), 5.54 (1H, d, J=7.3 Hz), 5.89 (1H, d, J=8.0 Hz), 6.01 (1H, t, J=7.3 Hz), 6.08 (1H, d, J=5.3 Hz), 7.37 (2H, br), 7.48 (2H, t, J=7.8 Hz), 7.61 (1H, t, J=7.3 Hz), 8.03 (2H, d, J=7.3 Hz), 8.59 (2H, br). FAB mass: 877 ($MH^+$).

Inventive Example 56

9β-13-O-[3-(tert-Butoxycarbonylamino)-3-(2-furyl)-2-hydroxy-2-methylpropionyl]-4-O-cyclopropanecarbonyl-4,10-dideacetyl-9-dihydro-9,10-O-(2-propenylidene)baccatin III Melting point: 230–233° C. (lyophilization from dioxane); $^1$H-NMR (400 MHz, CDCl$_3$/TMS.) δ (ppm); 1.20–1.80 (4H, m), 1.31 (3H, s), 1.37 (9H, s), 1.45 (3H, s), 1.60 (3H, s), 1.69 (3H, s), 1.89–2.02 (2H, m), 2.92 (1H, d, J=3.9 Hz), 3.86 (1H, d, J=7.3 Hz), 4.05–4.13 (1H, m), 4.22 (1H, br s), 4.29 (1H, d, J=8.3 Hz), 4.33 (1H, d, J=8.3 Hz), 4.61 (1H, d, J=7.9 Hz), 5.07 (1H, s like), 5.16–5.29 (3H, m), 5.44 (1H, d, J=10.8 Hz), 5.50 (1H, d, J=9.7 Hz), 5.56 (1H, d, J=17.1 Hz), 5.98–6.10 (1H, m), 6.08 (1H, d, J=3.9 Hz), 6.20 (1H, t, J=8.0 Hz), 6.30 (1H, d, J=3.5 Hz), 6.35 (1H, m), 7.36 (1H, s like), 7.49 (2H, t, J=7.4 Hz), 7.61 (1H, t, J=7.4 Hz), 8.06 (2H, d, J=7.4 Hz). FAB mass: 878 ($MH^+$).

Inventive Example 57

9β-13-O-[3-(tert-Butoxycarbonylamino)-3-(2-furyl)-2-hydroxy-2-methylpropionyl]-4-O-cyclopropanecarbonyl-4,10-dideacetyl-9-dihydro-9,10-O-(2-morpholinoethylidene)baccatin III Melting point: 140–143° C. (lyophilization from dioxane); $^1$H-NMR (400 MHz, CDCl$_3$/TMS) δ (ppm); 1.10–1.82 (4H, m), 1.31 (3H, s), 1.37 (9H, s), 1.58 (3H, s), 1.66 (6H, s), 1.67 (3H, s), 1.90–2.03 (1H, m), 1.92 (1H, s), 2.04–2.36 (4H, m), 2.50–2.70 (4H, m), 2.74 (1H, dd, J=13.6 Hz, J=5.3 Hz), 2.82 (1H, dd, J=13.6 Hz, J=3.4 Hz), 2.90 (1H, d, J=3.9 Hz), 3.73 (4H, t, J=4.8 Hz), 3.78 (1H, d, J=7.3 Hz), 4.02–4.10 (1H, m), 4.18 (1H, br), 4.28 (1H, d, J=8.8 Hz), 4.34 (1H, d, J=8.8 Hz), 4.69 (1H, d, J=8.3 Hz), 5.02 (1H, t, J=4.9 Hz), 5.07 (1H, s), 5.15–5.26 (2H, m), 5.48 (1H, d, J=9.8 Hz), 6.06 (1H, d, J=3.9 Hz), 6.19 (1H, t, J=8.3 Hz), 6.30 (1H, d, J=3.0 Hz), 6.35 (1H, dd, J=3.0 Hz, J=2.9 Hz), 7.36 (1H, d, J=2.9 Hz), 7.49 (2H, t, J=7.8 Hz), 7.61 (1H, t, J=7.8 Hz), 8.06 (2H, d, J=7.8 Hz). FAB mass: 951 ($MH^+$).

Inventive Example 58

9β-13-O-[(2R,3S)-3-(tert-Butoxycarbonylamino)-2-hydroxy-3-(4-pyridyl)propionyl]-4-O-cyclopropanecarbonyl-4,10-dideacetyl-9-dihydro-9,10-O-(2-propenylidene)baccatin III Melting point: 156–157° C. (lyophilization from dioxane); $^1$H-NMR (400 MHz, CDCl$^3$/TMS) δ (ppm); 1.04–1.16 (2H, m), 1.20–1.80 (2H, m), 1.23 (3H, s), 1.41 (9H, s), 1.63 (6H, s), 1.67 (3H, s), 1.95–2.28 (4H, m), 2.36–2.47 (1H, m), 2.87 (1H, d, J=4.4 Hz), 3.85 (1H, d, J=7.2 Hz), 4.08 (1H, br), 4.27 (1H, d, J=8.8 Hz), 4.30 (1H, d, J=8.8 Hz), 4.47–4.65 (2H, m), 5.05 (1H, s like), 5.21 (1H, d, J=5.8 Hz), 5.23–5.34 (2H, m), 5.45 (1H, d, J=10.3 Hz), 5.56 (1H, d, J=17.2 Hz), 5.79 (1H, d, J=9.8 Hz), 6.00–6.12 (3H, m), 7.35 (2H, d, J=5.8 Hz), 7.47 (2H, t, J=7.8 Hz), 7.60 (1H, t, J=7.8 Hz), 8.02 (2H, d, J=7.8 Hz), 8.57 (2H, d, J=5.8 Hz). FAB mass 875 ($MH^+$).

Inventive Example 59

9β-13-O-[(2R,3S)-3-(tert-Butoxycarbonylamino)-2-hydroxy-(4-pyridyl)propionyl]-10-deacetyl-7-deoxy-9-dihydro-9,10-O-isopropylidenebaccatin III Melting point: 162.5–167.5° C. (lyophilization from dioxane); $^1$H-NMR (400 MHz, CDCl$_3$/TMS) δ (ppm); 1.23 (3H, s), 1.43 (9H, s), 1.51 (3H, s), 1.55 (3H, s), 1.57 (3H, s), 1.61 (3H, s), 1.71 (3H, s), 1.60–2.10 (5H, m), 1.97 (1H, s), 2.28 (3H, s), 2.34 (1H, dd, J=10.2, 15.1 Hz), 2.91 (1H, d, J=4.9 Hz), 4.12 (1H, d, J=7.1 Hz), 4.27 (1H, d, J=8.3 Hz), 4.32 (1H, d, J=8.3 Hz), 4.63 (1H, br s), 4.82 (1H, br s), 4.93 (1H, br s), 5.30 (1H, d, J=9.1 Hz), 5.56 (1H, d, J=7.1 Hz), 5.81 (1H, d, J=9.1 Hz), 6.00 (1H, d, J=4.9 Hz), 6.09 (1H, br t, J=7.8 Hz), 7.36 (2H, d, J=5.9 Hz), 7.47 (2H, t, J=7.3 Hz), 7.60 (1H, t, J=7.3 Hz), 8.12 (2H, d, J=7.3 Hz), 8.59 (2H, d, J=5.9 Hz).

Inventive Example 60

9β-13-O-[3-(tert-Butoxycarbonylamino)-2-hydroxy-2-methyl-3-(4-pyridyl)propionyl]-4-O-cyclopropanecarbonyl-4,10-dideacetyl-9-dihydro-9,10-O-isopropylidenebaccatin III Melting point: 152–158° C. (lyophilization from dioxane); $^1$H-NMR (400 MHz, CDCl$_3$/TMS) δ (ppm); 1.16 (4H, m), 1.28 (3H, s), 1.39 (9H, s), 1.40 (3H, s), 1.42 (3H, s), 1.58 (3H, s), 1.60 (3H, s), 1.67 (3H, s), 1.83–2.36 (5H, m), 2.89 (1H, d, J=3.9 Hz), 3.74 (1H, d, J=7.3 Hz), 4.07 (1H, m), 4.32 (2H, s), 4.70 (1H, d, J=8.3 Hz), 5.00 (1H, d, J=10.3 Hz), 5.07 (1H, s), 5.49 (1H, d, J=6.8 Hz), 5.87 (1H, d, J=9.8 Hz), 6.08 (1H, d, J=4.4 Hz), 6.20 (1H, m), 7.38 (2H, d, J=5.9 Hz), 7.49 (2H, t, J=7.8 Hz), 7.62 (1H, t, J=7.3 Hz), 8.04 (2H, d, J=7.3 Hz), 8.57 (2H, d, J=5.4 Hz). FAB mass: 891 ($MH^+$).

Inventive Example 61

9β-13-O-[(2R,3S)-3-(tert-Butoxycarbonylamino)-2-hydroxy-3-phenylpropionyl]-4-O-cyclopropanecarbonyl-4,10-dideacetyl-7-deoxy-9-dihydro-9,10-O-(2-propenylidene)baccatin III Melting point: 130–133° C. (lyophilization from dioxane); $^1$H-NMR (400 MHz, CDCl$_3$/TMS) δ (ppm); 1.00–1.10 (2H, m), 1.20–1.40 (2H, m), 1.24 (3H, s), 1.41 (9H, s), 1.45 (3H, s), 1.62 (3H, s), 1.62–2.10 (6H, m), 2.01 (3H, s), 2.38 (1H, dd, J=14.7 Hz, J=8.8 Hz), 2.89 (1H, d, J=4.4 Hz), 4.14 (1H, d, J=7.0 Hz), 4.18 (1H, d, J=8.8 Hz), 4.27 (1H, d, J=8.8 Hz), 4.60 (1H, br s), 4.65 (1H, br s), 4.87 (1H, s), 5.23 (1H, d, J=5.9 Hz), 5.20–5.20 (1H, m), 5.29 (1H, d, J=5.9 Hz), 5.46 (1H, d, J=10.7 Hz), 5.57 (1H, d, J=17.6 Hz), 5.74 (1H, d, J=9.8 Hz), 5.95–6.08 (3H, m), 7.29 (1H, d, J=7.3 Hz), 7.34 (2H, t, J=7.3 Hz), 7.42 (2H, d, J=7.3 Hz), 7.47 (2H, t, J=7.3 Hz), 7.60 (1H, t, J=7.3 Hz), 8.04 (2H, d, J=7.3 Hz). FAB mass: 858 (MH$^+$).

Inventive Example 62

9β-13-O-[(2R,3R)-3-(tert-Butoxycarbonylamino)-3-(2-furyl)-2-hydroxypropionyl]-4-O-cyclopropanecarbonyl-4,10-dideacetyl-7-deoxy-9-dihydro-9,10-O-(2-propenylidene)baccatin III Melting point: 132–135° C. (lyophilization from dioxane); $^1$H-NMR (400 MHz, CDCl$_3$/TMS) δ (ppm); 1.03–1.13 (2H, m), 1.25 (3H, s), 1.30–1.50 (2H, m), 1.41 (9H, s), 1.46 (3H, s), 1.63 (3H, s), 1.71–1.95 (5H, m), 1.78 (3H, br s), 2.01–2.21 (2H, m), 2.40 (1H, dd, J=15.1 Hz, J=9.8 Hz), 2.91 (1H, d, J=4.9 Hz), 4.14–4.22 (2H, m), 4.29 (1H, d, J=8.3 Hz), 4.33 (1H, br s), 4.71 (1H, s), 4.87 (1H, s), 5.24 (1H, d, J=6.3 Hz), 5.31 (1H, d, J=6.8 Hz), 5.37 (1H, br d, J=9.8 Hz), 5.44 (1H, br d, J=9.8 Hz), 5.46 (1H, d, J=10.8 Hz), 5.57 (1H, d, J=17.1 Hz), 5.93–6.10 (3H, m), 6.31 (1H, d, J=2.9 Hz), 6.34 (1H, dd, J=2.9 Hz, J=1.9 Hz), 7.36 (1H, s like), 7.48 (2H, t, J=7.4 Hz), 7.61 (1H, t, J=7.43 Hz), 8.06 (2H, d, J=7.4 Hz). FAB mass: 848 (MH$^+$).

Inventive Example 63

9β-13-O-[(2R,3S)-3-(tert-Butoxycarbonylamino)-2-hydroxy-3-phenylpropionyl]-4-O-cyclopropanecarbonyl-4,10-dideacetyl-7-deoxy-9-dihydro-9,10-O-(2-morpholinoethylidene)baccatin III Melting point: 118–121° C. (lyophilization from dioxane); $^1$H-NMR (400 MHz, CDCl$_3$/TMS) δ (ppm); 1.00–1.09 (2H, m), 1.24 (3H, s), 1.20–1.40 (2H, m), 1.40 (9H, s), 1.43 (3H, s), 1.50–2.21 (6H, m), 1.55–1.62 (6H, m), 2.39 (1H, dd, J=14.5 Hz, J=10.2 Hz), 2.53–2.82 (5H, m), 2.86 (1H, D, J=3.9 Hz), 3.74 (4H, t, J=4.9 Hz), 4.08 (1H, d, J=7.3 Hz), 4.18 (1H, d, J=8.8 Hz), 4.26 (1H, d, J=8.8 Hz), 4.61 (1H, br), 4.86 (1H, br s), 5.04 (1H, dd, J=4.4 Hz, J=3.4 Hz), 5.23 (1H, d, J=7.3 Hz), 5.29 (1H, d, J=8.3 Hz), 5.73 (1H, d, J=8.3 Hz), 5.95–6.06 (2H, m), 7.21–7.30 (1H, ), 7.41 (2H, d, J=7.3 Hz), 7.47 (2H, t, J=7.3 Hz), 7.60 (1H, t, J=7.3 Hz), 8.04 (2H, d, J=7.3 Hz). FAB mass: 931 (MH$^+$).

Inventive Example 64

9β-13-O-[(2R,3R)-3-(tert-Butoxycarbonylamino)-3-(2-furyl)-2-hydroxypropionyl]-4-O-cyclopropanecarbonyl-4,10-dideacetyl-7-deoxy-9-dihydro-9,10-O-(2-morpholinoethylidene)baccatin III Melting point: 129–132° C. (lyophilization from dioxane); $^1$H-NMR (400 MHz, CDCl$_3$/TMS) δ (ppm); 1.02–1.12 (2H, m), 1.26 (3H, s), 1.34–1.49 (2H, m), 1.41 (9H, s), 1.60 (6H, s), 1.70–2.21 (6H, m), 1.76. (3H, s) 2.39 (1H, dd, J=15.2 Hz, J=9.7 Hz), 2.53–2.82 (6H, m), 2.90 (1H, d, J=4.8 Hz), 3.74 (4H, t, J=4.4 Hz), 4.11 (1H, d, J=7.3 Hz), 4.18 (1H, d, J=8.8 Hz), 4.29 (1H, d, J=8.8 Hz), 4.71 (1H, s), 4,86 (1H, br s), 5.04 (1H, t like, J=5.4 Hz), 5.24 (1H, d, J=7.3 Hz), 5.37 (1H, d, J=8.8 Hz), 5.44 (1H, d, J=8.8 Hz), 5.98–6.09 (2H, m), 6.31 (1H, d, J=2.9 Hz), 6.34 (1H, dd, J=2.9 Hz, J=1.4 Hz), 7.36 (1H, d, J=1.4 Hz), 7.48 (2H, t, J=7.8 Hz), 7.61 (1H, t, J=7.8 Hz), 8.06 (2H, d, J=7.8 Hz). FAB mass: 921 (MH$^+$).

Inventive Example 65

9β-13-O-[3-(tert-Butoxycarbonylamino)-2-hydroxy-2-methyl-3-(4-pyridyl)propionyl]-4-O-cyclopropanecarbonyl-4,10-dideacetyl-7-deoxy-9-dihydro-9,10-O-isopropylidenebaccatin III Melting point: 160–163° C. (lyophilization from dioxane); $^1$H-NMR (400 MHz, CDCl$_3$/TMS) δ (ppm); 1.00–2.30 (11H, m), 1.26 (3H, s), 1.38 (9H, s), 1.42 (3H, s), 1.46 (6H, s), 1.56 (3H, s), 1.61 (6H, s), 2.91 (1H, d, J=4.0 Hz), 4.10 (1H, d, J=7.3 Hz), 4.22 (1H, d, J=8.8 Hz), 4.27 (1H, d, J=8.8 Hz), 4.80–4.90 (2H, m), 5.00 (1H, d, J=9.8 Hz), 5.52 (1H, d, J=7.3 Hz), 5.90 (1H, d, J=9.8 Hz), 6.01 (1H, d, J=4.0 Hz), 6.15–6.25 (1H, m), 7.36 (2H, d, J=5.3 Hz), 7.48 (2H, t, J=7.3 Hz), 7.61 (1H, t, J=7.3 Hz), 8.05 (2H, d, J=7.3 Hz), 8.56 (2H, d, J=5.3 Hz). FAB mass: 875 (MH$^+$).

Inventive Example 66

9β-13-O-[3-(tert-Butoxycarbonylamino)-2-hydroxy-2-methyl-3-(2-pyridyl)propionyl]-4-O-cyclopropanecarbonyl-4,10-dideacetyl-9-dihydro-9,10-O-isopropylidenebaccatin III Melting point: 151–153° C. (lyophilization from dioxane); $^1$H-NMR (400 MHz, CDCl$_3$/TMS) δ (ppm); 1.15 (4H, m), 1.30 (3H, s), 1.39 (3H, s), 1.42 (9H, s), 1.51 (3H, s), 1.57 (6H, s), 1.63 (3H, s), 1.66 (3H, s), 2.09–2.42 (5H, m), 2.92 (1H, d, J=4.9 Hz), 3.82 (1H, m), 4.04 (1H, m), 4.34 (2H, ABq, J=7.8 Hz), 4.76 (1H, d, J=8.3 Hz), 5.10 (1H, s), 5.11 (1H, d, J=10.3 Hz), 5.48 (1H, d, J=7.3 Hz), 6.04 (1H, d, J=4.9 Hz), 6.16 (1H, t, J=8.3 Hz), 7.23 (1H, t, J=4.4 Hz), 7.42 (1H, d, J=7.8 Hz), 7.49 (2H, t, J=7.8 Hz), 7.61 (1H, t, J=7.3 Hz), 7.72 (1H, t, J=6.8 Hz), 8.07 (2H, d, J=7.3 Hz), 8.46 (1H, d, J=4.4 Hz). FAB mass 891 (MH$^+$).

Inventive Example 67

9β-13-O-[ (2R,3R)-3-(tert-Butoxycarbonylamino)-3-(2-furyl)-2-hydroxypropionyl]-10-deacetyl-7-deoxy-9,10-O-ethylidene-9-dihydrobaccatin III Melting point: 104–106° C. (lyophilization from dioxane); $^1$H-NMR (400 MHz, CDCl$_3$/TMS) δ (ppm); 1.20–2.10 (5H, m), 1.25 (3H, s), 1.42 (9H, s), 1.49 (3H, d, J=4.8 Hz), 1.50 (3H, s), 1.62 (3H, s), 1.74 (3H, s), 2.30–2.50 (1H, m), 2.32 (3H, s), 2.93 (1H, d, J=4.8 Hz), 4.12 (1H, d, J=7.4 Hz), 4.24 (1H, d, J=8.8 Hz), 4.29 (1H, br), 4.33 (1H, d, J=8.8 Hz), 4.72 (1H, d, J=2.0 Hz), 4.92 (1H, s), 5.06 (1H, q, J=4.8 Hz), 5.25 (1H, d, J=8.3 Hz), 5.39 (1H, d, J=10.0 Hz), 5.44 (1H, d, J=10.0 Hz), 6.01 (1H, d, J=4.8 Hz), 6.05–6.20 (1H, m), 6.31 (1H, d, J=2.9 Hz), 6.35 (1H, dd, J=2.9 Hz, J=1.9 Hz), 7.22 (1H, s like), 7.47 (2H, t, J=7.8 Hz), 7.59 (1H, t, J=7.8 Hz), 8.13 (2H, d, J=7.8 Hz). FAB mass: 810 (MH$^+$).

Inventive Example 68

9β-13-O-[(2R,3S)-3-(tert-Butoxycarbonylamino)-2-hydroxy-3-phenylpropionyl]-10-deacetyl-7-deoxy-9-dihydro-9,10-O-(2-propenylidene)baccatin III Melting point: 140–143° C. (lyophilization from dioxane); $^1$H-NMR (400 MHz, CDCl$_3$/TMS) δ (ppm); 1.20–2.20 (5H, m), 1.25 (3H, s), 1.41 (9H, s), 1.48 (3H, s), 1.63 (3H, s), 2.27 (3H, s), 2.37 (1H, dd, J=1.51 Hz, J=5.3

Hz), 2.90 (1H, d, J=4.4 Hz), 4.15 (1H, d, J=7.3 Hz), 4.23 (1H, d, J=8.3 Hz), 4.31 (1H, d, J=8.3 Hz), 4.50 (1H, s like), 4.62 (1H, s like), 4.91 (1H, s), 5.20–5.40 (2H, m), 5.23 (1H, d, J=5.9 Hz), 5.46 (1H, d, J=10.2 Hz), 5.57 (1H, d, J=17.6 Hz), 5.71 (1H, d, J=9.8 Hz), 5.90–6.20 (3H, m), 7.20–7.50 (7H, m), 7.60 (1H, t, J=7.9 Hz), 8.11 (2H, d, J=7.9 Hz). FAB mass: 832 (MH$^+$).

Inventive Example 69

9β-13-O-[(2R,3S)-3-(tert-Butoxycarbonylamino)-2-hydroxy-3-(2-pyridyl)propionyl]-4-O-cyclopropanecarbonyl-4,10-dideacetyl-9-dihydro-9,10-O-isopropylidenebaccatin III Melting point: 138–141° C. (lyophilization from dioxane); $^1$H-NMR (400 MHz, CDCl$_3$/TMS) δ (ppm); 1.23–1.29 (4H, m), 1.27 (3H, s), 1.39 (9H, s), 1.41 (3H, s), 1.58 (3H, s), 1.63 (3H, s), 1.66 (3H, s), 1.74 (3H, s), 1.85 (1H, s), 1.98–2.39 (5H, m), 2.94 (1H, d, J=4.9 Hz), 3.84 (1H, d, J=7.3 Hz), 4.06 (1H, m), 4.30 (2H, ABq, J=8.3 Hz), 4.55 (1H, br), 4.79 (1H, d, J=8.3 Hz), 4.88 (1H, s), 5.07 (1H, s), 5.34 (1H, d, J=9.3 Hz), 5.55 (1H, d, J=6.8 Hz), 5.83 (1H, d, J=9.8 Hz), 6.05 (2H, m), 7.22 (1H, dd, J=7.3 Hz, 4.9 Hz), 7.41 (1H, d, J=7.8 Hz), 7.47 (2H, t, J=7.8 Hz), 7.60 (1H, t, J=7.3 Hz), 7.71 (1H, t, J=6.4 Hz), 8.05 (2H, d, J=6.8 Hz), 8.50 (1H, d, J=4.4 Hz). FAB mass: 877 (MH$^+$).

Inventive Example 70

9β-13-O-[(2R,3S)-3-(tert-Butoxycarbonylamino)-2-hydroxy-3-(4-pyridyl)propionyl]-4-O-cyclopropanecarbonyl-4,10-dideacetyl-7-deoxy-9-dihydro-9,10-O-isopropylidenebaccatin III Melting point: 155–157° C. (lyophilization from dioxane); $^1$H-NMR (400 MHz, CDCl$_3$/TMS) δ (ppm); 1.00–1.20 (2H, m), 1.20–1.50 (2H, m), 1.22 (3H, s), 1.43 (9H, s), 1.47 (3H, s), 1.50–2.10 (6H, m), 1.56 (6H, s), 1.60 (6H, s), 2.35 (1H, t like, J=10.8 Hz), 2.87 (1H, d, J=4.4 Hz); 4.11 (1H, d, J=7.4 Hz), 4.20 (1H, d, J=8.8 Hz), 4.27 (1H, d, J=8,8 Hz), 4.59 (1H, s), 4.87 (1H, s), 5.28 (1H, d, J=8.8 Hz), 5.56 (1H, d, J=7.4 Hz), 5.84 (1H, d, J=8.8 Hz), 5.95–6.10 (2H, m), 7.36 (2H, d, J=5.9 Hz), 7.47 (2H, t, J=7.8 Hz), 7.61 (1H, t, J=7.8 Hz), 8.04 (2H, d, J=7.8 Hz), 8.58 (2H, d, J=5.9 Hz). FAB mass: 861 (MH$^+$).

Inventive Example 71

7α,9β-13-O-[(2R,3S)-3-(tert-Butoxycarbonylamino)-2-hydroxy-3-3-phenylpropionyl]-10-deacetyl-7-deoxy-9-dihydro-7-fluoro-9,10-O-(2-morpholinoethylidene)baccatin III Melting point: 139–142.5° C. (lyophilization from dioxane); $^1$H-NMR (400 MHz, CDCl$_3$/TMS) δ (ppm); 1.17 (3H, s), 1.40 (9H, s), 1.58 (3H, s), 1.63 (6H, s), 1.82 (1H, s), 2.08–2.35 (2H, m), 2.28 (3H, s), 2.37 (1H, dd, J=9.8, 15.1 Hz), 2.40–2.55 (1H, m), 2.55–2.67 (4H, m), 2.85 (1H, dd, J=4.4, 13.7 Hz), 2.89 (1H, dd, J=4.4, 13.7 Hz), 3.48 (1H, d, J=5.2 Hz), 3.74 (4H, t, J=4.6 Hz), 4.10–4.28 (1H, br), 4.18 (1H, d, J=8.3 Hz), 4.25 (1H, d, J=8.3 Hz), 4.38 (1H, d, J=8.3 Hz), 4.61 (1H, br s), 4.75 (1H, br d, J=46.4 Hz), 4.91 (1H, t, J=4.4 Hz), 4.95 (1H, br d, J=5.9 Hz), 5.31 (1H, br d, J=9.1 Hz), 5.37 (1H, d, J=8.3 Hz), 5.66 (1H, br d, J=9.1 Hz), 5.90 (1H, d, J=5.2 Hz), 6.07 (1H, br t, J=8.3 Hz), 7.28 (1H, t, J=7.3 Hz), 7.35 (2H, t, J=7.3 Hz), 7.41 (2H, t, J=7.3 Hz), 7.48 (2H, t, J=7.8 Hz), 7.61 (1H, t, J=7.8 Hz), 8.09 (2H, d, J=7.8 Hz). FAB mass: 923 (MH$^+$).

Inventive Example 72

7α,9β-13-O-[(2R,3S)-3-(tert-Butoxycarbonylamino)-2-hydroxy-3-(4-pyridyl)propionyl]-10-deacetyl-7-deoxy-9-dihydro-7-fluoro-9,10-O-isopropylidenebaccatin III Melting point: 154–158° C. (lyophilization from dioxane); $^1$H-NMR (400 MHz, CDCl$_3$/TMS) δ (ppm); 1.19 (3H, s), 1.41 (9H, s), 1.42 (3H, s), 1.56 (3H, s), 1.61 (3H, s), 1.62 (3H, s), 1.63 (3H, s), 1.87 (1H, s), 2.32 (3H, s), 2.08–2.47 (4H, m), 3.46 (1H, d, J=5.4 Hz), 4.28–4.40 (1H, br), 4.31 (1H, d, J=8.5 Hz), 4.36 (1H, d, J=8.5 Hz), 4.59 (1H, d, J=8.6 Hz), 4.63 (1H, br s), 4.87 (1H, ddd, J=3.9, 7.8, 45.9 Hz), 4.93–4.97 (1H, m), 5.31 (1H, br d, J=9.6 Hz), 5.52 (1H, d, J=8.6 Hz), 5.69 (1H, br d, J=9.6 Hz), 5.92 (1H, d, J=5.4 Hz), 6.12 (1H, br t, J=8.3 Hz), 7.35 (2H, d, J=6.2 Hz), 7.48 (2H, t, J=7.6 Hz), 7.62 (1H, t, J=7.6 Hz), 8.10 (2H, d, J=7.6 Hz), 8.60 (2H, d, J=6.2 Hz). FAB mass: 853 (MH$^+$).

Inventive Example 73

7α,9β-13-O-[(2R,3R)-3-(tert-Butoxycarbonylamino)-3-(2-furyl)-2-hydroxypropionyl]-10-deacetyl-7-deoxy-9-dihydro-7-fluoro-9,10-O-(2-morpholinoethylidene)baccatin III Melting point: 134–138.5° C. (lyophilization from dioxane); $^1$H-NMR (400 MHz, CDCl$_3$/TMS) δ (ppm); 1.19 (3H, s), 1.41 (9H, s), 1.57 (3H, s), 1.63 (3H, s), 1.72 (3H, s), 1.81 (1H, s), 2.10–2.50 (4H, m), 2.33 (3H, s), 2.50–2.75 (4H, m), 2.82–2.93 (2H, m), 3.49 (1H, d, J=5.2 Hz), 3.75 (4H, t, J=4.6 Hz), 4.00 (1H, br s), 4.21 (1H, br d, J=8.8 Hz), 4.26 (1H, d, J=8.3 Hz), 4.49 (1H, d, J=8.3 Hz), 4.71 (1H, br s), 4.76 (1H, br d, J=46.5 Hz), 4.91 (1H, t, J=4.2 Hz), 4.96 (1H, br d, J=6.4 Hz), 5.33–5.42 (3H, m), 5.91 (1H, d, J=5.2 Hz), 6.10 (1H, br t, J=8.3 Hz), 6.32 (1H, d, J=2.9 Hz), 6.34–6.38 (1H, m), 7.38 (1H, br s), 7.49 (2H, t, J=7.3 Hz), 7.61 (1H, t, J=7.3 Hz), 8.10 (2H, d, J=7.3 Hz). FAB mass: 913 (MH$^+$).

Inventive Example 74

9β-13-O-[(2R,3S)-3-(tert-Butoxycarbonylamino)-2-hydroxy-3-phenylpropionyl]-10-deacetyl-7-deoxy-9-dihydro-9,10-O-(2-morpholinoethylidene)baccatin III Melting point: 146–149° C. (lyophilization from dioxane); $^1$H-NMR (400 MHz, CDCl$_3$/TMS) δ (ppm); 1.24 (3H, s), 1.40 (9H, s) 1.46 (3H, s), 1.59 (3H, s), 1.60–2.10 (5H, m), 2.27 (3H, s), 2.30–2.45 (1H, m), 2.58–2.94 (6H, m), 2.90 (1H, d, J=4.4 Hz), 3.74 (4H, t, J=4.8 Hz), 4.09 (1H, d, J=7.4 Hz), 4.23 (1H, d, J=8.8 Hz), 4.31 (1H, d, J=8.8 Hz), 4.50 (1H, br), 4.62 (1H, s), 4.91 (1H, s), 5.04 (1H, t, J=3.9 Hz), 5.22 (1H, d, J=7.4 Hz), 5.31 (1H, d, J=9.3 Hz), 5.70 (1H, d, J=9.3 Hz), 6.05 (1H, d, J=4.4 Hz), 6.05–6.18 (1H, m), 7.20–7.48 (7H, m), 7.60 (1H, t, J=7.3 Hz), 8.11 (2H, d, J=7.3 Hz). FAB mass: 905 (MH$^+$).

Inventive Example 75

9β-13-O-[(2R,3S)-3-(tert-Butoxycarbonylamino)-2-hydroxy-3-(4-pyridyl)propionyl]-10-deacetyl-7-deoxy-9,10-O-ethylidene-9-dihydrobaccatin III Melting point: 120–122° C. (lyophilization from dioxane); $^1$H-NMR (400 MHz, CDCl$_3$/TMS) δ (ppm); 1.10–2.10 (5H, m), 1.23 (3H, s), 1.25 (3H, s), 1.42 (9H, s), 1.49 (3H, d, J=5.3 Hz), 1.57 (3H, s), 1.61 (3H, s), 2.20–2.40 (1H, m), 2.26 (3H, s), 2.90 (1H, d, J=4.9 Hz), 4.08 (1H, d, J=7.3 Hz), 4.25 (1H, d, J=8.8 Hz), 4.32 (1H, d, J=8.8 Hz), 4.62 (1H, s), 4.80–5.00 (2H, m), 5.06 (1H, q, J=5.3 Hz), 5.22 (1H, d, J=7.3 Hz), 5.32 (1H, d like, J=9.3 Hz), 5.79 (1H, d like, J=9.3 Hz), 6.03 (1H, d, J=4.9 Hz), 6.05–6.20 (1H, m), 7.38 (2H, d, J=4.8 Hz), 7.47 (2H, t, J=7.8 Hz), 7.60 (1H, t, J=7.8 Hz), 8.11 (2H, d, J=7.8 Hz), 8.61 (2H, d, J=4.8 Hz). FAB mass: 821 (MH$^+$).

Inventive Example 76

9β-13-O-(3-(tert-Butoxycarbonylamino)-2-ethyl-2-hydroxy-3-(4-pyridyl)propionyl]-4-O-cyclopropanecarbonyl-4,10-dideacetyl-9-dihydro-9,10-O-isopropylidenebaccatin III Melting point: 125–164° C. (lyophilization from dioxane); $^1$H-NMR (400 MHz, CDCl$_3$/TMS) δ (ppm); 0.95 (3H, t, J=6.8 Hz), 1.11–1.48 (6H, m), 1.25 (6H, s), 1.29 (3H, s), 1.66 (3H, s), 1.90–2.37 (5H, m), 2.89 (1H, d, J=4.4 Hz), 3.71 (1H, d, J=7.3 Hz), 4.06 (1H, m), 4.31 (2H, s), 4.67 (1H, d, J=8.3 Hz), 5.01 (1H, d, J=9.8 Hz), 5.05 (1H, s), 5.45 (1H, d, J=6.8 Hz), 5.91 (1H, d, J=9.8 Hz), 6.07 (1H, d, J=4.4 Hz), 6.21 (1H, t, J=8.0 Hz), 7.36 (2H, d, J=5.9 Hz), 7.49 (2H, t, J=7.3 Hz), 7.62 (1H, t, J=7.3 Hz), 8.04 (2H, d, J=8.3 Hz), 8.56 (2H, d, J=5.4 Hz). FAB mass: 905 (MH$^+$).

Inventive Example 77

9β-13-O-[(2R,3R)-3-(tert-Butoxycarbonylamino)-3-(2-furyl)-2-hydroxypropionyl]-10-deacetyl-7-deoxy-9-dihydro-9,10-O-(2-propenylidene)baccatin III Melting point: 133–136° C. (lyophilization from dioxane); $^1$H-NMR (400 MHz, CDCl$_3$/TMS) δ (ppm); 1.26 (3H, s), 1.42 (9H, s), 1.49 (3H, s), 1.63 (3H, s), 1.75 (3H, s), 1.80–2.15 (5H, m), 2.30–2.44 (1H, m), 2.33 (3H, s), 2.93 (1H, d, J=4.9 Hz), 4.17 (1H, d, J=6.8 Hz), 4.23 (1H, d, J=8.8 Hz), 4.33 (1H, d, J=8.8 Hz), 4.72 (1H, s), 4.92 (1H, s), 5.24 (1H, d, J=6.3 Hz), 5.30 (1H, d, J=6.8 Hz), 5.38 (1H, d, J=10.2 Hz), 5.42–5.54 (2H, m), 5.58 (1H, d, J=17.5 Hz), 5.96–6.08 (2H, m), 6.11 (1H, t, J=7.9 Hz), 6.31 (1H, d, J=3.4 Hz), 6.34 (1H, dd, J=3.4 Hz, J=1.9 Hz), 7.39 (1H, s like), 7.47 (2H, t, J=7.8 Hz), 7.60 (1H, t, J=7.8 Hz), 8.12 (2H, d, J=7.8 Hz). FAB mass 822 (MH$^+$).

Inventive Example 78

9β-13-O-[3-(tert-Butoxycarbonylamino)-2-ethyl-2-hydroxy-3-(4-pyridyl)propionyl]-10-deacetyl-9-dihydro-9,10-O-isopropylidenebaccatin III Melting point: 161–163° C. (lyophilization from dioxane); $^1$H-NMR (400 MHz, CDCl$_3$/TMS) δ (ppm); 0.95 (3H, t, J=7.3 Hz), 1.26 (3H, s), 1.30 (3H, s), 1.36 (9H, s), 1.39 (3H, s), 1.57 (3H, s), 1.62 (3H, s), 1.67 (3H, s), 1.82–2.35 (4H, m), 2.49 (3H, s), 2.89 (1H, d, J=4.4 Hz), 3.75 (1H, d, J=7.3 Hz), 4.06 (1H, br), 4.38 (2H, s), 4.67 (1H, d, J=7.8 Hz), 5.01 (1H, d, J=9.8 Hz), 5.10 (1H, s), 5.45 (1H, d, J=6.8 Hz), 5.82 (1H, brd, J=9.3 Hz), 6.04 (1H, d, J=4.4 Hz), 6.24 (1H, t, J=8.0 Hz), 7.36 (2H, d, J=5.4 Hz), 7.48 (2H, t, J=7.8 Hz), 7.60 (1H, t, J=7.3 Hz), 8.24 (2H, d, J=7.3 Hz), 8.56 (2H, d, J=5.4 Hz). FAB mass: 879 (MH$^+$).

Inventive Example 79

9β-13-O-[ (2R,3R)-3-(tert-Butoxycarbonylamino)-3-(2-furyl)-2-hydroxypropionyl]-10-deacetyl-7-deoxy-9-dihydro-9,10-O-(2-morpholinoethylidene)baccatin III Melting point: 140–143° C. (lyophilization from dioxane); $^1$H-NMR (400 MHz, CDCl$_3$/TMS) δ (ppm); 1.25 (3H, s), 1.41 (9H, s), 1.47 (3H, s), 1.60 (3H, s), 1.60–2.15 (5H, m), 1.73 (3H, s), 2.20–2.42 (1H, m), 2.32 (3H, s), 2.52–2.84 (6H, m), 3.74 (4H, t, J=4.4 Hz), 4.11 (1H, d, J=6.9 Hz), 4.23 (1H, d, J=8.3 Hz), 4.32 (1H, d, J=8.3 Hz), 4.72 (1H, s), 4.91 (1H, s), 5.0481 H, t, J=3.9 Hz), 5.24 (1H, d, J=6.9 Hz), 5.45 (1H, d, J=9.3 Hz), 5.99 (1H, d, J=4.9 Hz), 6.03–6.18 (1H, m), 6.31 (1H, s like), 6.34 (1H, s like), 7.38 (1H, s like), 7.47 (2H, t, J=7.8 Hz), 7.60 (1H, t, J=7.8 Hz), 8.12 (2H, d, J=7.8 Hz). FAB mass: 895 (MH$^+$).

Inventive Example 80

9β-13-O-[ (2R,3S)-3-(tert-Butoxycarbonylamino)-2-hydroxy-3-(2-pyridyl)propionyl]-10-deacetyl-7-deoxy-9-dihydro-9,10-O-isopropylidenebaccatin III Melting point: 145–148° C. (lyophilization from dioxane); $^1$H-NMR (400 MHz, CDCl$_3$/TMS) δ (ppm); 1.26 (3H, s), 1.43 (3H, s), 1.44 (9H, s), 1.52 (3H, s), 1.56 (3H, s), 1.61 (3H, s), 1.71 (3H, s), 1.80–2.20 (4H, m), 2.22–2.31 (2H, m), 2.35 (3H, s), 2.94 (1H, d, J=4.9 Hz), 4.17 (1H, d, J=7.3 Hz), 4.23 (1H, d, J=8.3 Hz), 4.32 (1H, d, J=8.3 Hz), 4.88 (1H, d, J=2.5 Hz), 4.92 (1H, s), 5.34 (1H, d, J=9.3 Hz), 5.56 (1H, d, J=7.3 Hz), 5.94 (1H, d, J=9.3 Hz), 5.96 (1H, d, J=4.9 Hz), 6.09 (1H, t, J=8.3 Hz), 7.22 (1H, dd, J=7.3 Hz, J=4.9 Hz), 7.38–7.50 (3H, m), 7.59 (1H, t, J=7.8 Hz), 7.72 (1H, t, J=7.3 Hz), 8.12 (2H, d, J=7.8 Hz), 8.54 (1H, d, J=4.4 Hz). FAB mass: 835 (MH$^+$).

Inventive Example 81

7α,9β-4-O-Butanoyl-13-O-[(2R,3R)-3-(tert-butoxycarbonylamino)-3-(2-furyl)-2-hydroxypropionyl]-7-deoxy-4,10-dideacetyl-9-dihydro-7-fluoro-9,10-O-(2-morpholinoethylidene)baccatin III Melting point: 124.5–129.5° C. (lyophilization from dioxane); $^1$H-NMR (400 MHz, CDCl$_3$/TMS) δ (ppm); 1.02 (3H, t, J=7.3 Hz), 1.19 (3H, s), 1.40 (9H, s), 1.57 (3H, s), 1.63 (3H, s), 1.72 (3H, s), 1.81 (1H, s), 1.75–1.90(2H, m), 2.15–2.55 (6H, m), 2.55–2.67 (4H, m), 2.82–2.93 (2H, m), 3.49 (1H, d, J=5.4 Hz), 3.74 (4H, t, J=5.1 Hz), 3.92 (1H, br s), 4.22 (1H, d, J=8.3 Hz), 4.27 (1H, d, J=8.3 Hz), 4.39 (1H, d, J=8.3 Hz), 4.66–4.73 (1H, br), 4.68–4.85 (1H, m), 4.87–4.95 (2H, m), 5.30–5.41 (3H, m), 5.91 (1H, d, J=5.4 Hz), 6.08 (1H, br t, J=8.1 Hz), 6.33 (1H, d, J=3.4 Hz), 6.36 (1H, dd, J=3.4, 1.5 Hz), 7.39 (1H, d, J=1.5 Hz), 7.48 (2H, t, J=7.8 Hz), 7.62 (1H, t, J=7.8 Hz), 8.11 (2H, d, J=7.8 Hz).

Inventive Example 82

9β-13-O-[(2R,3S)-3-(tert-Butoxycarbonylamino)-2-hydroxy-2-methyl-3-(2-pyridyl)propionyl]-10-deacetyl-7-deoxy-9-dihydro-9,10-O-isopropylidenebaccatin III Melting point: 147–150° C. (lyophilization from dioxane); $^1$H-NMR (400 MHz, CDCl$_3$/TMS) δ (ppm); 1.29 (3H, s), 1.40 (3H, s), 1.42 (9H, s), 1.52 (3H, s), 1.54 (3H, s), 1.55 (6H, s), 1.61 (3H, s), 1.80–2.23 (6H, m), 2.51 (3H, s), 2.94 (1H, d, J=4.9 Hz), 4.18 (1H, d, J=7.3 Hz), 4.22 (1H, d, J=7.3 Hz), 4.34 (1H, d, J=8.3 Hz), 4.94 (1H, s), 5.10 (1H, d, J=10.2 Hz), 5.49 (1H, d, J=7.3 Hz), 6.03 (1H, d, J=10.2 Hz), 6.15 (1H, t, J=8.8 Hz), 7.18–7.33 (1H, m), 7.37–7.55 (3H, m), 7.60 (1H, t, J=7.4 Hz), 7.67–7.80 (1H ,m), 8.15 (2H, d, J=7.4 Hz), 8.49 (1H, d, J=4.4 Hz). FAB mass: 849 (MH$^+$).

Inventive Example 83

9β-13-O-[(2R,3S)-3-(tert-Butoxycarbonylamino)-2-hydroxy-3-(2-pyridyl)propionyl]-4,10-dideacetyl-9-dihydro-9,10-O-isopropylidene-4-O-propionylbaccatin III Melting point: 148–150° C. (lyophilization from dioxane); $^1$H-NMR (400 MHz, CDCl$_3$/TMS) δ (ppm); 1.28

(3H, s), 1.32 (3H, t, J=7.5 Hz), 1.40 (3H, s), 1.44 (9H, s), 1.58 (3H, s), 1.65 (3H, s), 1.66 (3H, s), 2.18 (2H, br), 2.27 (1H, m), 2.68 (2H, q, J=7.5 Hz), 2.96 (1H, d, J=4.9 Hz), 3.88 (1H, d, J=7.3 Hz), 4.06 (1H, m), 4.32 (1H, d, J=8.3 Hz), 4.41 (1H, d, J=8.3 Hz), 4.68 (1H, d, J=7.8 Hz), 4.85 (1H, br), 5.05 (1H, t-br), 5.32 (1H, m), 5.52 (1H, d, J=7.3 Hz), 5.87 (1H, d, J=9.9 Hz), 6.03 (1H, d, J=4.9 Hz), 6.09 (1H, t, J=8.8 Hz), 7.24 (1H, m), 7.42 (1H, d, J=7.8 Hz), 7.47 (2H, t, J=7.5 Hz), 7.60 (1H, t, J=7.5 Hz), 7.73 (1H, td, J=7.8 Hz, 2 Hz), 8.13 (2H, m), 8.52 (1H, d, J=4.4 Hz). FAB mass: 866 (MH$^+$).

Inventive Example 84

9β-13-O-[3-(tert-Butoxycarbonylamino)-2-hydroxy-2-methyl-3-(2-pyridyl)propionyl]-10-deacetyl-9-dihydro-9,10-O-isopropylidenebaccatin III Melting point: 145–151° C. (lyophilization from dioxane); $^1$H-NMR (400 MHz, CDCl$_3$/TMS) δ (ppm); 1.29 (3H, s), 1.38 (3H, s), 1.44 (9H, s), 1.50 (3H, s), 1.55 (3H, s), 1.56 (3H, s), 1.64 (3H, s), 1.66 (3H, s), 2.07–2.30 (4H, m), 2.55 (3H, s), 2.94 (1H, d, J=5.4 Hz), 3.86 (1H, d, 7.3 Hz), 4.05 (1H, m), 4.36 (2H, ABq, J=8.3 Hz), 4.69 (1H, d, J=7.8 Hz), 5.10 (1H, d, J=10.3 Hz), 5.11 (1H, s like), 5.45 (1H, d, J=7.8 Hz), 5.99–6.03 (2H, m), 6.16 (1H, t, J=9.3 Hz), 7.24 (1H, m), 7.43–7.48 (3H, m), 7.60 (1H, t, J=7.3 Hz), 7.73 (1H, t, J=6.8 Hz), 8.14 (2H, d, J=7.8 Hz), 8.47 (1H, d, J=4.4 Hz). FAB mass: 865 (MH$^+$).

Inventive Example 85

9β-13-O-[3-(tert-Butoxycarbonylamino)-2-hydroxy-2-methyl-3-(2-pyridyl)propionyl]-4,10-dideacetyl-9-dihydro-9,10-O-isopropylidene-4-O-propionylbaccatin III Melting point: 147–150° C. (lyophilization from dioxane); $^1$H-NMR (400 MHz, CDCl$_3$/TMS) δ (ppm); 1.30 (s), 1.38 (s), 1.40 (3H, t, J=7.3 Hz), 1.44 (9H, s), 1.50 (s) 1.55 (s), 1.57 (s), 1.64 (s), 1.65 (s), 2.12 (1H, dd, J=14.7 Hz, 8.8 Hz), 2.20 (2H, t, J=3.4 Hz), 2.29 (1H, dd, J=14.7 Hz, 8.8 Hz), 2.88 (2H, q, J=7.5 Hz), 2.94 (1H, d, J=5.4 Hz), 3.88 (1H, d, J=7.3 Hz), 4.05 (1H, m), 4.32 (1H, d, J=8.3 Hz), 4.44 (1H, d, J=8.3 Hz), 4.67 (1H, d, J=7.8 Hz), 5.07 (1H, m), 5.45 (1H, d, J=7.3 Hz), 6.01 (2H, m), 6.14 (1H, t, J=9 Hz), 7.24 (1H, m), 7.44 (1H, d, J=8.3 Hz), 7.48 (2H, t, J=7.8 Hz), 7.60 (1H, t, J=7.3 Hz), 7.73 (1H, td, J=7.5 Hz, 1.5 Hz), 8.14 (2H, m), 8.47 (1H, d, J=4.4 Hz). FAB mass: 879 (M$^+$).

Inventive Example 86

9β-13-O-[(2R,3S)-3-(tert-Butoxycarbonylamino)-2-hydroxy-3-(2-pyridyl)propionyl]-10-deacetyl-9-dihydro-9,10-O-isopropylidenebaccatin III Melting point: 150–153° C. (lyophilization from dioxane); $^1$H-NMR (400 MHz, CDCl$_3$/TMS) δ (ppm); 1.27 (3H, s), 1.40 (3H, s), 1.44 (9H, s), 1.58 (3H, s), 1.64 (3H, s), 1.66 (3H, s), 1.69 (3H, s), 2.05–2.32 (4H, m), 2.40 (3H, s), 2.95 (1H, d, J=4.9 Hz), 3.86 (1H, d, J=7.8 Hz), 4.06 (1H, m), 4.35 (2H, ABq, J=8.3 Hz), 4.70 (d, J=8.3 Hz), 4.85 (1H, d, J=2.4 Hz), 5.11 (1H, s), 5.35 (1H, d, J=9.3 Hz), 5.53 (1H, d, J=7.3 Hz), 5.90 (1H, d, J=9.8 Hz), 6.03 (1H, d, J=5.4 Hz), 6.10 (1H, t, J=8.3 Hz), 7.24 (1H, m), 7.41 (1H, d, J=7.8 Hz), 7.47 (2H, t, J=7.8 Hz), 7.59 (1H, t, J=7.3 Hz), 7.73 (1H, t, J=5.9 Hz), 8.11 (2H, d, J=8.8 Hz), 8.52 (1H, d, J=4.9 Hz). FAB mass: 852 (MH$_2{}^+$).

Inventive Example 87

9β-13-O-[3-(tert-Butoxycarbonylamino)-2-hydroxy-2-methyl-3-(2-pyridyl)propionyl]-10-deacetyl-9-dihydro-9,10-O-(2-propenylidene)baccatin III Melting point: 140–145° C. (lyophilization from dioxane); $^1$H-NMR (400 MHz, CDCl$_3$/TMS) δ (ppm); 1.30 (3H, s), 1.44 (9H, s), 1.52 (3H, s), 1.54 (3H, s), 1.62 (3H, s), 1.68 (3H, s), 2.13–2.30 (4H, m), 2.55 (3H, s), 2.95 (1H, d, J=4.9 Hz), 3.89 (1H, d, J=6.8 Hz), 4.08 (1H, m), 4.35 (2H, ABq, J=8.3 Hz), 4.61 (1H, d, J=8.3 Hz), 5.12 (3H, m), 5.19 (1H, d, J=6.4 Hz), 5.45 (1H, d, J=10.7 Hz), 5.56 (1H, d, J=17.6 Hz), 6.01 (2H, m), 6.17 (2H, m), 7.24 (1H, m), 7.43–7.51 (3H, m), 7.61 (1H, t, J=7.3 Hz), 7.73 (1H, t, J=6.4 Hz), 8.13 (2H, d, J=7.3 Hz), 8.48 (1H, d, J=4.4 Hz). FAB mass: 864 (MH$_2{}^+$).

Inventive Example 88

9β-13-O-[3-(tert-Butoxycarbonylamino)-2-hydroxy-2-methyl-3-(2-pyridyl)propionyl]-10-deacetyl-9-dihydro-9,10-O-(2-morpholinoethylidene)baccatin III Melting point: 135–139° C. (lyophilization from dioxane); $^1$H-NMR (400 MHz, CDCl$_3$/TMS) δ (ppm); 1.30 (3H, s), 1.43 (9H, s), 1.51 (3H, s), 1.54 (3H, s), 1.61 (3H, s), 1.64 (3H, s), 2.09–2.34 (4H, m), 2.55 (3H, s), 2.62 (4H, m), 2.77 (2H, ABdq, J=26.9 Hz, 3.4 Hz), 2.95 (1H, d, J=4.9 Hz), 3.73 (4H, t like, 4.9 Hz), 3.81 (1H, d, J=7.3 Hz), 4.07 (1H, m), 4.35 (2H, ABq, J=8.3 Hz), 4.71 (1H, d, J=8.3 Hz), 4.99 (1H, t, J=4.4 Hz), 5.10 (1H, d, J=10.3 Hz), 5.12 (1H, d, J=7.3 Hz), 6.01 (1H, d, J=5.4 Hz), 6.02 (1H, d, J=4.9 Hz), 6.16 (1H, t, J=7.8 Hz), 7.23 (1H, m), 7.43 (1H, d, J=7.8 Hz), 7.49 (2H, t, J=7.8 Hz), 7.61 (1H, t, J=7.8 Hz), 7.73 (1H, t, J=7.8 Hz), 8.13 (2H, d, J=7.3 Hz), 8.47 (1H, d, J=4.9 Hz). FAB mass: 936 (MH$^+$).

Inventive Example 89

9β-13-O-[(2R,3S)-3-(Benzoylamino)-2-hydroxy-3-phenylpropionyl]-4-O-cyclopropanecarbonyl-4,10-dideacetyl-7-deoxy-9-dihydro-9,10-O-(2-propenylidene)baccatin III Melting point: 150–153° C. (lyophilization from dioxane); $^1$H-NMR (400 MHz, CDCl$_3$/TMS) δ (ppm); 1.05–1.13 (2H, m), 1.21 (3H, s), 1.38–1.50 (2H, m), 1.43 (3H, s), 1.46 (3H, s), 1.55–1.75 (2H, m), 1.60 (3H, s), 1.78–2.11 (5H, m), 2.38 (1H, dd, J=15.1 Hz, J=9.7 Hz), 2.85 (1H, d, J=4.9 Hz), 4.09 (1H, d, J=6.9 Hz), 4.18 (1H, d, J=8.8 Hz), 4.27 (1H, d, J=8.8 Hz), 4.73 (1H, s like), 4.88 (1H, s like), 4.93 (1H, s like), 5.18–5.27 (2H, m), 5.44 (1H, d, J=10.3 Hz), 5.55 (1H, d, J=17.1 Hz), 5.85 (1H, dd, J=9.3 Hz, J=2.5 Hz), 5.94–6.09 (3H, m), 7.24–7.57 (11H, m), 7.60 (1H, t, J=7.3 Hz), 7.84 (2H, d like, J=8.3 Hz), 8.04 (2H, d, J=7.3 Hz). FAB mass: 862 (MH$^+$).

Inventive Example 90

9β-13-O-[3-(tert-Butoxycarbonylamino)-2-hydroxy-2-methyl-3-(4-pyridyl)propionyl]-4,10-dideacetyl-9-dihydro-9,10-O-isopropylidene-4-O-propionylbaccatin III Melting point: 152–155° C. (lyophilization from dioxane); $^1$H-NMR (400 MHz, CDCl$_3$/TMS) δ (ppm); 1.30 (s), 1.38 (s), 1.40 (s), 1.41 (s), 1.44 (s), 1.58 (s), 1.68 (s), 2.06 (1H, m), 2.10 (1H, m), 2.22 (1H, m), 2.26 (1H, m), 2.63 (1H, m), 2.75 (1H, m), 2.91 (1H, d, J=4.4 Hz), 3.78 (1H, d, J=7.8 Hz), 4.08 (1H, br), 4.39 (2H, ABq, J=8.8 Hz), 4.70 (1H, d, J=7.8 Hz), 4.99 (1H, d, J=9.8 Hz), 5.48 (1H, d, J=7.3 Hz), 5.78 (1H, d, J=9.8 Hz), 6.06 (1H, d, J=4.3 Hz), 6.21 (1H, t-br), 7.35 (2H, d, J=5 Hz), 7.48 (2H, t, J=7.8 Hz), 7.61 (1H, t, J=7.3 Hz), 8.14 (2H, m), 8.59 (2H, d, J=5 Hz). FAB mass: 879 (M$^+$).

Inventive Example 91

9β-13-O-[(2R,3S)-3-(Benzoylamino)-2-hydroxy-3-phenylpropionyl]-4-O-cyclopropanecarbonyl-4,10-dideacetyl-7-deoxy-9-dihydro-9,10-O-(2-morpholinoethylidene)baccatin III Melting point: 150–153° C. (lyophilization from dioxane); $^1$H-NMR (400 MHz, CDCl$_3$/TMS) δ (ppm); 1.04–1.13 (2H, m), 1.21 (3H, s), 1.36–1.47 (2H, m), 1.42 (3H, s), 1.44 (3H, s), 1.53–2.08 (7H, m), 1.57 (3H, s), 2.37 (1H, dd, J=15.1 Hz, J=9.8 Hz), 2.53–2.73 (5H, m), 2.77 (1H, dd, J=13.6 Hz, J=3.9 Hz), 2.85 (1H, d, J=4.4 Hz), 3.73 (4H, t, J=4.4 Hz), 4.17 (1H, d, J=6.8 Hz), 4.26 (1H, d, J=8.8 Hz), 4.30 (1H, d, J=8.8 Hz), 4.73 (1H, d, J=2.4 Hz), 4.87 (1H, br s), 5.00 (1H, t, J=4.4 Hz), 5.14 (1H, d, J=6.8 Hz), 5.85 (1H, dd, J=9.3 Hz, J=2.5 Hz), 5.97–6.06 (2H, m), 7.23–7.56 (10H, m), 7.60 (1H, t, J=7.3 Hz), 7.84 (1H, d, J=7.3 Hz), 8.04 (2H, d, J=7.3 Hz). FAB mass: 935 (MH$^+$).

Inventive Example 92

9β-13-O-[(2R,3S)-3-(tert-Butoxycarbonylamino)-2-hydroxy-3-phenylpropionyl]-4-O-ethoxycarbonyl-4,10-dideacetyl-9-dihydro-9,10-O-(2-propenylidene)baccatin III Melting point: 117–120° C. (lyophilization from dioxane); $^1$H-NMR (400 MHz, CDCl$_3$/TMS) δ (ppm); 1.24 (3H, s), 1.34 (3H, t, J=7.4 Hz), 1.40 (9H, s), 1.62 (3H, s), 1.65 (3H, br s), 1.67 (3H, s), 1.88 (1H, s), 1.99–2.29 (3H, m), 2.47 (1H, dd, J=15.1 Hz, J=9.7 Hz), 2.86 (1H, d, J=4.3 Hz), 3.87 (1H, d, J=6.8 Hz), 3.97 (1H, br), 4.08 (1H, m), 4.30–4.66 (6H, m), 5.17–5.36 (3H, m), 5.45 (1H, d, J=10.8 Hz), 5.57 (1H, d, J=17.1 Hz), 5.66 (1H, d, J=9.7 Hz), 5.92 (1H, br t, J=7.3 Hz), 6.03 (1H, ddd, J=17.1 Hz, J=10.8 Hz, J=6.3 Hz), 6.11 (1H, d, J=4.3 Hz), 7.24–7.49 (7H, m), 7.58 (1H, t, J=7.3 Hz), 8.03 (2H, d, J=7.3 Hz). FAB mass 878 (MH$^+$).

Inventive Example 93

9β-13-O-[(2R,3R)-3-(tert-Butoxycarbonylamino)-3-(2-furyl)-2-hydroxypropionyl]-4-O-ethoxycarbonyl-4,10-dideacetyl-9-dihydro-9,10-O-(2-propenylidene)baccatin III Melting point: 121–123° C. (lyophilization from dioxane); $^1$H-NMR (400 MHz, CDCl$_3$/TMS) δ (ppm); 1.26 (3H, s), 1.37 (3H, t, J=6.9 Hz), 1.38 (9H, s), 1.63 (3H, s), 1.68 (3H, s), 1.75 (3H, s), 1.88 (1H, s), 2.02–2.12 (1H, m), 2.18–2.37 (2H, m), 2.45 (1H, dd, J=15.2 Hz, J=9.8 Hz), 2.88 (1H, d, J=4.9 Hz), 3.80–3.94 (2H, m), 4.08 (1H, br), 4.29–4.61 (5H, m), 4.70 (1H, s like), 5.18–5.29 (2H, m), 5.29 (1H, d, J=7.0 Hz), 5.30–5.45 (2H, m), 5.46 (1H, d, J=10.7 Hz), 5.57 (1H, d, J=17.0 Hz), 5.97–6.15 (2H, m), 6.10 (1H, d, J=4.9 Hz), 7.38 (1H, s like), 7.44 (2H, t, J=7.8 Hz), 7.58 (1H, t, J=7.8 Hz), 8.05 (2H, d, J=7.8 Hz). FAB mass 868 (MH$^+$).

Inventive Example 94

9β-13-O-[(2R,3S)-3-(tert-Butoxycarbonylamino)-2-hydroxy-3-phenylpropionyl]-4-O-ethoxycarbonyl-4,10-dideacetyl-9-dihydro-9,10-O-(2-morpholinoethylidene)baccatin III Melting point: 128–131° C. (lyophilization from dioxane); $^1$H-NMR (400 MHz, CDCl$_3$/TMS) δ (ppm); 1.24 (3H, s), 1.33 (3H, t, J=7.3 Hz), 1.40 (9H, s), 1.60 (3H, s), 1.64 (6H, s), 1.86 (1H, s), 2.00–2.09 (1H, m), 2.14–2.30 (2H, m), 2.46 (1H, dd, J=15.1 Hz, J=9.7 Hz), 2.56–2.71 (4H, m), 2.75 (1H, dd, J=13.6 Hz, J=5.3 Hz), 2.80–2.91 (2H, m), 3.73 (4H, t, J=5.3 Hz), 3.78 (1H, d, J=7.3 Hz), 4.06 (1H, br), 4.29–4.48 (3H, m), 4.50–4.68 (3H, m), 5.03 (1H, t like, J=5.3 Hz), 5.19–5.35 (3H, m), 5.65 (1H, d, J=9.8 Hz), 5.92 (1H, br t, J=6.8 Hz), 6.09 (1H, d, J=4.4 Hz), 7.25–7.50 (7H, m), 7.59 (1H, t, J=7.8 Hz), 8.03 (2H, d, J=7.8 Hz). FAB mass: 951 (MH$^+$).

Inventive Example 95

9β-13-O-[3-(tert-Butoxycarbonylamino)-2-hydroxy-2-methyl-3-(4-pyridyl)propionyl]-10-deacetyl-7-deoxy-9-dihydro-9,10-O-isopropylidenebaccatin III Melting point: 182–184° C. (lyophilization from dioxane); $^1$H-NMR(400 MHz, CDCl$_3$/TMS) δ (ppm); 1.27 (3H, s), 1.37 (9H, s), 1.42 (6H, s), 1.47 (3H, br s), 1.50 (3H, s), 1.56 (3H, s), 1.62 (3H, s), 1.75–2.11 (6H, m), 2.22 (1H, dd, J=14.2 Hz, J=10.2 Hz), 2.30–2.50 (1H, m), 2.42 (3H, s), 2.91 (1H, d, J=4.4 Hz), 4.12 (1H, d, J=7.3 Hz), 4.28 (1H, d, J=8.3 Hz), 4.32 (1H, d, J=8.3 Hz), 4.58 (1H, br), 4.92 (1H, s), 5.00 (1H, d, J=10.2 Hz), 5.51 (1H, d, J=7.3 Hz), 5.92 (1H, d, J=10.2 Hz), 5.98 (1H, d, J=4.4 Hz), 6.17–6.29 (1H, m), 7.36 (2H, d, J=5.4 Hz), 7.47 (2H, t, J=7.9 Hz), 7.60 (1H, t, J=7.9 Hz), 8.13 (2H, d, J=7.9 Hz), 8.58 (2H, d, J=5.4 Hz). FAB mass: 849 (MH$^+$).

Inventive Example 96

9β-13-O-[(2R,3R)-3-(tert-Butoxycarbonylamino)-3-(2-furyl)-2-hydroxypropionyl]-4-O-ethoxycarbonyl-4,10-dideacetyl-9-dihydro-9,10-O-(2-morpholinoethylidene)baccatin III Melting point: 130–132° C. (lyophilization from dioxane); $^1$H-NMR (400 MHz, CDCl$_3$/TMS) δ (ppm); 1.26 (3H, s), 1.36 (3H, t, J=6.8 Hz), 1.41 (9H, s), 1.61 (3H, s), 1.65 (3H, s), 1.73 (3H, s), 1.85 (1H, s), 2.00–2.10 (1H, m), 2.19–2.39 (2H, m), 2.42 (1H, dd, J=15.1 Hz, J=9.8 Hz), 2.54–2.93 (7H, m), 3.73 (4H, t, J=4.4 Hz), 3.80 (1H, d, J=7.3 Hz), 4.06 (1H, br), 4.25–4.50 (3H, m), 4.53 (1H, d, J=8.8 Hz), 4.61 (1H, d, J=7.8 Hz), 4.70 (1H, s), 5.03 (1H, t, J=4.4 Hz), 5.17–5.45 (4H, m), 5.99 (1H, t, J=7.8 Hz), 6.08 (1H, d, J=4.4 Hz), 6.28–6.42 (2H, m), 7.38 (1H, s like), 7.45 (2H, t, J=7.8 Hz), 7.59 (1H, t, J=7.8 Hz), 8.05 (2H, d, J=7.8 Hz). FAB mass: 941 (MH$^+$).

Inventive Example 97

9β-13-O-[(2R,3R)-3-(tert-Butoxycarbonylamino)-2-hydroxy-3-(2-thienyl)propionyl]-10-deacetyl-7-deoxy-9-dihydro-9,10-O-(2-propenylidene)baccatin III Melting point: 135–137° C. (lyophilization from dioxane); $^1$H-NMR (400 MHz, CDCl$_3$/TMS) δ (ppm); 1.24 (3H, s), 1.41 (9H, s), 1.48 (3H, s), 1.63 (3H, s), 1.66 (3H, s), 1.80–2.22 (5H, m), 2.31 (3H, s), 2.37 (1H, dd, J=15.1 Hz, J=10.2 Hz), 2.92 (1H, d, J=5.3 Hz), 4.16 (1H, d, J=6.9 Hz), 4.24 (1H, d, J=8.8 Hz), 4.33 (1H, d, J=8.8 Hz), 4.57 (1H, s), 4.64 (1H, s), 4.93 (1H, s), 5.23 (1H, d, J=6.4 Hz), 5.29 (1H, d, J=6.9 Hz), 5.46 (1H, d, J=10.8 Hz), 5.50–5.74 (3H, m), 5.96–6.18 (3H, m), 6.98 (1H, dd, J=5.4 Hz, J=4.0 Hz), 7.10 (1H, d, J=4.0 Hz), 7.22–7.27 (1H, m), 7.47 (2H, t, J=7.8 Hz), 7.60 (1H, t, J=7.8 Hz), 8.12 (2H, d, J=7.8 Hz). FAB mass: 838 (MH$^+$).

Inventive Example 98

9β-13-O-[(2R,3R)-3-(tert-Butoxycarbonylamino)-2-hydroxy-3-(2-thienyl)propionyl]-10-deacetyl-7-deoxy-9-dihydro-9,10-O-(2-morpholinoethylidene)baccatin III Melting point: 135–138° C. (lyophilization from dioxane); $^1$H-NMR (400 MHz, CDCl$_3$/TMS) δ (ppm); 1.24

(3H, s), 1.41 (9H, s), 1.47 (3H, s), 1.59 (3H, s), 1.60–2.15 (5H, m), 1.65 (3H, s), 2.31 (3H, s), 2.36 (1H, dd, J=15.2 Hz, J=9.8 Hz), 2.57–2.86 (6H, m), 2.91 (1H, d, J=4.9 Hz), 3.74 (4H, t, J=4.8 Hz), 4.10 (1H, d, J=6.8 Hz), 4.23 (1H, d, J=8.3 Hz), 4.32 (1H, d, J=8.3 Hz), 4.64 (1H, s), 4.92 (1H, s), 5.04 (1H, t, J=3.9 Hz), 5.22 (1H, d, J=6.8 Hz), 5.54 (1H, d, J=9.8 Hz), 5.60 (1H, d, J=9.8 Hz), 5.99 (1H, d, J=4.9 Hz), 6.08 (1H, t, J=7.8 Hz), 6.97 (1H, dd, J=5.3 Hz, J=3.4 Hz), 7.10 (1H, d, J=3.4 Hz), 7.20–7.20 (1H, m), 7.47 (2H, t, J=7.8 Hz), 7.61 (1H, t, J=7.8 Hz), 8.12 (2H, d, J=7.8 Hz). FAB mass: 911 (MH$^+$).

Inventive Example 99

9β-13-O-[(2R,3S)-3-(tert-Butoxycarbonylamino)-2-hydroxy-3-(2-pyridyl)propionyl]-4,10-dideacetyl-9-dihydro-4-O-ethoxycarbonyl-9,10-O-isopropylidenebaccatin III Melting point: 131–135° C. (lyophilization from dioxane); $^1$H-NMR (400 MHz, CDCl$_3$/TMS) δ (ppm); 1.25 (3H, s), 1.37 (3H, t, J=7.3 Hz), 1.41 (3H, s), 1.45 (9H, s), 1;59 (3H, s), 1.65 (6H, s), 1.74 (3H, s), 1.87–2.39 (1H, d, J=4.4 Hz), 2.86 (1H, d, J=4.4 Hz), 3.63 (1H, d, J=7.3 Hz), 4.04 (1H, m), 4.34 (2H, m), 4.48 (1H, q, 7.3 Hz), 4.53 (1H, d, J=8.8 Hz), 4.67 (1H, d, J=7.8 Hz), 4.80 (1H, d, J=2.8 Hz), 5.23 (1H, d, J=7.8 Hz), 5.57 (1H, d, J=7.3 Hz), 5.59 (2H, m), 6.07 (1H, d, J=4.9 Hz), 7.24 (1H, dd, J=7.3 Hz, 4.9 Hz), 7.45 (2H, t, J=7.8 Hz), 7.58 (1H, t, J=7.3 Hz), 7.73 (1H, dt, 7.8 Hz, 2.0 Hz), 8.05 (2H, d, J=7.2 Hz), 8.50 (1H, d, J=3.9 Hz). FAB mass 881 (MH$^+$).

Inventive Example 100

9β-13-O-[(2R,3S)-3-(tert-Butoxycarbonylamino)-2-hydroxy-3-(4-pyridyl)propionyl]-4,10-dideacetyl-9-dihydro-4-O-ethoxycarbonyl-9,10-O-isopropylidenebaccatin III Melting point: 132–137° C. (lyophilization from dioxane); $^1$H-NMR (400 MHz, CDCl$_3$/TMS) δ (ppm); 1.23 (3H, s), 1.37 (3H, t, J=7.3 Hz), 1.41 (9H, s), 1.59 (3H, s), 1.62 (3H, s), 1.64 (3H, s), 1.66 (6H, s), 2.02–2.48 (4H, m), 2.87 (1H, d, J=4.4 Hz), 3.79 (1H, d, J=7.3 Hz), 4.06 (1H, m), 4.35 (1H, d, J=8.8 Hz), 4.43 (2H, q, J=7.3 Hz), 4.52 (1H, d, J=8.8 Hz), 4.62 (2H, s), 5.21 (1H, s), 5.30 (1H, d, J=8.3 Hz), 5.66 (1H, d, J=7.3 Hz), 5.75 (1H, d, J=9.8 Hz), 5.94 (1H, t, J=8.0 Hz), 6.12 (1H, d, J=4.4 Hz), 7.37 (2H, d, J=4.9 Hz), 7.44 (2H, t, J=7.8 Hz), 7.60 (1H, t, J=7.8 Hz), 8.03 (2H, d, J=7.3 Hz), 8.60 (2H, d, J=5.4 Hz), FAB mass: 881 (MH$^+$).

Inventive Example 101

9β-13-O-[3-(tert-Butoxycarbonylamino)-2-hydroxy-2-methyl-3-(4-pyridyl)propionyl]-4,10-dideacetyl-9-dihydro-4-O-ethoxycarbonyl-9,10-O-isopropylidenebaccatin III Melting point: 149–153° C. (lyophilization from dioxane); $^1$H-NMR (400 MHz, CDCl$_3$/TMS) δ (ppm); 1.28 (3H, s), 1.38 (9H, s), 1.41 (3H, s), 1.42 (3H, s), 1.45 (3H, t, J=7.3 Hz), 1.53 (3H, s), 1.59 (3H, s), 1.65 (3H, s), 1.67 (3H, s), 2.02–2.27 (4H, m), 2.91 (1H, d, J=3.9 Hz), 3.78 (1H, d, J=7.3 Hz), 4.06 (1H, m), 4.53 (1H, d, J=8.8 Hz), 4.54 (3H, m), 4.63 (1H, d, 7.8 Hz), 5.09 (1H, d, J=10.3 Hz), 5.21 (1H, s), 5.53 (1H, d, J=7.3 Hz), 5.82 (1H, d, J=9.8 Hz), 6.10 (1H, d, J=4.4 Hz), 6.17 (1H, t, J=8.3 Hz), 7.39 (2H, d, J=4.9 Hz), 7.44 (2H, t, J=7.8 Hz), 7.59 (1H, t, J=7.3 Hz), 8.05 (2H, d, J=7.3 Hz), 8.58 (2H, d, J=4.9 Hz). FAB mass: 895 (MH$^+$).

Inventive Example 102

9β-13-O-[(2R,3S)-3-(tert-Butoxycarbonylamino)-2-hydroxy-3-phenylpropionyl]-10-deacetyl-7-deoxy-9-dihydro-9,10-O-thiocarbonatebaccatin III Melting point: 162–165° C. (lyophilization from dioxane); $^1$H-NMR (400 MHz, CDCl$_3$/TMS) δ (ppm); 1.25 (3H, s), 1.30 (3H, s), 1.40 (9H, s), 1.50–2.15 (5H, m), 1.61 (3H, s), 1.62 (3H, s), 2.29 (3H, s), 2.41 (1H, dd, J=15.2 Hz, J=9.8 Hz), 2.87 (1H, d, J=4.9 Hz), 4.10 (1H, br), 4.20 (1H, d, J=8.8 Hz), 4.32 (1H, d, J=8.8 Hz), 4.63 (1H, br), 4.85 (1H, d, J=8.7 Hz), 4.90 (1H, s), 5.28 (1H, d, J=9.2 Hz), 5.58 (1H, d, J=9.2 Hz), 5.99 (1H, d, J=4.9 Hz), 6.04–6.18 (2H, m), 7.20–7.45 (5H, m), 7.48 (2H, t, J=7.8 Hz), 7.62 (1H, t, J=7.8 Hz), 8.10 (2H, d, J=7.8 Hz). FAB mass: 836 (MH$^+$).

Inventive Example 103

7α,9β-13-O-[(2R,3S)-3-(tert-Butoxycarbonylamino)-2-hydroxy-(2-pyridyl)propionyl]-10-deacetyl-7-deoxy-9-dihydro-7-fluoro-9,10-O-isopropylidenebaccatin III Melting point: 136–141° C. (lyophilization from dioxane); $^1$H-NMR (400 MHz, CDCl$_3$/TMS) δ (ppm); 1.21 (3H, s), 1.42 (3H, s), 1.44 (9H, s), 1.52 (3H, s), 1.59 (3H, s), 1.65 (3H, s), 1.70 (1H, s), 1.74 (3H, s), 2.07–2.45 (4H, m), 2.27 (1H, d, J=9.3 Hz), 2.41 (3H, s), 3.50 (1H, d, J=5.4 Hz), 4.29 (1H, d, J=8.8 Hz), 4.36 (1H, d, J=8.8 Hz), 4.62 (1H, d, J=9.1 Hz), 4.84 (1H, br s), 4.83–5.02 (1H, m), 4.95–5.02 (1H, m), 5.36 (1H, br d, J=9.8 Hz), 5.53 (1H, d, J=9.1 Hz), 5.86–5.95 (2H, m), 6.10 (1H, br t, J=8.5 Hz), 7.23 (1H, dd, J=4.9, 7.1 Hz), 7.41 (1H, d, J=7.8 Hz), 7.48 (2H, t, J=7.3 Hz), 7.60 (1H, t, J=7.3 Hz), 7.73 (1H, dt, J=1.5, 7.8 Hz), 8.21 (2H, d, J=7.6 Hz), 8.46 (1H, d, J=4.9 Hz), FAB mass: 853 (MH$^+$).

Inventive Example 104

9β-13-O-[(2R,3R)-3-(tert-Butoxycarbonylamino)-3-(2-furyl)-2-hydroxypropionyl]-10-deacetyl-7-deoxy-9-dihydro-9,10-O-[2-(1-methylpiperazin-4-yl)ethylidene]baccatin III Melting point: 128–130° C. (lyophilization from dioxane); $^1$H-NMR (400 MHz, CDCl$_3$/TMS) δ (ppm); 1.25 (3H, s), 1.42 (9H, s), 1.47 (3H, s), 1.58–2.10 (6H, m), 1.60 (3H, s), 1.73 (3H, s), 2.20–2.88 (9H, m), 2.32 (6H, s), 2.91 (1H, d, J=4.9 Hz), 4.11 (1H, d, J=6.9 Hz), 4.23 (1H, d, J=8.3 Hz), 4.32 (1H, d, J=8.3 Hz), 4.77 (1H, s like), 4.91 (1H, s like), 5.03 (1H, t, J=3.9 Hz), 5.23 (1H, d, J=6.9 Hz), 5.37 (1H, d, J=9.3 Hz), 5.43 (1H, d, J=9.3 Hz), 5.99 (1H, d, J=4.9 Hz), 6.10 (1H, t, J=8.0 Hz), 6.31 (1H, d, J=3.4 Hz), 6.35 (1H, dd, J=3.4 Hz, J=1.9 Hz), 7.39 (1H, d, J=1.9 Hz), 7.47 (2H, t, J=7.8 Hz), 7.60 (1H, t, J=7.8 Hz), 8.12 (2H, d, J=7.8 Hz). FAB mass: 908 (MH$^+$).

Inventive Example 105

9β-13-O-[(2R,3R)-3-(tert-Butoxycarbonylamino)-3-(2-furyl)-2-hydroxypropionyl]-10-deacetyl-7-deoxy-9-dihydro-9,10-O-(2-dimethylaminoethylidene)baccatin III Melting point: 135–136° C. (lyophilization from dioxane); $^1$H-NMR (400 MHz, CDCl$_3$/TMS) δ (ppm); 1.25 (3H, s), 1.42 (9H, s), 1.47 (3H, s), 1.61 (3H, s), 1.70–2.10 (5H, m), 1.74 (3H, s), 2.20–2.35 (1H, m), 2.32 (3H, s), 2.39 (6H, s), 2.67 (1H, dd, J=13.2 Hz, J=4.9 Hz), 2.77 (1H, dd, J=13.2 Hz, J=4.9 Hz), 2.92 (1H, d, J=4.8 Hz), 4.12 (1H, d, J=7.4 Hz), 4.23 (1H, d, J=8.3 Hz), 4.32 (1H, d, J=8.3 Hz), 4.72 (1H, s), 4.92 (1H, s), 5.03 (1H, t like, J=4.9 Hz), 5.25 (1H, d, J=7.4 Hz), 5.37 (1H, d, J=10.3 Hz), 5.45 (1H, d, J=10.3 Hz), 6.00 (1H, d, J=4.8 Hz), 6.10 (1H, t, J=8.3 Hz), 6.31 (1H, d, J=3.4 Hz), 6.35 (1H, dd, J=3.4 Hz, J=2.1 Hz), 7.39 (1H, d, J=2.1 Hz), 7.47 (2H, t, J=7.4 Hz), 7.60 (1H, t, J=7.4 Hz), 8.12 (2H, d, J=7.4 Hz). FAB mass 853 (MH$^+$).

Inventive Example 106

9β-13-O-[(3-(tert-Butoxycarbonylamino)-2-hydroxy-2-methyl-3-(2-pyridyl)propionyl]-4,10-dideacetyl-9-dihydro-4-O-ethoxycarbonyl-9,10-O-isopropylidenebaccatin III Melting point: 118–122° C. (lyophilization from dioxane); $^1$H-NMR (400 MHz, CDCl$_3$/TMS) δ (ppm); 1.27 (3H, s), 1.40 (3H, s), 1.42 (3H, t, J=7.3 Hz), 1.45 (9H, s), 1.56 (3H, s), 1.58 (3H, s), 1.64 (3H, s), 1.67 (3H, s), 2.02–2.48 (4H, m), 2.83 (1H, d, J=4.9 Hz), 3.86 (1H, d, J=7.8 Hz), 4.09 (1H, br), 4.12 (1H, d, J=7.3 Hz), 4.51 (3H, m), 4.64 (1H, d, J=7.3 Hz), 5.13 (1H, d, J=10.3 Hz), 5.23 (1H, br), 5.51 (1H, d, J=9.9 Hz), 6.05 (2H, m), 7.23 (1H, m), 7.45 (3H, m), 7.58 (1H, t, J=7.3 Hz), 7.82 (1H, t, J=6.8 Hz), 8.06 (2H, d, J=7.3 Hz), 8.46 (1H, m). FAB mass: 895 (MH$^+$).

Inventive Example 107

9β-4-O-Butanoyl-13-O-[(2R,3R)-3-(tert-butoxycarbonylamino)-3-(2-furyl)-2-hydroxypropionyl]-4,10-dideacetyl-9-dihydro-9,10-O-[2-(1-methylpiperazin-4-yl)ethylidene]baccatin III Melting point: 118–128° C. (lyophilization from dioxane); $^1$H-NMR (400 MHz, CDCl$_3$/TMS) δ (ppm); 1.02 (3H, t, J=7.3 Hz), 1.28 (3H, s), 1.41 (9H, s), 1.61 (3H, s), 1.65 (3H, s), 1.70 (3H, s), 1.84 (2H, m), 2.03–3.07 (20H, m), 3.82 (1H, d, J=7.3 Hz), 4.08 (1H, br), 4.36 (2H, ABq, J=8.3 Hz), 4.70 (1H, s), 5.01 (1H, t, J=2.8 Hz), 5.06 (1H, s), 5.20 (1H, d, J=7.3 Hz), 5.33 (2H, br), 6.03 (1H, d, J=4.4 Hz), 6.09 (1H, t, J=8.2 Hz), 6.33 (1H, d, J=2.8 Hz), 6.36 (1H, d, J=2.4 Hz), 7.39 (1H, s), 7.48 (2H, t, J=7.8 Hz), 7.61 (1H, t, J=6.8 Hz), 8.12 (2H, d, J=7.4 Hz). FAB mass 952 (MH$^+$).

Inventive Example 108

9β-13-O-[(2R,3R)-3-(tert-Butoxycarbonylamino)-2-hydroxy-3-(2-thienyl)propionyl]-4-O-ethoxycarbonyl-4,10-dideacetyl-9-dihydro-9,10-O-(2-morpholinoethylidene)baccatin III Melting point: 126–130° C. (lyophilization from dioxane); $^1$H-NMR (400 MHz, CDCl$_3$/TMS) δ (ppm); 1.24 (3H, s), 1.30–1.45 (3H, m), 1.41 (3H, s), 1.61 (3H, s), 1.64 (3H, s), 1.67 (3H, s), 1.84 (1H, s), 2.00–2.12 (1H, m), 2.17–2.30 (2H, m), 2.45 (1H, dd, J=15.1 Hz, J=9.8 Hz), 2.52–2.94 (7H, m), 3.73 (4H, t like, J=4.4 Hz), 3.79 (1H, d, J=7.3 Hz), 4.06 (1H, br), 4.13–4.46 (3H, m), 4.46–4.70 (3H, m), 5.03 (1H, t, J=3.9 Hz), 5.16–5.27 (2H, m), 5.53 (2H, br), 5.86–6.02 (1H, m), 6.10 (1H, d, J=4.4 Hz), 6.97 (1H, dd, J=4.9 Hz, J=3.4 Hz), 7.11 (1H, d, J=3.4 Hz), 7.18–7.35 (1H, m), 7.44 (2H, t, J=7.8 Hz), 7.59 (1H, t, J=7.8 Hz), 8.04 (2H, d, J=7.8 Hz). FAB mass 957 (MH$^+$).

Inventive Example 109

9β-13-O-[(2R,3R)-3-(tert-Butoxycarbonylamino)-2-hydroxy-3-(2-thienyl)propionyl]-4-O-ethoxycarbonyl-4,10-dideacetyl-9-dihydro-9,10-O-[2-(1-methylpiperazin-4-yl)ethylidene]baccatin III Melting point: 132–135° C. (lyophilization from dioxane); $^1$H-NMR (400 MHz, CDCl$_3$/TMS) δ (ppm); 1.20–1.50 (3H, s), 1.24 (3H, s), 1.40 (9H, s), 1.60 (3H, s), 1.64 (3H, s), 1.67 (3H, s), 1.84 (1H, s), 2.00–2.10 (1H, m), 2.10–2.95 (11H, m), 2.31 (3H, s), 3.79 (1H, d, J=7.3 Hz), 4.06 (1H, s), 4.11–4.50 (3H, m), 4.53 (1H, d, J=8.8 Hz), 4.63 (1H, s), 5.01 (1H, t, J=4.4 Hz), 5.21 (2H, s like), 5.52 (2H, br), 5.84–6.02 (1H, m), 6.09 (1H, d, J=4.9 Hz), 6.97 (1H, dd, J=14.9 Hz, J=3.9 Hz), 7.10 (1H, d, J=3.9 Hz), 7.20–7.35 (1H, m), 7.44 (2H, t, J=7.8 Hz), 7.59 (1H, t, J=7.8 Hz), 8.04 (2H, d, J=7.8 Hz). FAB mass 970 (MH$^+$).

Inventive Example 110

9β-13-O-[(2R,3R)-3-(Benzylamino)-3-(2-furyl)-2-hydroxypropionyl]-4-O-cyclopropanecarbonyl-4,10-dideacetyl-9-dihydro-9,10-O-(2-propenylidene)baccatin III Melting point: 151–153° C. (lyophilization from dioxane); $^1$H-NMR (400 MHz, CDCl$_3$/TMS) δ (ppm); 1.04–1.30 (2H, m), 1.25 (3H, s), 1.30–1.55 (2H, m), 1.59 (3H, s), 1.64 (3H, s), 1.67 (3H, s), 1.70–1.86 (1H, m), 1.97 (1H, s), 2.03–2.32 (3H, m), 2.41 (1H, dd, J=15.1 Hz, J=9.7 Hz), 2.90 (1H, d, J=4.8 Hz), 3.85 (1H, d, J=7.3 Hz), 4.07 (1H, br s), 4.27 (1H, d, J=8.8 Hz), 4.32 (1H, d, J=8.8 Hz), 4.42 (1H, br), 4.57 (1H, br d, J=7.3 Hz), 4.79 (1H, d, J=2.9 Hz), 5.06 (1H, s), 5.19 (1H, d, J=6.3 Hz), 5.23 (1H, d, J=7.3 Hz), 5.44 (1H, d, J=10.7 Hz), 5.55 (1H, d, J=17.6 Hz), 5.89–6.18 (4H, m), 6.36 (1H, dd, J=3.4 Hz, J=2.0 Hz), 6.39 (1H, d, J=3.4 Hz). FAB mass: 868 (MH$^+$).

Inventive Example 111

9β-13-O-[(2R,3R)-3-(tert-Butoxycarbonylamino)-3-(2-furyl)-2-hydroxypropionyl]-4-O-cyclopropanecarbonyl-4,10-dideacetyl-9-dihydro-9,10-O-[2-(i-methylpiperazin-4-yl)ethylidene]baccatin III Melting point: 124–127° C. (lyophilization from dioxane); $^1$H-NMR (400 MHz, CDCl$_3$-CD$_3$OD (4:1 (v/v))/TMS) δ (ppm); 1.10 (4H, m), 1.28 (3H, s), 1.41 (9H, s), 1.57 (3H, s), 1.63 (3H, s), 1.74 (3H, s), 2.04–3.20 (16H, m), 2.70 (3H, s), 3.84 (1H, d, J=7.8 Hz), 4.04 (1H, br), 4.39 (2H, ABq, J=7.8 Hz), 4.72 (1H, br), 5.00 (1H, t, J=3.6 Hz), 5.05 (1H, s), 5.23 (1H, d, J=6.8 Hz), 5.38 (1H, d, J=6.8 Hz), 6.03 (2H, m), 6.33 (1H, d, J=2.8 Hz), 6.35 (1H, t, J=2.0 Hz), 7.37 (1H, s), 7.48 (2H, t, J=7.8 Hz), 7.61 (1H, t, J=7.3 Hz), 8.05 (2H, d, J=7.3 Hz). FAB mass: 951 (MH$_2^+$).

Inventive Example 112

9β-13-O-[(2R,3R)-3-(tert-Butoxycarbonylamino)-3-(2-furyl)-2-hydroxypropionyl]-4-O-cyclopropanecarbonyl-4,10-dideacetyl-9-dihydro-9,10-O-(2-dimethylaminoethylidene)baccatin III Melting point: 129–136° C. (lyophilization from dioxane); $^1$H-NMR (400 MHz, CDCl$_3$/TMS) δ (ppm); 1.10 (4H, m), 1.28 (3H, s), 1.42 (9H, s), 1.58 (3H, s), 1.63 (3H, s), 1.75 (3H, s), 2.03–2.36 (5H, m), 2.71 (3H, s), 2.91 (3H, s), 3.12 (2H, m), 3.90 (1H, d, J=6.8 Hz), 4.05 (1H, m), 4.30 (2H, ABq, J=8.8 Hz), 4.72 (1H, s), 5.06 (1H, s), 5.21 (1H, br), 5.30 (1H, d, J=6.8 Hz), 5.38 (2H, m), 6.03 (2H, m), 6.33 (1H, d, J=2.8 Hz), 6.35 (1H, d, J=2.0 Hz), 7.37 (1H, s), 7.49 (2H, t, J=7.3 Hz), 7.60 (1H, t, J=7.3 Hz), 8.04 (2H, d, J=7.8 Hz). FAB mass 896 (MH$_2^+$).

Inventive Example 113

9β-13-O-[(2R,3R)-3-(Benzoylamino)-3-(2-furyl)-2-hydroxypropionyl]-4-O-cyclopropanecarbonyl-4,10-dideacetyl-9-dihydro-9,10-O-(2-morpholinoethylidene)baccatin II Melting point: 148–151° C. (lyophilization from dioxane); $^1$H-NMR (400 MHz, CDCl$_3$/TMS) δ (ppm);

1.04–1.30 (2H, m), 1.25 (3H, s), 1.34–1.53 (2H, m), 1.58 (3H, s), 1.62 (3H, s), 1.63 (3H, s), 1.72–1.84 (1H, m), 1.93 (1H, s), 2.00–2.24 (3H, m), 2.40 (1H, dd, J=15.1 Hz, J=9.8 Hz), 2.52–2.70 (4H, m), 2.73 (1H, dd, J=13.2 Hz, J=4.9 Hz), 2.81 (1H, dd, J=13.2 Hz, J=3.9 Hz), 3.66–3.83 (4H, m), 3.77 (1H, d, J=6.8 Hz), 4.05–4.08 (1H, m), 4.27 (1H, d, J=8.8 Hz), 4.33 (1H, d, J=8.8 Hz), 4.66 (1H, d, J=8.3 Hz), 4.79 (1H, s like), 5.00 (1H, t, J=3.9 Hz), 5.06 (1H, s), 5.17 (1H, d, J=6.8 Hz), 5.93 (1H, dd, J=9.3 Hz, J=2.5 Hz), 6.02–6.15 (2H, m), 6.35 (1H, d, J=1.9 Hz), 6.36 (1H, dd, J=3.4 Hz, J=1.9 Hz), 7.12 (1H, d, J=9.3 Hz), 7.37 (1H, s like), 7.40–7.59 (5H, m), 7.61 (1H, t, J=7.8 Hz), 7.80 (2H, d, J=8.3 Hz), 8.04 (2H, d, J=8.3 Hz). FAB mass: 941 (MH$^+$).

Inventive Example 114

9β-13-O-[(2R,3R)-3-(tert-Butoxycarbonylamino)-3-(2-furyl)-2-hydroxypropionyl)-4,10-dideacetyl-7-deoxy-4-O-ethoxycarbonyl-9-dihydro-9,10-O-(2-morpholinoethylidene)baccatin III Melting point: 118–119° C. (lyophilization from dioxane); $^1$H-NMR (400 MHz, CDCl$_3$/TMS) δ (ppm); 1.25 (3H, s), 1.37 (3H, t, J=5.8 Hz), 1.41 (9H, s), 1.49 (3H, s), 1.50–2.10 (4H, m), 1.60 (3H, s), 1.77 (3H, s), 1.85 (1H, s), 2.20 (1H, dd, J=15.3 Hz, J=3.4 Hz), 2.45 (1H, dd, J=15.3 Hz, J=9.3 Hz), 2.52–2.94 (7H, m), 3.74 (4H, t, J=4.4 Hz), 4.02 (1H, br), 4.11 (1H, d, J=7.3 Hz), 4.22 (1H, d, J=8.8 Hz), 4.25–4.57 (3H, m), 4.71 (1H, s), 5.00 (1H, s), 5.05 (1H, t, J=8.9 Hz), 5.26 (1H, d, J=7.3 Hz), 5.35 (1H, d, J=10.2 Hz), 5.41 (1H, d, J=10.2 Hz), 5.97 (1H, t, J=7.3 Hz), 6.04 (1H, d, J=4.4 Hz), 6.25–6.40 (2H, m), 7.38 (1H, s), 7.44 (2H, t, J=7.8 Hz), 7.59 (1H, t, J=7.8 Hz), 8.07 (2H, d, J=7.8 Hz). FAB mass: 925 (MH$^+$).

Inventive Example 115

9β-13-O-((2R,3R)-3-(tert-butoxycarbonylamino)-3-(2-furyl)-2-hydroxypropionyl]-4,10-dideacetyl-7-deoxy-4-O-ethoxycarbonyl-9-dihydro-9,10-O-(2-dimethylaminoethylidene)baccatin III Melting point: 114–115° C. (lyophilization from dioxane); $^1$H-NMR (400 MHz, CDCl$_3$/TMS) δ (ppm); 1.25 (3H, s), 1.36 (3H, t, J=6.9 Hz), 1.41 (9H, s), 1.49 (3H, s), 1.50–2.30 (6H, m), 1.61 (3H, s), 1.78 (3H, s), 2.35–2.51 (1H, m), 2.39 (6H, m), 2.67 (1H, dd, J=13.2 Hz, J=5.4 Hz), 2.76 (1H, dd, J=13.2 Hz, J=3.9 Hz), 2.85 (1H, d, J=4.9 Hz), 4.11 (1H, d, J=7.3 Hz), 4.22 (1H, d, J=8.8 Hz), 4.23–4.57 (3H, m), 4.71 (1H, s), 4.95–5.08 (2H, m), 5.27 (1H, d, J=7.3 Hz), 5.35 (1H, d, J=8.8 Hz), 5.42 (1H, d, J=8.8 Hz), 5.98 (1H, t, J=7.8 Hz), 6.04 (1H, d, J=4.9 Hz), 6.23–6.39 (2H, m), 7.38 (1H, s), 7.44 (2H, t, J=7.8 Hz), 7.60 (1H, t, J=7.8 Hz), 8.07 (2H, d, J=7.8 Hz). FAB mass: 883 (MH$^+$).

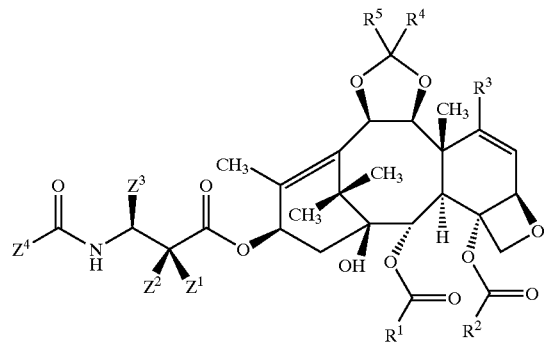

| Example No. | R$^1$ | R$^2$ | R$^3$ | R$^4$ | R$^5$ | Z$^1$ | Z$^2$ | Z$^3$ | Z$^4$ |
|---|---|---|---|---|---|---|---|---|---|
| 116 | Ph | CH$_3$ | H | —CH=CH$_2$ | H | OH | H | Ph | OC(CH$_3$)$_3$ |
| 117 | Ph | CH$_3$ | H | —CH$_2$—N(morpholino) | H | OH | H | Ph | OC(CH$_3$)$_3$ |
| 118 | Ph | CH$_3$ | H | CH$_3$ | CH$_3$ | OH | H | 4-pyridyl | OC(CH$_3$)$_3$ |
| 119 | Ph | (CH$_2$)$_2$CH$_3$ | H | —CH=CH$_2$ | H | OH | H | 2-furyl | OC(CH$_3$)$_3$ |
| 120 | Ph | (CH$_2$)$_2$CH$_3$ | H | —CH$_2$—N(morpholino) | H | OH | H | 2-furyl | OC(CH$_3$)$_3$ |

-continued

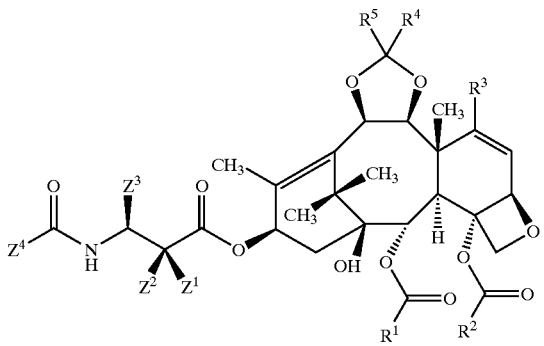

| Example No. | R¹ | R² | R³ | R⁴ | R⁵ | Z¹ | Z² | Z³ | Z⁴ |
|---|---|---|---|---|---|---|---|---|---|
| 121 | Ph | △ | H | CH₃ | CH₃ | OH | CH₃ | 4-pyridyl | OC(CH₃)₃ |
| 122 | Ph | CH₃ | H | CH₃ | CH₃ | OH | CH₃ | 4-pyridyl | OC(CH₃)₃ |
| 123 | Ph | △ | H | —CH₂—N(morpholino) | H | OH | H | 2-furyl | OC(CH₃)₃ |
| 124 | Ph | CH₃ | H | CH₃ | CH₃ | OH | H | 2-pyridyl | OC(CH₃)₃ |

Ph: Phenyl group.

Inventive Example 116

9β-13-O-[(2R,3S)-3-(tert-Butoxycarbonylamino)-2-hydroxy-3-phenylpropionyl]-10-deacetyl-7-deoxy-6,7-didehydro-9-dihydro-9,10-O-(2-propenylidene)baccatin III Melting point: 148–151° C. (lyophilization from dioxane); $^1$H-NMR(400 MHz, CDCl$_3$/TMS) δ (ppm); 1.24 (3H, s), 1.40 (9H, br s), 1.52 (3H, s), 1.58 (3H, s), 1.59 (3H, s), 1.84 (1H, s), 2.14 (1H, dd, J=7.8, 15.1 Hz), 2.33 (3H, s), 2.44 (1H, dd, J=9.9, 15.1 Hz), 3.08 (1H, d, J=5.9 Hz), 3.97 (1H, d, J=7.3 Hz), 4.07–4.16 (1H, br s), 4.24 (1H, d, J=8.1 Hz), 4.34 (1H, d, J=8.1 Hz), 4.63 (1H, br s), 4.86 (1H, br d, J=4.2 Hz), 5.22 (1H, d, J=7.3 Hz), 5.26 (1H, d, J=6.4 Hz), 5.30 (1H, br d, J=8.8 Hz), 5.49 (1H, d, J=10.7 Hz), 5.61 (1H, d, J=17.1 Hz), 5.52–5.63 (1H, m), 5.70 (1H, dd, J=10.3, 4.2 Hz), 5.97–6.10 (3H, m), 6.11 (1H, d, J=10.3 Hz), 7.25–7.43 (5H, m), 7.48 (2H, t, J=7.5 Hz), 7.61 (1H, t, J=7.5 Hz), 8.13 (2H, d, J=7.5 Hz). FAB mass: 830 (MH⁺).

Inventive Example 117

9β-13-O-[(2R,3S)-3-(tert-Butoxycarbonylamino)-2-hydroxy-3-phenylpropionyl]-10-deacetyl-7-deoxy-6,7-didehydro-9-dihydro-9,10-O-(2-morpholinoethylidene)baccatin III Melting point: 150–153° C. (lyophilization from dioxane); $^1$H-NMR (400 MHz, CDCl$_3$/TMS) δ (ppm); 1.23 (3H, s), 1.39 (9H, s), 1.51 (3H, s), 1.57 (3H, s), 1.64 (3H, br s), 1.84 (1H, s), 2.15 (1H, dd, J=7.3, 14.8 Hz), 2.32 (3H, s), 2.39 (1H, dd, J=9.5, 14.8 Hz), 2.55–2.70 (4H, m), 2.75 (1H, dd, J=4.9, 13.7 Hz), 2.82 (1H, dd, J=3.9, 13.7 Hz), 3.07 (1H, d, J=5.9 Hz), 3.74 (4H, t, J=4.6 Hz), 3.91 (1H, d, J=7.6 Hz), 4.00–4.15 (1H, br s), 4.24 (1H, d, J=7.8 Hz), 4.34 (1H, d, J=7.8 Hz), 4.63 (1H, br s), 4.85 (1H, d, J=4.2 Hz), 5.05 (1H, dd, J=3.9, 4.9 Hz), 5.15 (1H, d, J=7.6 Hz), 5.30 (1H, br d, J=9.3 Hz), 5.62 (1H, br d, J=9.3 Hz), 5.69 (1H, dd, J=10.3, 4.2 Hz), 5.96 (1H, d, J=5.9 Hz), 6.03–6.09 (1H, m), 6.07 (1H, d, J=10.3 Hz), 7.30–7.43 (5H, m), 7.49 (2H, t, J=7.3 Hz), 7.61 (1H, t, J=7.3 Hz), 8.13 (2H, d, J=7.3 Hz).

Inventive Example 118

9β-13-O-[(2R,3S)-3-(tert-Butoxycarbonylamino)-2-hydroxy-3-(4-pyridyl)propionyl)-10-deacetyl-7-deoxy-6,7-didehydro-9-dihydro-9,10-O-isopropylidenebaccatin III Melting point: 162–165° C. (lyophilization from dioxane); $^1$H-NMR (400 MHz, CDCl$_3$/TMS) δ (ppm); 1.22 (3H, s), 1.41 (9H, s), 1.42 (3H, s), 1.52 (3H, s), 1.53 (3H, s), 1.57 (3H, s), 1.60 (3H, s), 1.86 (1H, s), 2.34 (3H, s), 2.05–2.17 (1H, m), 2.32–2.43 (1H, m), 3.07 (1H, d, J=5.7 Hz), 3.97 (1H, d, J=7.3 Hz), 4.22 (1H, d, J=7.8 Hz), 4.37 (1H, d, J=7.8 Hz), 4.39 (1H, br s), 4.63 (1H, br s), 4.86 (1H, d, J=4.0 Hz), 5.32 (1H, br d, J=9.6 Hz), 5.47 (1H, d, J=7.3 Hz), 5.69 (1H, dd, J=4.0, 10.3 Hz), 5.73 (1H, br d, J=9.6 Hz), 5.98 (1H, d, J=5.7 Hz), 6.10 (1H, d, J=10.3 Hz), 6.02–6.14 (1H, br), 7.36 (2H, d, J=5.9 Hz), 7.48 (2H, t, J=7.4 Hz), 7.61 (1H, t, J=7.4 Hz), 8.14 (2H, d, J=7.4 Hz), 8.60 (2H, d, J=5.9 Hz). FAB mass: 833 (MH⁺).

Inventive Example 119

9β-4-O-Butanoyl-13-O-[(2R,3R)-3-(tert-butoxycarbonylamino)-3-(2-furyl)-2-hydroxypropionyl]-7-deoxy-4,10-dideacetyl-6,7-didehydro-9-dihydro-9,10-O-(2-propenylidene)baccatin III Melting point: 127–130° C. (lyophilization from dioxane); $^1$H-NMR (400 MHz, CDCl$_3$/TMS) δ (ppm); 1.23–1.29 (3H, m), 1.41 (9H, s), 1.53 (3H, s), 1.60 (6H, s), 1.70 (3H, s), 1.77–1.92 (2H, m), 2.27 (1H, dd, J=8.3, 15.3 Hz), 2.39 (1H, dd, J=9.5, 15.3 Hz), 2.44–2.70 (2H, m), 3.12 (1H, d, J=5.9 Hz), 3.76 (1H, br s), 4.01 (1H, d, J=7.3 Hz), 4.27 (1H, d, J=8.3 Hz), 4.34 (1H, d, J=8.3 Hz), 4.71 (1H, br d, J=3.9 Hz), 4.81 (1H, d, J=4.2 Hz), 5.22 (1H, d, J=7.3 Hz), 5.25 (1H, d, J=6.4 Hz), 5.33 (2H, br s), 5.48 (1H, d, J=10.7 Hz), 5.60 (1H, d, J=17.1 Hz), 5.70 (1H, dd, J=10.3, 4.2 Hz), 5.99 (1H, d, J=5.9 Hz), 6.00–6.13 (2H, m), 6.12 (1H, d, J=10.3 Hz), 6.34 (1H, d, J=2.9 Hz), 6.35–6.38 (1H, m), 7.40 (1H, br s), 7.49 (2H, t, J=7.3 Hz), 7.62 (1H, t, J=7.3 Hz), 8.16 (2H, d, J=7.3 Hz).

Inventive Example 120

9β-4-O-Butanoyl-13-O-[(2R,3R)-3-(tert-butoxycarbonylamino)-3-(2-furyl)-2-hydroxypropionyl]-7-deoxy-4,10-dideacetyl-6,7-didehydro-9-dihydro-9,10-O-(2-morpholinoethylidene)baccatin III Melting point: 132–135° C. (lyophilization from dioxane); $^1$H-NMR (400 MHz, CDCl$_3$/TMS) δ (ppm); 1.01 (3H, t, J=7.3 Hz), 1.25 (3H, s), 1.40 (9H, s), 1.52 (3H, s), 1.56 (3H, s), 1.68 (3H, s), 1.78–1.90 (2H, m), 2.28 (1H, dd, J=8.3, 14.9 Hz), 2.39 (1H, dd, J=9.5, 14.9 Hz), 2.44–2.55 (1H, m), 2.55–2.70 (5H, m), 2.76 (1H, dd, J=13.7, 5.1 Hz), 2.81 (1H, dd, J=13.7, 3.9 Hz), 3.10 (1H, d, J=6.2 Hz), 3.75 (4H, t, J=4.7 Hz), 3.97 (1H, d, J=7.5 Hz), 4.26 (1H, d, J=8.3 Hz), 4.33 (1H, d, J=8.3 Hz), 4.71 (1H, br s), 4.81 (1H, d, J=3.9 Hz), 5.04 (1H, dd, J=5.1, 3.9 Hz), 5.16 (1H, d, J=7.5 Hz), 5.32 (2H, br s), 5.70 (1H, dd, J=10.3, 3.9 Hz), 5.96 (1H, d, J=6.2 Hz), 6.03–6.13 (1H, m), 6.09 (1H, d, J=10.3 Hz), 6.30–6.40 (2H, m), 7.40 (1H, s), 7.50 (2H, t, J=7.3 Hz), 7.62 (1H, t, J=7.3 Hz), 8.16 (2H, d, J=7.3 Hz).

Inventive Example 121

9β-13-O-(3-(tert-Butoxycarbonylamino)-2-hydroxy-2-methyl-3-(4-pyridyl)propionyl]-4-O-cyclopropanecarbonyl-7-deoxy-4,10-dideacetyl-6,7-didehydro-9-dihydro-9,10-O-isopropylidenebaccatin III Melting point: 165–168° C. (lyophilization from dioxane); $^1$H-NMR (400 MHz, CDCl$_3$/TMS) δ (ppm); 1.25 (s), 1.38 (s), 1.42 (s), 1.51 (s), 1.57 (s), 1.59 (s), 2.20 (1H, m), 2.28 (1H, m), 3.11 (1H, d, J=5 Hz), 3.94 (1H, d, J=7.5 Hz), 4.14 (1H, d, J=8 Hz), 4.33 (4H, d, J=8 Hz), 4.54 (8H, br), 4.75 (1H, d, J=4 Hz), 5.00 (1H, d, J=9.5 Hz), 5.45 (1H, d, J=7.5 Hz), 5.67 (1H, dd, J=1 Hz, 4 Hz), 5.85 (1H, d, J=9.5 Hz), 6.00 (1H, d, J=5 Hz), 6.07 (1H, d, J=10 Hz), 6.18 (1H, t-br), 7.34 (2H, d, J=5.5 Hz), 7.50 (2H, t, J=7.5 Hz), 7.62 (1H, t, J=7.5 Hz), 8.07 (2H, d, J=7.5 Hz), 8.57 (2H, d, J=5.5 Hz). FAB mass: 873 (M$^+$).

Inventive Example 122

9β-13-O-[3-(tert-Butoxycarbonylamino)-2-hydroxy-2-methyl-3-(4-pyridyl)propionyl]-10-deacetyl-7-deoxy-6,7-didehydro-9-dihydro-9,10-O-isopropylidenebaccatin III Melting point: 161–164° C. (lyophilization from dioxane); $^1$H-NMR (400 MHz, CDCl$_3$/TMS) δ (ppm); 1.27 (s), 1.34 (9H, s), 1.42 (s), 1.54 (s), 1.58 (s), 1.59 (s), 2.22 (2H, m), 2.52 (3H, s), 3.10 (1H, d, J=5.5 Hz), 3.98 (1H, d, J=7.5 Hz), 4.24 (1H, d, J=8 Hz), 4.38 (1H, d, J=8 Hz), 4.85 (1H, d, J=4 Hz), 5.02 (1H, d, J=10 Hz), 5.44 (1H, d, J=7.5 Hz), 5.69 (1H, dd, J=10 Hz, 4 Hz), 5.74 (1H, d, J=10 Hz), 5.96 (1H, d, J=5.5 Hz), 6.10 (1H, d, J=10 Hz), 6.23 (1H, t, J=9 Hz), 7.35 (2H, d, J=5 Hz), 7.49 (2H, t, J=7.5 Hz), 7.61 (1H, t, J=7.5 Hz), 8.15 (2H, d, J=7.5 Hz), 8.60 (2H, d, J=5 Hz). FAB mass: 847 (M$^+$).

Inventive Example 123

9β-13-O-[(2R,3R)-3-(tert-Butoxycarbonylamino)-3-(2-furyl)-2-hydroxypropionyl]-4-O-cyclopropanecarbonyl-7-deoxy-4,10-dideacetyl-6,7-didehydro-9-dihydro-9,10-O-(2-morpholinoethylidene)baccatin III Melting point: 105–110° C. (lyophilization from dioxane); $^1$H-NMR (400 MHz, CDCl$_3$/TMS) δ (ppm); 1.25 (7H, s like), 1.41 (9H, s), 1.50 (3H, s), 1.56 (3H, s), 1.71 (3H, s), 2.33–2.44 (3H, m), 2.64 (4H, m), 2.79 (2H, ABq, J=8.3 Hz), 3.10 (1H, d, J=5.9 Hz), 3.72–7.76 (4H, m), 3.94 (1H, d, J=7.3 Hz), 4.25 (2H, ABq, J=8.3 Hz), 4.73 (1H, s), 4.78 (1H, d, J=4.4 Hz), 5.05 (1H, dd, J=4.9 Hz, 3.9 Hz), 5.45 (1H, d, J=17.2 Hz), 5.69 (1H, dd, 10.3 Hz, 3.9 Hz), 5.98 (1H, d, J=5.9 Hz), 6.04 (1H, m), 6.07 (1H, d, J=10.7 Hz), 6.32 (1H, d, J=3.4 Hz), 6.35 (1H, dd, J=3.4 Hz, 2.0 Hz), 7.36 (1H, s), 7.50 (2H, t, J=7.3 Hz), 7.62 (1H, t, J=7.3 Hz), 8.10 (2H, d, J=7.3 Hz). FAB mass: 919 (MH$^+$). $^1$H-NMR (400 MHz, CDCl$_3$/TMS) δ (ppm); 1.59 (3H, s), 1.60 (3H, s), 1.66 (3H, s), 1.80 (1H, s), 2.23–2.38 (2H, m), 2.42 (3H, s), 3.12 (1H, d, J=5.9 Hz), 4.06 (1H, d, J=7.6 Hz), 4.28 (1H, d, J=8.3 Hz), 4.33 (1H, d, J=8.3 Hz), 4.78 (1H, br s), 4.87 (1H, br s), 4.88 (1H, d, J=4.2 Hz), 5.35 (1H, br d, J=9.8 Hz), 5.47 (1H, d, J=7.8 Hz), 5.68 (1H, dd, J=4.2, 10.6 Hz), 5.91 (1H, d, J=9.8 Hz), 5.94 (1H, d, J=5.9 Hz), 6.09 (1H, d, J=10.6 Hz), 6.05–6.15 (1H, m), 7.20–7.28 (1H, m), 7.41 (1H, d, J=7.8 Hz), 7.48 (2H, t, J=7.3 Hz), 7.60 (1H, t, J=7.3 Hz), 7.73 (1H, d, J=7.8 Hz), 8.14 (2H, d, J=7.3 Hz), 8.52 (1H, d, J=4.4 Hz).

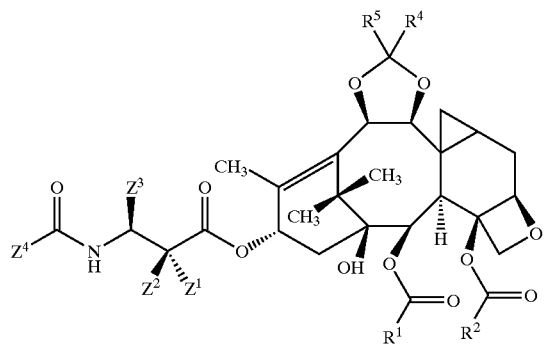

| Example No. | R¹ | R² | R³ | R⁴ | R⁵ | Z¹ | Z² | Z³ | Z⁴ |
|---|---|---|---|---|---|---|---|---|---|
| 125 | Ph | $CH_3(CH_2)_2$ | — | —$CH_2$—N(morpholine) | H | OH | H | 2-furyl | $OC(CH_3)_3$ |
| 126 | Ph | $CH_3$ | — | —$CH_2$—N(morpholine) | H | OH | H | Ph | $OC(CH_3)_3$ |

Ph: Phenyl group.

Inventive Example 125

9β-4-O-Butanoyl-13-O-[(2R,3R)-3-(tert-butoxycarbonylamino)-3-(2-furyl)-2-hydroxypropionyl]-7-deoxy-4,10-dideacetyl-9-dihydro-7β,8β-methylene-9,10-O-[2-morpholinoethylidene]-19-norbaccatin III ¹H-NMR (400 MHz, CDCl₃/TMS) δ (ppm); 0.74 (1H, br t, J=5.0 Hz), 0.99 (3H, t, J=7.6 Hz), 1.18–1.80 (9H, m), 1.20 (3H, s), 1.35 (9H, s), 1.53 (3H, s), 2.29 (1H, dd, J=8.8 Hz, 15.6 Hz), 2.40–2.77 (10H, m), 3.12 (1H, d, J=8.3 Hz), 3.36 (1H, br s), 3.72 (4H, t, J=4.6 Hz), 4.13 (1H, dd, J=7.8 Hz, 2.6 Hz), 4.32 (1H, d, J=7.8 Hz), 4.47–4.55 (2H, m), 4.67 (1H, br s), 4.91 (1H, t, J=4.4 Hz), 5.09 (1H, d, J=7.3 Hz), 5.24 (1H, d, J=9.7 Hz), 5.38 (1H, br d, J=9.7 Hz), 5.52 (1H, d, J=8.3 Hz), 6.22 (1H, br t, J=8.8 Hz), 6.35 (1H, d, J=2.9 Hz), 6.39 (1H, dd, J=2.9 Hz, 1.5 Hz), 7.42 (1H, d, J=1.5 Hz), 7.49 (2H, t, J=7.8 Hz), 7.57 (1H, t, J=7.8 Hz), 8.08 (2H, d, J=7.8 Hz).

Inventive Example 126

9β-13-O-[(2R,3S)-3-(tert-butoxycarbonylamino)-2-hydroxy-3-phenylpropionyl]-10-deacetyl-7-deoxy-9-dihydro-7β,8β-methylene-9,10-O-(2-morpholinoethylidene)-19-norbaccatin III ¹H-NMR (400 MHz, CDCl₃/TMS) δ (ppm); 0.77 (1H, br s), 1.10–1.80 (3H, m), 1.21 (3H, s), 1.34 (9H, s), 1.54 (3H, s), 1.68 (9H, s), 1.75 (1H, s), 2.23 (3H, s), 2.31 (1H, dd, J=8.8 Hz, 15.6 Hz), 2.50–2.78 (8H, m), 3.12 (1H, d, J=8.3 Hz), 3.48 (1H, br s), 3.65–3.78 (4H, m), 4.17 (1H, dd, J=7.8 Hz, 2.0 Hz), 4.32–4.48 (2H, m), 4.54 (1H, t, J=8.8 Hz), 4.60 (1H, br s), 4.91 (1H, t, J=4.2 Hz), 5.09 (1H, d, J=7.3 Hz), 5.31 (1H, br d, J=9.1 Hz), 5.47 (1H, d, J=9.1 Hz), 5.53 (1H, d, J=8.3 Hz), 6.20 (1H, br t, J=8.3 Hz), 7.30–7.43 (5H, m), 7.49 (2H, t, J=7.8 Hz), 7.57 (1H, t, J=7.8 Hz), 8.08 (2H, d, J=7.8 Hz).

Reference Example 1

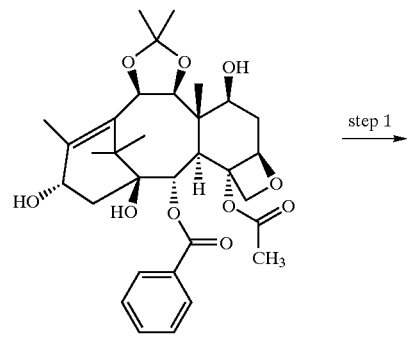

step 1 →

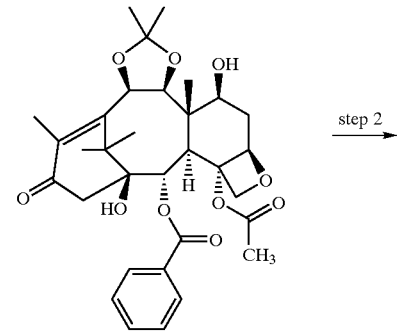

step 2 →

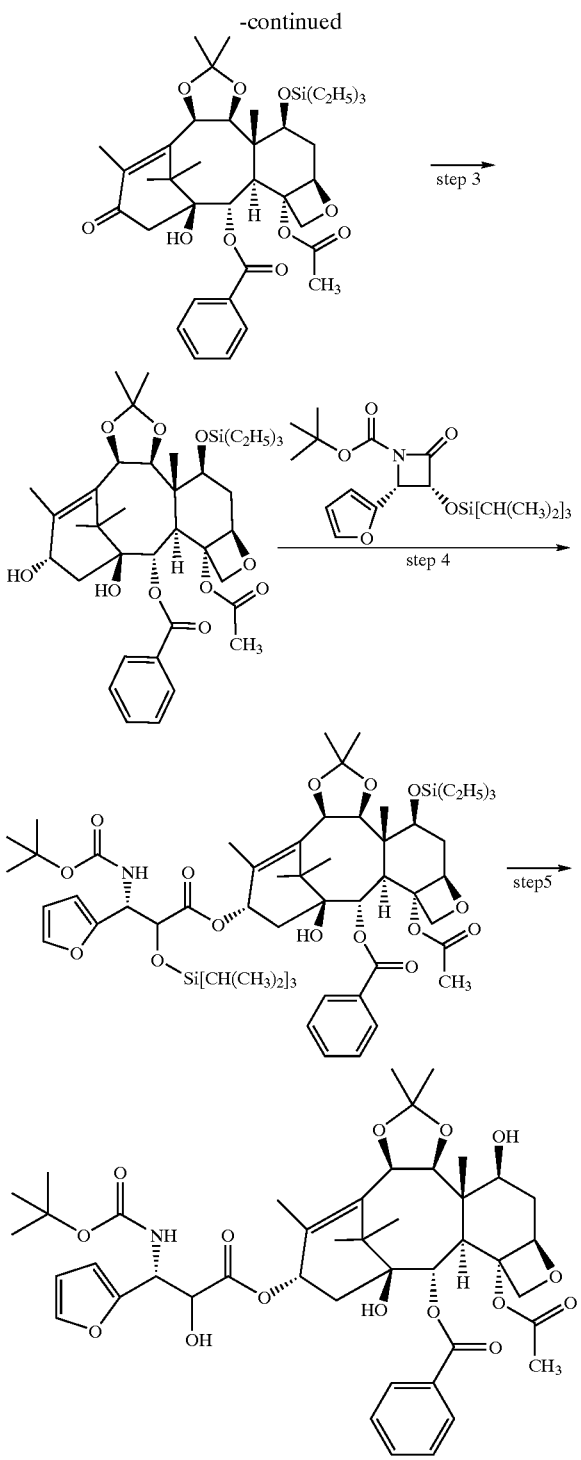

Step 1: 9β-10-Deacetyl-13-deoxy-9-dihydro-9,10-O-isopropylidene-13-oxobaccatin III A 0.1301 g portion of the compound obtained in the step 2 of Inventive Example 1 was dissolved in 6.5 ml of dioxane, and the solution was mixed with 0.823 g of manganese dioxide at room temperature and stirred vigorously for 15 hours at room temperature. The reaction mixture was filtered through celite, the filtered material was washed with chloroform and then solvent in the resulting filtrate was evaporated under a reduced pressure. Thereafter, the thus obtained residue was purified by a silica gel thin layer chromatography (developing solvent; chloroform:acetone=10:1 (v/v)) to obtain 0.1154 g of the title compound as a colorless transparent syrup.

Rf=0.60 (chloroform:acetone=10:1 (v/v)) $^1$H-NMR (400 MHz, CDCl$_3$/TMS) δ (ppm); 1.27 (3H, s), 1.43 (3H, s), 1.61 (3H, s), 1.66 (3H, s), 1.68 (3H, s), 1.94 (3H, s), 2.01 (1H, s), 2.17 (2H, m), 2.22 (3H, s), 2.64 (1H, AB type d, J=20.0 Hz), 2.90 (1H, AB type d, J=20.0 Hz), 3.15 (1H, d, J=4.4 Hz), 3.99 (1H, d, J=7.3 Hz), 4.07 (1H, m), 4.24 (1H, AB type d, J=7.8 Hz), 4.65 (1H, AB type d, J=7.8 Hz), 4.41 (1H, dd, J=1.5 Hz, 8.8 Hz), 5.04 (1H, s), 5.68 (1H, d, J=7.3 Hz), 6.16 (1H, d, J=4.8 Hz), 7.49 (2H, t, J=7.8 Hz), 7.60 (1H, t, J=7.8 Hz), 8.11 (2H, d, J=7.8 Hz).

Step 2: 9β-10-Deacetyl-13-deoxy-9-dihydro-9,10-O-isopropylidene-13-oxo-7-O-triethylsilylbaccatin III A 73.0 mg portion of the compound obtained in the above step 1 was dissolved in 2.2 ml of methylene chloride, and the solution was mixed with 0.075 ml of 2,6-lutidine and 0.112 ml of triethylsilyl trifluoromethanesulfonate at −32° C. After 30 minutes, this solution was mixed with saturated sodium bicarbonate aqueous solution at −30° C. and extracted with chloroform, and the extract was washed with saturated brine and dried over anhydrous sodium sulfate. Thereafter, the solvent was evaporated under a reduced pressure and the resulting residue was purified by a silica gel column chromatography (developing solvent; chloroform:methanol=8.5:1 (v/v)) to obtain 48.3 mg of the title compound as a white solid.

Rf=0.40 (hexane:ethyl acetate=7:1 (v/v)) $^1$H-NMR (400 MHz, CDCl$_3$/TMS) δ (ppm); 0.60 (6H, q, J=7.8 Hz), 0.95 (9H, t, J=7.8 Hz), 1.24 (3H, s), 1.44 (3H, s), 1.54 (3H, s), 1.61 (3H, s), 1.67 (3H, s), 1.94 (3H, s), 2.21 (3H, s), 1.98–2.13 (2H, m), 2.62 (1H, AB type d, J=20.0 Hz), 2.93 (1H, AB type d, J=20.0 Hz), 3.23 (1H, d, J=5.4 Hz), 4.07 (1H, t, J=2.9 Hz), 4.21 (1H, AB type d, J=7.8 Hz), 4.43 (1H, AB type d, J=7.8 Hz), 4.30 (1H, br-d), 4.78 (1H, t, J=4.0 Hz), 5.61 (1H, d, J=7.8 Hz), 6.07 (1H, d, J=5.4 Hz), 6.94 (1H, d, J=7.8 Hz), 7.49 (2H, t, J=7.8 Hz), 7.60 (1H, t, J=7.8 Hz), 8.12 (2H, d, J=7.8 Hz).

Step 3: 9β-10-Deacetyl-9-dihydro-9,10-O-isopropylidene-7-O-triethylsilylbaccatin III A 48.3 mg portion of the compound obtained in the above step 2 was dissolved in a tetrahydrofuran-methanol (20:1 (v/v)) mixture solvent, and the solution was mixed with 11.0 mg of sodium borohydride at room temperature. After 1.5 hours, this solution was neutralized by adding saturated ammonium chloride aqueous solution at 0° C. and extracted with ethyl acetate. The extract was washed with saturated brine and dried over anhydrous sodium sulfate. After evaporation of the solvent under a reduced pressure, 48.3 mg of the thus obtained residue was dissolved in 2.5 ml of methylene chloride to which was subsequently added dropwise 1.0 N aluminum diisobutylhydride (toluene solution, 0.17 ml) at −82° C., followed by 10 minutes of stirring. Methanol was poured into the reaction mixture at −78° C., and aqueous solution (1.5 ml water) of Rochelle salt (0.23 g) was added thereto and the mixture was vigorously stirred for 1 hour at room temperature. After extraction with chloroform, the resulting extract was washed with saturated brine and dried over anhydrous sodium sulfate. Thereafter, the solvent was evaporated under a reduced pressure and the resulting resi due was purified by a silica gel thin layer chromatography (developing solvent; hexane:ethyl acetate=2:1 (v/v)) to obtain 10.8 mg of the title compound as a colorless transparent syrup.

Rf=0.49 (hexane:ethyl acetate=2:1 (v/v)) $^1$H-NMR (400 MHz, CDCl$_3$/TMS) δ (ppm); 0.61 (6H, q, J=7.8 Hz), 0.95 (9H, t, J=7.8 Hz), 1.12 (3H, s), 1.40 (3H, s), 1.49 (3H, s), 1.56 (3H, s), 1.57 (3H, s), 1.93 (3H, s), 1.95–2.11 (3H, m), 2.26–2.44 (2H, m), 2.32 (3H, s), 3.16 (1H, d, J=4.9 Hz), 4.06 (1H, t, J=4.8 Hz), 4.21 (1H, AB type d, J=7.8 Hz), 4.54 (1H, AB type d, J=7.8 Hz), 4.72–4.84 (2H, m), 5.51 (1H, d, J=7.8 Hz), 5.91 (1H, d, J=4.9 Hz), 7.48 (2H, t, J=7.3 Hz), 7.59 (1H, t, J=7.3 Hz), 8.13 (2H, d, J=7.3 Hz).

Step 4: 9β-13-O-[(2R,3R)-3-(tert-Butoxycarbonylamino)-3-(2-furyl)-2-(triisopropylsilyloxy)propionyl]-10-deacetyl-9-dihydro-9,10-O-isopropylidene-7-O-triethylsilylbaccatin III Reaction of the compound obtained in the above step 3 with (3R,4R)-1-(tert-butoxycarbonyl)-4-(2-furyl)-3-(triisopropylsilyloxy)azetidin-2-one and subsequent purification were carried out in accordance with the procedure of the step 3 of Inventive Example 1 to obtain the title compound.

Rf=0.25 (hexane:ethyl acetate=6:1 (v/v)) $^1$H-NMR (400 MHz, CDCl$_3$/TMS) δ (ppm); 0.62 (6H, q, J=7.8 Hz), 0.85–1.01 (30H, m), 1.06 (3H, s), 1.23 (3H, s), 1.38 (9H, s), 1.46 (6H, s), 1.50 (3H, s), 1.76 (3H, s), 2.04–2.29 (3H, m), 2.43 (3H, s), 2.36–2.45 (1H, m), 3.16 (1H, d, J=5.4 Hz), 3.98 (1H, dd, J=8.4 Hz, 3.2 Hz), 4.25 (1H, d, J=8.0 Hz), 4.40–4.48 (1H, m), 4.50 (1H, d, J=8.0 Hz), 4.83 (1H, t, J=6.8 Hz), 4.96 (1H, s), 5.25–5.36 (2H, m), 5.41 (1H, d, J=4.8 Hz), 5.89 (1H, d, J=5.4 Hz), 6.12 (1H, t), 6.24 (1H, d, J=3.2 Hz), 6.34 (1H, d, J=3.2 Hz), 7.36 (1H, s), 7.48 (2H, t, J=7.2 Hz), 7.57 (1H, t, J=7.2 Hz), 8.11 (2H, d, J=7.2 Hz).

Step 5: 9β-13-O-[(2R,3R)-3-(tert-Butoxycarbonylamino)-3-(2-furyl)-2-hydroxypropionyl]-10-deacetyl-9-dihydro-9,10-O-isopropylidenebaccatin III Reaction of the compound obtained in the above step 3 was carried out in the same manner as described in the step 4 of Inventive Example 1 to obtain the same title compound as obtained in the step 4 of Inventive Example 1.

Reference Example 2

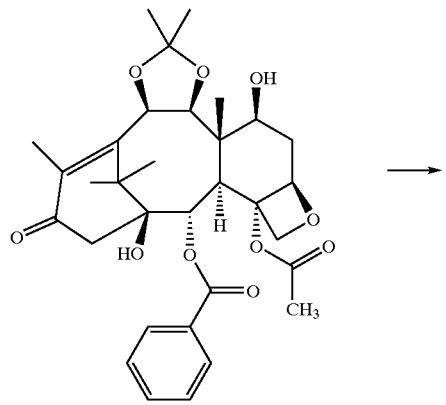

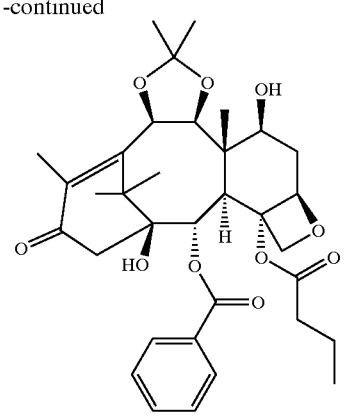

9β-4-O-Butanoyl-4,10-dideacetyl-13-deoxy-9-dihydro-9,10-O-isopropylidene-13-O-oxobaccatin III A 84.9 mg portion of the compound obtained in the step 1 of Reference Example 1 was dissolved in 2.9 ml of tetrahydrofuran to which was added dropwise 0.73 ml of 1 N sodium hexamethyldisilazide (tetrahydrofuran solution) at −58° C., followed by the addition of 0.058 ml of ethyl iodide 5 minutes thereafter. After 1.5 hours, this was mixed with saturated ammonium chloride aqueous solution at −52° C. and extracted with ethyl acetate. The thus obtained extract was washed with saturated brine and dried over anhydrous sodium sulfate. Thereafter, the solvent was evaporated under a reduced pressure and the resulting residue was purified by a silica gel thin layer chromatography (developing solvent; hexane:ethyl acetate=5:2 (v/v)) to obtain 19.1 mg of the title compound as a colorless transparent syrup.

Rf=0.23 (hexane:ethyl acetate=5:2 (v/v)) $^1$H-NMR (400 MHz, CDCl$_3$/TMS) δ (ppm); 1.06 (3H, t, J=7.3 Hz), 1.26 (3H, s), 1.43 (3H, s), 1.61 (3H, s), 1.67 (3H, s), 1.68 (3H, s), 1.68–1.80 (2H, m), 1.93 (3H, s), 1.97 (1H, s), 2.12–2.23 (2H, m), 2.38–2.54 (2H, m), 2.62 (1H, AB type d, J=19.5 Hz), 2.89 (1H, AB type d, J=19.5 Hz), 3.17 (1H, d, J=4.4 Hz), 3.99 (1H, d, J=7.3 Hz), 4.05–4.11 (1H, m), 4.24 (1H, AB type d, J=8.8 Hz), 4.67 (1H, type AB d, J=8.8 Hz), 4.42 (1H, dd, J=8.3 Hz, 0.9 Hz), 5.00 (1H, s), 5.67 (1H, d, J=7.3 Hz), 6.15 (1H, d, J=4.4 Hz), 7.49 (2H, t, J=8.3 Hz), 7.62 (1H, t, J=8.3 Hz), 8.11 (2H, d, J=8.3 Hz).

Reference Example 3

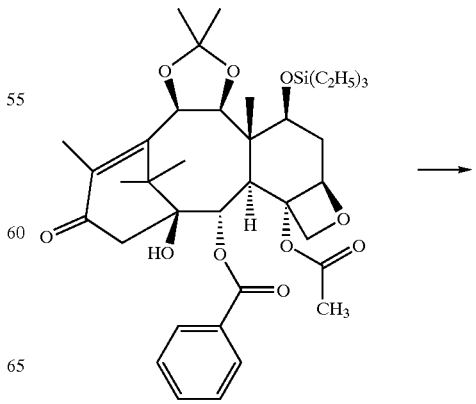

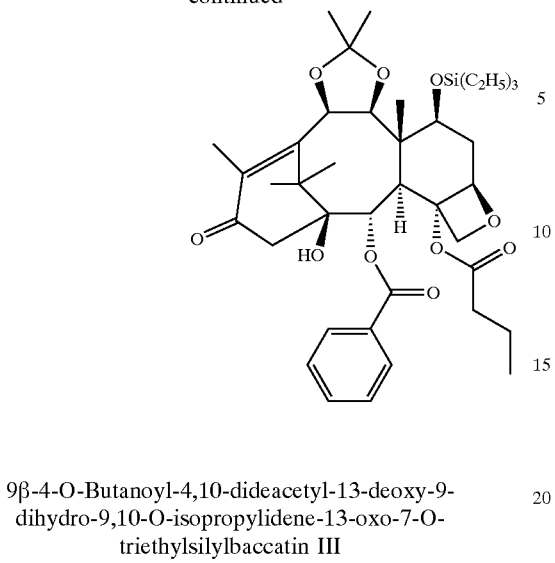

9β-4-O-Butanoyl-4,10-dideacetyl-13-deoxy-9-dihydro-9,10-O-isopropylidene-13-oxo-7-O-triethylsilylbaccatin III Using the compound obtained in the step 2 of Reference Example 1, the reaction procedure of the Reference Example 2 was repeated to obtain the title compound as a colorless transparent syrup.

Rf=0.33 (hexane:ethyl acetate=4:1 (v/v)) $^1$H-NMR (400 MHz, CDCl$_3$/TMS) δ (ppm); 0.60 (6H, q, J=8.0 Hz), 0.94 (9H, t, J=8.0 Hz), 1.05 (3H, t, J=7.6 Hz), 1.22 (3H, s), 1.43 (3H, s), 1.53 (3H, s), 1.61 (3H, s), 1.65 (3H, s), 1.66–1.82 (2H, m), 1.93 (3H, s), 1.98–2.13 (2H, m), 2.32–2.53 (2H, m), 2.59 (1H, AB type d, J=19.5 Hz), 2.91 (1H, AB type d, J=19.5 Hz), 3.22 (1H, d, J=4.8 Hz), 4.08 (1H, t, J=4.0 Hz), 4.21 (1H, AB type d, J=7.7 Hz), 4.44 (1H, AB total d, J=7.7 Hz), 4.24–4.35 (1H, m), 4.74 (1H, t, J=4.0 Hz), 5.61 (1H, d, J=7.5 Hz), 6.07 (1H, d, J=4.8 Hz), 7.48 (2H, t, J=7.7 Hz), 7.61 (1H, t, J=7.7 Hz), 8.13 (2H, d, J=7.7 Hz). FAB mass: 838 (MH$^+$).

Reference Example 4

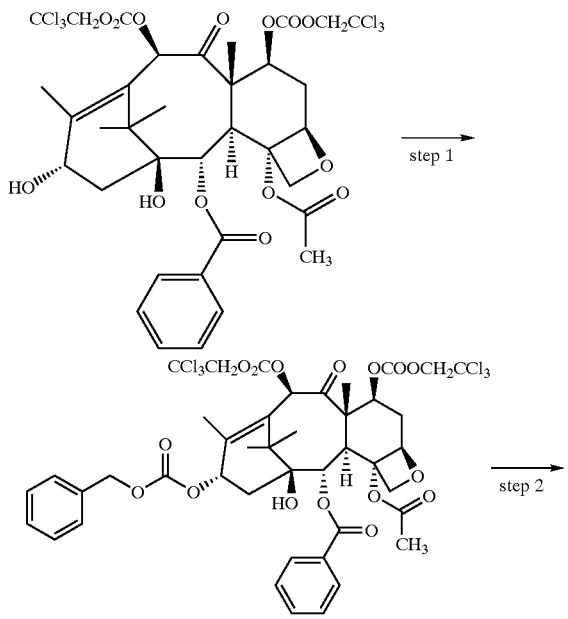

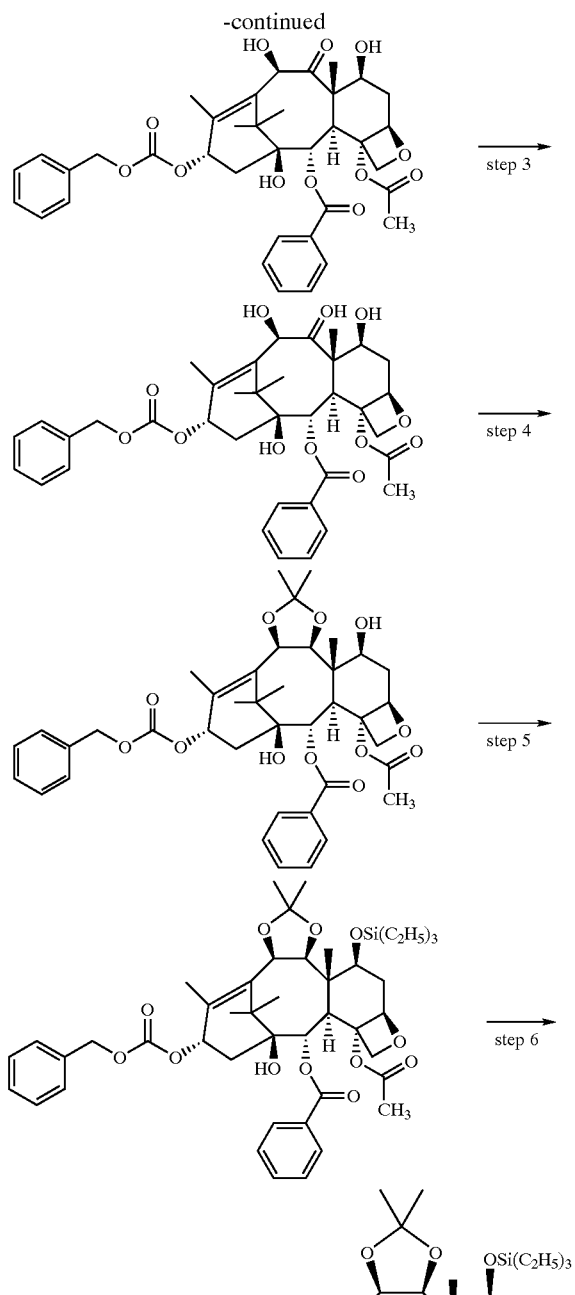

Step 1: 13-O-Benzyloxycarbonyl-10-deacetyl-7,10-bis-O-(2,2,2-trichloroethoxycarbonyl)baccatin III A 2.409 g portion of 10-deacetyl-7,10-bis-O-(2,2,2-trichloroethoxycarbonyl)baccatin III was dissolved in 15 ml of a dry tetrahydrofuran to which were added 0.92 g of benzyloxycarbonyl chloride under cooling at −50° C. Then, 5.38 ml of 1 N sodium hexamethyldisilazide (tetrahydrofuran solution) was added dropwise thereto, followed by 3 hours of stirring at the same temperature. The reaction solution was mixed with ammonium chloride aqueous solution and extracted with ethyl acetate. The thus obtained extract was washed with saturated brine and dried on anhydrous sodium sulfate. Thereafter, the solvent was evaporated under a reduced pressure and the resulting residue was purified by a silica gel column chromatography (developing solvent; hexane containing 10% (v/v) of ethyl acetate which was changed to 15% and then to 20%) to obtain 1.607 g of the title compound as a colorless glassy solid.

$^1$H-NMR (400 MHz, CDCl$_3$/TMS) δ (ppm); 1.18 (3H, s), 1.19 (3H, s), 1.84 (3H, s), 2.0–2.2 (1H, m), 2.06 (1H, d, J=1 Hz), 2.28 (3H, s), 2.35 (2H, m), 2.62 (1H, ddd, J=15 Hz, 9 Hz, 7 Hz), 3.94 (1H, d, J=7 Hz), 4.13 (1H, d, J=8 Hz), 4.32 (1H, d, J=8 Hz), 4.60 (1H, d, J=12 Hz), 4.76 (1H, AB type d, J=12 Hz), 4.79 (1H, AB type d, J=12 Hz), 4.91 (1H, d, J=12 Hz), 4.96 (1H, d, J=8 Hz), 5.25 (2H, s), 5.60 (1H, dd, J=11 Hz, 7 Hz), 5.66 (1H, d, J=7 Hz), 5.95 (1H, t, J=8 Hz), 6.26 (1H, s), 7.40 (5H, s), 7.48 (2H, t, J=7.5 Hz), 7.62 (1H, t, J=7.5 Hz), 8.07 (2H, m).

Step 2: 13-O-Benzyloxycarbonyl-10-deacetylbaccatin III

Reaction of the compound obtained in the above step 1 was carried out in the same manner as described in the step 3 of Inventive Example 9 to obtain the title compound.

$^1$H-NMR (400 MHz, CDCl$_3$/TMS) δ (ppm); 1.11 (3H, s), 1.16 (3H, s), 1.74 (3H, s), 1.82 (1H, m), 1.97 (3H, s), 2.25 (3H, s), 2.32 (2H, m), 2.59 (1H, ddd, J=14 Hz, 9.5 Hz, 6.5 Hz), 3.96 (1H, d, J=7 Hz), 4.16 (2H, m), 4.30 (2H, m), 4.95 (1H, d, J=8 Hz), 5.24 (3H, m), 5.65 (1H, d, J=7 Hz), 5.92 (1H, t, J=8 Hz), 7.40 (5H, s), 7.48 (2H, t, J=7.5 Hz), 7.62 (1H, t, J=7.5 Hz), 8.07 (2H, m).

Step 3: 9β-13-O-Benzyloxycarbonyl-10-deacetyl-9-dihydrobaccatin III

A 119 mg portion of the compound obtained in the above step 2 was dissolved in 10 ml of a dry methylene chloride, and the solution was mixed with 180 mg of tetrabutylammonium borohydride at room temperature and stirred for 15 hours at room temperature. The reaction solution was mixed, with 1 N hydrochloric acid and stirred until foaming ceased. The organic layer was collected, washed with saturated brine and then dried over anhydrous sodium sulfate. The solvent was evaporated under a reduced pressure, and the resulting residue was dissolved in methanol and allowed to stand for 3 hours. Thereafter, the solvent was evaporated under a reduced pressure and the resulting residue was purified by a silica gel thin layer chromatography (developing solvent; chloroform containing 6% (v/v) methanol) to obtain 86 mg of the title compound as a white powder.

$^1$H-NMR (400 MHz, CDCl$_3$/TMS) δ (ppm); 1.25 (3H, s), 1.64 (3H, s), 1.75 (3H, s), 1.80 (3H, s), 1.91 (1H, m), 2.19 (3H, s), 2.29 (2H, m), 2.49 (1H, m), 3.08 (1H, d, J=5 Hz), 4.11 (1H, br), 4.16 (1H, d, J=8 Hz), 4.34 (2H, m), 4.98 (1H, d, J=7 Hz), 5.17 (2H, d and br, J=12 Hz), 5.27 (1H, d, J=12 Hz), 5.96 (1H, t, J=8 Hz), 6.09 (1H, d, J=5 Hz), 7.39 (5H, m), 7.46 (2H, t, J=7.5 Hz), 7.58 (1H, t, J=7.5 Hz), 8.08 (2H, d, J=7.5 Hz).

Step 4: 9β-13-O-Benzyloxycarbonyl-10-deacetyl-9-dihydro-9,10-O-isopropylidenebaccatin III Reaction of the compound obtained in the above step 3 was carried out in the same manner described in the step 2 of Inventive Example 1 to obtain the title compound as a glassy solid.

$^1$H-NMR (400 MHz, CDCl$_3$/TMS) δ (ppm); 1.23 (3H, s), 1.40 (3H, s), 1.57 (3H, s), 1.63 (3H, s), 1.65 (3H, s), 1.79 (3H, s), 2.18 (2H, m), 2.23 (3H, s), 2.30 (2H, m), 2.97 (1H, d, J=5 Hz), 3.89 (1H, d, J=7.5 Hz), 4.03 (1H, m), 4.26 (1H, d, J=8 Hz), 4.38 (1H, d, J=8 Hz), 4.66 (1H, d, J=8 Hz), 5.09 (1H, br), 5.18 (1H, d, J=12 Hz), 5.26 (1H, d, J=12 Hz), 5.55 (1H, d, J=7.5 Hz), 5.92 (1H, t, J=8 Hz), 5.99 (1H, d, J=5 Hz), 7.39 (5H, m), 7.46 (2H, t, J=7.5 Hz), 7.59 (1H, t, J=7.5 Hz), 8.09 (2H, d, J=7.5 Hz).

Step 5: 9β-13-O-Benzyloxycarbonyl-10-deacetyl-9-dihydro-9,10-O-isopropylidene-7-O-triethylsilylbaccatin III Reaction of the compound obtained in the above step 3 was carried out in the same manner as described in the step 2 of Inventive Example 3 to obtain the title compound as a glassy solid.

$^1$H-NMR (400 MHz, CDCl$_3$/TMS) δ (ppm); 0.62 (6H, q, J=8 Hz), 0.97 (9H, t, J=7 Hz), 1.15 (3H, s), 1.38 (3H, s), 1.47 (3H, s), 1.51 (3H, s), 1.79 (3H, d, J=1 Hz), 2.08 (1H, m), 2.24 (3H, s), 2.28–2.39 (3H, m), 3.21 (1H, d, J=6 Hz), 3.94 (1H, dd, J=10 Hz, 4 Hz), 4.27 (1H, d, J=8 Hz), 4.46 (1H, d, J=8 Hz), 4.54 (1H, br), 4.80 (1H, t, J=7 Hz), 5.19 (1H, d, J=12 Hz), 5.25 (1H, d, J=12 Hz), 5.42 (1H, d, J=9 Hz), 5.84 (1H, d, J=6 Hz), 5.88 (1H, t, J=10 Hz), 7.39 (5H, m), 7.46 (2H, t, J=7.5 Hz), 7.59 (1H, t, J=7.5 Hz), 8.08 (2H, d, J=7.5 Hz).

Step 6: 9β-10-Deacetyl-9-dihydro-9,10-O-isopropylidene-7-O-triethylsilylbaccatin III A 122 mg portion of the compound obtained in the above step 5 was dissolved in 10 ml of ethanol, and the solution was mixed with 40 mg of 10% palladium-carbon and stirred for 1 hour in an atmosphere of hydrogen. Insoluble material was removed by filtration, and solvent in the resulting filtrate was evaporated under a reduced pressure. The thus obtained residue was purified by a silica gel thin layer chromatography (developing solvent; chloroform containing 5% (v/v) of acetone) to obtain 80 mg of the same title compound obtained in the step 3 of Inventive Example 3.

Reference Example 5

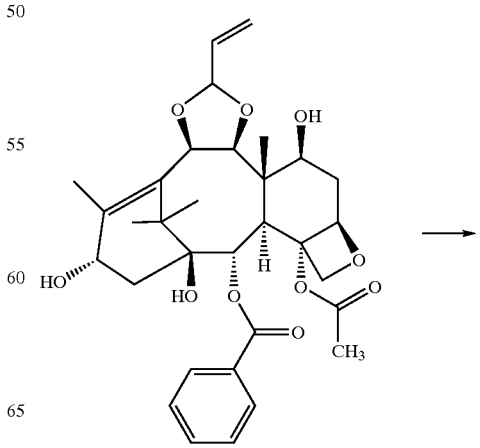

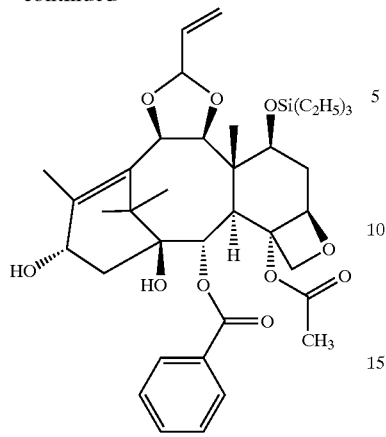

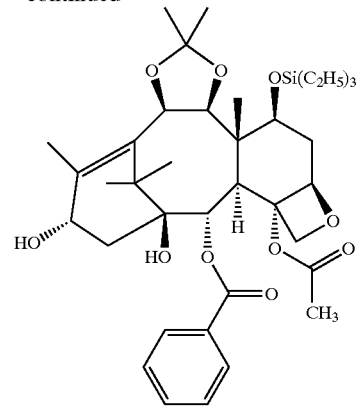

9β-10-Deacetyl-9-dihydro-9,10-O-isopropylidene-7-O-triethylsilylbaccatin III Using 9β-10-deacetyl-9-dihydro-9,10-O-isopropylidenebaccatin III as the starting material, the reaction procedure of the step 1 of Reference Example 5 was repeated to obtain the title compound.

$^{1}$H-NMR (400 MHz, CDCl$_3$/TMS) δ (ppm); 0.61 (6H, q, J=7.8 Hz), 0.96 (9H, t, J=7.8 Hz), 1.11 (3H, s), 1.40 (3H, s), 1.50 (3H, s), 1.57 (3H, s), 1.59 (3H, s), 1.93 (3H, s), 1.88–2.15 (2H, m), 2.23–2.47 (2H, m), 2.32 (3H, s), 3.16 (1H, d, J=5.3 Hz), 4.17 (1H, t, J=4.8 Hz), 4.17–4.29 (1H, m), 4.20 (1H, d, J=7.8 Hz), 4.54 (1H, d, J=7.8 Hz), 4.73–4.88 (2H, m), 5.51 (1H, d, J=7.8 Hz), 5.91 (1H, d, J=5.3 Hz), 7.48 (2H, t, J=7.3 Hz), 7.59 (1H, t, J=7.3 Hz), 8.14 (2H, t, J=7.3 Hz).

β-10-Deacetyl-9-dihydro-9,10-O-(2-propenylidene)-7-O-triethylsilylbaccatin III A 0.4030 g portion of 9β-10-deacetyl-9-dihydro-9,10-O-(2-propenylidene)baccatin III was dissolved in 80 ml of methylene chloride, and the solution was mixed with 0.232 ml of 2,6-di-tert-butylpyridine at room temperature and then cooled to −78° C. Thereto was added dropwise 0.202 ml of triethylsilyl trifluoromethanesulfonate. After 16 minutes, this solution was mixed with methanol and saturated sodium bicarbonate aqueous solution at −78° C. and extracted with chloroform, and the extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=20:1 (v/v)→chloroform:acetone=7:1 (v/v)) to obtain 0.4126 g of the title compound in a white foamy form.

$^{1}$H-NMR (400 MHz, CDCl$_3$/TMS) δ (ppm); 0.58–0.71 (6H, m), 0.98 (9H, t, J=7.8 Hz), 1.09 (3H, s), 1.56 (3H, s), 1.60 (3H, s), 1.75 (1H, s), 1.94 (3H, s), 2.00–2.45 (4H, m), 2.30 (3H, s), 3.19 (1H, d, J=5.3 Hz), 3.95 (1H, dd, J=8.8 Hz, J=5.8 Hz), 4.32 (1H, d, J=8.3 Hz), 4.35 (1H, d, J=8.3 Hz), 4.61 (1H, d, J=7.8 Hz), 4.72–4.89 (2H, m), 5.09 (1H, d, J=5.8 Hz), 5.33 (1H, d, J=7.8 Hz), 5.46 (1H, d, J=10.7 Hz), 5.56 (1H, d, J=17.1 Hz), 5.90 (1H, d, J=5.3 Hz), 6.16 (1H, ddd, J=17.1 Hz, J=10.7 Hz, J=5.8 Hz), 7.47 (2H, t, J=7.3 Hz), 7.59 (1H, t, J=7.3 Hz), 8.11 (2H, d, J=7.3 Hz).

Reference Example 6

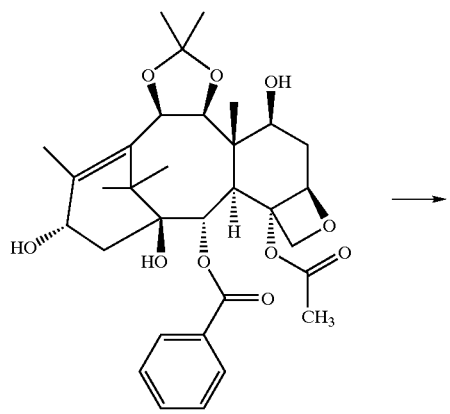

Reference Example 7

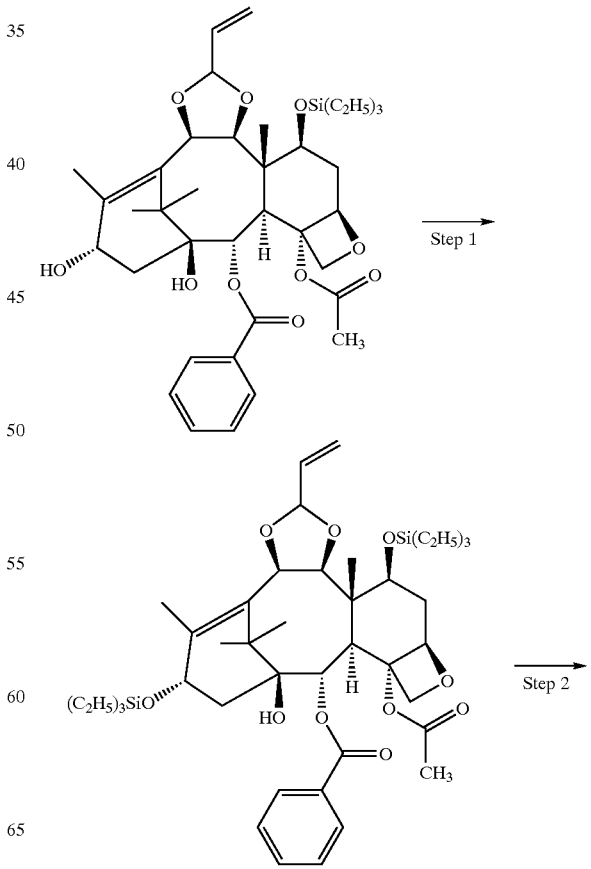

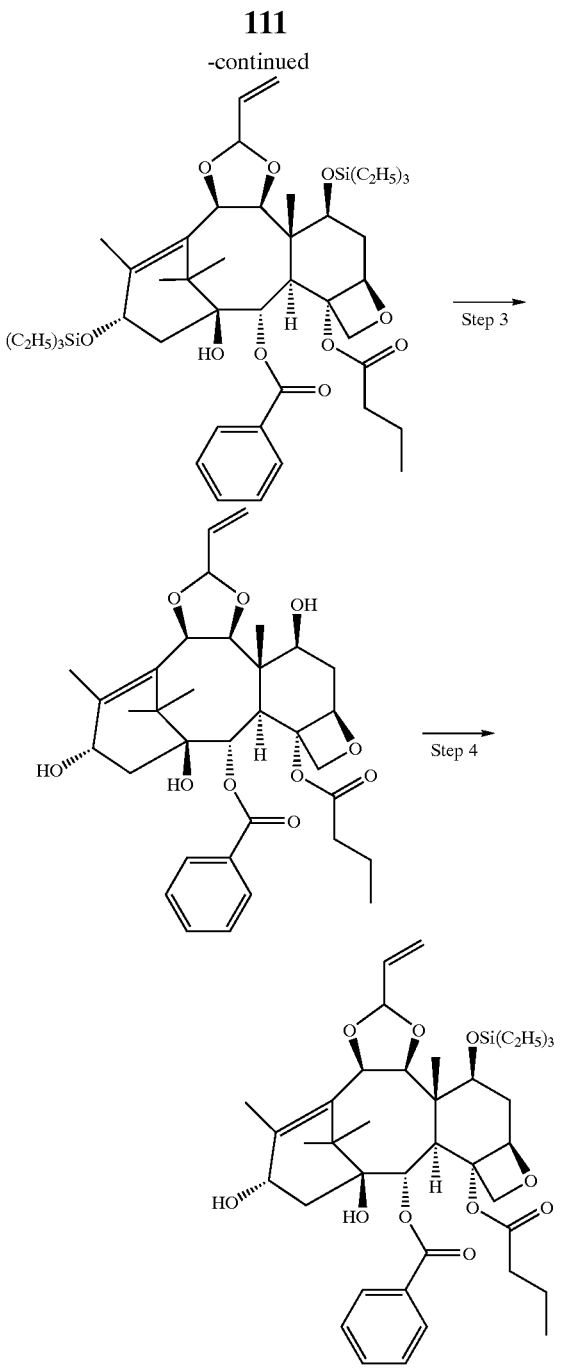

Step 1: 9β-10-Deacetyl-9-dihydro-9,10-O-(2-propenylidene)-7,13-bis-O-triethylsilylbaccatin III A 2.115 g portion of the compound obtained in the step 1 of Reference Example 5 was dissolved in 150 ml of methylene chloride, and the solution was mixed with 0.528 ml of 2,6-lutidine at room temperature and then cooled to −58° C., followed by dropwise addition of 0.88 ml of triethylsilyl trifluoromethanesulfonate. After 40 minutes, this solution was further supplemented with 0.176 ml of 2,6-lutidine and 0.293 ml of triethylsilyl trifluoromethanesulfonate at −52° C. The resulting solution was mixed with methanol and saturated sodium bicarbonate aqueous solution at −52° C. and extracted with chloroform, and the extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=6:1 (v/v)) to obtain 1.7763 g of the title compound in a white foamy form.

$^1$H-NMR (400 MHz, CDCl$_3$/TMS) δ (ppm); 0.55–0.73 (6H, m), 0.99 (9H, t, J=7.8 Hz), 1.01 (9H, t, J=7.8 Hz), 1.14 (3H, s), 1.52 (3H, s), 1.53 (3H, s), 1.72 (1H, s), 1.87 (3H, s), 2.01–2.16 (2H, m), 2.26 (3H, s), 3.21 (1H, d, J=5.9 Hz), 3.92 (1H, dd, J=10.7 Hz, J=5.3 Hz), 4.32 (1H, d, J=8.3 Hz), 4.39 (1H, d, J=8.3 Hz), 4.59 (1H, d, J=9.3 Hz), 4.83 (1H, dd, J=8.7 Hz, J=5.3 Hz), 4.94 (1H, t, J=7.3 Hz), 5.05 (1H, d, J=5.9 Hz), 5.30 (1H, d, J=9.3 Hz), 5.44 (1H, d, J=10.7 Hz), 5.82 (1H, d, J=5.9 Hz), 6.12 (1H, ddd, J=17.6 Hz, J=10.7 Hz, J=5.9 Hz), 7.46 (2H, t, J=7.3 Hz), 7.57 (1H, t, J=7.3 Hz), 8.08 (2H, d, J=7.3 Hz).

Step 2: 9β-4-O-Butanoyl-4,10-dideacetyl-9-dihydro-9,10-O-(2-propenylidene)-7,13-bis-O-triethylsilylbaccatin III A 0.7671 g portion of the compound obtained in the above step 1 was dissolved in 37 ml of a dry tetrahydrofuran to which was subsequently added dropwise 4.7 ml of sodium bistrimethylsilylamide (1.0 mol/L tetrahydrofuran solution) at 0° C. After 15 minutes of the dropwise addition, this solution was mixed with 0.37 ml of ethyl iodide and stirred for 30 minutes at the same temperature. The resulting solution was mixed with saturated sodium bicarbonate aqueous solution at 0° C., diluted with ethyl acetate to effect phase separation and then extracted with ethyl acetate. The thus obtained extract was washed with saturated brine, dried over anhydrous sodium sulfate and then concentrated under a reduced pressure, and the resulting residue was purified by a silica gel column chromatography (developing solvent; hexane:ethyl acetate=7:1 (v/v)) to obtain 0.2604 g of the title compound in a white glassy form.

$^1$H-NMR (400 MHz, CDCl$_3$/TMS) δ (ppm); 0.58–0.73 (12H, m), 0.93–1.10 (21H, m), 1.15 (3H, s), 1.52 (3H, s), 1.53 (3H, s), 1.70 (1H, s), 1.74–1.90 (2H, m), 1.85 (3H, s), 2.01–2.12 (2H, m), 2.17–2.30 (1H, m), 2.32–2.43 (1H, m), 2.45–2.63 (2H, m), 3.19 (1H, d, J=5.9 Hz), 3.93 (1H, dd, J=11.3 Hz, J=5.4 Hz), 4.32 (1H, d, J=8.3 Hz), 4.39 (1H, d, J=8.3 Hz), 4.58 (1H, d, J=8.8 Hz), 4.79 (1H, dd, J=8.8 Hz, J=4.9 Hz), 4.94 (1H, t, J=8.3 Hz), 5.05 (1H, d, J=5.9 Hz), 5.29 (1H, d, J=8.8 Hz), 5.44 (1H, d, J=10.8 Hz), 5.55 (1H, d, J=17.6 Hz), 5.81 (1H, d, J=5.9 Hz), 6.11 (1H, ddd, J=17.6 Hz, J=10.8 Hz, J=5.9 Hz), 7.46 (2H, t, J=7.8 Hz), 7.58 (1H, t, J=7.8 Hz), 8.09 (2H, d, J=7.8 Hz).

Step 3: 9β-4-O-Butanoyl-4,10-dideacetyl-9-dihydro-9,10-O-(2-propenylidene)baccatin III A 0.1414 g portion of the compound obtained in the above step 2 was dissolved in 7.0 ml of pyridine to which was gradually added dropwise 1.41 ml of hydrogen fluoride-pyridine at 0° C. After completion of the dropwise addition, this solution was mixed with cold water of 0° C., diluted with ethyl acetate to effect phase separation and then extracted with ethyl acetate. The thus obtained extract was washed with saturated brine and dried over anhydrous sodium sulfate. Thereafter, the extract was concentrated under a reduced pressure and the resulting residue was purified by a silica gel column chromatography (developing solvent; chloroform:acetone=7:1 (v/v)) to obtain 69.7 mg of the title compound in a white glassy form.

$^1$H-NMR (400 MHz, CDCl$_3$/TMS) δ (ppm); 1.06 (3H, s), 1.16 (3H, s), 1.62 (3H, s), 1.65 (3H, s), 1.73–1.86 (2H, m), 1.90–2.00 (1H, m), 1.93 (3H, s), 2.10–2.29 (3H, m), 2.34 (1H, dd, J=15.6 Hz, J=9.7 Hz), 2.60 (2H, t, J=7.8 Hz), 3.05 (1H, d, J=4.9 Hz), 3.88 (1H, d, J=6.8 Hz), 4.06–4.18 (1H, m), 4.33 (1H, d, J=8.4 Hz), 4.40 (1H, dd, J=8.4 Hz, J=1.5 Hz), 4.59 (1H, d, J=8.3 Hz), 4.78 (1H, br q, J=7.4 Hz), 5.02 (1H, s), 5.22 (1H, d, J=5.9 Hz), 5.30 (1H, d, J=6.8 Hz), 5.44 (1H, d, J=10.8 Hz), 5.56 (1H, d, J=17.1 Hz), 5.95–6.13 (2H, m), 7.48 (2H, t, J=7.8 Hz), 7.60 (1H, t, J=7.8 Hz), 8.14 (2H, d, J=7.8 Hz).

Step 4: 9β-4-O-Butanoyl-4,10-dideacetyl-9-dihydro-9,10-O-(2-propenylidene)-7-O-triethylsilylbaccatin III Using the compound obtained in the above step 3 as the starting material, the reaction procedure of the step 1 of Reference Example 5 was repeated to obtain the title compound.

¹H-NMR (400 MHz, CDCl₃/TMS) δ (ppm); 0.64 (6H, q like, J=7.8 Hz), 0.98 (9H, t, J=7.8 Hz), 1.05 (3H, s), 1.41 (3H, s), 1.56 (3H, s), 1.61 (3H, s), 1.71–1.84 (2H, m), 1.76 (1H, s), 1.94 (3H, s), 1.95–2.63 (7H, m), 3.18 (1H, d, J=4.8 Hz), 3.96 (1H, dd, J=8.3 Hz, J=5.8 Hz), 4.32 (1H, d, J=8.3 Hz), 4.37 (1H, d, J=8.3 Hz), 4.58 (1H, br d, J=7.8 Hz), 4.70–4.81 (2H, m), 5.10 (1H, d, J=5.9 Hz), 5.33 (1H, d, J=8.4 Hz), 5.46 (1H, d, J=10.2 Hz), 5.57 (1H, d, J=17.6 Hz), 5.90 (1H, d, J=4.8 Hz), 6.16 (1H, ddd, J=17.6 Hz, J=10.2 Hz, J=5.9 Hz), 7.47 (2H, t, J=7.8 Hz), 7.59 (1H, t, J=7.8 Hz), 8.11 (2H, d, J=7.8 Hz).

Reference Example 8

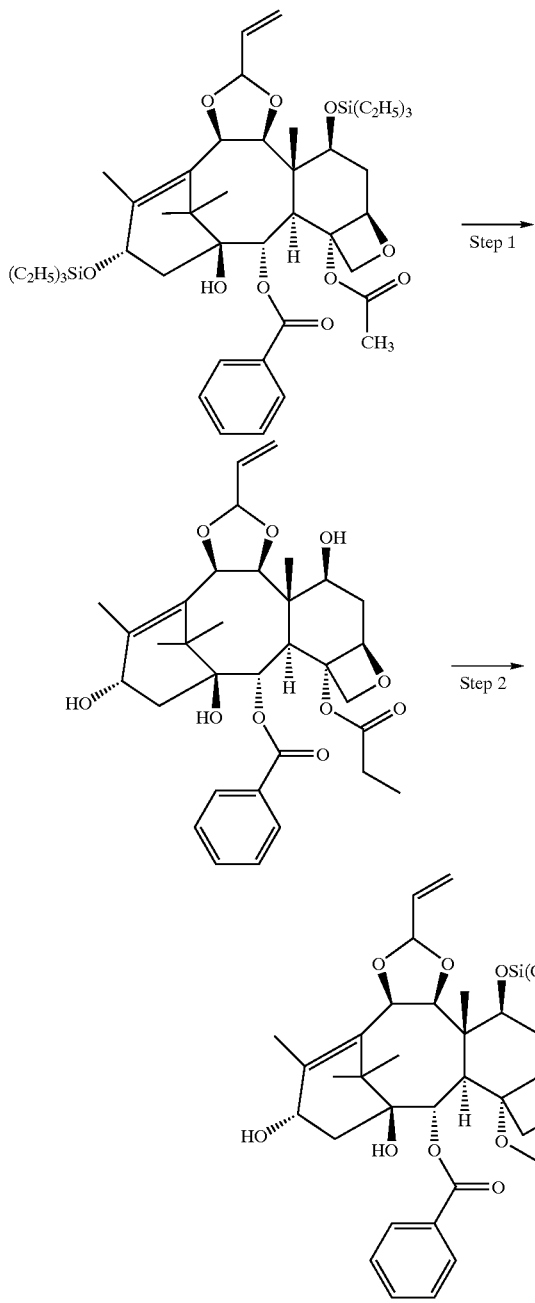

Step 1: 9β-4,10-Dideacetyl-9-dihydro-4-O-propanoyl-9,10-O-(2-propenylidene)baccatin III Using the compound obtained in the step 1 of Reference Example 7 as the starting material, the reaction procedure of the step 2 of Reference Example 7 was repeated except that methyl iodide was used in stead of ethyl iodide. Thereafter, the reaction procedure of the step 3 of Reference Example 7 was repeated to obtain the title compound in a white glassy form.

¹H-NMR (400 MHz, CDCl₃/TMS) δ (ppm); 1.16 (3H, s), 1.26 (3H, t, J=7.4 Hz), 1.62 (3H, s), 1.65 (3H, s), 1.82 (1H, br s), 1.93 (3H, s), 2.09–2.25 (3H, m), 2.33 (1H, dd, J=14.0 Hz, J=10.0 Hz), 2.66 (2H, q, J=7.4 Hz), 3.05 (1H, d, J=4.9 Hz), 3.89 (1H, d, J=7.4 Hz), 4.06–4.16 (1H, br), 4.33 (1H, d, J=8.8 Hz), 4.39 (1H, d, J=8.8 Hz), 4.53–4.63 (1H, br), 4.72–4.84 (1H, br), 5.02 (1H, s like), 5.22 (1H, d, J=6.4 Hz), 5.30 (1H, d, J=7.4 Hz), 5.45 (1H, d, J=10.8 Hz), 5.56 (1H, d, J=17.6 Hz), 5.96–6.10 (2H, m), 7.47 (2H, t, J=7.4 Hz), 7.60 (1H, t, J=7.4 Hz), 8.13 (2H, d, J=7.4 Hz).

Step 2: 9β-4,10-Dideacetyl-9-dihydro-4-O-propanoyl-9,10-(2-propenylidene)-7-triethylsilylbaccatin III Using the compound obtained in the above step 1 as the starting material, the reaction procedure of the step 1 of Reference Example 5 was repeated to obtain the title compound. in a white glassy form.

¹H-NMR (400 MHz, CDCl₃/TMS) δ (ppm); 0.58–0.71 (6H, m), 0.98 (9H, t, J=7.8 Hz), 1.09 (3H, s), 1.25 (3H, s), 1.56 (3H, s), 1.60 (3H, s), 1.75 (1H, s), 1.94 (3H, s), 1.98–2.16 (2H, m), 2.23–2.44 (2H, m), 2.62 (2H, q, J=7.3 Hz), 3.19 (1H, d, J=5.4 Hz), 3.96 (1H, dd, J=8.8 Hz, J=5.8 Hz), 4.32 (1H, d, J=8.3 Hz), 4.37 (1H, d, J=8.3 Hz), 4.59 (1H, d, J=8.7 Hz), 4.71–4.82 (2H, m), 5.09 (1H, d, J=5.9 Hz), 5.33 (1H, d, J=8.7 Hz), 5.46 (1H, d, J=10.8 Hz), 5.56 (1H, d, J=17.6 Hz), 5.90 (1H, d, J=5.4 Hz), 6.16 (1H, ddd, J=17.6 Hz, J=10.8 Hz, J=5.9 Hz), 7.46 (2H, t, J=7.3 Hz), 7.58 (1H, t, J=7.3 Hz), 8.12 (2H, d, J=7.3 Hz).

Reference Example 9

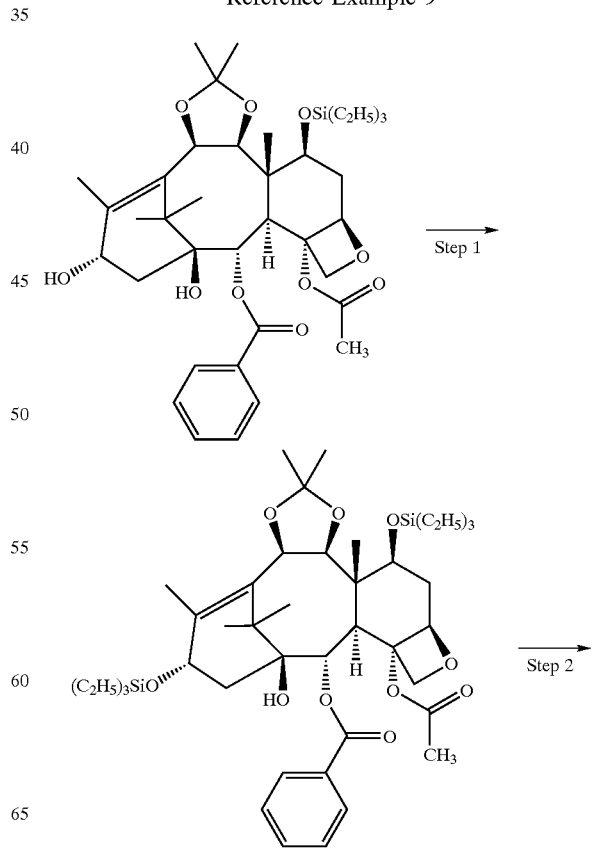

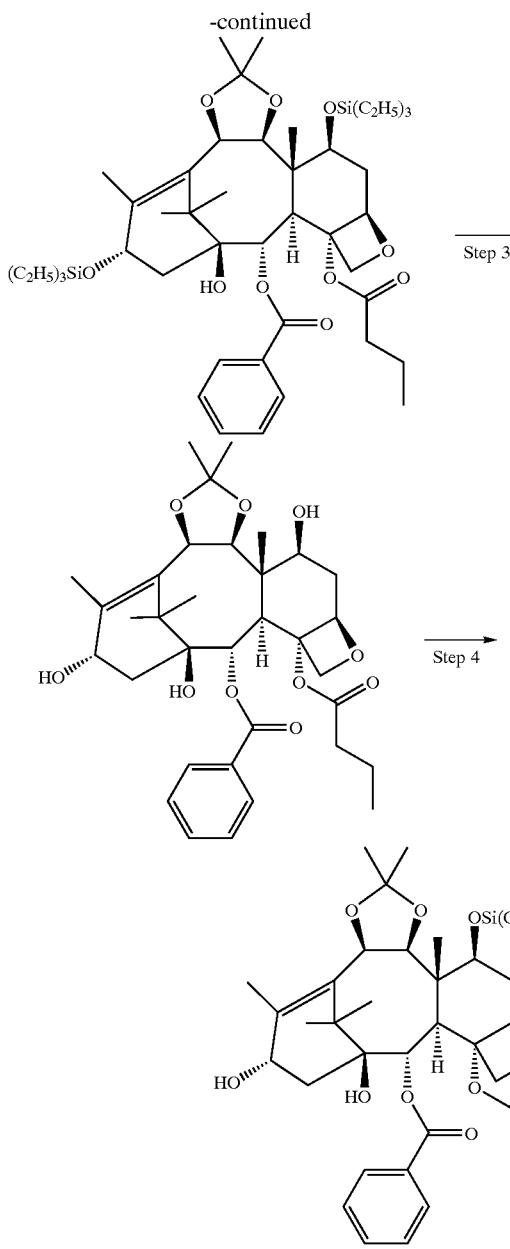

Step 1: 9β-10-Deacetyl-9-dihydro-9,10-O-isopropylidene-7,13-bis-O-triethylsilylbaccatin III Using the compound obtained in the step 1 of Reference Example 6 as the starting material, the reaction procedure of the step 1 of Reference Example 7 was repeated to obtain the title compound.

¹H-NMR (400 MHz, CDCl₃/TMS) δ (ppm); 0.56–0.70 (12H, m), 0.90–1.04 (18H, m), 1.15 (3H, s), 1.31 (3H, s), 1.37 (3H, s), 1.45 (3H, s), 1.55 (3H, s), 1.87 (3H, s), 2.03–2.36 (4H, m), 2.27 (3H, s), 3.20 (1H, d, J=5.8 Hz), 3.94 (1H, dd, J=9.2 Hz, J=3.6 Hz), 4.42 (1H, d, J=8.0 Hz), 4.50 (1H, d, J=8.0 Hz), 4.54 (1H, d, J=9.2 Hz), 4.83 (1H, t, J=7.3 Hz), 4.94 (1H, dd, J=8.2 Hz, J=7.8 Hz), 5.41 (1H, d, J=9.2 Hz), 5.7 (1H, d, J=5.8H), 7.44–7.84 (2H, m), 7.56–7.59 (1H, m), 8.07–8.09 (2H, m).

Step 2: 9β-4-O-Butanoyl-4,10-dideacetyl-9-dihydro-9,10-O-isopropylidene-7,13-bis-O-triethylsilylbaccatin III Using the compound obtained in the above step 1 as the starting material, the reaction procedure of the step 2 of Reference Example 7 was repeated to obtain the title compound as a colorless glassy solid.

¹H-NMR (400 MHz, CDCl₃/TMS) δ (ppm); 0.58–0.70 (12H, m), 0.91–1.07 (21H, m), 1.16 (3H, s), 1.38 (3H, s), 1.46 (3H, s), 1.47 (3H, s), 1.56 (3H, s), 1.85 (3H, s), 2.04–2.28 (6H, m), 2.53 (1H, dt, J=8.0 Hz, J=6.0 Hz), 2.54 (1H, dt, J=8.0 Hz, J=6.0 Hz), 3.19 (1H, d, J=5.9 Hz), 3.97 (1H, dd, J=9.9 Hz, J=3.9 Hz), 4.37 (2H, ABq, J=7.8 Hz), 4.54 (1H, d, J=9.3 Hz), 4.80 (1H, t, J=7.3 Hz), 4.94 (1H, t, J=7.8 Hz), 5.41 (1H, d, J=9.3 Hz), 5.79 (1H, d, J=5.9 Hz), 7.46 (2H, t, J=7.8 Hz), 7.57 (1H, t, J=7.8 Hz), 8.10 (2H, d, J=7.8 Hz). FAB mass: 843 (MH⁺).

Step 3: 9β-4-O-Butanoyl-4,10-dideacetyl-9-dihydro-9,10-O-isopropylidenebaccatin III Using the compound obtained in the above step 2 as the starting material, the reaction procedure of the step 3 of Reference Example 7 was repeated to obtain the title compound as a colorless glassy solid.

¹H-NMR (400 MHz, CDCl₃/TMS) δ (ppm); 1.07 (3H, s), 1.16 (3H, s), 1.42 (3H, s), 1.58 (3H, s), 1.63 (3H, s), 1.64 (3H, s), 1.84 (3H, s), 1.93 (3H, s), 1.97–2.40 (4H, m), 2.59 (2H, dd, J=7.8 Hz, J=7.3 Hz), 3.06 (1H, d, J=4.9 Hz), 3.85 (1H, d, J=7.3 Hz), 4.10 (1H, s), 4.37 (2H, ABq, J=8.5 Hz), 4.67 (1H, d, J=7.8 Hz), 4.79 (1H, dd, J=8.5 Hz, J=5.7 Hz), 5.02 (1H, br), 5.59 (1H, d, J=7.3 Hz), 6.03 (1H, d, J=4.9 Hz), 7.48 (2H, t, J=7.8 Hz), 7.60 (1H, t, J=7.3 Hz), 8.13 (2H, d, J=7.3 Hz).

Step 4: 9β-4-O-Butanoyl-4,10-dideacetyl-9-dihydro-9,10-O-isopropylidene-7-O-triethylsilylbaccatin III Using the compound obtained in the above step 3 as the starting material, the reaction procedure of the step 1 of Reference Example 5 was repeated to obtain the title compound as a colorless glassy solid.

¹H-NMR (400 MHz, CDCl₃/TMS) δ (ppm); 0.61 (6H, q, J=7.8 Hz), 0.95 (9H, t, J=7.8 Hz), 1.06 (3H, t, J=7.3 Hz), 1.13 (3H, s), 1.41 (3H, s), 1.51 (3H, s), 1.57 (3H, s), 1.59 (3H, s), 1.77–1.83 (2H, m), 1.94 (3H, s), 2.27–2.39 (4H, m), 2.59 (2H, m), 3.65 (1H, d, J=5.4 Hz), 3.65 (1H, dd, J=7.8 Hz, J=4.4 Hz), 4.18 (2H, ABq, J=7.8 Hz), 4.56 (1H, d, J=7.8 Hz), 4.48–4.83 (2H, m), 5.52 (1H, d, J=7.8 Hz), 5.93 (1H, d, J=5.4 Hz), 7.43 (2H, t, J=7.8 Hz), 7.59 (1H, t, J=7.8 Hz), 8.15 (2H, d, J=7.8 Hz).

Reference Example 10

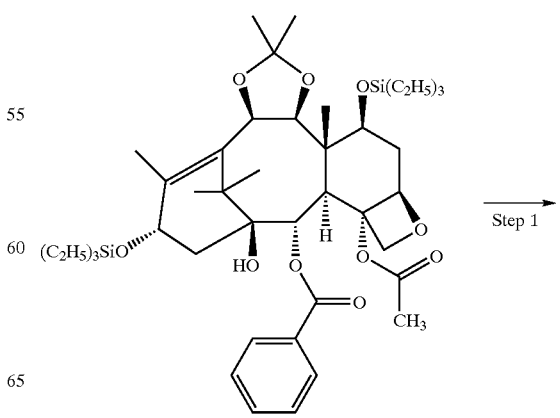

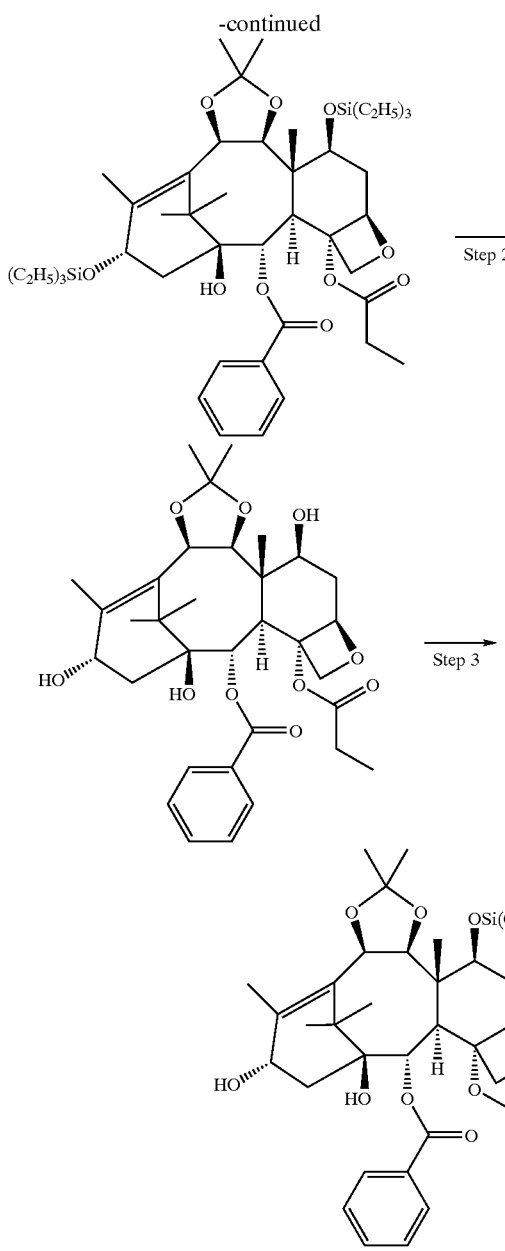

Step 1: 9β-4,10-Dideacetyl-9-dihydro-9,10-O-isopropylidene-4-O-propanoyl-7,13-bis-O-triethylsilylbaccatin III In an atmosphere of nitrogen, 1.17 ml of diisopropylamine was dissolved in 21 ml of a dry tetrahydrofuran at 0° C., and the solution was mixed with n-butyl lithium (1.69 mol/L, hexane solution) and stirred for 20 minutes. After cooling to −78° C., thereto was added dropwise 7 ml of a dry tetrahydrofuran solution containing 728 mg of the compound obtained in the step 1 of Reference Example 9. One hour thereafter, this solution was mixed with 1.11 ml of methyl iodide at −78° C. and stirred for 4 hours while gradually increasing the temperature to −5° C. The resulting solution was mixed with saturated ammonium chloride aqueous solution and extracted with ethyl acetate. The thus obtained extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=10:1 (v/v)) to obtain 706 mg of the title compound as a colorless glassy solid.

$^1$H-NMR (400 MHz, CDCl$_3$/TMS) δ (ppm); 0.61–0.72 (12H, m), 0.91–1.02 (18H, m), 1.16 (3H, s), 1.25 (3H, t, J=7.3 Hz), 1.38 (3H, s), 1.46 (3H, s), 1.50 (3H, s), 1.56 (3H, s), 1.85 (3H, s), 2.02–2.26 (4H, m), 2.63 (2H, q, J=7.3 Hz), 3.19 (1H, d, J=5.9 Hz), 3.96 (1H, dd, J=9.3 Hz, J=3.4 Hz), 4.30 (2H, ABq, J=7.8 Hz), 4.54 (1H, d, J=8.8 Hz), 4.80 (1H, t, J=7.3 Hz), 4.95 (1H, t, J=8.3 Hz), 5.40 (1H, d, J=9.3 Hz), 5.78 (1H, d, J=5.9 Hz), 7.46 (2H, t, J=7.3 Hz), 7.58 (1H, t, J=7.3 Hz), 8.10 (2H, d, J=7.3 Hz). FAB mass: 829 (MH$^+$).

Step 2: 9β-4,10-Dideacetyl-9-dihydro-9,10-O-isopropylidene-4-O-propanoylbaccatin III Using the compound obtained in the above step 1 as the starting material, the reaction procedure of the step 3 of Reference Example 7 was repeated to obtain the title compound as a colorless glassy solid $^1$H-NMR (400 MHz, CDCl$_3$/TMS) δ (ppm); 1.16 (3H, s), 1.27 (3H, t, J=7.3 Hz), 1.42 (3H, s), 1.50 (3H, s), 1.63 (3H, s), 1.64 (3H, s), 1.94 (3H, s), 2.11–2.36 (4H, m), 2.66 (2H, q, J=7.3 Hz), 3.06 (1H, d, J=4.9 Hz), 3.85 (1H, d, J=7.3 Hz), 4.52 (2H, ABq, J=8.3 Hz), 4.67 (1H, d, J=8.3 Hz), 4.79 (1H, m), 5.02 (1H, s), 5.59 (1H, d, J=7.3 Hz), 6.02 (1H, d, J=4.9 Hz), 7.47 (2H, t, J=7.8 Hz), 7.60 (1H, t, J=7.8 Hz), 8.14 (2H, d, J=7.8 Hz).

Step 3: 9β-4,10-Dideacetyl-9-dihydro-9,10-O-isopropylidene-4-O-propanoyl-7-O-triethylsilylbaccatin III Using the compound obtained in the above step 2 as the starting material, the reaction procedure of the step 1 of Reference Example 5 was repeated to obtain the title compound as a colorless glassy solid.

$^1$H-NMR (400 MHz, CDCl$_3$/TMS) δ (ppm); 0.57–0.64 (6H, m), 0.93–0.98 (9H, m), 1.12 (3H, s), 1.26 (3H, t, J=7.3 Hz), 1.40 (3H, s), 1.51 (3H, s), 1.57 (3H, s), 1.58 (3H, s), 1.77 (1H, s), 1.94 (3H, s), 1.96–2.35 (4H, m), 2.65 (2H, q, J=7.3 Hz), 3.16 (1H, d, J=5.6 Hz), 4.08 (1H, t, J=4.9 Hz), 4.20 (2H, d, J=7.8 Hz), 4.56 (1H, d, J=7.8 Hz), 4.74–4.78 (2H, m), 5.20 (1H, d, J=8.3 Hz), 5.93 (1H, d, J=5.4 Hz), 7.46 (2H, t, J=7.8 Hz), 7.59 (1H, t, J=7.8 Hz), 8.15 (2H, d, J=7.8 Hz). FAB mass: 715 (MH$^+$).

Reference Example 11

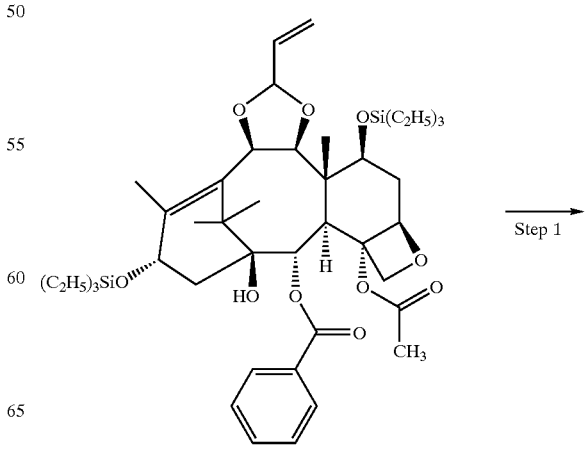

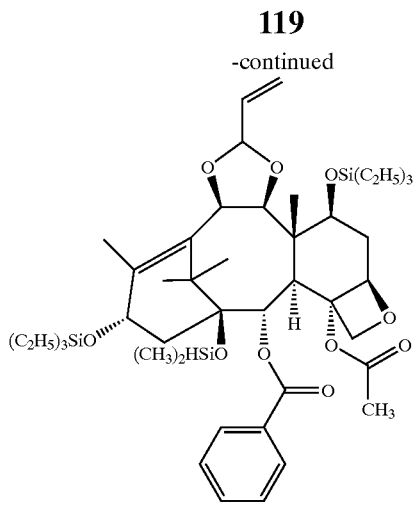

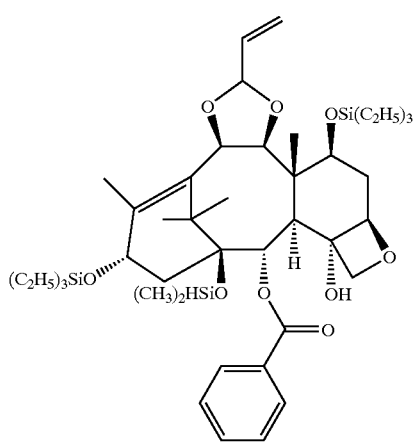

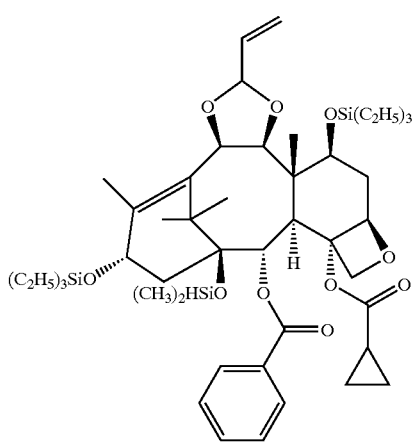

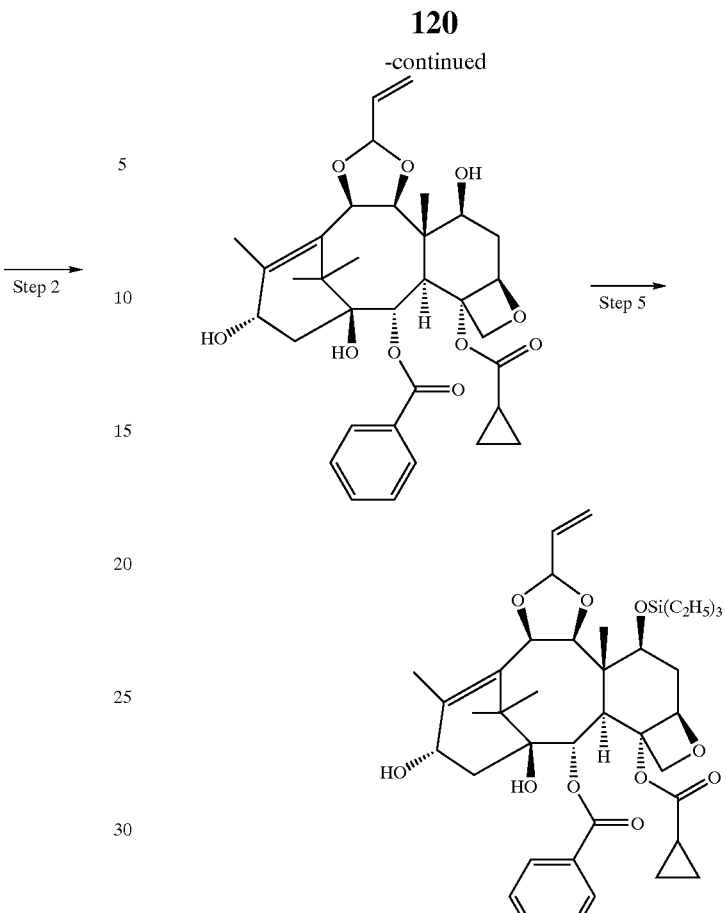

Step 1: 9β-10-Deacetyl-9-dihydro-1-O-dimethylsilyl-9,10-O-(2-propenylidene)-7,13-bis-O-triethylsilylbaccatin III A 1.0789 g portion of the compound obtained in the step 1 of Reference Example 7 was dissolved in 26.9 ml of N,N-dimethylformamide, and the solution was mixed with 0.595 g of imidazole at room-temperature. Thereto was added dropwise 0.736 ml of dimethylchlorosilane at 0° C. After 1 hour of stirring, this solution was mixed with cold water at 0° C. and extracted with a hexane-ethyl acetate mixture solvent (1:1 (v/v)). The thus obtained extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=9:1 (v/v)) to obtain 0.994 g of the title compound in a white foamy form.

$^1$H-NMR (400 MHz, CDCl$_3$/TMS) δ (ppm); −0.34 (3H, d, J=2.9 Hz), 0.03 (3H, d, J=2.9 Hz), 0.58–0.76 (12H, m), 0.92–1.09 (18H, m), 1.11 (3H, s), 1.522 (3H, s), 1.528 (3H, s), 1.86 (3H, s), 2.02–2.16 (1H, m), 2.23–2.44 (3H, m), 2.26 (3H, s), 3.19 (1H, d, J=5.3 Hz), 3.88 (1H, dd, J=10.7 Hz, J=4.9 Hz), 4.33 (1H, d, J=7.8 Hz), 4.41 (1H, d, J=7.8 Hz), 4.52–4.68 (2H, m), 4.83 (1H, dd, J=8.8 Hz, J=5.4 Hz), 4.98 (1H, t, J=9.0 Hz), 5.04 (1H, d, J=6.4 Hz), 5.27 (1H, d, J=9.3 Hz), 5.42 (1H, d, J=10.7 Hz), 5.53 (1H, d, J=17.5 Hz), 5.89 (1H, d, J=5.3 Hz), 6.11 (1H, ddd, J=17.5 Hz, J=10.7 Hz, J=6.4 Hz), 7.45 (2H, t, J=7.8 Hz), 7.56 (1H, t, J=7.8 Hz), 8.10 (2H, d, J=7.8 Hz).

Step 2: 9β-4,10-Dideacetyl-9-dihydro-1,O-dimethylsilyl-9,10-O-(2-propenylidene)-7,13-bis-O-triethylsilylbaccatin III A 0.994 g portion of the compound obtained in the above step 1 was dissolved in 50 ml of a dry tetrahydrofuran to which was subsequently added dropwise 2.7 ml of sodium bis(2-methoxyethoxy)aluminum hydride (65% (w/v), toluene solution) at 0° C., followed by 50 minutes of stirring at the same temperature. Thereto were added 250 ml of diethyl ether at 0° C. and then gradually 70 ml of water in which 12.8 g of potassium sodium tartrate tetrahydrate has been dissolved. After completion of the addition, the resulting mixture was warmed up to room temperature and vigorously stirred for 1 hour. The resulting solution was extracted with ethyl acetate, and the extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=9:1 (v/v)) to obtain 0.8413 g of the title compound in a colorless glassy form.

$^1$H-NMR (400 MHz, CDCl$_3$/TMS) δ (ppm); −0.27 (3H, d, J=2.4 Hz), −0.01 (3H, d, J=2.4 Hz), 0.54–0.67 (6H, m), 0.69–0.85 (6H, m), 0.95 (3H, t, J=7.8 Hz), 0.97 (3H, s), 1.05 (9H, t, J=7.9 Hz), 1.44 (3H, s), 1.55 (3H, s), 1.81 (3H, s), 2.10 (1H, ddd, J=13.6 Hz, J=9.6 Hz, J=4.2 Hz), 2.20 (1H, ddd, J=13.6 Hz, J=8.2 Hz, J=6.0 Hz), 2.52 (1H, dd, J=14.7 Hz, J=9.8 Hz), 2.87 (1H, d, J=3.4 Hz), 3.01 (1H, dd, J=14.7 Hz, J=1.4 Hz), 3.62 (1H, dd, J=9.6 Hz, J=6.0 Hz), 3.78 (1H, s like), 4.28 (1H, d, J=7.9 Hz), 4.38–4.50 (2H, m), 4.50–4.69 (2H, m), 5.07 (1H, d, J=6.4 Hz), 5.33 (1H, d, J=7.9 Hz), 5.44 (1H, d, J=10.2 Hz), 5.55 (1H, d, J=17.1 Hz), 5.97 (1H, d, J=3.5 Hz), 6.20 (1H, ddd, J=17.1 Hz, J=10.2 Hz, J=6.4 Hz), 7.43 (2H, t, J=7.4 Hz), 7.53 (1H, t, J=7.4 Hz), 8.15 (2H, d, J=7.4 Hz).

Step 3: 9β-4-O-Cyclopropanecarbonyl-4,10-dideacetyl-9-dihydro-1-O-dimethylsilyl-9,10-O-(2-propenylidene)-7,13-bis-O-triethylsilylbaccatin III A 0.8413 g portion of the compound obtained in the above step 2 was dissolved in 40 ml of a dry tetrahydrofuran to which was subsequently added dropwise 3.1 ml of 1.0 mol/L lithium bistrimethylsilylamide (tetrahydrofuran solution) at 0° C., followed by the addition of 0.24 ml of cyclopropanecarbonyl chloride 15 minutes thereafter. After 45 minutes, this solution was mixed with saturated ammonium chloride aqueous solution at 0° C. and extracted with ethyl acetate. The thus obtained extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=10:1 (v/v)→hexane:ethyl acetate=6:1 (v/v)) to obtain 0.8104 g of the title compound in a colorless glassy form.

$^1$H-NMR (400 MHz, CDCl$_3$/TMS) δ (ppm); −0.33 (3H, d, J=2.4 Hz), 0.04 (3H, d, J=2.4 Hz), 0.57–0.75 (12H, m), 0.97 (9H, t, J=7.8 Hz), 1.02 (9H, t, J=7.8 Hz), 1.13 (3H, s), 1.20–1.46 (2H, m), 1.52 (3H, s), 1.56 (3H, s), 1.64–1.76 (1H, m), 1.87 (3H, s), 2.02 (1H, ddd, J=14.4 Hz, J=10.4 Hz, J=4.4 Hz), 2.22–2.41 (3H, m), 3.15 (1H, d, J=5.4 Hz), 3.88 (1H, dd, J=10.4 Hz, J=5.4 Hz), 4.25 (1H, d, J=8.3 Hz), 4.34 (1H, d, J=8.3 Hz), 4.52–4.64 (2H, m), 4.72 (1H, dd, J=8.8 Hz, J=4.4 Hz), 4.97 (1H, t, J=8.3 Hz), 5.05 (1H, d, J=5.7 Hz), 5.28 (1H, d, J=8.8 Hz), 5.42 (1H, d, J=10.3 Hz), 5.53 (1H, d, J=17.6 Hz), 5.91 (1H, d, J=5.4 Hz), 6.13 (1H, ddd, J=17.6 Hz, J=10.3 Hz, J=5.7 Hz), 7.45 (2H, t, J=7.4 Hz), 7.56 (1H, t, J=7.4 Hz), 8.08 (2H, d, J=7.4 Hz).

Step 4: 9β-4-O-Cyclopropanecarbonyl-4,10-dideacetyl-9-dihydro-9,10-O-(2-propenylidene)baccatin III Using the compound obtained in the above step 3 as the starting material, the reaction procedure of the step 3 of Reference Example 7 was repeated to obtain the title compound in a colorless glassy form.

$^1$H-NMR (400 MHz, CDCl$_3$/TMS) δ (ppm); 1.05–1.40 (4H, m), 1.17 (3H, s), 1.61 (3H, s), 1.73–2.48(m), 1.92 (3H, s), 3.04 (1H, d, J=4.4 Hz), 3.86 (1H, d, J=6.9 Hz), 4.03–4.18 (1H, m), 4.36 (1H, d, J=8.3 Hz), 4.42 (1H, d, J=8.3 Hz), 4.57 (1H, d, J=8.3 Hz), 4.68–4.82 (1H, m), 4.98 (1H, s like), 5.22 (1H, d, J=5.9 Hz), 5.29 (1H, d, J=6.9 Hz), 5.45 (1H, d, J=10.2 Hz), 5.56 (1H, d, J=17.1 Hz), 5.94–6.11 (2H, m), 7.48 (2H, t, J=7.8 Hz), 7.60 (1H, t, J=7.8 Hz), 8.13 (2H, d, J=7.8 Hz).

Step 5: 9β-4-O-Cyclopropanecarbonyl-4,10-dideacetyl-9-dihydro-9,10-O-(2-propenylidene)-7-O-triethylsilylbaccatin III Using the compound obtained in the above step 4 as the starting material, the reaction procedure of the step 1 of Reference Example 5 was repeated to obtain the title compound in a colorless glassy form.

$^1$H-NMR (400 MHz, CDCl$_3$/TMS) δ (ppm); 0.58–0.72 (6H, m), 0.97 (9H, t, J=7.8 Hz), 1.06–1.39 (4H, m), 1.10 (3H, s), 1.56 (3H, s), 1.62 (3H, s), 1.74–1.88 (2H, m), 1.98 (3H, s), 1.98–2.21 (3H, m), 2.28–2.44 (2H, m), 3.16 (1H, d, J=5.3 Hz), 3.95 (1H, dd, J=8.3 Hz, J=5.9 Hz), 4.30 (1H, d, J=8.3 Hz), 4.38 (1H, d, J=8.3 Hz), 4.54 (1H, d, J=7.8 Hz), 4.68–4.82 (2H, m), 5.10 (1H, d, J=5.8 Hz), 5.33 (1H, d, J=7.8 Hz), 5.45 (1H, d, J=10.3 Hz), 5.56 (1H, d, J=17.6 Hz), 5.93 (1H, d, J=5.3 Hz), 6.16 (1H, ddd, J=17.6 Hz, J=10.3 Hz, J=5.8 Hz), 7.47 (2H, t, J=7.8 Hz), 7.60 (1H, t, J=7.8 Hz), 8.11 (2H, d, J=7.8 Hz).

Reference Example 12

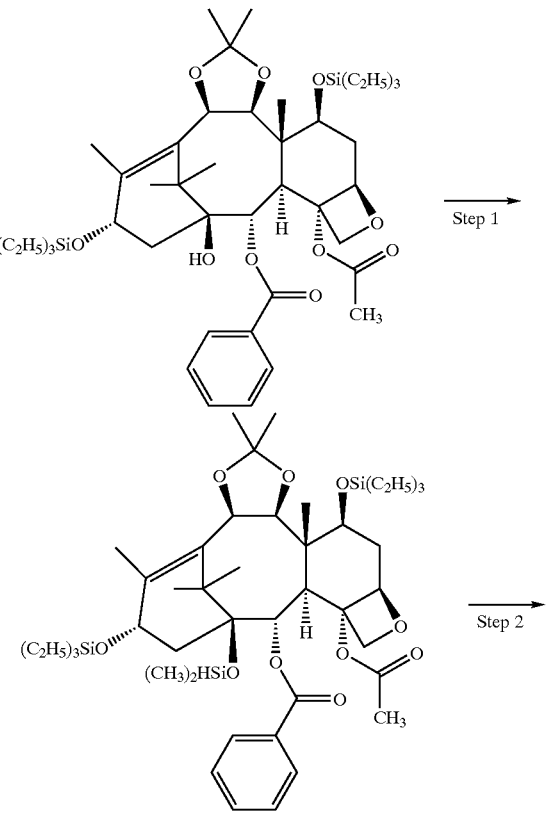

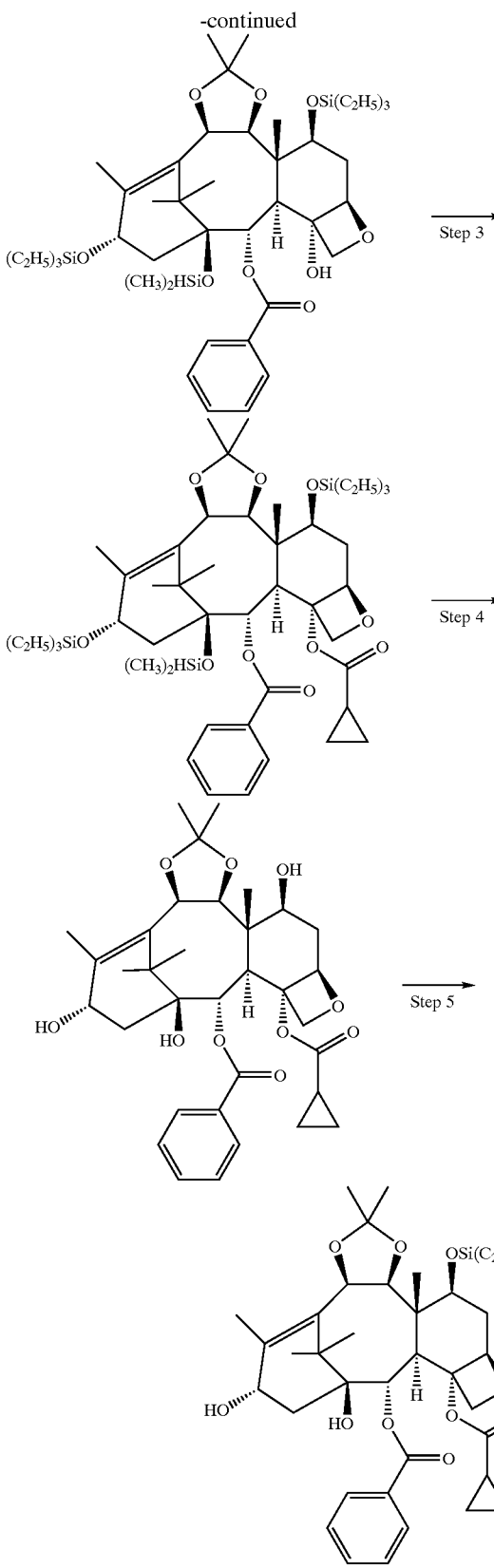

Step 1: 9β-10-Deacetyl-9-dihydro-1-O-dimethylsilyl-9,10-O-isopropylidene-7,13-bis-O-triethylsilylbaccatin III Using the compound obtained in the step 1 of Reference Example 8 as the starting material, the reaction procedure of the step 1 of Reference Example 11 was repeated to obtain the title compound in a colorless glassy form.

¹H-NMR (400 MHz, CDCl₃/TMS) δ (ppm); −0.33 (3H, d, J=2.9 Hz), 0.04 (3H, d, J=2.9 Hz), 0.58–0.72 (12H, m), 0.94–1.05 (18H, m), 1.12 (3H, s), 1.37 (3H, s), 1.47 (3H, s), 1.49 (3H, s), 1.57 (3H, s), 1.86 (3H, s), 2.09–2.36 (4H, m), 2.30 (3H, s), 3.19 (1H, d, J=5.9 Hz), 3.91 (1H, dd, J=8.8 Hz, J=3.4 Hz), 4.40 (2H, ABq, J=8.8 Hz), 4.50 (1H, d, J=8.8 Hz), 4.57 (1H, m), 4.83 (1H, t, J=7.3 Hz), 4.97 (1H, t, J=8.3 Hz), 5.40 (1H, d, J=8.8 Hz), 5.84 (1H, d, J=5.4 Hz), 7.46 (2H, t, J=7.8 Hz), 7.57 (1H, t, J=7.8 Hz), 8.09 (2H, d, J=7.8 Hz).

Step 2: 9β-4,10-Dideacetyl-9-dihydro-1-O-dimethylsilyl-9,10-O-isopropylidene-7,13-bis-O-triethylsilylbaccatin III Using the compound obtained in the above step 1 as the starting material, the reaction procedure of the step 2 of Reference Example 11 was repeated to obtain the title compound in a colorless glassy form.

¹H-NMR (400 MHz, CDCl₃/TMS) δ (ppm); −0.27 (3H, d, J=2.9 Hz), 0.01 (3H, d, J=2.9 Hz), 0.58–0.83 (12H, m), 0.93–1.10 (18H, m), 1.08 (3H, s), 1.39 (3H, s), 1.46 (3H, s), 1.55 (3H, s), 1.77 (3H, s), 1.84–2.40 (4H, m), 2.51 (1H, dd, J=15.1 Hz, J=10.0 Hz), 2.73 (1H, d, J=5.9 Hz), 3.03 (1H, dd, J=15.1 Hz, J=2.4 Hz), 3.64 (1H, s), 3.86 (1H, dd, J=7.3 Hz, J=2.9 Hz), 4.05 (1H, d, J=7.8 Hz), 4.09 (1H, d, J=6,8 Hz), 4.43 (1H, m), 4.52 (1H, d, J=6.8 Hz), 4.62–4.65 (2H, m), 5.54 (1H, d, J=7.3 Hz), 5.57 (1H, d, J=3.9 Hz), 7.44 (2H, t, J=7.8 Hz), 7.55 (1H, t, J=7.8 Hz), 8.19 (2H, d, J=7.8 Hz).

Step 3: 9β-4-O-Cyclopropanecarbonyl-4,10-dideacetyl-9-dihydro-1-O-dimethylsilyl-9,10-O-isopropylidene-7,13-bis-O-triethylsilylbaccatin III Using the compound obtained in the above step 2 as the starting material, the reaction procedure of the step 3 of Reference Example 11 was repeated to obtain the title compound in a colorless glassy form.

¹H-NMR (400 MHz, CDCl₃/TMS) δ (ppm); −0.32 (3H, d, J=2.4 Hz), 0.05 (3H, d, J=2.4 Hz), 0.58–0.71 (12H, m), 0.94–1.04 (18H, m), 1.16 (3H, s), 1.21–1.36 (4H, m), 1.38 (3H, s), 1.48 (3H, s), 1.53 (3H, s), 1.55 (3H, s), 1.71 (1H, m), 1.87 (3H, s), 2.05–2.38 (4H, m), 3.13 (1H, d, J=5.4 Hz), 3.87 (1H, dd, J=8.8 Hz, J=3.4 Hz), 4.20 (2H, ABq, J=7.8 Hz), 4.41 (1H, d, J=8.8 Hz), 4.60 (1H, m), 4.43 (1H, t, J=6.3 Hz), 4.99 (1H, t, J=8.3 Hz), 5.42 (1H, d, J=8.8 Hz), 5.88 (1H, d, J=5.4 Hz), 7.46 (2H, t, J=7.8 Hz), 7.57 (1H, t, J=7.8 Hz), 8.10 (2H, d, J=7.8 Hz). FAB mass: 899 (MH⁺).

Step 4: 9β-4-O-Cyclopropanecarbonyl-4,10-dideacetyl-9-dihydro-9,10-O-isopropylidenebaccatin III Using the compound obtained in the above step 3 as the starting material, the reaction procedure of the step 3 of Reference Example 7 was repeated to obtain the title compound in a colorless glassy form.

¹H-NMR (400 MHz, CDCl₃/TMS) δ (ppm); 1.15–1.37 (7H, m), 1;41 (3H, s), 1.58 (3H, s), 1.64 (6H, s), 1.82–2.41 (5H, m), 1.73 (3H, s), 3.05 (1H, d, J=4.9 Hz), 3.82 (1H, d, J=6.8 Hz), 4.08 (1H, br), 4.39 (2H, ABq, J=8.3 Hz), 4.67 (1H, br), 4.76 (1H, t, J=7.2 Hz), 4.99 (1H, s), 5.59 (1H, d, J=6.8 Hz), 6.06 (1H, d, J=4.9 Hz), 7.48 (2H, t, J=7.8 Hz), 7.60 (1H, t, J=7.8 Hz), 8.13 (2H, d, J=7.3 Hz). FAB mass: 813 (MH⁺).

Step 5: 9β-4-O-Cyclopropanecarbonyl-4,10-dideacetyl-9-dihydro-9,10-O-isopropylidene-7-O-triethylsilylbaccatin III Using the compound obtained in the above step 4 as the starting material, the reaction procedure of the step 1 of Reference Example 5 was repeated to obtain the title compound in a colorless glassy form.

¹H-NMR (400 MHz, CDCl₃/TMS) δ (ppm); 0.58–0.64 (6H, m), 0.71–0.88 (9H, m), 1.05–1.22 (4H, m), 1.14 (3H, s), 1.41 (3H, s), 1.57 (3H, s), 1.60 (3H, s), 1.86–2.08 (5H, m), 1.93 (3H, s), 3.11 (1H, d, J=4.9 Hz), 4.09–4.27 (2H, m), 4.50 (2H, ABq, J=7.8 Hz), 4.71–4.80 (2H, m), 5.53 (1H, d, J=7.8 Hz), 5.96 (1H, d, J=4.8 Hz), 7.48 (2H, t, J=7.8 Hz), 7.59 (1H, t, J=7.8 Hz), 8.15 (2H, d, J=7.3 Hz).

Reference Example 13

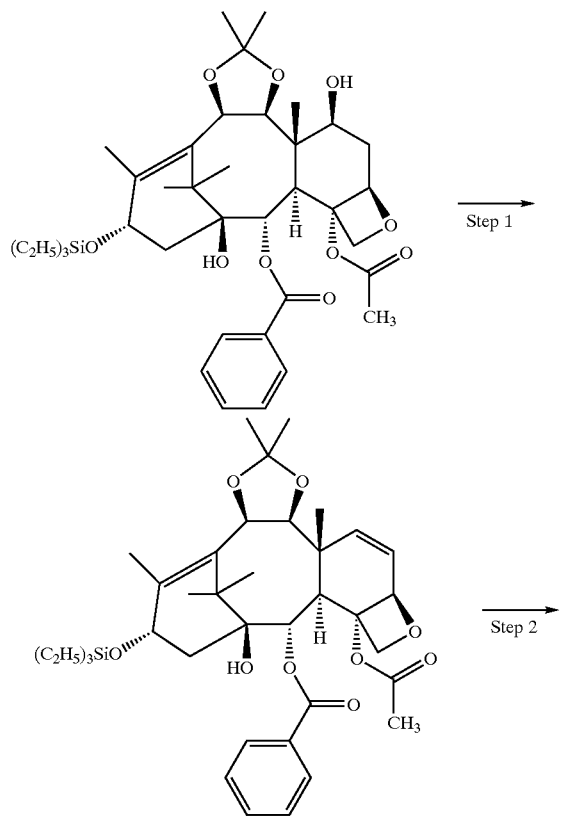

Step 1: 9β-10-Deacetyl-7-deoxy-6,7-didehydro-9-dihydro-9,10-O-isopropylidene-13-O-triethylsilylbaccatin III A 470 mg portion of the compound obtained in the step 3 of Inventive Example 10 was dissolved in 45 ml of methylene chloride, and the solution was mixed with 15 ml pyridine and 570 μl of trifluoromethanesulfonic acid anhydride at 0° C. After 1 hour of stirring at room temperature, the reaction solution was poured into stirred mixture of 100 ml of diethyl ether and 50 ml of saturated sodium bicarbonate aqueous solution, and extracted with diethyl ether. The thus obtained extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=4:1 (v/v)→2:1 (v/v)) to obtain 240 mg of the title compound as a white solid and to recover 107 mg of the starting material.

$^1$H-NMR (400 MHz, CDCl$_3$/TMS) δ (ppm); 0.57–0.74 (6H, m), 1.01 (9H, t, J=8.9 Hz), 1.20 (3H, s), 1.40 (3H, s), 1.51 (3H, s), 1.54 (3H, s), 1.57 (3H, s), 1.75 (1H, s), 1.84 (3H, s), 2.13 (1H, dd, J=8.1, 14.7 Hz), 2.22 (1H, dd, J=8.6, 14.7 Hz), 2.29 (3H, s), 3.09 (1H, d, J=6.2 Hz), 4.14 (1H, d, J=8.1 Hz), 4.27–4.33 (2H, m), 4.90 (1H, d, J=4.3 Hz), 4.97 (1H, br t, J=8.8 Hz), 5.48 (1H, d, J=8.1 Hz), 5.66 (1H, dd, J=10.3, 4.3 Hz), 5.87 (1H, d, J=6.2 Hz), 6.08 (1H, d, J=10.3 Hz), 7.49 (2H, t, J=7.8 Hz), 7.60 (1H, t, J=7.8 Hz), 8.15 (2H, d, J=7.8 Hz).

Step 2: 9β-10-Deacetyl-7-deoxy-6,7-didehydro-9-dihydro-9,10-O-isopropylidenebaccatin III Using the compound obtained in the above step 1 as the starting material, the reaction procedure of the step 4 of Inventive Example 1 was repeated to obtain the title compound as a white solid.

$^1$H-NMR (400 MHz, CDCl$_3$/TMS) δ (ppm); 1.13 (3H, s), 1.42 (3H, s), 1.53 (3H, s), 1.54 (3H, s), 1.59 (3H, s), 1.75 (1H, s), 1.91 (3H, s), 2.09 (1H, dd, J=6.8, 15.2 Hz), 2.20 (1H, br d, J=7.8 Hz), 2.34 (1H, dd, J=8.8, 15.2 Hz), 2.35 (3H, s), 3.22 (1H, d, J=5.9 Hz), 4.04 (1H, d, J=7.4 Hz), 4.26 (1H, d, J=8.1 Hz), 4.34 (1H, d, J=8.1 Hz), 4.72–4.87 (1H, m), 4.83 (1H, d, J=4.4 Hz), 5.54 (1H, d, J=7.4 Hz), 5.66 (1H, dd, J=10.3, 4.4 Hz), 5.93 (1H, d, J=5.9 Hz), 6.12 (1H, d, J=10.3 Hz), 7.48 (2H, t, J=7.3 Hz), 7.60 (1H, t, J=7.3 Hz), 8.18 (2H, d, J=7.3 Hz).

Reference Example 14

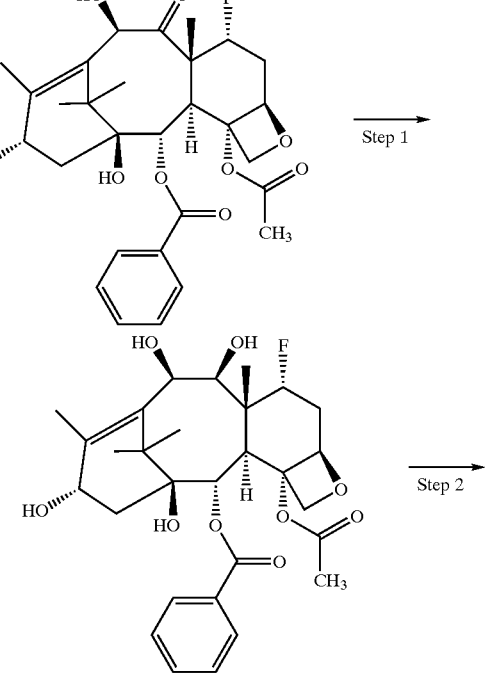

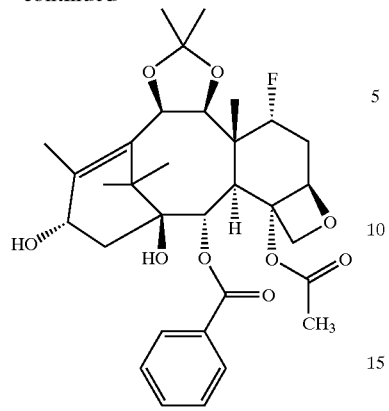

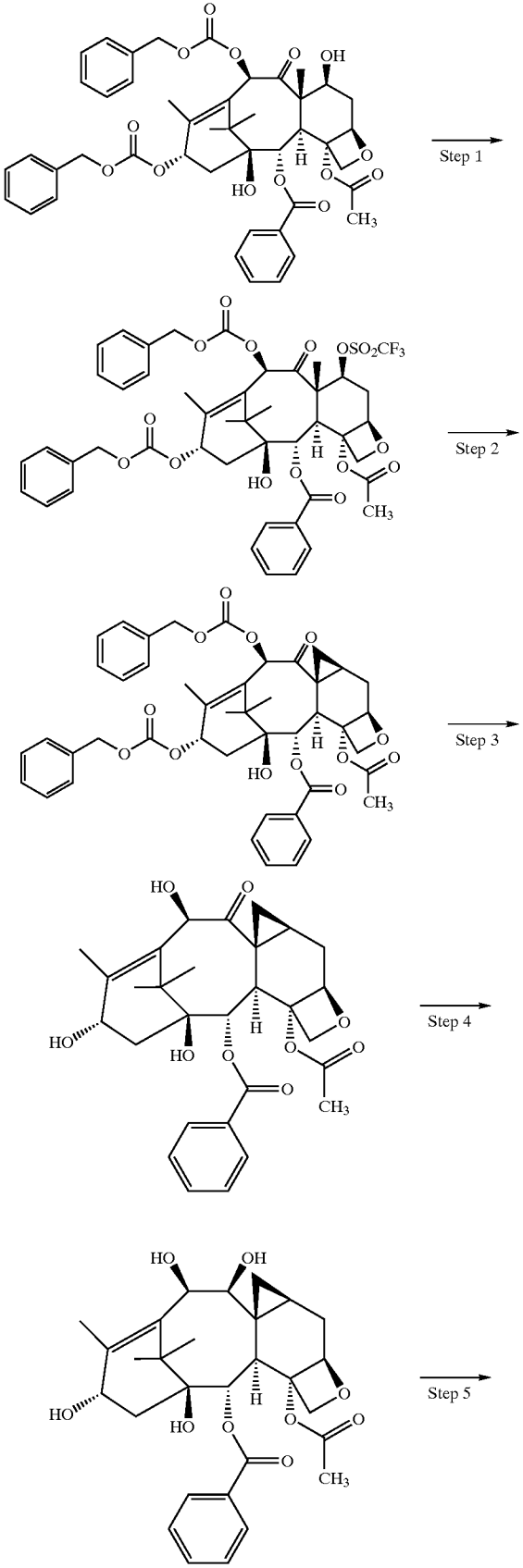

Reference Example 15

Step 1: 9β-10-Deacetyl-7-deoxy-9-dihydro-7α-fluorobaccatin III

A 26.1 mg portion of 10-deacetyl-7-deoxy-7α-fluorobaccatin III was dissolved in 1.5 ml of tetrahydrofuran, and the solution was mixed with 1.5 ml of borane-tetrahydrofuran (1.0 M tetrahydrofuran solution) at 0° C. After 6 hours of stirring at 0° C., 3.0 ml of methanol was added dropwise thereto and the mixture was stirred at room temperature for 30 minutes. Thereafter, the solvent was evaporated under a reduced pressure and the resulting residue was purified by a silica gel. thin layer chromatography (developing solvent; chloroform:acetone=3:1 (v/v)) to obtain 30.8 mg of the title compound in a colorless transparent glassy form.

$^1$H-NMR (400 MHz, CDCl$_3$/TMS) δ (ppm); 1.14 (3H, s), 1.63 (3H, s), 1.71 (3H, s), 1.77 (1H, s), 1.87–1.90 (3H, m), 2.11 (1H, dd, J=5.9, 15.6 Hz), 2.15–2.52 (4H, m), 2.32 (3H, s), 3.34 (1H, s), 3.56 (1H, d, J=4.9 Hz), 4.06 (1H, d, J=5.4 Hz), 4.22 (1H, d, J=8.3 Hz), 4.42 (1H, d, J=8.3 Hz), 4.71 (1H, dd, J=5.4, 48.3 Hz), 4.72–4.83 (1H, m), 4.99 (1H, d, J=7.8 Hz), 5.27 (1H, br s), 6.08 (1H, d, J=4.9 Hz), 7.48 (2H, t, J=7.8 Hz), 7.59 (1H, t, J=7.8 Hz), 8.11 (2H, d, J=7.8 Hz).

Step 2: 9β-10-Deacetyl-7-deoxy-9-dihydro-7α-fluoro-9,10-O-isopropylidenebaccatin III Using the compound obtained in the above step 1 as the starting material, the reaction procedure of the step 2 of Inventive Example 1 was repeated to obtain the title compound in a colorless transparent glassy form.

$^1$H-NMR (400 MHz, CDCl$_3$/TMS) δ (ppm); 1.12 (3H, s), 1.43 (3H, s), 1.49 (3H, s), 1.59 (3H, s), 1.65 (3H, s), 1.75 (1H, s), 1.98 (3H, d, J=1.5 Hz), 2.00–2.45 (5H, m), 2.33 (3H, s), 3.59 (1H, d, J=5.2 Hz), 4.30 (1H, d, J=8.8 Hz), 4.35 (1H, d, J=8.8 Hz), 4.61 (1H, d, J=8.8 Hz), 4.75–4.85 (1H, m), 4.92 (1H, ddd, J=3.4, 10.3, 45.9 Hz), 4.94 (1H, d, J=3.9 Hz), 5.59 (1H, d, J=8.8 Hz), 5.89 (1H, d, J=5.2 Hz), 7.48 (2H, t, J=7.4 Hz), 7.61 (1H, t, J=7.4 Hz), 8.12 (2H, d, J=7.4 Hz).

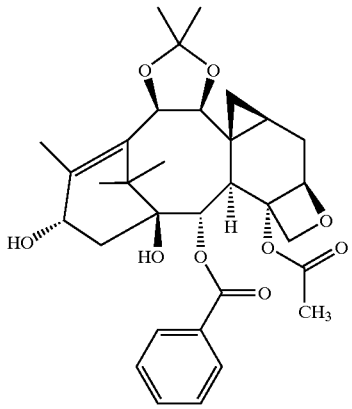

Step 1: 10,13-bis-O-Benzyloxycarbonyl-10-deacetyl-7-O-trifluoromethanesulfonylbaccatin III A 470 mg portion of 10,13-di-O-benzyloxycarbonyl-10-deacetylbaccatin III was dissolved in 20 ml of methylene chloride, and the solution was mixed with 700 mg of 4-dimethylaminopyridine and 480 μl of trifluoromethanesulfonic acid anhydride at 0° C. After 1 hour of stirring at 0° C., the reaction solution was poured into a stirred mixture of 50 ml ethyl acetate and 50 ml ice water and extracted with ethyl acetate. The thus obtained extract was washed with saturated sodium bicarbonate aqueous solution and dried over anhydrous sodium sulfate. Thereafter, the solvent was evaporated under a reduced pressure and the resulting residue was purified by a silica gel column chromatography (developing solvent; chloroform:ethyl acetate=1:1 (v/v)) to obtain 370 mg of the title compound as a white solid.

$^1$H-NMR (400 MHz, CDCl$_3$/TMS) δ (ppm); 1.10 (3H, s), 1.18 (3H, s), 1.68 (1H, s), 1.86 (3H, s), 2.13 (3H, d, J=1.5 Hz), 2.18–2.45 (3H, m), 2.28 (3H, s), 2.78–2.93 (1H, m), 3.94 (1H, d, J=6.8 Hz), 4.13 (1H, d, J=8.3 Hz), 4.33 (1H, d, J=8.3 Hz), 4.91 (1H, d, J=8.3 Hz), 5.20 (1H, d, J=12.2 Hz), 5.24 (2H, s), 5.25 (1H, d, J=12.2 Hz), 5.50 (1H, dd, J=7.3, 10.3 Hz), 5.67 (1H, d, J=6.8 Hz), 5.92 (1H, t, J=8.1 Hz), 6.48 (1H, s), 7.27–7.39 (10H, m), 7.48 (2H, t, J=7.3 Hz), 7.62 (1H, t, J=7.3 Hz), 8.05 (2H, d, J=7.3 Hz).

Step 2: 10,13-di-O-Benzyloxycarbonyl-10-deacetyl-7-deoxy-7β,8β-methylene-19-norbaccatin III A 220 mg portion of the compound obtained in the above step 1 was dissolved in 12 ml of tetrahydrofuran and 12 ml of acetonitrile, and the solution was mixed with 6.0 g of silica gel and stirred at 60° C. for 24 hours. After removing silica gel by filtration, the resulting filtrate was mixed with 50 ml of ethyl acetate and 50 ml of saturated sodium bicarbonate aqueous solution, and extracted with ethyl acetate. The thus obtained extract was washed with saturated brine and dried over anhydrous sodium sulfate. Thereafter, the solvent was evaporated under a reduced pressure and the resulting residue was purified by a silica gel column chromatography (developing solvent; hexane:ethyl acetate=3:1 (v/v)) to obtain 170 mg of the title compound as a white solid.

$^1$H-NMR (400 MHz, CDCl$_3$/TMS) δ (ppm); 1.14 (3H, s), 1.22 (3H, s), 1.39 (1H, br s), 1.58 (1H, s), 1.60–1.70 (1H, m), 1.94 (3H, d, J=1.0 Hz), 2.09 (1H, d, J=16.1 Hz), 2.23–2.40 (3H, m), 2.23 (3H, s), 2.45 (1H, dt, J=16.1, 4.4 Hz), 4.01 (1H, d, J=7.3 Hz), 4.10 (1H, d, J=8.8 Hz), 4.29 (1H, d, J=8.8 Hz), 4.72 (1H, d, J=3.9 Hz), 5.17–5.30 (4H, m), 5.63 (1H, d, J=7.3 Hz), 5.80–5.92 (1H, m), 6.12 (1H, s), 7.28–7.50 (10H, m), 7.48 (2H, t, J=7.3 Hz), 7.61 (1H, t, J=7.3 Hz), 8.08 (2H, d, J=7.3 Hz).

Step 3: 10-Deacetyl-7-deoxy-7β,8β-methylene-19-norbaccatin III

A 170 mg portion of the compound obtained in the above step 2 was dissolved in 10 ml of ethanol, and the solution was mixed with 34.0 ml of 10% palladium-carbon at room temperature. After 1 hour of stirring in an atmosphere of hydrogen, the catalyst was removed by filtration, the solvent in the resulting filtrate was evaporated under a reduced pressure and then the thus obtained residue was purified by a silica gel column chromatography (developing solvent; hexane:ethyl acetate=1:1 (v/v)) to obtain 110 mg of the title compound as a white solid.

$^1$H-NMR (400 MHz, CDCl$_3$/TMS) δ (ppm); 1.11 (3H, s), 1.15 (3H, s), 1.35–1.43 (1H, m), 1.74 (1H, dd, J=5.2, 7.1 Hz), 1.76 (1H, s), 2.03 (3H, d, J=1.0 Hz), 2.07–2.15 (2H, m), 2.27 (3H, s), 2.20–2.40 (2H, m), 2.45 (1H, dt, J=15.6, 4.4 Hz), 4.06 (1H, d, J=7.8 Hz), 4.22 (1H, d, J=1.0 Hz), 4.23 (1H, d, J=8.3 Hz), 4.32 (1H, d, J=8.3 Hz), 4.75 (1H, d, J=3.9 Hz), 4.82–4.90 (1H, m), 5.04 (1H, s), 5.62 (1H, d, J=7.8 Hz), 7.49 (2H, t, J=7.3 Hz), 7.61 (1H, t, J=7.3 Hz), 8.13 (2H, d, J=7.3 Hz).

Step 4: 9β-10-Deacetyl-7-deoxy-9-dihydro-7β,8β-methylene-19-norbaccatin III

Using the compound obtained in the above step 3 as the starting material, the reaction procedure of the step 1 of Reference Example 14 was repeated to obtain the title compound in a colorless transparent glassy form.

$^1$H-NMR (400 MHz, CDCl$_3$/TMS) δ (ppm); 0.92 (1H, br s), 1.06–1.18 (1H, m), 1.14 (3H, s), 1.39–1.48 (2H, m), 1.67 (3H, s), 1.78 (1H, s), 1.83 (3H, s), 2.16 (1H, d, J=4.9 Hz), 2.19 (3H, s), 2.34–2.40 (1H, m), 2.43 (1H, dd, J=9.3, 15.9 Hz), 2.53 (1H, dd, J=7.1, 15.9 Hz), 2.61 (1H, d, J=7.8 Hz), 2.58–2.68 (1H, m), 3.25 (1H, d, J=7.8 Hz), 3.87 (1H, dd, J=5.4, 7.8 Hz), 4.18 (1H, d, J=7.3 Hz), 4.58 (1H, dd, J=7.8, 10.7 Hz), 4.69 (1H, d, J=7.3 Hz), 4.70–4.80 (1H, m), 5.27 (1H, dd, J=4.4, 5.4 Hz), 5.55 (1H, d, J=7.8 Hz), 7.47 (2H, t, J=7.3 Hz), 7.58 (1H, t, J=7.3 Hz), 8.04 (2H, d, J=7.3 Hz).

Step 5: 9β-10-Deacetyl-7-deoxy-9-dihydro-7β,8β-methylene-9,10-O-isopropylidene-19-norbaccatin III Using the compound obtained in the above step 4 as the starting material, the reaction procedure of the step 2 of Inventive Example 1 was repeated to obtain the title compound in a colorless transparent glassy form.

$^1$H-NMR (400 MHz, CDCl$_3$/TMS) δ (ppm); 1.11 (3H, s), 1.20–1.40 (2H, m), 1.34 (3H, s), 1.48 (3H, s), 1,53 (3H, s), 1.68–1.80 (2H, m), 1.70 (1H, s), 1.76 (1H, t, J=5.3 Hz), 1.92 (3H, d, J=1.0 Hz), 2.09 (1H, d, J=5.4 Hz), 2.22 (3H, s), 2.37 (1H, dd, J=8.3, 15.6 Hz), 2.47 (1H, dd, J=7.3, 15.6 Hz), 2.70 (1H, dt, J=14.7, 8.3 Hz), 3.31 (1H, d, J=8.3 Hz), 4.22 (1H, d, J=7.8 Hz), 4.40 (1H, d, J=7.8 Hz), 4.49 (1H, d, J=7.8 Hz), 4.57 (1H, dd, J=8.2, 9.2 Hz), 4.75–4.85 (1H, m), 5.49 (1H, d, J=7.8 Hz), 5.50 (1H, d, J=8.3 Hz), 7.43 (2H, t, J=7.3 Hz), 7.59 (1H, t, J=7.3 Hz), 8.05 (2H, d, J=7.3 Hz).

Reference Example 16

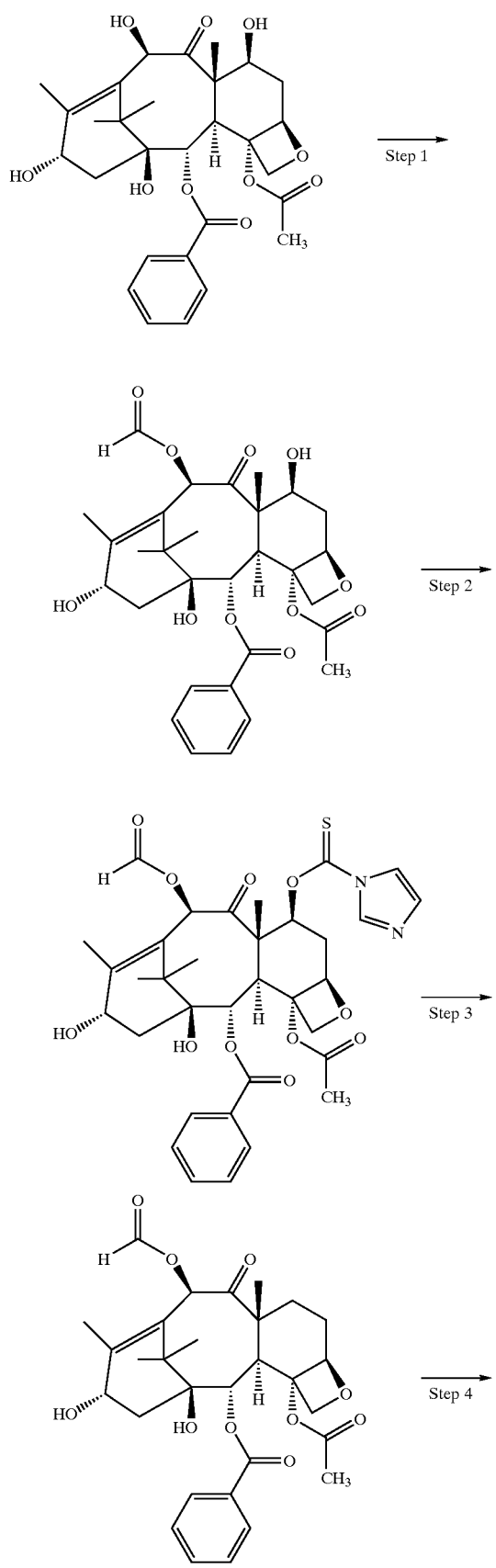

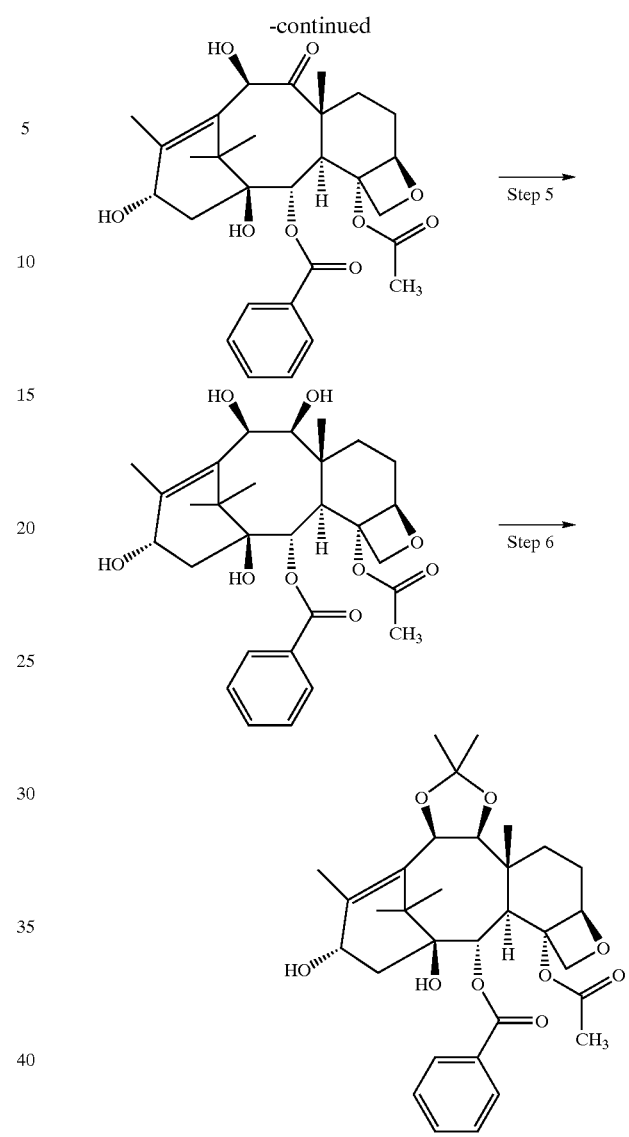

Step 1: 10-Deacetyl-10-O-formylbaccatin III

A 104 mg portion of 10-deacetylbaccatin III was dissolved in 1.0 ml of N,N-dimethylhormamido, and the solution was mixed with 70.7 ml of 4-dimethylaminopyridine and 96.0 µl of anhydrous trifluoromethanesulfonate at 0° C. After 10 minutes of stirring at 0° C., the reaction mixture was mixed with 10 ml of ethyl acetate and 40 ml of water under stirring, and then extracted with ethyl acetate. The thus obtained extract was washed with saturated brine, and dried over anhydrous sodium sulfate. Thereafter, the solvent was evaporated under a reduced pressure and the resulting residue was purified by a silica gel thin layer chromatography (developing solvent; chloroform:ethyl acetate=1:2 (v/v)) to obtain 94.3 mg of the title compound as a white solid.

$^1$H-NMR (400 MHz, CDCl$_3$/TMS) δ (ppm); 1.11 (3H, s), 1.12 (3H, s), 1.60 (3H, s), 1.69 (3H, s), 1.80–2.40 (5H, m), 2.29 (3H, s), 2.53–2.62 (1H, m), 3.89 (1H, d, J=6.8 Hz), 4.16 (1H, d, J=8.7 Hz), 4.31 (1H, d, J=8.7 Hz), 4.40–4.50 (1H, m), 4.90 (1H, br q, J=5.6 Hz), 4.98 (1H, d, J=7.9 Hz), 5.64 (1H, d, J=6.8 Hz), 6.46 (1H, s), 7.50 (2H, t, J=7.2 Hz), 7.61 (1H, t, J=7.2 Hz), 8.10 (2H, d, J=7.2 Hz), 8.22 (1H, s).

Step 2: 10-Deacetyl-10-O-formyl-7-O-[(1-imidazolyl)-thiocarbonyl]baccatin III 23.8 mg of the compound obtained in the above step 1 was dissolved in 0.50 ml of tetrahydrofuran, and the solution was mixed with 0.50 ml of benzene, 12.5 µl of 1,8-diazabicycloundecene and 12.5 mg of thiocarbonylimidazole at a room temperature. After 1 hour of stirring at the same temperature, the reaction mixture was mixed with 10 ml of ethyl acetate and 10 ml of saturated ammonium chloride aqueous solution, and then extracted with ethyl acetate. The thus obtained extract was washed with saturated brine, and dried over anhydrous sodium sulfate. Thereafter, the solvent was evaporated under a reduced pressure and the resulting residue was purified by a silica gel thin layer chromatography (developing solvent; chloroform:ethyl acetate 1:1 (v/v)) to obtain 21.4 mg of the title compound as a white solid.

$^1$H-NMR (400 MHz, CDCl$_3$/TMS) δ (ppm); 1.13 (3H, s), 1.18 (3H, s), 1.64 (3H, s), 1.85–2.45 (4H, m), 1.96 (3H, s), 2.34 (3H, s), 2.49 (1H, br s), 3.04 (1H, ddd, J=7.1, J=9.3, J=14.3 Hz), 4.12 (1H, d, J=7.3 Hz), 4.21 (1H, d, J=8.6 Hz), 4.38 (1H, d, J=8.6 Hz), 4.88 (1H, br s), 5.04 (1H, d, J=9.3 Hz), 5.69 (1H, d, J=7.3 Hz), 6.26 (1H, dd, J=7.1, J=10.5 Hz), 6.40 (1H, s), 7.00 (1H, s), 7.50 (2H, t, J=7.2 Hz), 7.52 (1H, s), 7.63 (1H, t, J=7.2 Hz), 7.99 (1H, s), 8.12 (2H, d, J=7.2 Hz), 8.18 (1H, s).

Step 3: 10-Deacetyl-7-deoxy-10-O-formyl-7-O-baccatin III 140 mg of the compound obtained in the above step 2 was dissolved in 5.0 ml of dioxane, and the solution was mixed with 280 µl of tin tributyl hydride and 10.0 mg of 2,2'-azobisisobutyronitrile at a room temperature. After 40 minutes of stirring at 75–80° C., the reaction mixture was mixed with 10 ml of ethyl acetate, 10 ml of water and 10 ml of saturated brine, and then extracted with ethyl acetate. The thus obtained extract was dried over anhydrous sodium sulfate. Thereafter, the solvent was evaporated under a reduced pressure and the resulting residue was purified by a silica gel thin layer chromatography (developing solvent; hexane:ethyl acetate=5:7 (v/v)) to obtain 52.0 mg of the title compound as a white solid. $^1$H-NMR (400 MHz, CDCl$_3$/TMS) δ (ppm); 1.09 (3H, s), 1.12 (3H, s), 1.50–2.50 (8H, m), 1.75 (3H, s), 2.04 (3H, s), 2.29 (3H, s), 3.85 (1H, d, J=7.3 Hz), 4.19 (1H, d, J=8.3 Hz), 4.32 (1H, d, J=8.3 Hz), 4.85 (1H, br s), 4.97 (1H, dd, J=9.3, J=2.5 Hz), 5.63 (1H, d, J=7.3 Hz), 6.60 (1H, s), 7.49 (2H, t, J=7.3 Hz), 7.63 (1H, t, J=7.3 Hz), 8.12 (2H, d, J=7.3 Hz), 8.24 (1H, s).

Step 4: 10-Deacetyl-7-deoxybaccatin III 50.0 mg of the compound obtained in the above step 3 was dissolved in 2.0 ml of 95% ethanol, and the solution was mixed with 200 µl of hydrazine hydrate at a room temperature. After 30 minutes of stirring at a room temperature, the reaction mixture was mixed with 10 ml of ethyl acetate and 50 ml of 7% hydrochloric acid, and then extracted with ethyl acetate. The thus obtained. extract was washed with saturated sodium bicarbonate aqueous solution and dried over anhydrous sodium sulfate. Thereafter, the solvent was evaporated under a reduced pressure and the resulting residue was purified by a silica gel thin layer chromatography (developing solvent; hexane:ethyl acetate=2:3 (v/v)) to obtain 30.0 mg of the title compound as a white solid.
$^1$H-NMR (400 MHz, CDCl$_3$/TMS) δ (ppm); 1.06 (3H, s), 1.09 (3H, s), 1.50–1.55 (1H, m), 1.80 (1H, s), 1.90–2.41 (7H, m), 2.17 (3H, s), 2.29 (3H, s), 3.92 (1H, d, J=7.3 Hz), 4.17 (1H, d, J=1.5 Hz), 4.22 (1H, d, J=8.3 Hz), 4.33 (1H, d, J=8.3 Hz), 4.82–4.92 (1H, m), 4.96 (1H, dd, J=9.6, J=3.2 Hz), 5.24 (1H, d, J=1.5 Hz), 5.62 (1H, d, J=7.3 Hz), 7.48 (2H, t, J=7.3 Hz), 7.61 (1H, t, J=7.3 Hz), 8.12 (2H, d, J=7.3 Hz).

Step 5: 9β-10-Deacetyl-7-deoxy-9-dihydrobaccatin III

Using the compound obtained in the above step 4 as the starting material, the reaction procedure of the step 1 of Reference Example 14 was repeated to obtain the title compound in a colorless transparent glassy form.

$^1$H-NMR (400 MHz, CDCl$_3$/TMS) δ (ppm); 1.15 (3H, s), 1.51 (3H, s), 1.67 (3H, s), 1.91 (3H, s), 1.50–2.70 (9H, m), 2.35 (3H, s), 3.04 (1H, d, J=4.9 Hz), 3.14 (1H, br d, J=6.8 Hz), 3.75 (1H, br s), 4.21 (1H, d, J=8.3 Hz), 4.37 (1H, d, J=8.3 Hz), 4.71 (1H, br q, J=8.3 Hz), 4.86 (1H, br s), 5.45 (1H, br s), 6.05 (1H, d, J=4.9 Hz), 7.48 (2H, t, J=7.6 Hz), 7.61 (1H, t, J=7.6 Hz), 8.14 (2H, d, J=7.6 Hz).

Step 6: 9β-10-Deacetyl-7-deoxy-9-dihydro-9,10-O-isopropylidenebaccatin III

Using the compound obtained in the above step 5 as the starting material, the reaction procedure of the step 2 of Inventive Example 1 was repeated to obtain the title compound in a colorless transparent glassy form.

$^1$H-NMR (400 MHz, CDCl$_3$/TMS) δ (ppm); 1.16 (3H, s), 1.43 (3H, s), 1.51 (3H, s), 1.57 (3H, s), 1.59 (3H, s), 1.79 (1H, s), 1.99 (3H, s), 1.45–2.40 (6H, m), 2.35 (3H, s), 2.44 (1H, d, J=5.3 Hz), 3.10 (1H, d, J=4.9 Hz), 4.19 (1H, d, J=7.6 Hz), 4.27 (1H, d, J=8.3 Hz), 4.34 (1H, d, J=8.3 Hz), 4.70–4.84 (1H, m), 4.86 (1H, br s), 5.62 (1H, d, J=7.6 Hz), 5.97 (1H, d, J=4.9 Hz), 7.48 (2H, t, J=7.3 Hz), 7.60 (1H, t, J=7.3 Hz), 8.14 (2H, d, J=7.3 Hz).

Reference Example 17

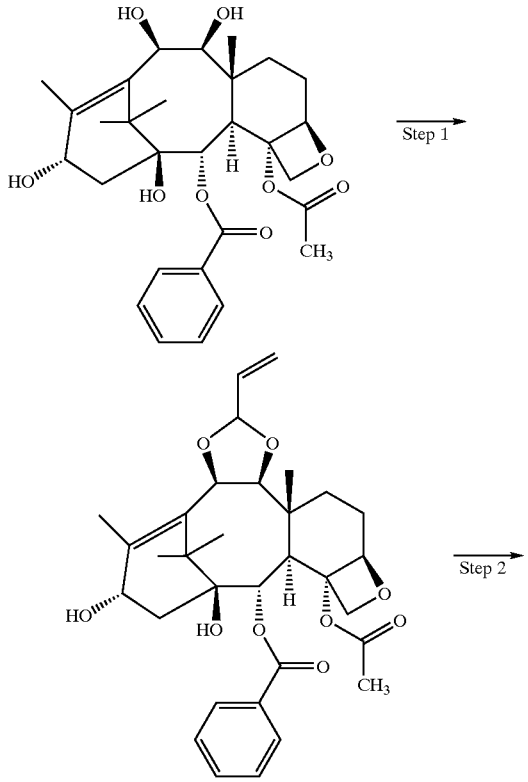

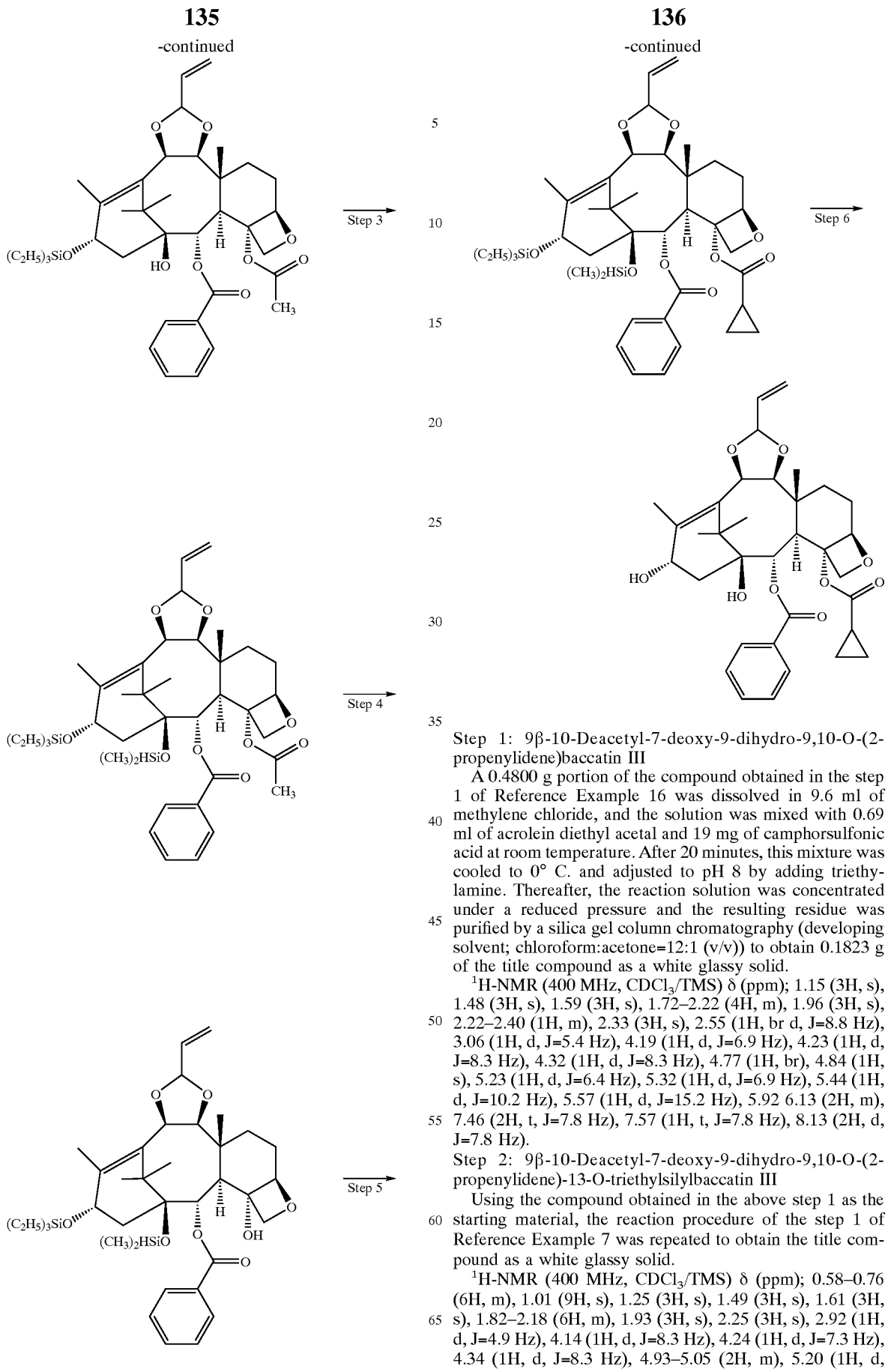

Step 1: 9β-10-Deacetyl-7-deoxy-9-dihydro-9,10-O-(2-propenylidene)baccatin III

A 0.4800 g portion of the compound obtained in the step 1 of Reference Example 16 was dissolved in 9.6 ml of methylene chloride, and the solution was mixed with 0.69 ml of acrolein diethyl acetal and 19 mg of camphorsulfonic acid at room temperature. After 20 minutes, this mixture was cooled to 0° C. and adjusted to pH 8 by adding triethylamine. Thereafter, the reaction solution was concentrated under a reduced pressure and the resulting residue was purified by a silica gel column chromatography (developing solvent; chloroform:acetone=12:1 (v/v)) to obtain 0.1823 g of the title compound as a white glassy solid.

$^{1}$H-NMR (400 MHz, CDCl$_3$/TMS) δ (ppm); 1.15 (3H, s), 1.48 (3H, s), 1.59 (3H, s), 1.72–2.22 (4H, m), 1.96 (3H, s), 2.22–2.40 (1H, m), 2.33 (3H, s), 2.55 (1H, br d, J=8.8 Hz), 3.06 (1H, d, J=5.4 Hz), 4.19 (1H, d, J=6.9 Hz), 4.23 (1H, d, J=8.3 Hz), 4.32 (1H, d, J=8.3 Hz), 4.77 (1H, br), 4.84 (1H, s), 5.23 (1H, d, J=6.4 Hz), 5.32 (1H, d, J=6.9 Hz), 5.44 (1H, d, J=10.2 Hz), 5.57 (1H, d, J=15.2 Hz), 5.92 6.13 (2H, m), 7.46 (2H, t, J=7.8 Hz), 7.57 (1H, t, J=7.8 Hz), 8.13 (2H, d, J=7.8 Hz).

Step 2: 9β-10-Deacetyl-7-deoxy-9-dihydro-9,10-O-(2-propenylidene)-13-O-triethylsilylbaccatin III Using the compound obtained in the above step 1 as the starting material, the reaction procedure of the step 1 of Reference Example 7 was repeated to obtain the title compound as a white glassy solid.

$^{1}$H-NMR (400 MHz, CDCl$_3$/TMS) δ (ppm); 0.58–0.76 (6H, m), 1.01 (9H, s), 1.25 (3H, s), 1.49 (3H, s), 1.61 (3H, s), 1.82–2.18 (6H, m), 1.93 (3H, s), 2.25 (3H, s), 2.92 (1H, d, J=4.9 Hz), 4.14 (1H, d, J=8.3 Hz), 4.24 (1H, d, J=7.3 Hz), 4.34 (1H, d, J=8.3 Hz), 4.93–5.05 (2H, m), 5.20 (1H, d, J=6.4 Hz), 5.28 (1H, d, J=7.3 Hz), 5.44 (1H, d, J=10.7 Hz), 5.56 (1H, d, J=17.1 Hz), 5.91–6.09 (2H, m), 7.47 (2H, t, J=7.8 Hz), 7.58 (1H, t, J=7.8 Hz), 8.14, (2H, d, J=7.8 Hz).

Step 3: 9β-10-Deacetyl-7-deoxy-9-dihydro-1-O-dimethylsilyl 9,10-O-(2-propenylidene)-13-O-triethylsilylbaccatin III Using the compound obtained in the above step 2 as the starting material, the reaction procedure of the step 1 of Reference Example 11 was repeated to obtain the title compound in a colorless transparent oily form.

$^1$H-NMR (400 MHz, CDCl$_3$/TMS) δ (ppm); −0.28 (3H, d, J=2.9 Hz), 0.05 (3H, d, J=2.9 Hz), 0.59–0.78 (6H, m), 1.02 (9H, t, J=7.8 Hz), 1.19 (3H, s), 1.50–1.64 (1H, m), 1.53 (3H, s), 1.59 (3H, s), 1.82–2.04 (3H, m), 1.89 (3H, s), 2.14 (1H, dd, J=15.1 Hz, J=8.3 Hz), 2.26 (3H, s), 2.33 (1H, dd, J=15.1 Hz, J=8.8 Hz), 2.88 (1H, d, J=4.8 Hz), 4.17 (1H, d, J=8.3 Hz), 4.23 (1H, d, J=7.3 Hz), 4.30 (1H, d, J=8.3 Hz), 4.54–4.62 (1H, m), 4.94 (1H, s), 4.99 (1H, t, J=8.3 Hz), 5.19 (1H, d, J=6.3 Hz), 5.27 (1H, d, J=7.3 Hz), 5.42 (1H, d, J=10.7 Hz), 5.55 (1H, d, J=17.1 Hz), 5.92–6.06 (2H, m), 7.45 (2H, t, J=7.9 Hz), 7.56 (1H, t, J=7.9 Hz), 8.14 (2H, d, J=7.9 Hz).

Step 4: 9β-4,10-Dideacetyl-7-deoxy-9-dihydro-1-O-dimethylsilyl-9,10-O-(2-propenylidene)-13-O-triethylsilylbaccatin III Using the compound obtained in the above step 3 as the starting material, the reaction procedure of the step 2 of Reference Example 11 was repeated to obtain the title compound in a pale yellow transparent oily form.

$^1$H-NMR (400 MHz, CDCl$_3$/TMS) δ (ppm); −0.26 (3H, d, J=2.9 Hz), 0.01 (3H, d, J=2.9 Hz), 0.68–0.87 (6H, m), 1.03 (3H, s), 1.05 (9H, t, J=7.8 Hz), 1.42 (3H, s), 1.52 (3H, s), 1.52–1.73 (2H, m), 1.80 (3H, s), 1.80–1.95 (2H, m), 2.52 (1H, dd, J=15.1 Hz, J=9.7 Hz), 2.71 (1H, d, J=4.4 Hz), 2.85 (1H, dd, J=15.1 Hz, J=2.4 Hz), 3.61 (1H, s), 4.12–4.31 (1H, m), 4.14 (1H, d, J=7.3 Hz), 4.18 (1H, d, J=7.3 Hz), 4.25 (1H, d, J=7.3 Hz), 4.57–4.70 (3H, m), 5.20 (1H, d, J=6.3 Hz), 5.36 (1H, d, J=7.3 Hz), 5.43 (1H, d, J=10.3 Hz), 5.55 (1H, d, J=17.1 Hz), 5.93–6.08 (2H, m), 7.44 (2H, t, J=7.3 Hz), 7.54 (1H, t, J=7.3 Hz), 8.17 (2H, d, J=7.3 Hz).

Step 5: 9β-4-O-Cyclopropanecarbonyl-4,10-dideacetyl-7-deoxy-9-dihydro-1-O-dimethylsilyl-9,10-O-(2-propenylidene)-13-O-triethylsilylbaccatin III Using the compound obtained in the above step 4 as the starting material, the reaction procedure of the step 3 of Reference Example 11 was repeated to obtain the title compound in a white glassy form.

$^1$H-NMR (400 MHz, CDCl$_3$/TMS) δ (ppm); −0.28 (3H, d, J=3.0 Hz), 0.05 (3H, d, J=3.0 Hz), 0.56–0.80 (6H, m), 1.02 (9H, t, J=7.8 Hz), 1.03–1.40 (4H, m), 1.21 (3H, s), 1.50–2.10 (5H, m), 1.51 (3H, s), 1.60 (3H, s), 1.90 (3H, s), 2.30 (2H, d, J=8.8 Hz), 2.83 (1H, d, J=4.9 Hz), 4.16 (1H, d, J=8.3 Hz), 4.22 (1H, d, J=7.4 Hz), 4.32 (1H, d, J=8.3 Hz), 4.60–4.72 (1H, m), 4.89 (1H, s), 5.01 (1H, t, J=8.3 Hz), 5.20 (1H, d, J=8.3 Hz), 5.26 (1H, d, J=7.4 Hz), 5.43 (1H, d, J=10.3 Hz), 5.55 (1H, d, J=17.6 Hz), 5.92–6.06 (2H, m), 7.45 (2H, t, J=7.9 Hz), 7.57 (1H, t, J=7.9 Hz), 8.11 (2H, d, J=7.9 Hz).

Step 6: 9β-4-O-Cyclopropanecarbonyl-4,10-dideacetyl-7-deoxy-9-dihydro-9,10-O-(2-propenylidene)baccatin III Using the compound obtained in the above step 5 as the starting material, -the reaction procedure of the step 3 of Reference Example 7 was repeated to obtain the title compound in a white glassy form.

$^1$H-NMR (400 MHz, CDCl$_3$/TMS) δ (ppm); 1.08–1.24 (3H, m), 1.17 (3H, s), 1.34–1.41 (1H, m), 1.47 (3H, s), 1.60 (3H, s), 1.60–1.94 (5H, m), 1.97 (3H, s), 2.04–2.12 (1H, m), 2.37 (1H, d, J=9.8 Hz), 2.40 (1H, d, J=11.7 Hz), 3.07 (1H, d, J=5.4 Hz), 4.18 (1H, d, J=6.8 Hz), 4.27 (1H, d, J=8.7 Hz), 4.36 (1H, d, J=8.7 Hz), 4.69–4.82 (2H, m), 5.23 (1H, d, J=6.3 Hz), 5.33 (1H, d, J=10.2 Hz), 5.57 (1H, d, J=17.1 Hz), 5,96–6.08 (2H, m), 7.48 (2H, t, J=7.3 Hz), 7.60 (1H, t like, J=7.3 Hz), 8.15 (2H, d like, J=7.3 Hz).

Reference Example 18

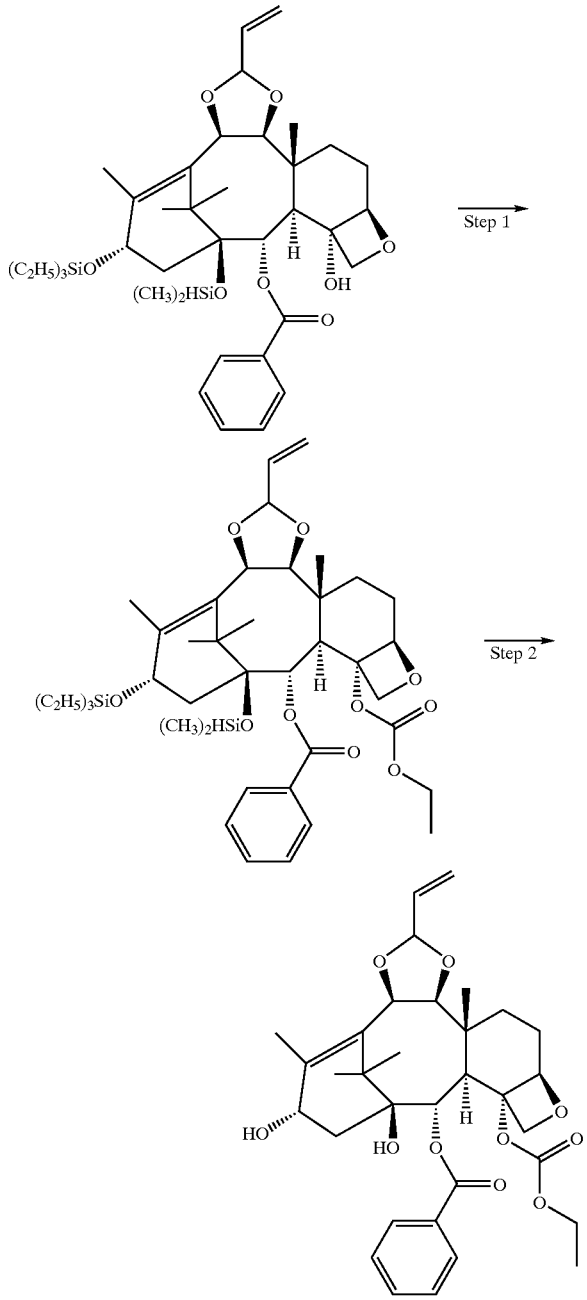

Step 1: 9β-4,10-Dideacetyl-7-deoxy-9-dihydro-1-O-dimethylsilyl-4-O-ethoxycarbonyl-9,10-O-(2-propenylidene)-13-O-triethylsilylbaccatin III Using the compound obtained in the step 4 of Reference Example 17 as the starting material, the reaction procedure of the step 3 of Reference Example 11 was repeated, except that ethyl chloroformate was used in stead of cyclopropanecarbonyl chloride, to obtain the title compound in a colorless transparent oily form.

$^1$H-NMR (400 MHz, CDCl$_3$/TMS) δ (ppm); −0.28 (3H, d, J=2.9 Hz), 0.03 (3H, d, J=2.9 Hz), 0.56–0.75 (6H, m), 1.00 (9H, t, J=7.8 Hz), 1.22 (3H, s), 1.39 (3H, t, J=7.3 Hz), 1.50–1.70 (2H, m), 1.52 (3H, s), 1.60 (3H, s), 1.75–2.10 (2H, m), 1.89 (3H, s), 2.20–2.37 (2H, m), 2.80 (1H, d, J=4.4 Hz), 4.15–4.26 (3H, m), 4.36–4.44 (2H, m), 4.60–4.68 (1H, m), 4.98–5.04 (2H, m), 5.20 (1H, d, J=6.3 Hz), 5.26 (1H, d, J=7.3 Hz), 5.43 (1H, d, J=10.3 Hz), 5.55 (1H, d, J=17.1 Hz), 5.91–6.07 (2H, m), 7.45 (2H, t, J=7.8 Hz), 7.55 (1H, t, J=7.8 Hz), 8.13 (2H, d, J=7.8 Hz).

Step 2: 9β-4,10-Dideacetyl-7-deoxy-9-dihydro-4-O-ethoxycarbonyl-9,10-O-(2-propenylidene)baccatin III Using the compound obtained in the above step 1 as the starting material, the reaction procedure of the step 3 of Reference Example 7 was repeated to obtain the title compound in a white glassy form.

$^1$H-NMR (400 MHz, CDCl$_3$/TMS) δ (ppm); 1.16 (3H, s), 1.43 (3H, t, J=7.3 Hz), 1.48 (3H, s), 1.54–2.15 (5H, m), 1.60 (3H, s), 1.97 (3H, s), 2.37 (1H, dd, J=15.7 Hz, J=9.8 Hz), 2.50 (1H, d, J=10.3 Hz), 3.00 (1H, d, J=4.9 Hz), 4.10–4.40 (5H, m), 4.65–4.80 (1H, m), 4.89 (1H, s), 5.23 (1H, d, J=6.3 Hz), 5.34 (1H, d, J=6.9 Hz), 5.46 (1H, d, J=10.2 Hz), 5.57 (1H, d, J=17.1 Hz), 5.92–6.08 (2H, m), 7.47 (2H, t, J=7.8 Hz), 7.58 (1H, t, J=7.8 Hz), 8.14 (2H, d, J=7.8 Hz).

INDUSTRIAL APPLICABILITY

Antitumor effects of the compound of the present invention are shown by the following test examples.

Test Example

Cells of each of three tumor cell lines, P388, PC-6 and PC-12, were inoculated into a 96 well microplate in an inoculum size of 5.0×10$^2$ cells/150 μl/well (P388), 5.0×10$^3$ cells/150 μl/well (PC-6) or 1.0×10$^3$ cells/150 μl/well (PC-12), and 50 μl/well of each sample was added to the plate 2 hours thereafter in the case of P388 or 24 hours thereafter in the case of the other two. Thereafter, the cells were cultured for 3 days and then 5 mg/ml solution of MTT [3-(4,5-dimethylthiazol-2-yl)-2,5-diphenyl-2H-tetrazolium bromide] was dispensed in 20 μl/well portions into wells of the microplate. Four hours thereafter, the culture medium was removed, 150 μl of dimethyl sulfoxide was added to each well and then absorbance at 540 nm was measured. The antitumor effect is shown as GI$_{50}$ value (ng/ml) of each drug which decreases cell proliferation in each drug-added group to 50% of that in the control group. The results are shown in below.

|  | P388 | PC-6 | PC-12 |
|---|---|---|---|
| Taxol | 4.36 | 1.20 | 82.2 |
| Taxotere | 1.62 | 1.16 | 19.1 |
| Inventive Example 22 | 0.0193 | 0.187 | 0.181 |
| Inventive Example 25 | 0.0549 | 1.31 | 0.234 |
| Inventive Example 51 | 0.00754 | 0.354 | 0.0669 |
| Inventive Example 53 | 0.0128 | 0.874 | 0.0758 |
| Inventive Example 57 | 0.0135 | 0.734 | 0.0739 |
| Inventive Example 60 | 0.0129 | 0.395 | 0.0698 |
| Inventive Example 65 | 0.00509 | 0.278 | 0.0684 |
| Inventive Example 69 | 0.0161 | 0.0915 | 0.0466 |
| Inventive Example 70 | 0.00137 | 0.160 | 0.0184 |
| Inventive Example 79 | 0.00689 | 0.0673 | 0.0264 |
| Inventive Example 81 | 0.0048 | 0.0604 | 0.050 |
| Inventive Example 90 | 0.0519 | 0.209 | 0.0943 |
| Inventive Example 95 | 0.0034 | 0.0992 | 0.0121 |
| Inventive Example 98 | 0.0126 | 0.0696 | 0.022 |
| Inventive Example 101 | 0.0301 | 0.409 | 0.125 |

-continued

|  | P388 | PC-6 | PC-12 |
|---|---|---|---|
| Inventive Example 105 | 0.0475 | 0.190 | 0.0643 |
| Inventive Example 121 | 0.00173 | 0.803 | 0.0498 |
| Inventive Example 123 | 0.0158 | 0.366 | 0.167 |

We claim:

1. A compound represented by the following formula (Ia) or a salt thereof:

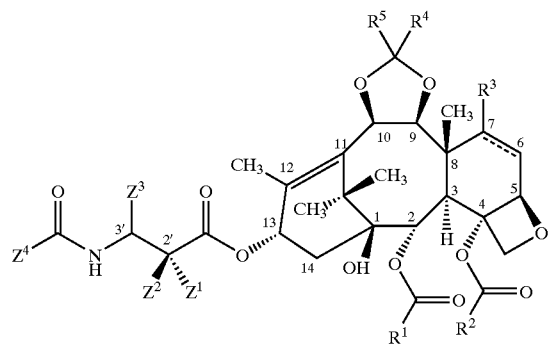

(Ia)

wherein:

R$^1$ represents a phenyl group, which may have one or more substituent(s) selected from the group consisting of a halogen atom, an alkyl group and an alkoxyl group;

R$^2$ represents a cycloalkyl group, and this cycloalkyl group may have one or more substituents selected from the group consisting of a halogen atom, a hydroxyl group, a carboxyl group, an alkoxyl group, an aryloxy group, a phenyl group, an amino group, an alkylamino group, an alkoxycarbonyl group, an aryloxycarbonyl group, an acyl group, an acylamino group and an acyloxy group;

R$^3$ represents a hydrogen atom, a hydroxyl group, a halogen atom, an alkoxyl group, a group —O—R$^{31}$, an acyloxy group or a group —O—CO—R$^{31}$, in which the alkoxyl and acyloxy groups may have one or more substituent(s) selected from the group consisting of a halogen atom, a hydroxyl group, a carboxyl group, a cycloalkyl group, an alkoxyl group, an aryl group, an aryloxy group, an amino group, an alkylamino group, an alkoxycarbonyl group, an aryloxycarbonyl group, an acyl group, an acylamino group, an acyloxy group and a heterocyclic group wherein the heterocyclic group may have one or more alkyl group(s) on the constituent atoms of its ring, wherein R$^{31}$ represents an alkylamino group, an alkenyl group, an alkynyl group, a cycloalkyl group, an aryl group or a heterocyclic group, in which these alkylamino, alkenyl, alkynyl, cycloalkyl, aryl and heterocyclic groups may have one or more substituent(s) selected from the group consisting of a halogen atom, a hydroxyl group, a carboxyl group, an alkyl group, an alkoxyl group, an aryloxy group, a phenyl group, an amino group, an alkylamino group, an aminoalkyl group, an alkylaminoalkyl group, an alkoxycarbonyl group, an aryloxycarbonyl group, aii acyl group, an acylamino group, an a carbon atom acyloxy group and a nitrogen-containing heterocyclic group having a size of a three- to eight-membered ring wherein the nitrogen-containing heterocyclic group may have one or more alkyl group(s) on the constituent atoms of its ring;

or $R^3$ may form a three-membered ring together with the methyl group linked to adjacent to the carbon atom to which $R^3$ is linked;

$R^4$ and $R^5$ each represents a hydrogen atom, an alkyl group, an alkenyl group, an alkynyl group, an aryl group or a heterocyclic group, in which these alkyl, alkenyl, alkynyl, aryl and heterocyclic groups may have one or more substituent(s) selected from the group consisting of an alkoxyl group, an amino group, an alkylamino group, an aminoalkyl group, an alkylaminoalkyl group and a nitrogen-containing saturated heterocyclic group having a size of a five- or six-membered ring represented by the following formula:

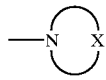

wherein X represents an oxygen atom, a sulfur atom, $CH_2$, CH—Y, NH or N—Y, in which Y is an alkyl group,
wherein said heterocyclic group may have one or more alkyl group(s) on a constituent atom of its ring;

or $R^4$ and $R^5$ may form a thiocarbonyl group or a carbonyl group together with the carbon atom liked thereto;

$Z^1$ represents a hydrogen atom, a hydroxyl group, a halogen atom or an alkyl group;

$Z^2$ represents a hydrogen atom, a hydroxyl group, a halogen atom or an alkyl group;

$Z^3$ represents an alkyl group, an alkenyl group, an alkynyl group, a cycloalkyl group, an aryl group or a heterocyclic group, in which these alkyl, alkenyl, alkynyl, cycloalkyl, aryl and heterocyclic groups may have one or more substituent(s) selected from the group consisting of a halogen atom, a hydroxyl group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group; and $Z^4$ represents an alkyl group, an aryl group or an alkoxyl group, in which these alkyl, aryl and alkoxyl groups may have one or more substituent (s) selected from the group consisting of a halogen atom, a hydroxyl group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group;

with the proviso that the dotted line of the following moiety:

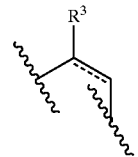

means that the corresponding bonding of the moiety may be a double bond, but $R^3$ is not a hydroxyl group in that case.

2. The compound or a salt thereof according to claim 1, wherein $R^2$ represents a cyclopropyl group.

* * * * *